(12) United States Patent
DeRoy et al.

(10) Patent No.: US 8,198,458 B2
(45) Date of Patent: Jun. 12, 2012

(54) NON-NUCLEOSIDE REVERSE TRANSCRIPTASE INHIBITORS

(75) Inventors: Patrick DeRoy, Blainville (CA);
Anne-Marie Faucher, St-Placide (CA);
Alexandre Gagnon, Montreal (CA);
Serge R. Landry, St. Jerome (CA);
Sebastien Morin, Montreal (CA);
Jeffrey O'Meara, Boisbriand (CA);
Bruno Simoneau, Laval (CA);
Bounkham Thavonekham, Longueuil (CA); Christiane Yoakim, Laval (CA)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 458 days.

(21) Appl. No.: 12/364,551

(22) Filed: Feb. 3, 2009

(65) Prior Publication Data
US 2009/0143370 A1 Jun. 4, 2009

Related U.S. Application Data

(62) Division of application No. 11/137,831, filed on May 24, 2005, now Pat. No. 7,517,998.

(60) Provisional application No. 60/575,888, filed on Jun. 1, 2004.

(51) Int. Cl.
*A61K 31/41* (2006.01)
*C07D 257/04* (2006.01)
(52) U.S. Cl. ........................ 548/251; 514/381
(58) Field of Classification Search .................. 548/251
See application file for complete search history.

(56) References Cited

U.S. PATENT DOCUMENTS

| | | | |
|---|---|---|---|
| 4,399,285 A | 8/1983 | Foerster et al. | |
| 6,245,817 B1 | 6/2001 | Connell et al. | |
| 7,642,277 B2 * | 1/2010 | Simoneau et al. | 514/381 |

FOREIGN PATENT DOCUMENTS

| | | |
|---|---|---|
| EP | 0035046 A1 | 9/1981 |
| JP | 63-185965 A | 8/1988 |
| WO | 2004/030611 A2 | 4/2004 |
| WO | 2004050643 A2 | 6/2004 |
| WO | 2005115147 A2 | 12/2005 |

OTHER PUBLICATIONS

EP Office Action, Application No. 05 757 660.5-2101, Dated Jul. 1, 2011.
JP Office Action, Application No. 2007-513640, Dated May 27, 2011.
Chemical Abstract English Language Translation of JP 63-185965, 1988.

* cited by examiner

*Primary Examiner* — Laura L. Stockton
(74) *Attorney, Agent, or Firm* — Michael P. Morris; Alan R. Stempel

(57) ABSTRACT

Compounds of formula (I):

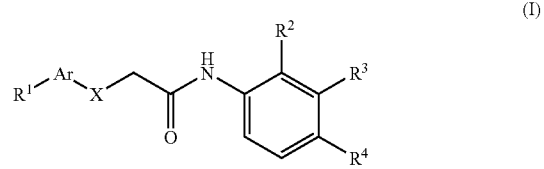

wherein Ar, X, $R^1$, $R^2$, $R^3$ and $R^4$ are as defined herein. The compounds are useful as reverse transcriptase inhibitors against wild type and single or double mutant strains of HIV.

28 Claims, No Drawings

NON-NUCLEOSIDE REVERSE TRANSCRIPTASE INHIBITORS

RELATED APPLICATIONS

This application is a divisional of U.S. application Ser. No. 11/137,831, now U.S. Pat. No. 7,517,998, filed on May 24, 2005, which claims priority benefit, as does the present application, to U.S. Application Ser. No. 60/575,888, filed on Jun. 1, 2004.

TECHNICAL FIELD OF THE INVENTION

The invention relates to novel compounds which inhibit HIV reverse transcriptase, a method for the treatment of HIV infection using such compounds, and to pharmaceutical compositions comprising such compounds.

BACKGROUND OF THE INVENTION

The disease known as acquired immune deficiency syndrome (AIDS) is caused by the human immunodeficiency virus (HIV), particularly the strain known as HIV-1. In order for HIV to be replicated by a host cell, the information of the viral genome must be integrated into the host cell's DNA. However, HIV is a retrovirus, meaning that its genetic information is in the form of RNA. The HIV replication cycle therefore requires a step of transcription of the viral genome (RNA) into DNA, which is the reverse of the normal chain of events. An enzyme that has been aptly dubbed reverse transcriptase (RT) accomplishes the transcription of the viral RNA into DNA. The HIV virion includes copies of RT along with the viral RNA.

Reverse transcriptase has three known enzymatic functions; it acts as an RNA-dependent DNA polymerase, as a ribonuclease, and as a DNA-dependent DNA polymerase. Acting as an RNA-dependent DNA polymerase, RT transcribes a single-stranded DNA copy of the viral RNA. Acting as a ribonuclease, RT destroys the original viral RNA, and frees the DNA just produced from the original RNA. Finally, acting as a DNA-dependent DNA polymerase, RT makes a second, complementary DNA strand, using the first DNA strand as a template. The two strands form double-stranded DNA, which is integrated into the host cell's genome by another enzyme called integrase.

Compounds that inhibit the enzymatic functions of HIV-1 reverse transcriptase will inhibit replication of HIV-1 in infected cells. Such compounds are useful in the prevention or treatment of HIV-1 infection in human subjects, as demonstrated by known RT inhibitors such as zidovudine, didanosine, zalcitabine, stavudine, lamivudine, emtricitabine, abacavir, tenofovir, nevirapine, delavirdine and efavirenz, the main reverse transcriptase inhibitors thus far approved for use in the treatment of AIDS.

As with any antiviral therapy, use of RT inhibitors in the treatment of AIDS eventually leads to a virus that is less sensitive to the given drug. Resistance (reduced sensitivity) to these drugs is the result of mutations that occur in the reverse transcriptase segment of the pol gene. Several mutant strains of HIV have been characterized, and resistance to known therapeutic agents is believed to be due to mutations in the RT gene. One of the more commonly observed mutants clinically for the non-nucleoside reverse transcriptase inhibitors is the K103N mutant, in which a lysine (K), at codon 103, has been mutated to a asparagine (N) residue. Other mutants, which emerge with varying frequency during treatment using known antivirals, include single mutants Y181C, G190A, Y188C, and P236L, and double mutants K103N/Y181C, K103N/P225H, K103N/V108I and K103N/L100I.

As antiviral use in therapy and prevention of HIV infection continues, the emergence of new resistant strains is expected to increase. There is therefore an ongoing need for new inhibitors of RT, which have different patterns of effectiveness against the various resistant mutants.

Antivirals active against HIV containing a thiadiazolyloxyacetamide or thiadiazolylthioacetamide moiety have been described in JP 07-188017 (Soyaku Gijutsu Kenkyusho) and non-nucleoside inhibitors of wild-type HIV reverse transcriptase containing triazolyl and imidazolyl moieties have been described in WO 2004/030611 (Ribapharm). The present invention provides novel compounds which show potent activity against wild type HIV reverse transcriptase as well as against single mutant and double mutant strains.

SUMMARY OF THE INVENTION

The invention provides compounds of formula (I) which are useful for treating HIV infection in a human infected by HIV. The compounds are potent inhibitors of wild-type (WT) and double mutant strains of HIV-1 RT, particularly the double mutation K103N/Y181C.

In a first aspect the invention provides a compound, represented by formula (I):

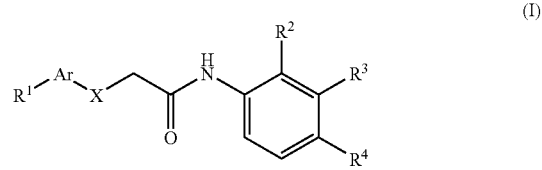

wherein

Ar is a 5-membered aromatic heterocycle containing 1 to 4 heteroatoms each independently selected from N, O and S; said heterocycle being optionally substituted at a substitutable position with $R^{Ar}$, wherein $R^{Ar}$ is H, $(C_{1-4})$alkyl, $CF_3$ or $(C_{3-7})$cycloalkyl and wherein the groups X and $R^1$ are attached to positions on the Ar ring which are immediately adjacent to each other;

X is selected from O and S;

$R^1$ is a group of formula:

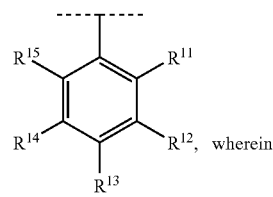, wherein $R^{11}$ is halo; and $R^{12}$, $R^{13}$, $R^{14}$ and $R^{15}$ are each independently selected from H, halo, $(C_{1-4})$alkyl, $CF_3$, $(C_{3-7})$cycloalkyl, $(C_{3-7})$cycloalkyl-$(C_{1-4})$alkyl-, cyano, —O—$(C_{1-4})$alkyl, —$OCF_3$ and —N($(C_{1-4})$alkyl)$_2$, wherein said $(C_{3-7})$cycloalkyl is optionally substituted with $(C_{1-4})$alkyl; or $R^{12}$ and $R^{13}$, $R^{13}$ and $R^{14}$, or $R^{14}$ and $R^{15}$ are linked, together with the carbon atoms to which they are attached, to form a five- or six-membered saturated, unsaturated or aromatic ring which optionally contains from one to three heteroatoms each independently selected from O, S and N, wherein the remaining of $R^{12}$, $R^{13}$, $R^{14}$ and $R^{15}$ are defined as hereinbefore;

$R^2$ is selected from halo, nitro and $(C_{1-4})$alkyl;
$R^3$ is selected from H and halo;
$R^4$ is selected from:

a)

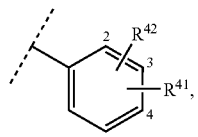

wherein $R^{42}$ is bonded to position 2 or position 3 of the phenyl ring and is selected from H, halo and $(C_{1-4})$alkyl; and $R^{41}$ is bonded to position 3 or position 4 of the phenyl ring and is selected from:
  i) $(C_{1-4})$alkyl substituted with —COOH, —COO$(C_{1-4})$alkyl, —C(=O)NH$_2$, —C(=O)NHSO$_2$—$(C_{1-4})$alkyl, or —OH;
  ii) $(C_{2-4})$alkenyl substituted with —COOH or —COO$(C_{1-4})$alkyl;
  iii) —O—$(C_{1-4})$alkyl optionally substituted with —COOH, Het, or —N(($C_{1-6}$)alkyl)$_2$, wherein said Het is optionally substituted with —OH or —COOH and wherein either or both of the $(C_{1-6})$alkyl groups in said —N(($C_{1-6}$)alkyl)$_2$ are optionally substituted with —COOH or —COO$(C_{1-4})$alkyl; and
  iv) —OH, —COOH, —COO$(C_{1-4})$alkyl, —SO$_2$NH$_2$, or —SO$_2$—$(C_{1-4})$alkyl;
provided that $R^{42}$ and $R^{41}$ may not both be bonded to position 3 of the phenyl ring at the same time;

b) $(C_{2-4})$alkenyl substituted with —COOH or —COO$(C_{1-4})$alkyl;

c) Het optionally substituted with $(C_{1-6})$alkyl, —NH$_2$, —COOH, or $(C_{2-4})$alkenyl substituted with —COOH;

d) —SO$_2$N($R^{43}$)$R^{44}$, wherein $R^{43}$ is H or $(C_{1-6})$alkyl and $R^{44}$ is selected from $(C_{1-6})$alkyl, phenyl, phenyl-$(C_{1-4})$alkyl-, —C(=O)NH$(C_{1-4})$alkyl, —C(=O)O$(C_{1-4})$alkyl, and Het; wherein said $(C_{1-6})$alkyl is optionally substituted with —OH or —COOH and wherein said Het is optionally substituted with $(C_{1-6})$alkyl;
  or $R^{43}$ and $R^{44}$, together with the N to which they are attached, are linked together to form a 5- or 6-membered heterocycle which may be saturated or unsaturated and which may optionally contain from one to three further heteroatoms each independently selected from N, O and S; said heterocycle being optionally substituted with $(C_{1-6})$alkyl or —COOH;

e) —O—$(C_{1-4})$alkyl substituted with —OH, —COOH or Het, wherein said Het is optionally substituted with —COOH or —COO$(C_{1-6})$alkyl;
  provided that the carbon atom of —O—$(C_{1-4})$alkyl which is directly bonded to O is not also directly bonded to —OH;

f) —C(=O)N($R^5$)$R^6$ or —O—CH$_2$—C(=O)N($R^5$)$R^6$ wherein $R^5$ is H or $(C_{1-6})$alkyl and $R^6$ is selected from:
  i) phenyl optionally substituted with one or two substituents each independently selected from —OH, —COOH, —N(($C_{1-4}$)alkyl)$_2$, $(C_{1-4})$alkyl, $(C_{2-4})$alkenyl and Het; wherein said $(C_{1-4})$alkyl is optionally substituted with —COOH and said $(C_{2-4})$alkenyl is substituted with —COOH;
  ii) $(C_{1-4})$alkyl optionally substituted with one or two substituents each independently selected from —COOH, —OH, —S—$(C_{1-6})$alkyl and Het; provided that the carbon atom of $(C_{1-4})$alkyl which is directly bonded to N is not also directly bonded to —OH;
  iii) phenyl-$(C_{1-4})$alkyl- wherein the phenyl portion of said phenyl-$(C_{1-4})$alkyl- is optionally substituted with one or two substituents each independently selected from —OH, —NH$_2$, and —COOH;
  iv) $(C_{3-7})$cycloalkyl-$(C_{1-4})$alkyl- wherein the cycloalkyl portion of said $(C_{3-7})$cycloalkyl-$(C_{1-4})$alkyl- is optionally substituted with —COOH;
  v) Het optionally substituted with one or two substituents each independently selected from $(C_{1-6})$alkyl, phenyl-$(C_{1-4})$alkyl- and —COOH;
  vi) $(C_{3-7})$cycloalkyl; and
  vii) —SO$_2$—$R^{61}$ wherein $R^{61}$ is $(C_{1-4})$alkyl or phenyl;
  or $R^5$ and $R^6$, together with the N to which they are attached, are linked together to form a 5- or 6-membered heterocycle which may be saturated or unsaturated and which may optionally contain from one to three further heteroatoms each independently selected from N, O and S; said heterocycle being optionally substituted with one or two substituents each independently selected from $(C_{1-6})$alkyl, —COOH and —COO$(C_{1-6})$alkyl;

g) —NHC(=O)—$R^7$ wherein $R^7$ is selected from:
  i) $(C_{1-6})$alkyl optionally substituted with one or two substituents each independently selected from —COOH, —O—$(C_{1-4})$alkyl, —NHC(=O)—$(C_{1-4})$alkyl, phenyl and Het; wherein said phenyl is optionally substituted with one or two substituents each independently selected from halo, —OH, —O—$(C_{1-4})$alkyl, —NO$_2$, —COOH, —NH$_2$, —NH$(C_{1-4})$alkyl, —N(($C_{1-4}$)alkyl)$_2$, and $(C_{1-6})$alkyl optionally substituted with from one to three halo substituents;
  ii) phenyl optionally substituted with —OH, halo or —COOH;
  iii) -NHR$^{71}$ wherein $R^{71}$ is phenyl or phenyl-$(C_{1-4})$alkyl-, wherein said phenyl is optionally substituted with —COOH or —COO$(C_{1-4})$alkyl; and
  iv) $(C_{1-6})$alkynyl, $(C_{3-7})$cycloalkyl or $(C_{3-7})$cycloalkyl-$(C_{1-4})$alkyl-;

h) —NHSO$_2$$R^8$ wherein $R^8$ is selected from phenyl, phenyl-$(C_{1-4})$alkyl- and Het; and i) —C≡C—$R^9$ wherein $R^9$ is selected from:
  i) H, —COOH, —COO$(C_{1-6})$alkyl, phenyl or $(C_{2-4})$alkenyl;
  ii) $(C_{3-7})$cycloalkyl optionally substituted with —OH, —COOH, —COO$(C_{1-6})$alkyl, or $(C_{1-4})$alkyl wherein said $(C_{1-4})$alkyl is optionally substituted with —OH or —N($R^{91}$)$R^{92}$, wherein $R^{91}$ is H and $R^{92}$ is $(C_{1-4})$alkyl substituted with Het; or $R^{91}$ and $R^{92}$, together with the N to which they are attached, are linked together to form a 5- or 6-membered heterocycle which may be saturated, unsaturated or aromatic and which may optionally contain from one to three further heteroatoms each independently selected from N, O and S; said heterocycle being optionally substituted with one or two substituents each independently selected from $(C_{1-6})$alkyl and —OH; and
  iii) $(C_{1-6})$alkyl optionally substituted with one, two or three substituents each independently selected from:
    a) —OH, —O(C=O)NH$_2$, —O(C=O)NH$(C_{1-4})$alkyl, CF$_3$, —COOH or —COO—$(C_{1-4})$alkyl;
    b) Het optionally substituted with $(C_{1-6})$alkyl or —OH;

c) —N(R$^{93}$)R$^{94}$ wherein R$^{93}$ is H or (C$_{1-4}$)alkyl and R$^{94}$ is selected from H, —(C$_{1-4}$)alkyl optionally substituted with R$^{941}$, —SO$_2$—(C$_{1-4}$)alkyl and —C(=O)—R$^{942}$;
  wherein R$^{941}$ is —COOH, —C(=O)NH$_2$, (C$_{3-7}$)cycloalkyl, Het, or phenyl optionally substituted with —OH,
  and R$^{942}$ is —O—(C$_{1-4}$)alkyl, —NH—(C$_{1-4}$)alkyl, phenyl, (C$_{3-7}$)cycloalkyl or Het, wherein said (C$_{3-7}$)cycloalkyl is optionally substituted with —COOH and wherein said Het is optionally substituted with one or two substituents each independently selected from (C$_{1-6}$)alkyl and —OH; or
  R$^{942}$ is (C$_{1-4}$)alkyl optionally substituted with —COOH, —NH$_2$, —NH(C$_{1-4}$)alkyl, —NH-Het, —N((C$_{1-4}$)alkyl)$_2$, or Het; wherein said Het is optionally substituted with one or two substituents each independently selected from —OH, —COOH and (C$_{1-6}$)alkyl optionally substituted with Het and wherein the (C$_{1-4}$)alkyl portion of said —NH(C$_{1-4}$)alkyl is optionally substituted with Het;

d) —C(=O)N(R$^{95}$)R$^{96}$, wherein R$^{95}$ is H and R$^{96}$ is selected from (C$_{3-7}$)cycloalkyl, —SO$_2$—R$^{961}$ and —(C$_{1-4}$)alkyl-R$^{962}$, wherein
  R$^{961}$ is (C$_{1-4}$)alkyl, phenyl, (C$_{3-7}$)cycloalkyl, or —N((C$_{1-4}$)alkyl)$_2$; and
  R$^{962}$ is phenyl, —COOH, —N((C$_{1-4}$)alkyl)$_2$, or Het, wherein said phenyl is optionally substituted with —N((C$_{1-4}$)alkyl)$_2$ and said Het is optionally substituted with oxo;
  or R$^{95}$ and R$^{96}$, together with the N to which they are attached, are linked together to form a 5- or 6-membered heterocycle which may be saturated or unsaturated and which may optionally contain from one to three further heteroatoms each independently selected from N, O and S; said heterocycle being optionally substituted with —COOH; and e) —O(C$_{1-4}$)alkyl optionally substituted with R$^{97}$ wherein R$^{97}$ is selected from —OH, —COOH, —C(=O)O—(C$_{1-4}$)alkyl-NH(C$_{1-4}$)alkyl, —C(=O)N(R$^{971}$)R$^{972}$—NH$_2$, —NH—(C$_{3-7}$)cycloalkyl, —O-Het, and Het;
  provided that the carbon atom of —O—(C$_{1-4}$)alkyl which is directly bonded to O is not also directly bonded to —OH, —NH$_2$ or —NH—(C$_{3-7}$)cycloalkyl;
  wherein each of said Het and the Het portion of said —O-Het is optionally substituted with one or two substituents each independently selected from halo, oxo, (C$_{1-4}$)alkyl, and —OH; and
  wherein R$^{971}$ is H or (C$_{1-4}$)alkyl and R$^{972}$ is selected from H, —OH, —NHC(=O)—(C$_{1-4}$)alkyl, —NHC(=O)—NH$_2$, (C$_{1-4}$)alkyl, (C$_{3-7}$)cycloalkyl, phenyl and Het, wherein said (C$_{1-4}$)alkyl is optionally substituted with —OH, —COOH, —N((C$_{1-4}$)alkyl)$_2$ or Het, provided that when R$^{972}$ is (C$_{1-4}$)alkyl, the carbon atom of (C$_{1-4}$)alkyl which is directly bonded to N is not also directly bonded to —OH;
  and wherein said (C$_{3-7}$)cycloalkyl is optionally substituted with —COOH, and wherein said phenyl is optionally substituted with —OH, —COOH or —(C$_{2-4}$)alkenyl-COOH;
  or R$^{971}$ and R$^{972}$, together with the N to which they are attached, are linked together to form a 5- or 6-membered heterocycle which may be saturated or unsaturated and which may optionally contain from one to three further heteroatoms each independently selected from N, O and S; said heterocycle being optionally substituted with (C$_{1-4}$)alkyl or —COOH;

wherein Het is a 4, 5- or 6-membered heterocycle or a 9- or 10-membered heterobicycle, each of which may be saturated, unsaturated or aromatic and each of which containing from one to four heteroatoms each independently selected from N, O and S, wherein each said N heteroatom may, independently and where possible, exist in an oxidized state such that it is further bonded to an O atom to form an N-oxide group and wherein each said S heteroatom may, independently and where possible, exist in an oxidized state such that it is further bonded to one or two oxygen atoms to form the groups SO or SO$_2$;

or an enantiomer, diastereoisomer or tautomer thereof, including a salt or ester thereof.

According to a further aspect of the invention, there is provided a pharmaceutical composition, comprising a compound of formula (I) as defined hereinbefore and hereinafter, or a pharmaceutically acceptable salt or ester thereof, and optionally one or more pharmaceutically acceptable carriers.

According to yet another aspect of the invention, there is provided a pharmaceutical composition, comprising a compound of formula (I) as defined hereinbefore and hereinafter, or a pharmaceutically acceptable salt or ester thereof, in combination with one or more other antiretroviral drugs.

According to another aspect of the invention, there is provided a pharmaceutical composition for the treatment or prevention of HIV infection, comprising a compound of formula (I) as defined hereinbefore and hereinafter, or a pharmaceutically acceptable salt or ester thereof, and optionally one or more pharmaceutically acceptable carriers.

A further aspect of the invention provides a pharmaceutical composition for the treatment or prevention of HIV infection, comprising a compound of formula (I) as defined hereinbefore and hereinafter, or a pharmaceutically acceptable salt or ester thereof, and optionally one or more pharmaceutically acceptable carriers, in combination with one or more other antiretroviral drugs.

Another important aspect of the invention involves a method of treating or preventing an HIV infection in a mammal by administering to the mammal an anti-HIV effective amount of a compound of formula (I) as defined hereinbefore and hereinafter, a pharmaceutically acceptable salt or ester thereof, or a composition as described above, alone or in combination with at least one other antiretroviral agent, administered together or separately.

Still another aspect of the invention provides the use of a compound of formula (I) as defined hereinbefore and hereinafter, or a pharmaceutically acceptable salt or ester thereof, for the treatment or prevention of HIV infection in a mammal.

According to another aspect of the invention, there is provided a method of inhibiting HIV-1 replication by exposing the virus to an inhibitory amount of a compound of formula (I) as defined hereinbefore and hereinafter, or a pharmaceutically acceptable salt or ester thereof.

Yet another aspect of the invention provides the use of a compound of formula (I) as defined hereinbefore and hereinafter, or a pharmaceutically acceptable salt or ester thereof, to inhibit HIV-1 replication.

According to another aspect of the invention, there is provided the use of a compound of formula (I) as defined hereinbefore and hereinafter, or a pharmaceutically acceptable salt or ester thereof, for the manufacture of a medicament for the treatment or prevention of an HIV infection.

According to yet another aspect of the invention, there is provided the use of a compound of formula (I) as defined hereinbefore and hereinafter, or a pharmaceutically acceptable salt or ester thereof, for the manufacture of a medicament for the treatment or prevention of an HIV infection, in combination with one or more other antiretroviral drugs.

Another aspect of the invention provides an article of manufacture comprising a composition effective to treat an HIV infection or to inhibit the reverse transcriptase of HIV; and packaging material comprising a label which indicates that the composition can be used to treat infection by the human immunodeficiency virus; wherein the composition comprises a compound of formula (I) as defined hereinbefore and hereinafter, or a pharmaceutically acceptable salt or ester thereof.

DETAILED DESCRIPTION OF THE INVENTION

Definitions

The following definitions apply unless otherwise noted:

As used herein, the term "$(C_{1-n})$alkyl", either alone or in combination with another radical, is intended to mean acyclic straight or branched chain alkyl radicals containing from one to n carbon atoms respectively. Examples of such radicals include, but are not limited to, methyl (Me), ethyl (Et), propyl (Pr), 1-methylethyl (iPr), butyl (Bu), 1-methylpropyl, 2-methylpropyl (iBu), and 1,1-dimethylethyl (tBu), wherein the abbreviations commonly used herein are given in brackets.

As used herein, the term "—O—$(C_{1-n})$alkyl", either alone or in combination with another radical, refers to alkoxy radicals containing for one to n carbon atoms and includes, but is not limited to, methoxy (—OMe), ethoxy (—OEt), propoxy (—OPr), 1-methylethoxy (—OiPr), butoxy (—OBu) and 1,1-dimethylethoxy (—OtBu), wherein the abbreviations commonly used herein are given in brackets. When an —O—$(C_{1-n})$alkyl group is substituted, it is understood to be substituted on the $(C_{1-n})$alkyl portion thereof.

As used herein, the term "—S—$(C_{1-n})$alkyl", either alone or in combination with another radical, refers to alkylthio radicals containing one to n carbon atoms and includes methylthio (—SMe), ethylthio (—SEt), propylthio (—SPr), 1-methylethylthio (—S-iPr), butylthio (—SBu) and 1,1-dimethylethylthio (—StBu), wherein the abbreviations commonly used herein are given in brackets. When an —S—$(C_{1-n})$alkyl group is substituted, it is understood to be substituted on the $(C_{1-n})$alkyl portion thereof.

The term "oxo" as used herein means an oxygen atom attached to a carbon atom as a substituent by a double bond (=O).

The term "thioxo" as used herein means an sulfur atom attached to a carbon atom as a substituent by a double bond (=S).

As used herein, the term "halo" means a halo radical selected from bromo, chloro, fluoro or iodo.

As used herein, the term "$(C_{2-n})$alkenyl", either alone or used with another radical, means an unsaturated, acyclic radical containing two to n carbon atoms, at least two of which are bonded to each other by a double bond and includes, but is not limited to, —CH=CH$_2$, —CH$_2$CH=CH$_2$, —CH$_2$CH=CHCH$_3$ and —CH(Me)CH=CH$_2$. The cis and trans isomers, and mixtures thereof, of the $(C_{2-n})$alkenyl radical can be encompassed by the term. A $(C_{2-n})$alkenyl radical may be substituted on any of the carbon atoms thereof which would otherwise bear a hydrogen atom.

The term "$(C_{2-n})$alkynyl", as used herein, wherein n is an integer, either alone or in combination with another radical, is intended to mean an unsaturated, acyclic straight chain radical containing two to n carbon atoms, at least two of which are bonded to each other by a triple bond. Examples of such radicals include, but are not limited to, ethynyl, 1-propynyl, 2-propynyl, and 1-butynyl.

The term "$(C_{3-m})$cycloalkyl" as used herein, wherein m is an integer, either alone or in combination with another substituent, means a cycloalkyl substituent containing from 3 to m carbon atoms and includes, but is not limited to, cyclopropyl, cyclobutyl, cyclopentyl, cyclohexyl and cycloheptyl.

The term "$(C_{3-m})$cycloalkyl-$(C_{1-n})$alkyl-" as used herein, wherein n and m are both integers, means an alkyl radical containing from 1 to n carbon atoms to which a cycloalkyl radical containing from 3 to m carbon atoms is directly linked; including, but not limited to, cyclopropylmethyl, cyclobutylmethyl, cyclopentylmethyl, 1-cyclopentylethyl, 2-cyclopentylethyl, cyclohexylmethyl, 1-cyclohexylethyl and 2-cyclohexylethyl. When a $(C_{3-m})$cycloalkyl-$(C_{1-n})$alkyl- group is substituted, it is understood, unless otherwise specified, that the substituent may be attached to either the cycloalkyl or the alkyl portion thereof.

The term "phenyl-$(C_{1-n})$alkyl-" as used herein, wherein n is an integer, means an alkyl radical containing from 1 to n carbon atoms to which a phenyl radical is directly linked; including, but not limited to, phenylmethyl (also known as benzyl), 1-phenylethyl, 2-phenylethyl, 2-phenyl-1-methylethyl, 1-phenyl-1-methylethyl, 1-phenylpropyl, 2-phenylpropyl, and 3-phenylpropyl. When a phenyl-$(C_{1-n})$alkyl- group is substituted, it is understood, unless otherwise specified, that the substituent may be attached to either the phenyl or the alkyl portion thereof.

As used herein, the term "Het" is defined as a 4, 5- or 6-membered heterocycle or a 9- or 10-membered heterobicycle, each of which may be saturated, unsaturated or aromatic and each of which containing from one to four heteroatoms each independently selected from N, O and S, wherein each said N heteroatom may, independently and where possible, exist in an oxidized state such that it is further bonded to an O atom to form an N-oxide group and wherein each said S heteroatom may, independently and where possible, exist in an oxidized state such that it is further bonded to one or two oxygen atoms to form the groups SO or SO$_2$, unless otherwise specified.

As used herein, the term "heterocycle", either alone or in combination with another radical, is intended to mean a monovalent radical derived by removal of a hydrogen from a 5- or 6-membered saturated or unsaturated (including aromatic) heterocycle containing 1 to 4 heteroatoms selected from N, O and S. Examples of such heterocycles include, but are not limited to, azetidine, pyrrolidine, tetrahydrofuran, thiazolidine, pyrrole, furan, thiophene, 1H-imidazole, isoxazole, oxazole, thiazole, tetrazole, piperidine, piperazine, 1,4-dioxane, 4-morpholine, 4-thiomorpholine, pyridine, pyridine-N-oxide, pyridazine, pyrazine or pyrimidine, or the following heterocycles:

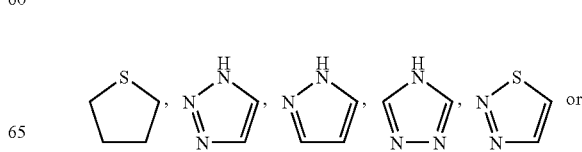

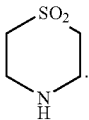

As used herein, the term "heterobicycle" either alone or in combination with another radical, means a heterocycle as defined above fused to another cycle, be it a heterocycle, a phenyl or any other cycle. Examples of such heterobicycles include, but are not limited to, indole, benzimidazole, benzofuran, thiazolo[4,5-b]-pyridine, quinoline, isoquinoline, or coumarin, or the following:

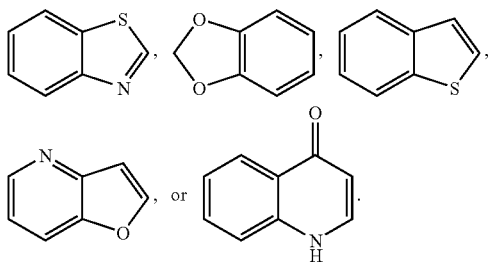

As used herein, the term "inhibitor of HIV replication" refers to an agent capable of substantially reducing or essentially eliminating the ability of HIV-1 reverse transcriptase to replicate a DNA copy from an RNA template.

As used herein, the term "single or double mutant strains" means that either one or two amino acid residues that are present in WT HIV-1 strain have been replaced by residues not found in the WT strain. For example, for the single mutant Y181C, the tyrosine at residue 181 has been replaced by a cysteine residue. Similarly, for the double mutant K103N/Y181C, an asparagine residue has replaced the lysine at residue 103 and a cysteine residue has replaced the tyrosine at residue 181.

The term "salt thereof" means any acid and/or base addition salt of a compound according to the invention; preferably a pharmaceutically acceptable salt thereof.

As used herein, the term "pharmaceutically acceptable salt" means a salt of a compound which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. Where applicable and compatible with the chemical properties of the compound of formula (I), the term includes pharmaceutically-acceptable acid addition salts and pharmaceutically-acceptable base addition salts. Lists of suitable salts are found in, e.g., S. M. Birge et al., J. Pharm. Sci., 1977, 66, pp. 1-19.

The term "pharmaceutically-acceptable acid addition salt" means those salts which retain the biological effectiveness and properties of the free bases and which are not biologically or otherwise undesirable, formed with inorganic acids such as hydrochloric acid, hydrobromic acid, hydroiodic acid, sulfuric acid, sulfamic acid, nitric acid, phosphoric acid, and the like, and organic acids such as acetic acid, trichloroacetic acid, trifluoroacetic acid, adipic acid, alginic acid, ascorbic acid, aspartic acid, benzenesulfonic acid, benzoic acid, 2-acetoxybenzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, heptanoic acid, hexanoic acid, formic acid, fumaric acid, 2-hydroxyethanesulfonic acid (isethionic acid), lactic acid, maleic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, picric acid, pivalic acid, propionic acid, pyruvic acid, salicylic acid, stearic acid, succinic acid, sulfanilic acid, tartaric acid, p-toluenesulfonic acid, undecanoic acid, and the like.

The term "pharmaceutically-acceptable base addition salt" means those salts which retain the biological effectiveness and properties of the free acids and which are not biologically or otherwise undesirable, formed with inorganic bases such as ammonia or hydroxide, carbonate, or bicarbonate of ammonium or a metal cation such as sodium, potassium, lithium, calcium, magnesium, iron, zinc, copper, manganese, aluminum, and the like. Particularly preferred are the ammonium, potassium, sodium, calcium, and magnesium salts. Salts derived from pharmaceutically-acceptable organic nontoxic bases include salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins, and the like. Particularly preferred organic nontoxic bases are isopropylamine, diethylamine, ethanolamine, trimethylamine, dicyclohexylamine, choline, and caffeine.

The term "ester thereof" means any ester of a compound in which any of the carboxyl functions of the molecule is replaced by an alkoxycarbonyl function, including but not limited to pharmaceutically acceptable esters thereof.

The term "pharmaceutically acceptable ester" as used herein, either alone or in combination with another substituent, means esters of the compound of formula (I) in which any of the carboxyl functions of the molecule, but preferably the carboxy terminus, is replaced by an alkoxycarbonyl function:

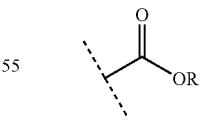

in which the R moiety of the ester is selected from alkyl (e.g. methyl, ethyl, n-propyl, tert-butyl, n-butyl); alkoxyalkyl (e.g. methoxymethyl); alkoxyacyl (e.g. acetoxymethyl); aralkyl (e.g. benzyl); aryloxyalkyl (e.g. phenoxymethyl); aryl (e.g. phenyl), optionally substituted with halogen, $(C_{1-4})$alkyl or $(C_{1-4})$alkoxy. Other suitable esters can be found in Design of prodrugs, Bundgaard, H. Ed. Elsevier (1985). Such pharmaceutically acceptable esters are usually hydrolyzed in vivo when administered to a mammal and transformed into the acid form of the compound of formula (I). With regard to the esters described above, unless otherwise specified, any alkyl moiety present advantageously contains 1 to 16 carbon atoms, particularly 1 to 6 carbon atoms. Any aryl moiety present in such esters advantageously comprises a phenyl group. In particular the esters may be a $(C_{1-16})$alkyl ester, an unsubstituted benzyl ester or a benzyl ester substituted with at least one halogen, $(C_{1-6})$alkyl, $(C_{1-6})$alkoxy, nitro or trifluoromethyl.

As used herein, the designation whereby a bond is drawn as emanating from the center of a ring, such as, for example,

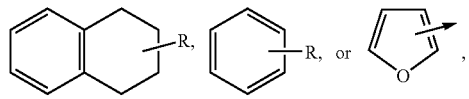

means that the bond may be attached to any free position on the ring that would otherwise be substituted by a hydrogen atom, unless specified otherwise. Such bonds may be linked to substituents of the ring or may indicate the linkage of the ring as a substituent on another structure.

As used herein, the term "treatment" means the administration of a compound or composition according to the present invention to alleviate or eliminate symptoms of the HIV disease and/or to reduce viral load in a patient.

As used herein, the terms "prevention" and "prophylaxis", used interchangeably, mean the administration of a compound or composition according to the present invention post-exposure of the individual to the virus but before the appearance of symptoms of the disease, and/or prior to the detection of the virus in the blood, to prevent the appearance of symptoms of the disease and/or to prevent the virus from reaching detectible levels in the blood and the administration of a compound or composition according to the present invention to prevent perinatal transmission of HIV-1 from mother to baby, by administration to the mother before giving birth and to the child within the first days of life.

The following signs

and

are used in sub-formulas to indicate the bond which is connected to the rest of the molecule as defined.

DETAILED DESCRIPTION OF PREFERRED EMBODIMENTS

In the following preferred embodiments, groups and substituents of the compounds of formula (I) according to this invention are described in detail.

Ar:

According to a preferred embodiment of the first aspect of the present invention there is provided a compound of formula (I)

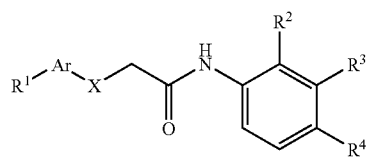

wherein X, $R^1$, $R^2$, $R^3$ and $R^4$ are as defined herein and wherein Ar is selected from:

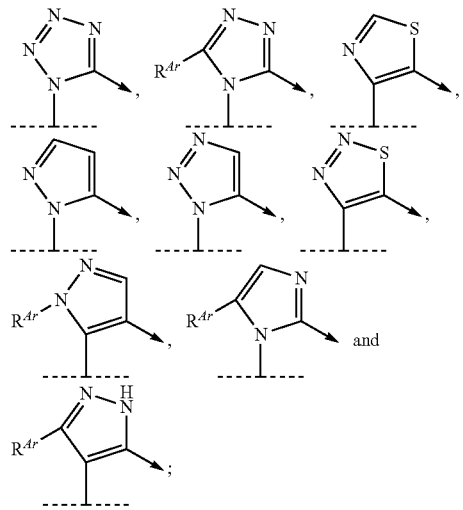

wherein $R^{Ar}$ is as defined herein and wherein the designation

represents the bond to $R^1$ and the designation

represents the bond to X.

More preferably, Ar is selected from

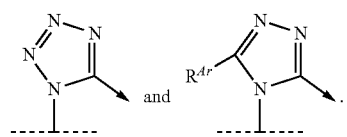

Most preferably, Ar is

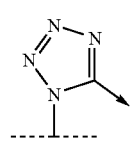

Therefore, the present invention preferably provides compounds of formulas (Ia) to (Ii):

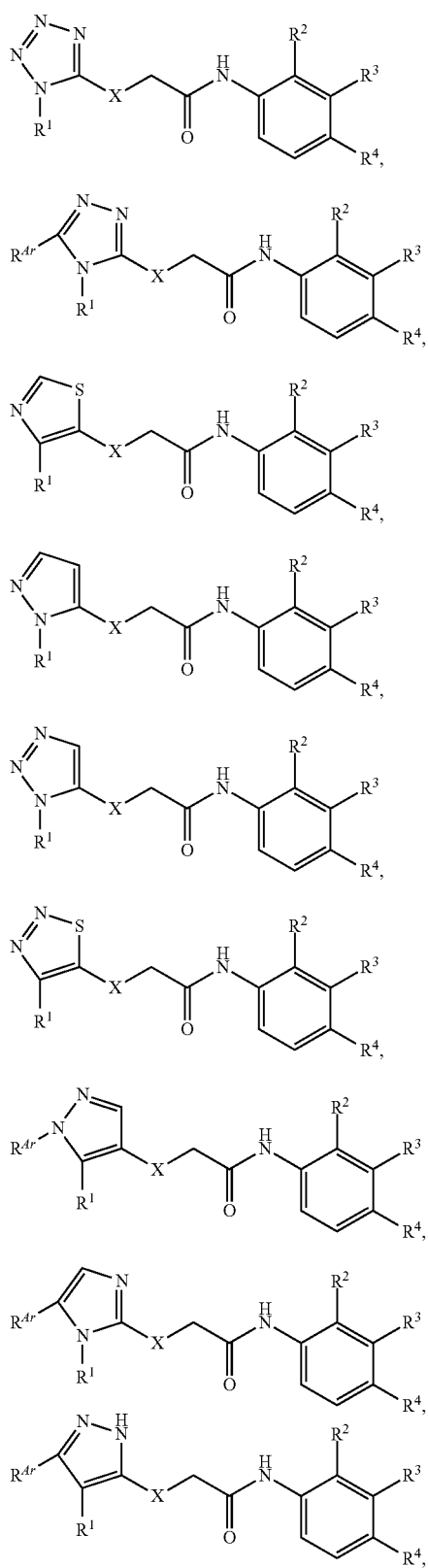

wherein X, $R^{Ar}$, $R^1$, $R^2$, $R^3$ and $R^4$ are as defined herein.

More preferably, the present invention provides compounds of formulas:

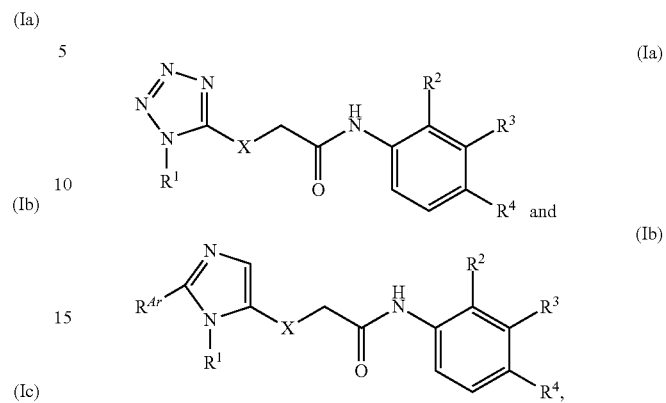

wherein X, $R^{Ar}$, $R^1$, $R^2$, $R^3$ and $R^4$ are as defined herein.

$R^{Ar}$ is preferably selected from H, $CH_3$, $CF_3$ and cyclopropyl.

Most preferably, the present invention provides compounds of formula (Ia)

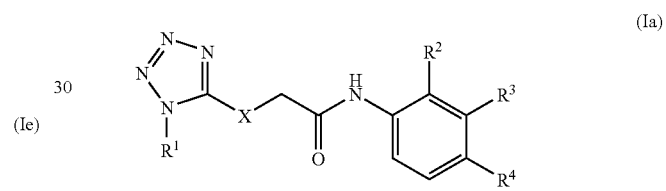

wherein X, $R^1$, $R^2$, $R^3$ and $R^4$ are as defined herein.

Any and each individual definition of Ar as set out herein may be combined with any and each individual definition of X, $R^1$, $R^2$, $R^3$ and $R^4$ as set out herein.

X:

When Ar, $R^1$, $R^2$, $R^3$ and $R^4$ are as defined hereinbefore and hereinafter, preferably, X is S.

Any and each individual definition of X as set out herein may be combined with any and each individual definition of Ar, $R^1$, $R^2$, $R^3$ and $R^4$ as set out herein.

$R^1$:

When Ar, X, $R^2$, $R^3$ and $R^4$ are as defined hereinbefore and hereinafter, $R^1$ is a group of formula:

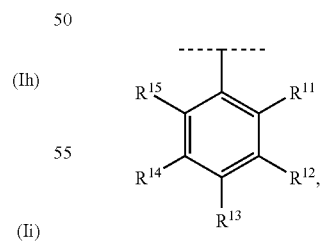

wherein $R^{11}$ is preferably chloro or bromo.

More preferably, $R^{11}$ is chloro.

Preferably, $R^{12}$ is selected from H, $(C_{1-4})$alkyl, $CF_3$, $(C_{3-7})$cycloalkyl and halo or $R^{12}$ and $R^{13}$ are linked, together with the carbon atoms to which they are attached, to form a five- or six-membered saturated, unsaturated or aromatic ring which optionally contains from one to three heteroatoms each independently selected from O, S and N.

More preferably, $R^{12}$ is selected from H, methyl, $CF_3$, chloro, bromo and cyclopropyl; or $R^{12}$ and $R^{13}$ are linked, together with the carbon atoms to which they are attached, so that $R^1$ is a fused ring system selected from naphthyl, benzothiazolyl and quinolyl.

Still more preferably, $R^{12}$ is H, $CF_3$ or cyclopropyl.

Most preferably, $R^{12}$ is H,

Preferably, $R^{13}$ is selected from H, $(C_{1-4})$alkyl, $CF_3$, $(C_{3-7})$cycloalkyl, $(C_{3-7})$cycloalkyl -$(C_{1-4})$alkyl-, —O—$(C_{1-4})$alkyl, —N$((C_{1-4})$alkyl$)_2$ and —$OCF_3$; wherein the $(C_{3-7})$cycloalkyl is optionally substituted with $(C_{1-4})$alkyl; or $R^{12}$ and $R^{13}$ or $R^{13}$ and $R^{14}$ are linked, together with the carbon atoms to which they are attached, to form a five- or six-membered saturated, unsaturated or aromatic ring which optionally contains from one to three heteroatoms each independently selected from O, S and N.

More preferably, $R^{13}$ is selected from H, methyl, $CF_3$, 1-methylethyl, 1,1-dimethylethyl, cyclopropyl, cyclopropylmethyl, 1-methylcyclopropyl, and —$OCF_3$; or $R^{12}$ and $R^{13}$ or $R^{13}$ and $R^{14}$ are linked, together with the carbon atoms to which they are attached, so that $R^1$ is a fused ring system selected from naphthyl, benzothiazolyl, indanyl and quinolyl.

Most preferably, $R^{13}$ is H, methyl, 1,1-dimethylethyl or cyclopropyl.

Preferably, $R^{14}$ is selected from H, halo, cyano, $(C_{1-4})$alkyl, $CF_3$, $(C_{3-7})$cycloalkyl, $(C_{3-7})$cycloalkyl-$(C_{1-4})$alkyl-, —O—$(C_{1-4})$alkyl, and —N$((C_{1-4})$alkyl$)_2$ or $R^{13}$ and $R^{14}$ are linked, together with the carbon atoms to which they are attached, to form a five- or six-membered saturated, unsaturated or aromatic ring which optionally contains from one to three heteroatoms each independently selected from O, S and N.

More preferably, $R^{14}$ is selected from H, fluoro, chloro, bromo, cyano, methyl, $CF_3$, 1,1-dimethylethyl, cyclopropyl, cyclopropylmethyl, methoxy, 1-methylethoxy, and dimethylamino, or $R^{13}$ and $R^{14}$ are linked, together with the carbon atoms to which they are attached, so that $R^1$ is a fused ring system selected from naphthyl and indanyl.

Still more preferably, $R^{14}$ is H, cyclopropyl or $CF_3$.

Most preferably, $R^{14}$ is H,

Preferably, $R^{15}$ is selected from H, halo, $(C_{1-4})$alkyl and $CF_3$.

More preferably, $R^{15}$ is H, fluoro, chloro, methyl or $CF_3$.

Most preferably, $R^{15}$ is H,

Therefore, preferred $R^1$ substituents are selected from:

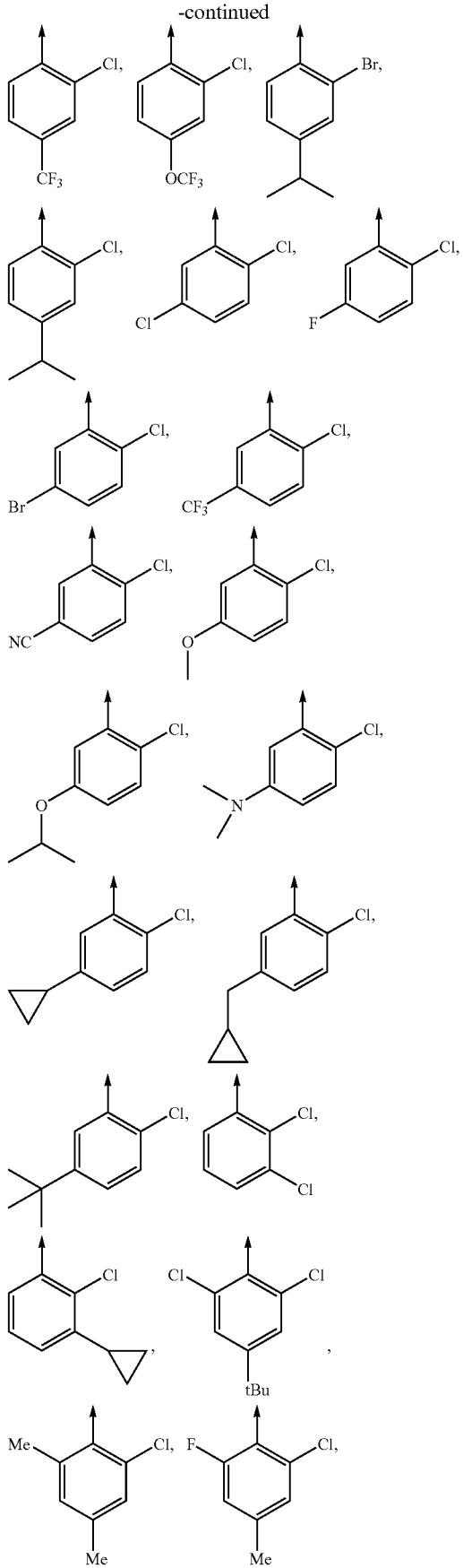

-continued

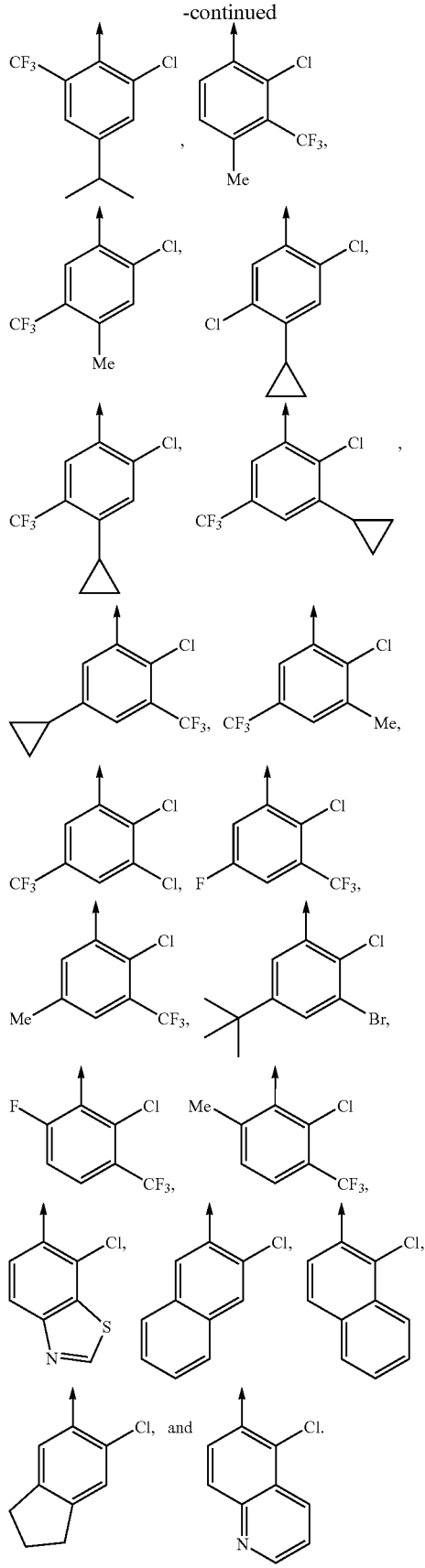

More preferably, $R^1$ is selected from:

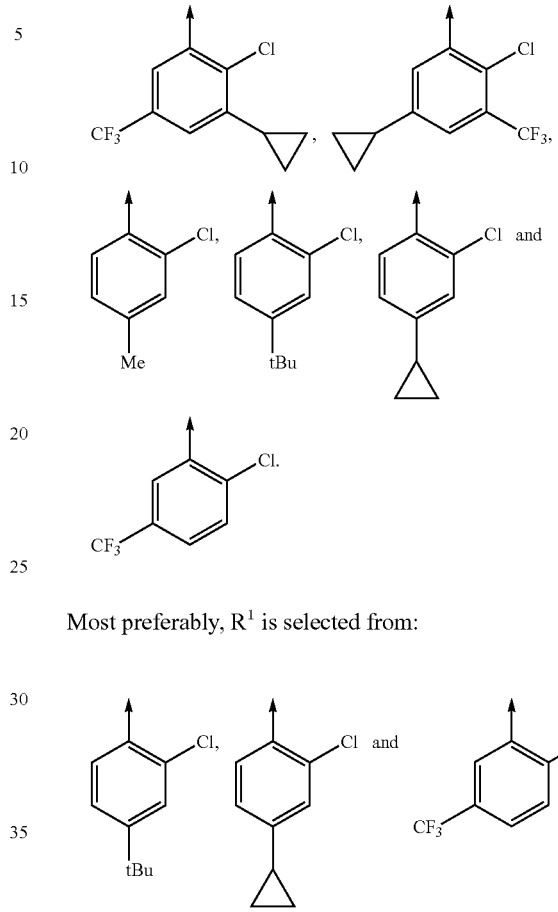

Most preferably, $R^1$ is selected from:

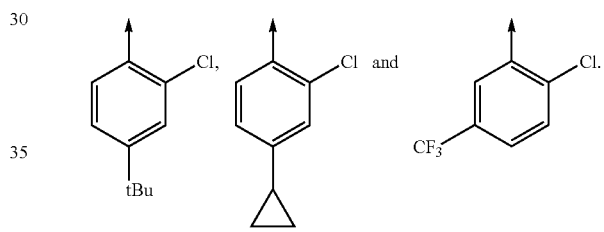

Any and each individual definition of $R^1$ as set out herein may be combined with any and each individual definition of Ar, X, $R^2$, $R^3$ and $R^4$ as set out herein.

$R^2$:

When Ar, X, $R^1$, $R^3$ and $R^4$ are as defined hereinbefore and hereinafter, preferably, $R^2$ is selected from halo, nitro and methyl.

More preferably, $R^2$ is halo or nitro.

Even more preferably, $R^2$ is halo.

Yet more preferably, $R^2$ is chloro or bromo.

Most preferably, $R^2$ is chloro.

Any and each individual definition of $R^2$ as set out herein may be combined with any and each individual definition of Ar, X, $R^1$, $R^3$ and $R^4$ as set out herein.

$R^3$:

When Ar, X, $R^1$, $R^2$ and $R^4$ are as defined hereinbefore and hereinafter, most preferably, $R^3$ is H or fluoro.

Any and each individual definition of $R^3$ as set out herein may be combined with any and each individual definition of Ar, X, $R^1$, $R^2$ and $R^4$ as set out herein.

$R^4$:

When Ar, X, $R^1$, $R^2$ and $R^3$ are as defined hereinbefore and hereinafter, $R^4$ is preferably defined as follows.

In one alternative embodiment, $R^4$ is

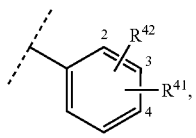

wherein $R^{42}$ is bonded to position 2 or position 3 of the phenyl ring and is selected from H, halo and $(C_{1-4})$alkyl; and $R^{41}$ is bonded to position 3 or position 4 of the phenyl ring and is selected from:
i) $(C_{1-4})$alkyl substituted with —COOH, —COO$(C_{1-4})$alkyl, —C(=O)NH$_2$, —C(=O)NHSO$_2$—$(C_{1-4})$alkyl, or —OH;
ii) $(C_{2-4})$alkenyl substituted with —COOH or —COO$(C_{1-4})$alkyl;
iii) —O—$(C_{1-4})$alkyl optionally substituted with —COOH, Het, or —N$((C_{1-6})$alkyl$)_2$, wherein Het is a 5- or 6-membered saturated, unsaturated or aromatic monocyclic heterocycle containing 1 to 4 heteroatoms each independently selected from O, S and N. wherein each said S heteroatom may, independently and where possible, exist in an oxidized state such that it is further bonded to one or two oxygen atoms to form the groups SO or SO$_2$, said Het being optionally substituted with —OH or —COOH; and wherein either or both of the $(C_{1-6})$alkyl groups in said —N$((C_{1-6})$alkyl$)_2$ are optionally substituted with —COOH or —COO$(C_{1-4})$alkyl; and
iv) —OH, —COOH, —COO$(C_{1-4})$alkyl, —SO$_2$NH$_2$, or —SO$_2$—$(C_{1-4})$alkyl;
provided that $R^{42}$ and $R^{41}$ may not both be bonded to position 3 of the phenyl ring at the same time.

Preferably $R^{42}$ is selected from H, Cl, F and CH$_3$. Most preferably, $R^{42}$ is H.

Preferably $R^{41}$ is selected from:
i) methyl, ethyl, propyl, 1-methylethyl, butyl, 1-methylpropyl, 2-methylpropyl and 1,1-dimethylethyl, each of which being substituted with —COOH, —COOCH$_3$, —COOCH$_2$CH$_3$—C(=O)NH$_2$, —C(=O)NHSO$_2$—CH$_3$, or —OH;
ii) —CH=CH—COOH, —CH=CH—COOCH$_3$ or —CH=CH—COOCH$_2$CH$_3$;
iii) —O—CH$_3$ or —O—CH$_2$CH$_3$, each of which being optionally substituted with —COOH, Het, or —N$((C_{1-4})$alkyl$)_2$, wherein Het is selected from

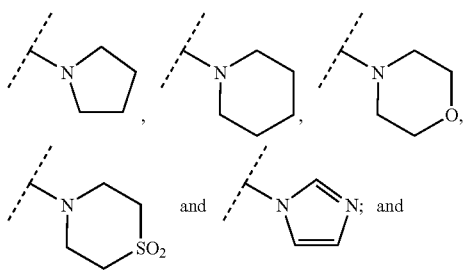

wherein said Het is optionally substituted with —OH or —COOH and wherein either or both of the $(C_{1-4})$alkyl groups in said —N$((C_{1-4})$alkyl$)_2$ are optionally substituted with —COOH, —COOCH$_3$ or —COOCH$_2$CH$_3$; and iv) —OH, —COOH, —COOCH$_3$, —COOCH$_2$CH$_3$, —SO$_2$NH$_2$, or —SO$_2$—CH$_3$.

More preferably within this embodiment, $R^{41}$ is selected from —OH, —OCH$_3$, —COOH, —COOCH$_3$, —SO$_2$CH$_3$, —SO$_2$NH$_2$, —CH$_2$COOH, —CH$_2$COOCH$_3$, —CH$_2$CONH$_2$, —CH$_2$CH$_2$OH, —CH$_2$CH$_2$COOH, —CH$_2$CONHSO$_2$CH$_3$, —C(CH$_3$)$_2$—COOH, —OCH$_2$COOH,

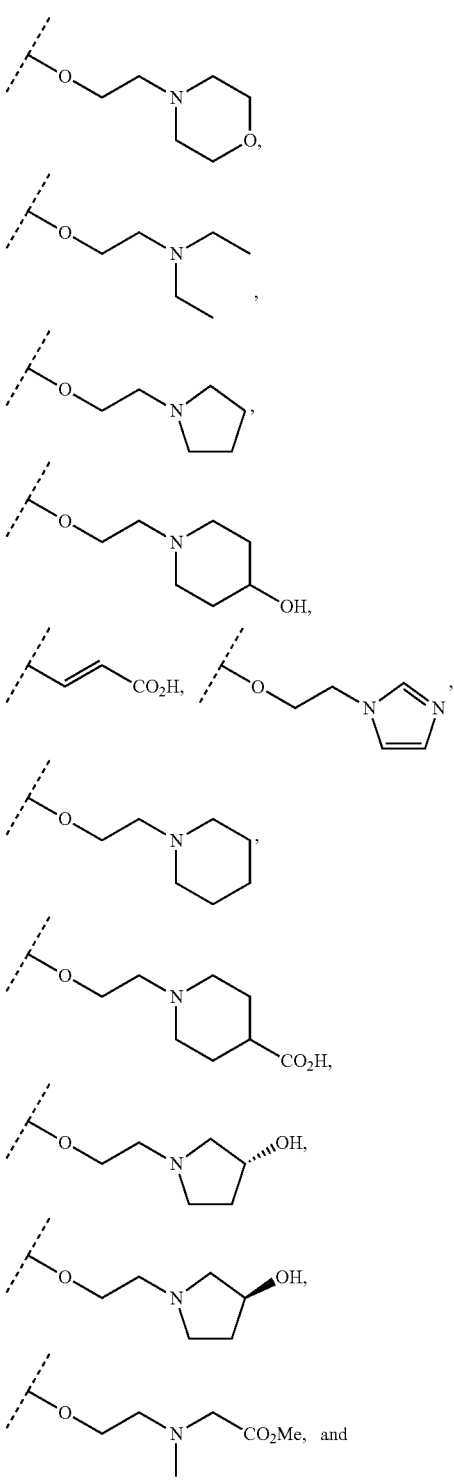

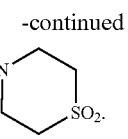

Most preferably, R⁴¹ is selected from —CH₂COOH, —C(CH₃)₂—COOH, —OCH₂COOH,

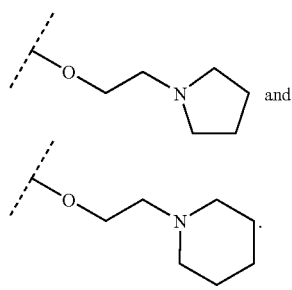

and

In a preferable embodiment, R⁴¹ is bonded to position 4 of the phenyl ring.

In another alternative embodiment, R⁴ is selected from:

b) (C₂₋₄)alkenyl substituted with —COOH or —COO(C₁₋₄)alkyl;

c) Het optionally substituted with (C₁₋₆)alkyl, —NH₂, —COOH, or (C₂₋₄)alkenyl substituted with —COOH, wherein Het is a 5- or 6-membered aromatic monocyclic heterocycle containing 1 to 4 heteroatoms each independently selected from O, S and N;

d) —SO₂N(R⁴³)R⁴⁴, wherein R⁴³ is H or (C₁₋₆)alkyl and R⁴⁴ is selected from (C₁₋₆)alkyl, phenyl, phenyl-(C₁₋₄)alkyl-, —C(=O)NH(C₁₋₄)alkyl, —C(=O)O(C₁₋₄)alkyl, and Het wherein Het is a 5- or 6-membered saturated, unsaturated or aromatic monocyclic heterocycle containing 1 to 4 heteroatoms each independently selected from O, S and N; wherein said (C₁₋₆)alkyl is optionally substituted with —OH or —COOH and wherein said Het is optionally substituted with (C₁₋₆)alkyl;

or R⁴³ and R⁴⁴, together with the N to which they are attached, are linked together to form a 5- or 6-membered heterocycle which may be saturated or unsaturated and which may optionally contain from one to three further heteroatoms each independently selected from N, O and S; said heterocycle being optionally substituted with (C₁₋₆)alkyl or —COOH;

e) —O—(C₁₋₄)alkyl substituted with —OH, —COOH or Het wherein Het is a 5- or 6-membered saturated, unsaturated or aromatic monocyclic heterocycle containing 1 to 4 heteroatoms each independently selected from O, S and N, wherein said Het is optionally substituted with —COOH or —COO(C₁₋₆)alkyl;

provided that the carbon atom of —O—(C₁₋₄)alkyl which is directly bonded to O is not also directly bonded to —OH; and h) —NHSO₂R⁸ wherein R⁸ is selected from phenyl, phenyl-(C₁₋₄)alkyl- and Het wherein Het is a 5- or 6-membered saturated, unsaturated or aromatic monocyclic heterocycle containing 1 to 4 heteroatoms each independently selected from O, S and N.

Preferably within the scope of this embodiment, R⁴ is selected from:

b) (C₂₋₄)alkenyl substituted with —COOH or —COOCH₃;

c) Het optionally substituted with CH₃, —NH₂, —COOH, or —CH=CH—COOH;

wherein Het is selected from

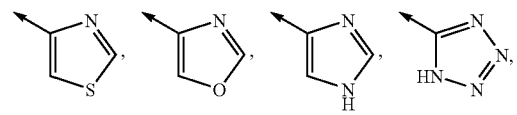

and

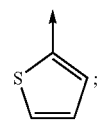

d) —SO₂N(R⁴³)R⁴⁴, wherein R⁴³ is H or CH₃ and R⁴⁴ is selected from (C₁₋₄)alkyl, phenyl, phenyl-(C₁₋₄)alkyl-, —C(=O)NHCH₃, —C(=O)OCH₃, and Het; wherein Het is selected from

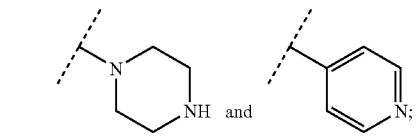

and wherein said (C₁₋₄)alkyl is optionally substituted with —OH or —COOH and wherein said Het is optionally substituted with CH₃;

or R⁴³ and R⁴⁴, together with the N to which they are attached, are linked together to form a 6-membered heterocycle which may be saturated or unsaturated and which may optionally contain one or two further heteroatoms each independently selected from N and O; said heterocycle being optionally substituted with CH₃ or —COOH;

e) —O—(C₁₋₄)alkyl substituted with —OH, —COOH or Het, wherein Het is selected from

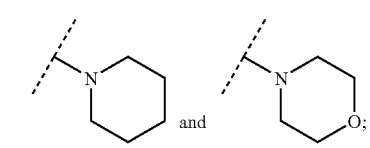

and wherein said Het is optionally substituted with —COOH, —COOCH₃ or —COOCH₂CH₃;

provided that the carbon atom of —O—(C₁₋₄)alkyl which is directly bonded to O is not also directly bonded to —OH; and h) —NHSO$_2$R$^8$ wherein R$^8$ is selected from phenyl, phenylmethyl and

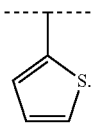

More preferably within the scope of this embodiment R$^4$ is selected from:

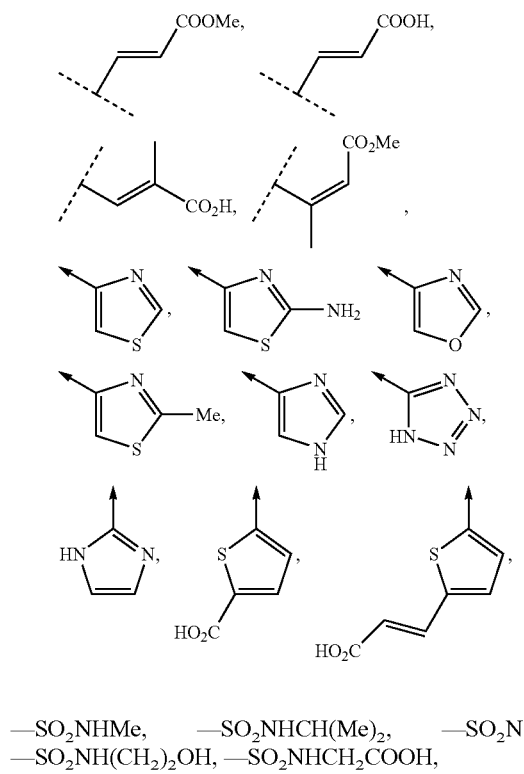

—SO$_2$NHMe, —SO$_2$NHCH(Me)$_2$, —SO$_2$N(Me)$_2$, —SO$_2$NH(CH$_2$)$_2$OH, —SO$_2$NHCH$_2$COOH,

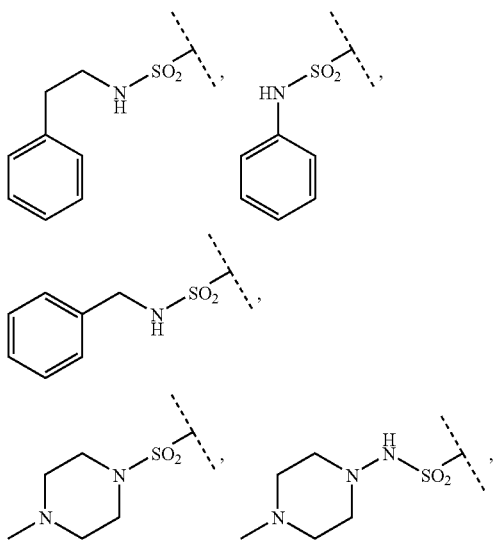

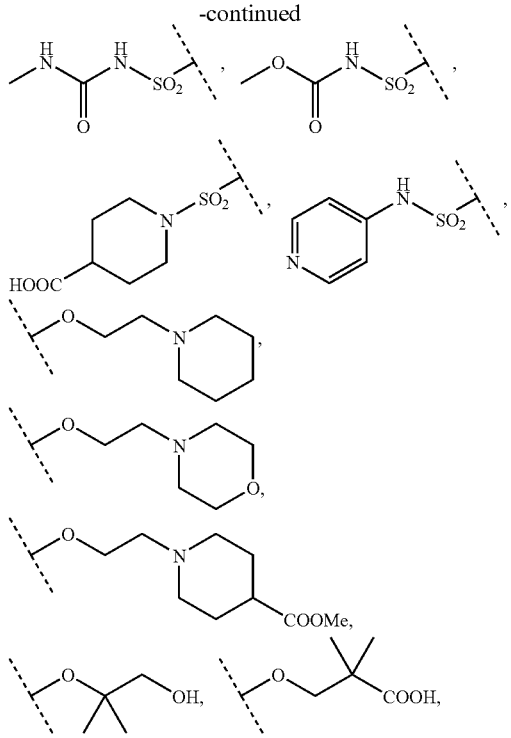

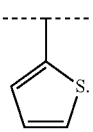

and —NHSO$_2$R$^8$ wherein R$^8$ is selected from phenyl, phenylmethyl and

In still another alternative embodiment, R$^4$ is —C(=O)N(R$^5$)R$^6$ or —O—CH$_2$—C(=O)N(R$^5$)R$^6$ wherein R$^5$ is H or (C$_{1-6}$)alkyl and R$^6$ is selected from:
  i) phenyl optionally substituted with one or two substituents each independently selected from —OH, —COOH, —N((C$_{1-4}$)alkyl)$_2$ (C$_{1-4}$)alkyl, (C$_{2-4}$)alkenyl and Het wherein Het is a 5- or 6-membered saturated, unsaturated or aromatic monocyclic heterocycle containing 1 to 4 heteroatoms each independently selected from O, S and N; wherein said (C$_{1-4}$)alkyl is optionally substituted with —COOH and said (C$_{2-4}$)alkenyl is substituted with —COOH;
  ii) (C$_{1-4}$)alkyl optionally substituted with one or two substituents each independently selected from —COOH, —OH, —S—(C$_{1-6}$)alkyl and Het wherein Het is a 5- or 6-membered saturated, unsaturated or aromatic monocyclic heterocycle containing 1 to 4 heteroatoms each independently selected from O, S and N wherein each said N heteroatom may, independently and where possible, exist in an oxidized state such that it is further bonded to an O atom to form an N-oxide group;
    provided that the carbon atom of (C$_{1-4}$)alkyl which is directly bonded to N is not also directly bonded to —OH;
  iii) phenyl-(C$_{1-4}$)alkyl- wherein the phenyl portion of said phenyl-(C$_{1-4}$)alkyl- is optionally substituted with one or two substituents each independently selected from —OH, —NH$_2$ and —COOH;

iv) $(C_{3-7})$cycloalkyl-$(C_{1-4})$alkyl- wherein the cycloalkyl portion of said $(C_{3-7})$cycloalkyl-$(C_{1-4})$alkyl- is optionally substituted with —COOH;
v) Het optionally substituted with one or two substituents each independently selected from $(C_{1-6})$alkyl, phenyl-$(C_{1-4})$alkyl- and —COOH wherein Het is a 5- or 6-membered heterocycle or a 9- or 10-membered heterobicycle, each of which may be saturated, unsaturated or aromatic and each of which may optionally contain from one to four heteroatoms each independently selected from N, O and S;
vi) $(C_{3-7})$cycloalkyl; and
vii) —$SO_2$—$R^{61}$ wherein $R^{61}$ is $(C_{1-4})$alkyl or phenyl;
or $R^5$ and $R^6$, together with the N to which they are attached, are linked together to form a 5- or 6-membered heterocycle which may be saturated or unsaturated and which may optionally contain from one to three further heteroatoms each independently selected from N, O and S; said heterocycle being optionally substituted with one or two substituents each independently selected from $(C_{1-6})$alkyl, —COOH and —COO$(C_{1-6})$alkyl.

More preferably within this embodiment, $R^4$ is —C(=O)N($R^5$)$R^6$ wherein $R^5$ and $R^6$ are as defined herein.

Preferably, $R^5$ is H or $CH_3$ and $R^6$ is selected from
i) phenyl optionally substituted with one or two substituents each independently selected from —OH, —COOH, —N(CH$_3$)$_2$, CH$_3$, —CH$_2$COOH, —CH$_2$CH$_2$COOH,

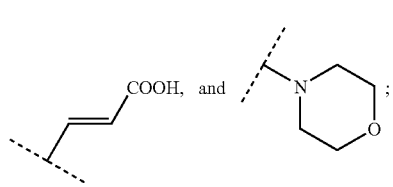

COOH, and ii) $(C_{1-4})$alkyl optionally substituted with one or two substituents each independently selected from —COOH, —OH, —S—CH$_3$ and Het, wherein Het is selected from

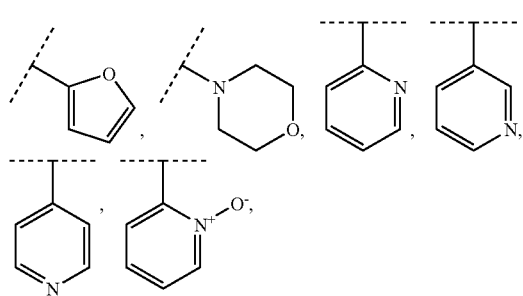

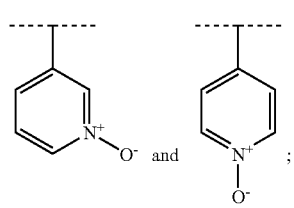

provided that the carbon atom of $(C_{1-4})$alkyl which is directly bonded to N is not also directly bonded to —OH;

iii) phenyl-CH$_2$— or phenyl-CH$_2$CH$_2$—, wherein the phenyl portion of said phenyl-CH$_2$— or phenyl-CH$_2$CH$_2$— is optionally substituted with one or two substituents each independently selected from —OH, —NH$_2$, and —COOH;
iv) (4-carboxycyclohexyl)methyl;
v) Het optionally substituted with one or two substituents each independently selected from methyl, phenylmethyl- and —COOH, wherein said Het is selected from

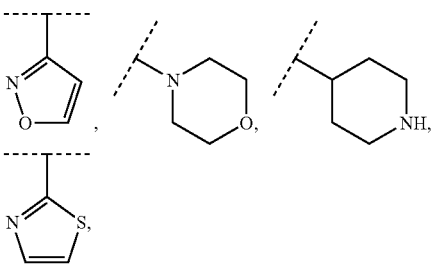

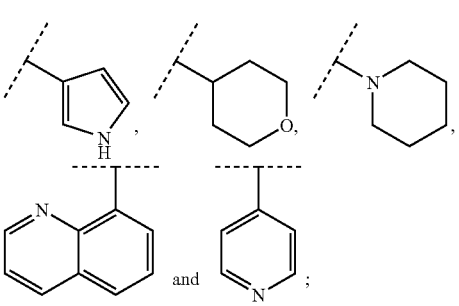

vi) cyclopropyl;
vii) —$SO_2$—$CH_3$ and —$SO_2$-Ph;
or $R^5$ and $R^6$, together with the N to which they are attached, are linked together to form a 6-membered saturated heterocycle which may optionally contain one further heteroatom independently selected from N and O; said heterocycle being optionally substituted with one or two substituents each independently selected from CH$_3$ and —COOH.

More preferably, the group —N($R^5$)$R^6$ is selected from —NHCH$_3$, —NHCH$_2$CH$_3$,

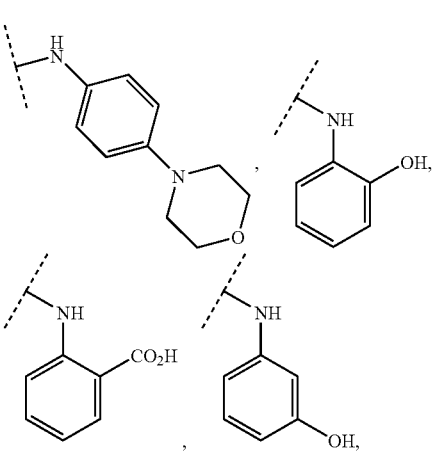

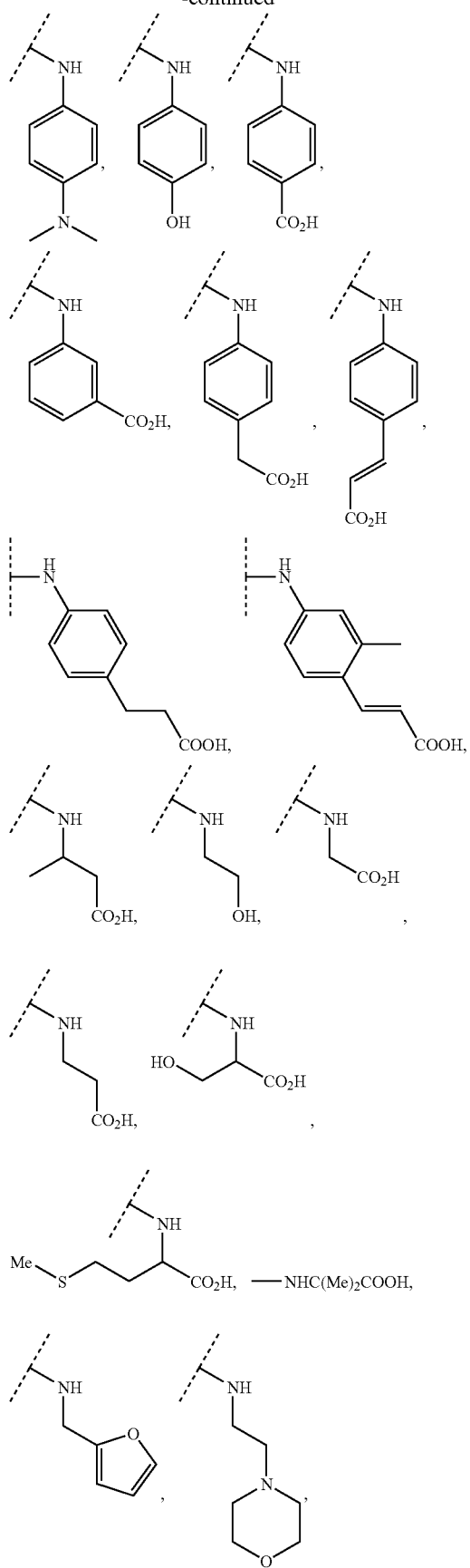
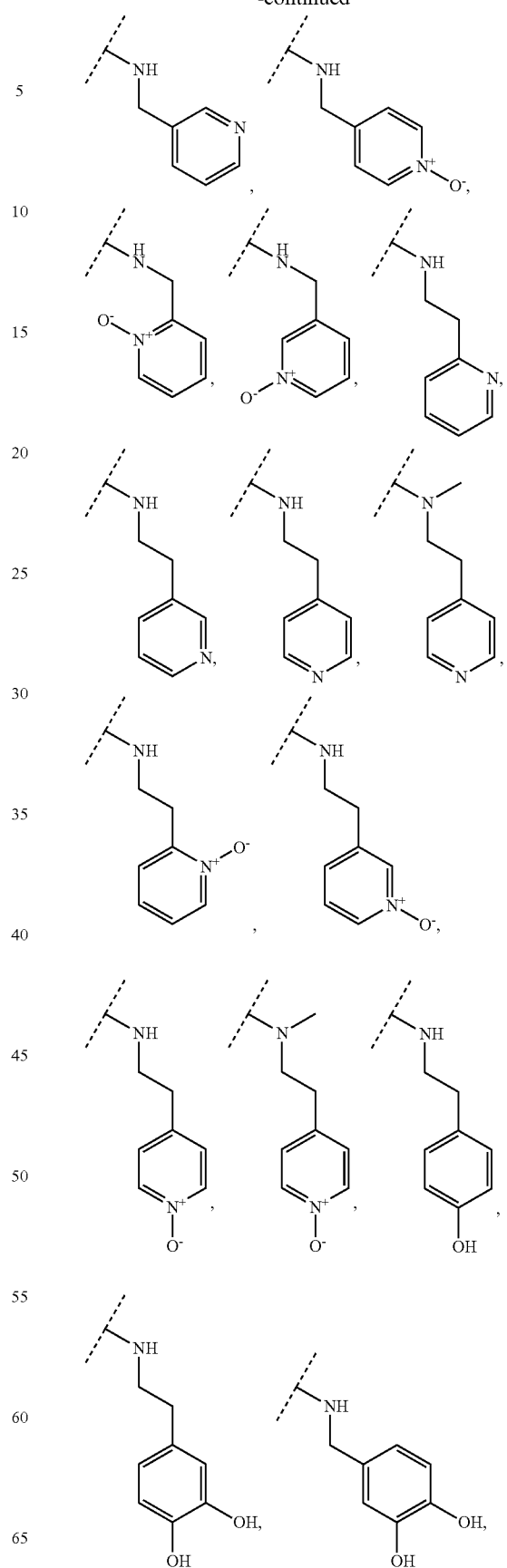

-continued

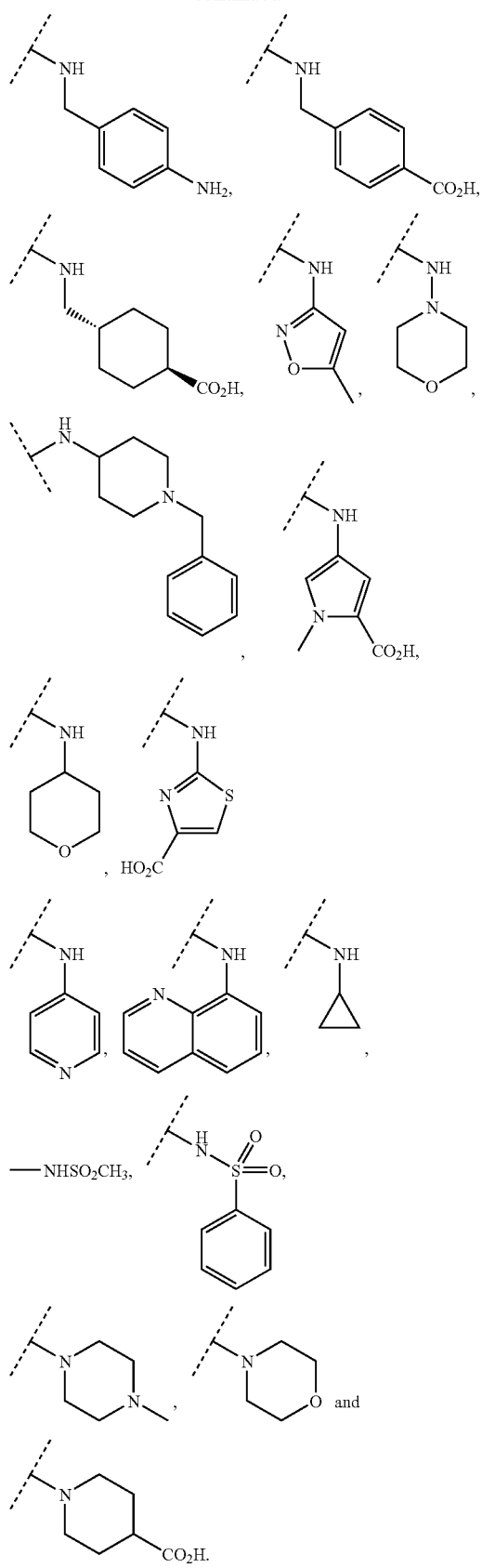

Most preferably, the group —N(R$^5$)R$^6$ is selected from

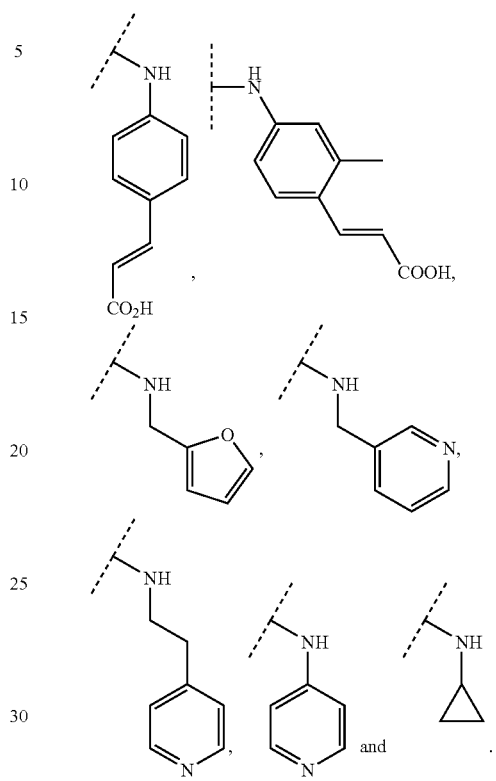

In a further alternative embodiment, R$^4$ is —NHC(=O)—R$^7$ wherein R$^7$ is selected from:
  i) (C$_{1-6}$)alkyl optionally substituted with one or two substituents each independently selected from —COOH, —O—(C$_{1-4}$)alkyl, —NHC(=O)—(C$_{1-4}$)alkyl, phenyl and Het wherein Het is a 5- or 6-membered heterocycle or a 9- or 10-membered heterobicycle, each of which may be saturated, unsaturated or aromatic and each of which may optionally contain from one to four heteroatoms each independently selected from N, O and S wherein each said N heteroatom may, independently and where possible, exist in an oxidized state such that it is further bonded to an O atom to form an N-oxide group; and wherein said phenyl is optionally substituted with one or two substituents each independently selected from halo, —OH, —O—(C$_{1-4}$)alkyl, —NO$_2$, —COOH, —NH$_2$, —NH(C$_{1-4}$)alkyl, —N((C$_{1-4}$)alkyl)$_2$, and (C$_{1-6}$) alkyl optionally substituted with from one to three halo substituents;
  ii) phenyl optionally substituted with —OH, halo or —COOH;
  iii) —NHR$^{71}$ wherein R$^{71}$ is phenyl or phenyl-(C$_{1-4}$)alkyl-, wherein said phenyl is optionally substituted with —COOH or —COO(C$_{1-4}$)alkyl; and
  iv) (C$_{1-6}$)alkynyl, (C$_{3-7}$)cycloalkyl or (C$_{3-7}$)cycloalkyl-(C$_{1-4}$)alkyl-.

Preferably, R$^7$ is selected from:
  i) methyl, ethyl, propyl, 1-methylethyl, butyl, 1-methylpropyl, 2-methylpropyl, 1,1-dimethylethyl, 1-methylbutyl, 2-methylbutyl or 3-methylbutyl, each of which being optionally substituted with one or two substituents each independently selected from —COOH, —O—CH$_3$, —NHC(=O)—CH$_3$, phenyl and Het; wherein Het is selected from

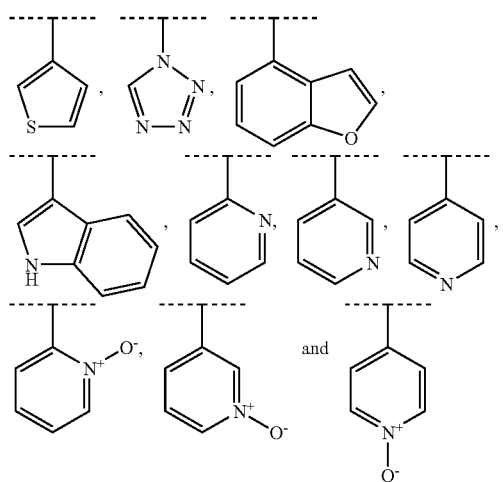

and wherein said phenyl is optionally substituted with one or two substituents each independently selected from halo, —OH, —O—$CH_3$, —$NO_2$, —COOH, —$NH_2$, —$NHCH_3$, —$N(CH_3)_2$, and $CF_3$;

ii) phenyl optionally substituted with —OH, Cl or —COOH;

iii) —NH-phenyl or phenyl-$CH_2$—NH—, wherein the phenyl portion of said —NH-phenyl and phenyl-$CH_2$—NH— is optionally substituted with —COOH, —$COOCH_3$ or —$COOCH_2CH_3$; and iv) ethynyl, 1-propynyl, 2-propynyl, 1-butynyl, 2-butynyl, 3-butynyl, cyclopropyl, cyclobutyl, cyclopentyl, cyclohexyl cyclopropylmethyl, cyclobutylmethyl, cyclopentylmethyl or cyclohexylmethyl.

More preferably, $R^7$ is selected from:

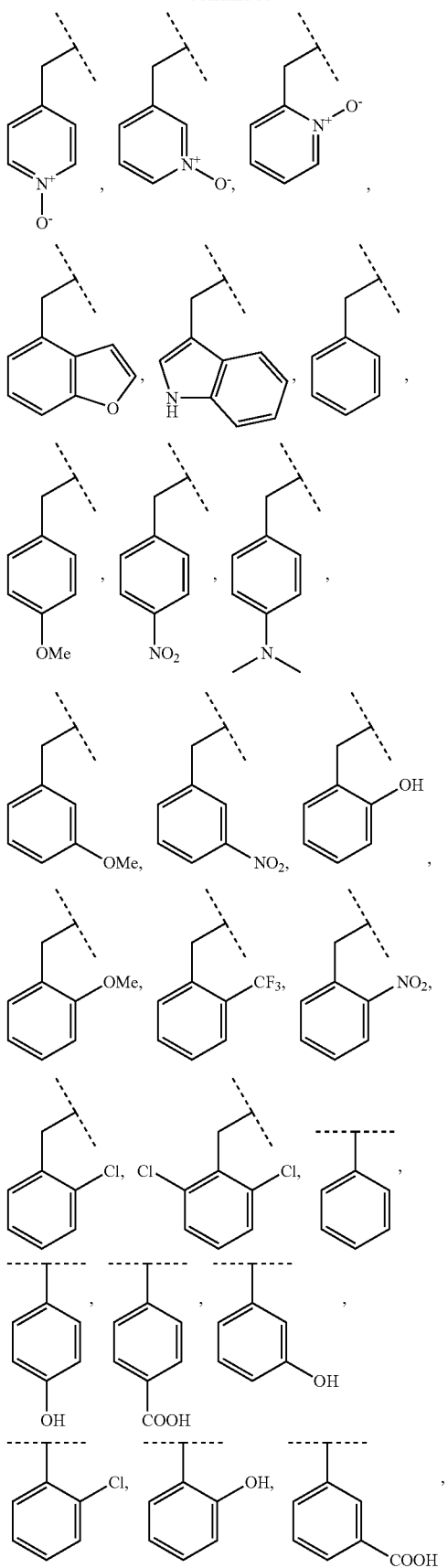

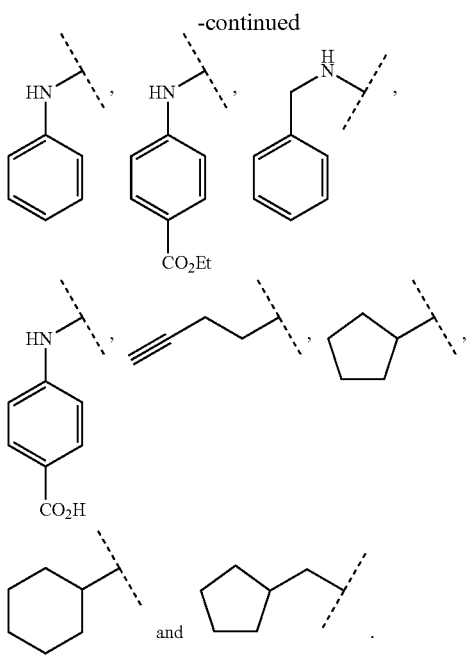

Most preferably, $R^7$ is selected from:

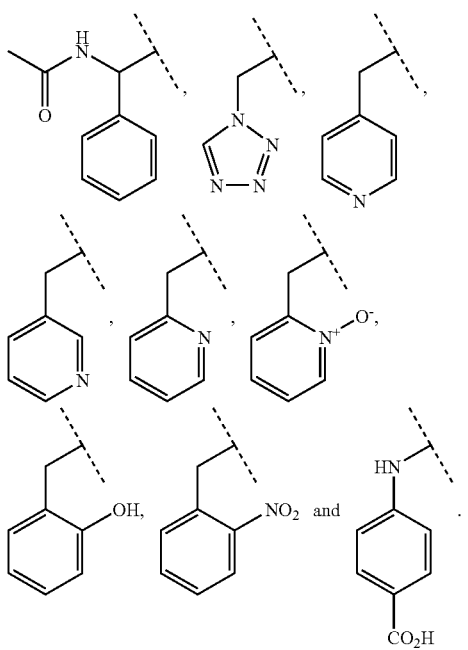

In yet another alternative embodiment, $R^4$ is —C≡C—$R^9$ wherein $R^9$ is selected from:
i) H, —COOH, —COO($C_{1-6}$)alkyl, phenyl or ($C_{2-4}$)alkenyl;
ii) ($C_{3-7}$)cycloalkyl optionally substituted with —OH, —COOH, —COO($C_{1-6}$)alkyl, or ($C_{1-4}$)alkyl wherein said ($C_{1-4}$)alkyl is optionally substituted with —OH or —N($R^{91}$)$R^{92}$, wherein $R^{91}$ is H and $R^{92}$ is ($C_{1-4}$)alkyl substituted with Het; or $R^{91}$ and $R^{92}$, together with the N to which they are attached, are linked together to form a 5- or 6-membered heterocycle which may be saturated, unsaturated or aromatic and which may optionally contain from one to three further heteroatoms each independently selected from N, O and S; said heterocycle being optionally substituted with one or two substituents each independently selected from ($C_{1-6}$)alkyl and —OH; and
iii) ($C_{1-6}$)alkyl optionally substituted with one, two or three substituents each independently selected from:
a) —OH, —O(C=O)$NH_2$, —O(C=O)NH($C_{1-4}$)alkyl, $CF_3$, —COOH or —COO—($C_{1-4}$)alkyl;
b) Het optionally substituted with ($C_{1-6}$)alkyl or —OH;
c) —N($R^{93}$)$R^{94}$ wherein $R^{93}$ is H or ($C_{1-4}$)alkyl and $R^{94}$ is selected from H, —($C_{1-4}$)alkyl optionally substituted with $R^{941}$—$SO_2$—($C_{1-4}$)alkyl and —C(=O)—$R^{942}$;
wherein $R^{941}$ is —COOH, —C(=O)$NH_2$, ($C_{3-7}$)cycloalkyl, Het, or phenyl optionally substituted with —OH,
and $R^{942}$ is —O—($C_{1-4}$)alkyl, —NH—($C_{1-4}$)alkyl, phenyl, ($C_{3-7}$)cycloalkyl or Het, wherein said ($C_{3-7}$)cycloalkyl is optionally substituted with —COOH and wherein said Het is optionally substituted with one or two substituents each independently selected from ($C_{1-6}$)alkyl and —OH; or
$R^{942}$ is ($C_{1-4}$)alkyl optionally substituted with —COOH, —$NH_2$, —NH($C_{1-4}$)alkyl, —NH-Het, —N(($C_{1-4}$)alkyl)$_2$, or Het; wherein said Het is optionally substituted with one or two substituents each independently selected from —OH, —COOH and ($C_{1-6}$)alkyl optionally substituted with Het and wherein the ($C_{1-4}$)alkyl portion of said —NH($C_{1-4}$)alkyl is optionally substituted with Het;
d) —C(=O)N($R^{95}$)$R^{96}$, wherein $R^{95}$ is H and $R^{96}$ is selected from ($C_{3-7}$)cycloalkyl, —$SO_2$—$R^{961}$ and —($C_{1-4}$)alkyl-$R^{962}$, wherein
$R^{961}$ is ($C_{1-4}$)alkyl, phenyl, ($C_{3-7}$)cycloalkyl, or —N(($C_{1-4}$)alkyl)$_2$; and
$R^{962}$ is phenyl, —COOH, —N(($C_{1-4}$)alkyl)$_2$, or Het, wherein said phenyl is optionally substituted with —N(($C_{1-4}$)alkyl)$_2$ and said Het is optionally substituted with oxo;
or $R^{95}$ and $R^{96}$, together with the N to which they are attached, are linked together to form a 5- or 6-membered heterocycle which may be saturated or unsaturated and which may optionally contain from one to three further heteroatoms each independently selected from N, O and S; said heterocycle being optionally substituted with —COOH; and
e) —O($C_{1-4}$)alkyl optionally substituted with $R^{97}$ wherein $R^{97}$ is selected from —OH, —COOH, —C(=O)O—($C_{1-4}$)alkyl-NH($C_{1-4}$)alkyl, —C(=O)N($R^{971}$)$R^{972}$—$NH_2$, —NH—($C_{3-7}$)cycloalkyl, —O-Het, and Het;
provided that the carbon atom of —O—($C_{1-4}$)alkyl which is directly bonded to O is not also directly bonded to —OH, —$NH_2$ or —NH—($C_{3-7}$)cycloalkyl;
wherein each of said Het and the Het portion of said —O-Het is optionally substituted with one or two substituents each independently selected from halo, oxo, ($C_{1-4}$)alkyl, and —OH; and
wherein $R^{971}$ is H or ($C_{1-4}$)alkyl and $R^{972}$ is selected from H, —OH, —NHC(=O)—($C_{1-4}$)alkyl, —NHC(=O)—$NH_2$, ($C_{1-4}$)alkyl, ($C_{3-7}$)cycloalkyl, phenyl and Het, wherein said ($C_{1-4}$)alkyl is optionally substituted with —OH, —COOH, —N(($C_{1-4}$)alkyl)$_2$ or Het, provided that when $R^{972}$ is $(C_{1-4})$alkyl, the carbon atom of $(C_{1-4})$alkyl which is directly bonded to N is not also directly bonded to —OH;

and wherein said $(C_{3-7})$cycloalkyl is optionally substituted with —COOH, and wherein said phenyl is optionally substituted with —OH, —COOH, or —$(C_{2-4})$alkenyl-COOH;

or $R^{971}$ and $R^{972}$, together with the N to which they are attached, are linked together to form a 5- or 6-membered heterocycle which may be saturated or unsaturated and which may optionally contain from one to three further heteroatoms each independently selected from N, O and S; said heterocycle being optionally substituted with $(C_{1-4})$alkyl or —COOH;

wherein Het is in each instance independently a 4,5- or 6-membered saturated, unsaturated or aromatic monocyclic heterocycle containing from one to four heteroatoms each independently selected from N, O and S. wherein each said N heteroatom may, independently and where possible, exist in an oxidized state such that it is further bonded to an O atom to form an N-oxide group and wherein each said S heteroatom may, independently and where possible, exist in an oxidized state such that it is further bonded to one or two oxygen atoms to form the groups SO or $SO_2$.

Preferably, $R^9$ is selected from:
i) H, —COOH, phenyl, ethenyl or 2-propenyl;
ii) cyclopropyl, cyclobutyl, cyclopentyl or cyclohexyl, each of which being optionally substituted with —OH, —COOH or $CH_3$, wherein said $CH_3$ is optionally substituted with —OH or —N($R^{91}$)$R^{92}$, wherein $R^{91}$ is H and $R^{92}$ is

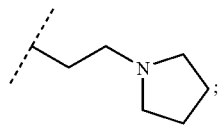

or $R^{91}$ and $R^{92}$, together with the N to which they are attached, are linked together to form a 5- or 6-membered heterocycle which may be saturated, unsaturated or aromatic and which may optionally contain one or two further heteroatoms each independently selected from N and O; said heterocycle being optionally substituted with one or two substituents each independently selected from $CH_3$ and —OH;

iii) methyl, ethyl, propyl, 1-methylethyl, butyl, 1-methylpropyl, 2-methylpropyl, 1,1-dimethylethyl, pentyl or 1-ethylpropyl, each of which being optionally substituted with one, two or three substituents each independently selected from:
a) —OH, —O(C=O)$NH_2$, —O(C=O)$NHCH_3$, $CF_3$, —COOH, —$COOCH_3$ or —$COOCH_2CH_3$;
b) Het optionally substituted with $CH_3$ or —OH; wherein Het is selected from

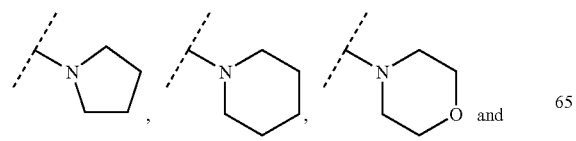

and

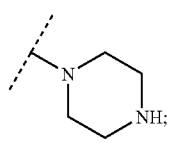

c) —N($R^{93}$)$R^{94}$ wherein $R^{93}$ is H, $CH_3$ or $CH_2CH_3$ and $R^{94}$ is selected from H, —$(C_{1-4})$alkyl optionally substituted with $R^{941}$—$SO_2$—$CH_3$ and —C(=O)—$R^{942}$;

wherein $R^{941}$ is —COOH, —C(=O)$NH_2$, cyclopropyl, Het, or phenyl optionally substituted with —OH; wherein Het is selected from

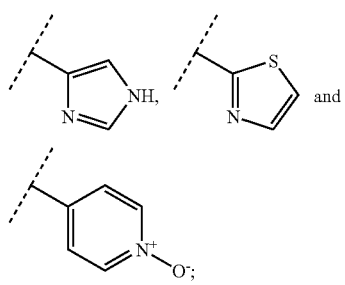

and $R^{942}$ is —O—$(C_{1-14})$alkyl, —NH—$(C_{1-4})$alkyl, phenyl, cyclopropyl or Het; wherein Het is selected from

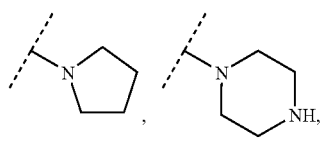

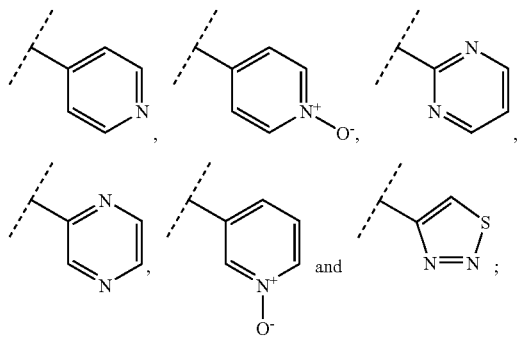

and wherein said cyclopropyl is optionally substituted with —COOH and wherein said Het is optionally substituted with $CH_3$ or —OH; or $R^{942}$ is $(C_{1-4})$alkyl optionally substituted with —COOH, —$NH_2$, —NH$(C_{1-4})$alkyl,

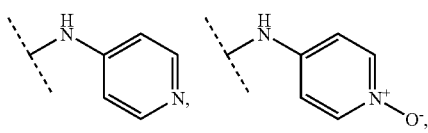

—N((C$_{1-4}$)alkyl)$_2$, or Het; wherein Het is selected from

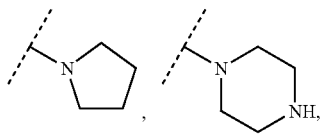

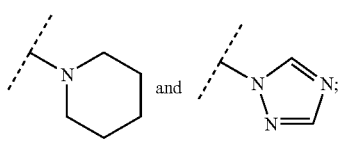

and wherein said Het is optionally substituted with one or two substituents each independently selected from —OH, —COOH and (C$_{1-4}$)alkyl optionally substituted with

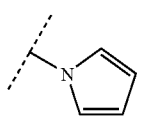

and wherein the (C$_{1-4}$)alkyl portion of said —NH(C$_{1-4}$)alkyl is optionally substituted with

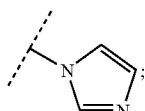

d) —C(=O)N(R$^{95}$)R$^{96}$, wherein R$^{95}$ is H and R$^{96}$ is selected from cyclopropyl, —SO$_2$—R$^{961}$ and —(C$_{1-4}$)alkyl-R$^{962}$, wherein
R$^{961}$ is CH$_3$, CH$_2$CH$_3$, phenyl, cyclopropyl, or —N(CH$_3$)$_2$; and
R$^{962}$ is phenyl, —COOH, —N(CH$_3$)$_2$, or Het; wherein Het is selected from

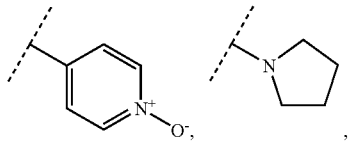

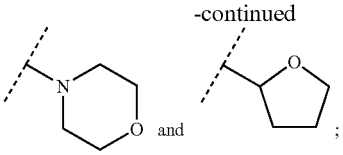

and wherein said phenyl is optionally substituted with —N(CH$_3$)$_2$ and said Het is optionally substituted with oxo; or R$^{95}$ and R$^{96}$, together with the N to which they are attached, are linked together to form a 6-membered heterocycle which may be saturated or unsaturated and which may optionally contain one or two further heteroatoms each independently selected from N and O; said heterocycle being optionally substituted with —COOH; and e) —O(C$_{1-4}$)alkyl optionally substituted with R$^{97}$ wherein R$^{97}$ is selected from —OH, —COOH, —C(=O)O—CH$_2$CH$_2$—NHCH$_3$, —C(=O)N(R$^{971}$)R$^{972}$—NH$_2$, —NH—(C$_{3-7}$)cycloalkyl,

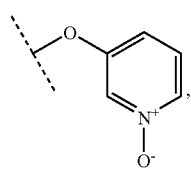

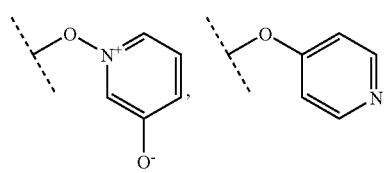

and Het;
provided that the carbon atom of —O—(C$_{1-4}$)alkyl which is directly bonded to O is not also directly bonded to —OH, —NH$_2$ or —NH—(C$_{3-7}$)cycloalkyl;
wherein Het is selected from

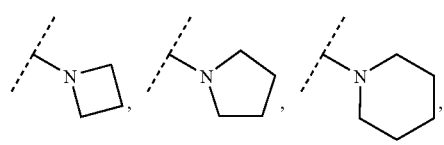

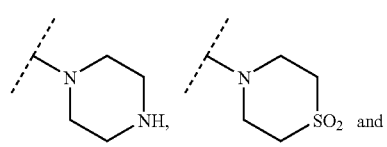

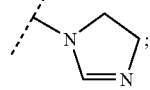

and wherein said Het is optionally substituted with one or two substituents each independently selected from halo, oxo, CH$_3$ and —OH; and wherein R$^{971}$ is H or CH$_3$ and R$^{972}$ is selected from H, —OH, —NHC(=O)—CH$_3$, —NHC(=O)—NH$_2$, (C$_{1-4}$)alkyl, cyclopropyl, phenyl and Het; wherein Het is selected from

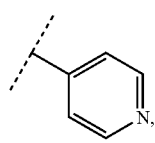

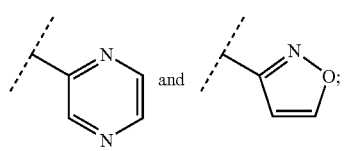

and wherein said (C$_{1-4}$)alkyl is optionally substituted with —OH, —COOH, —N(CH$_3$)$_2$ or

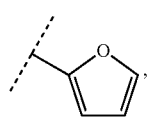

provided that when R$^{972}$ is (C$_{1-4}$)alkyl, the carbon atom of (C$_{1-4}$)alkyl which is directly bonded to N is not also directly bonded to —OH;

and wherein said cyclopropyl is optionally substituted with —COOH, and wherein said phenyl is optionally substituted with —OH, —COOH, or —CH=CH—COOH;

or R$^{971}$ and R$^{972}$, together with the N to which they are attached, are linked together to form a 5- or 6-membered heterocycle which may be saturated or unsaturated and which may optionally contain one or two further heteroatoms each independently selected from N and O; said heterocycle being optionally substituted with CH$_3$ or —COOH.

More preferably, R$^9$ is selected from H, —COOH,

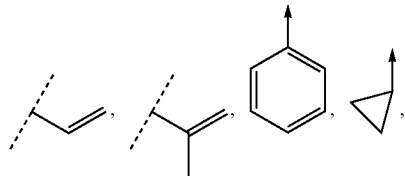

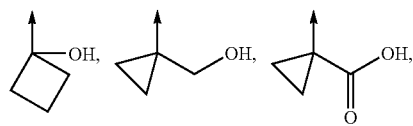

-continued

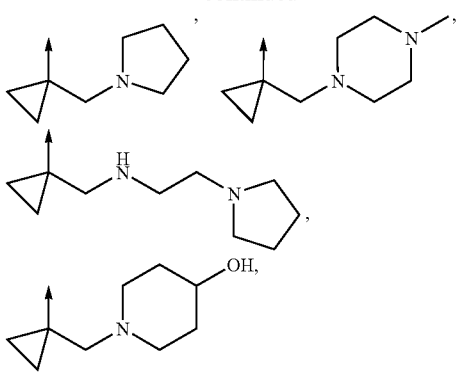

—(CH$_2$)$_2$CH$_3$, —CH$_2$OH, —(CH$_2$)$_2$OH, —(CH$_2$)$_3$OH, —(CH$_2$)$_4$OH, —C(Me)$_2$OH, —C(Me)$_2$CH$_2$OH,

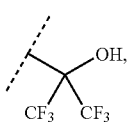

—C(Me)$_2$OMe,

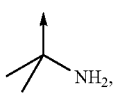

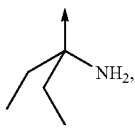

—CH$_2$N(Et)$_2$, —CH$_2$COOH, —(CH$_2$)$_2$COOH, —C(Me)$_2$CO$_2$H, —C(Me)$_2$COOMe, —C(Me)$_2$CH$_2$COOH, —CH$_2$OC(O)NH$_2$, —(CH$_2$)$_3$OC(O)NH$_2$,

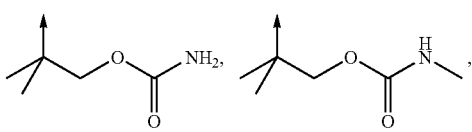

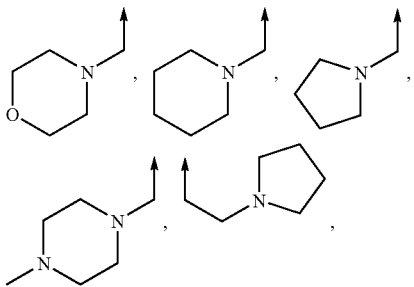

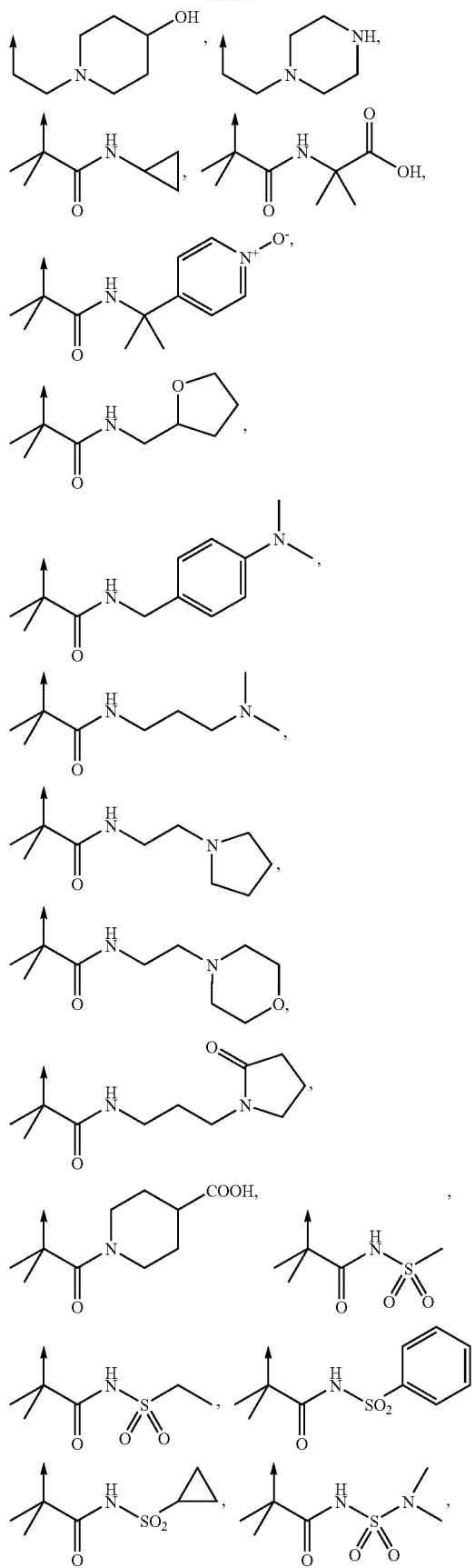
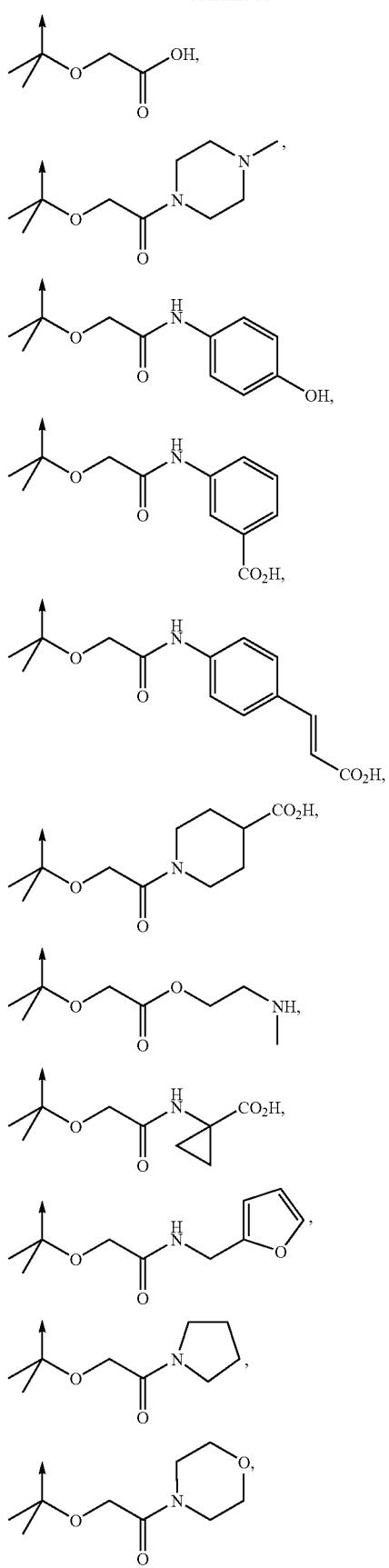

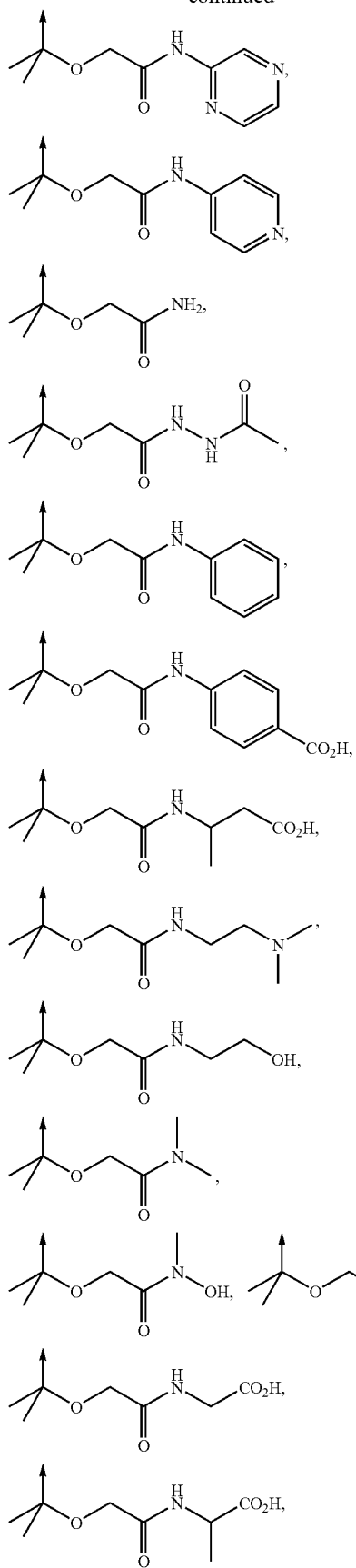
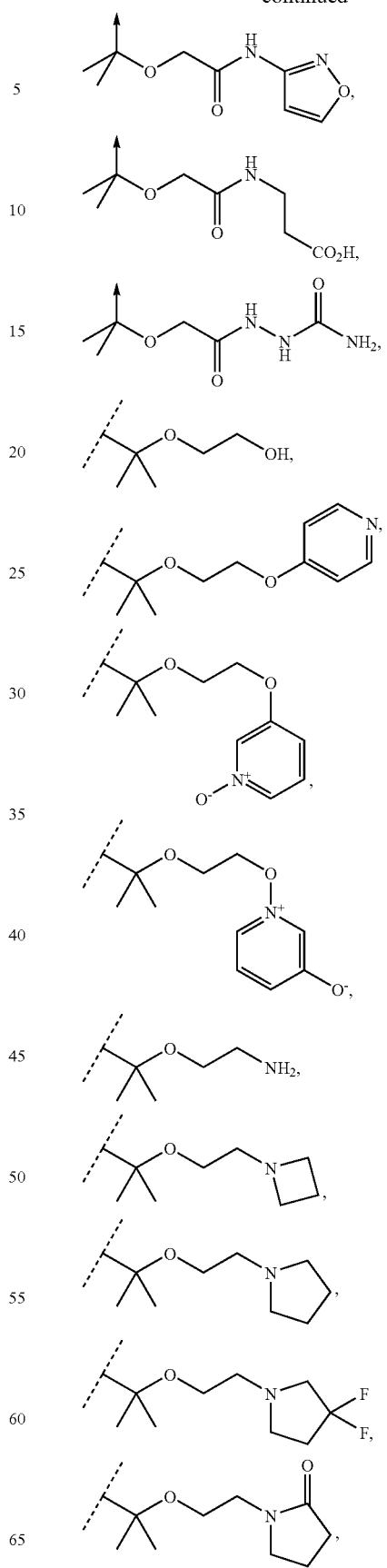

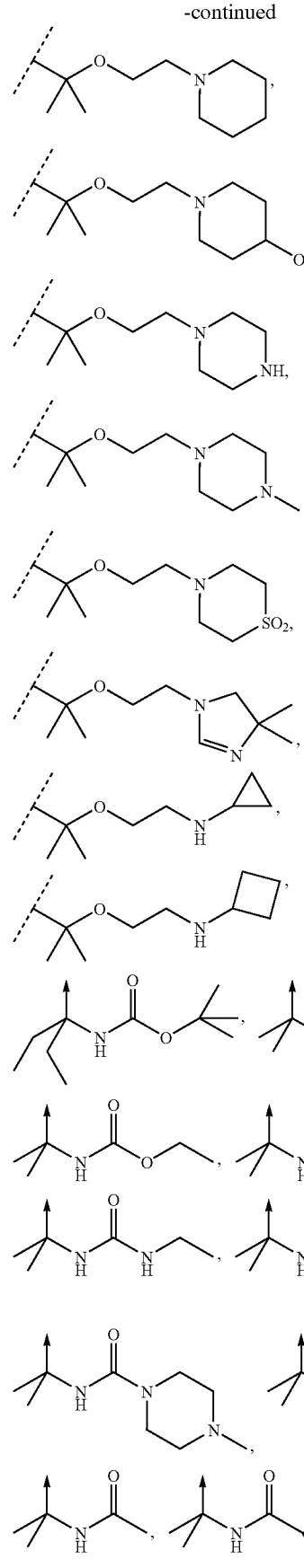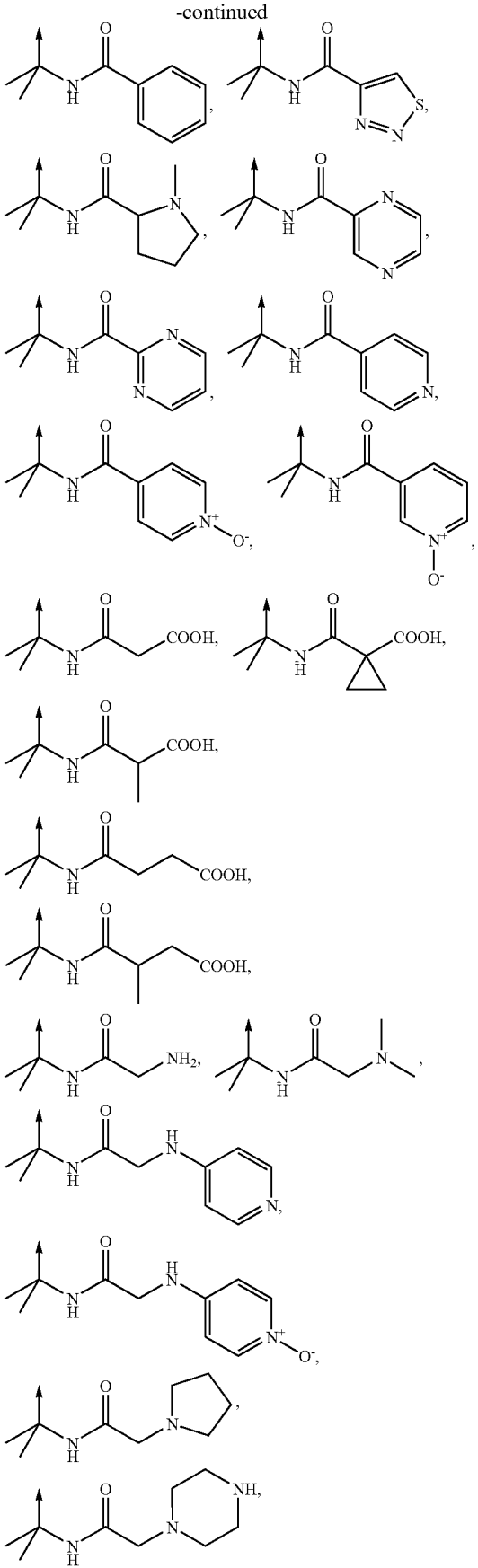

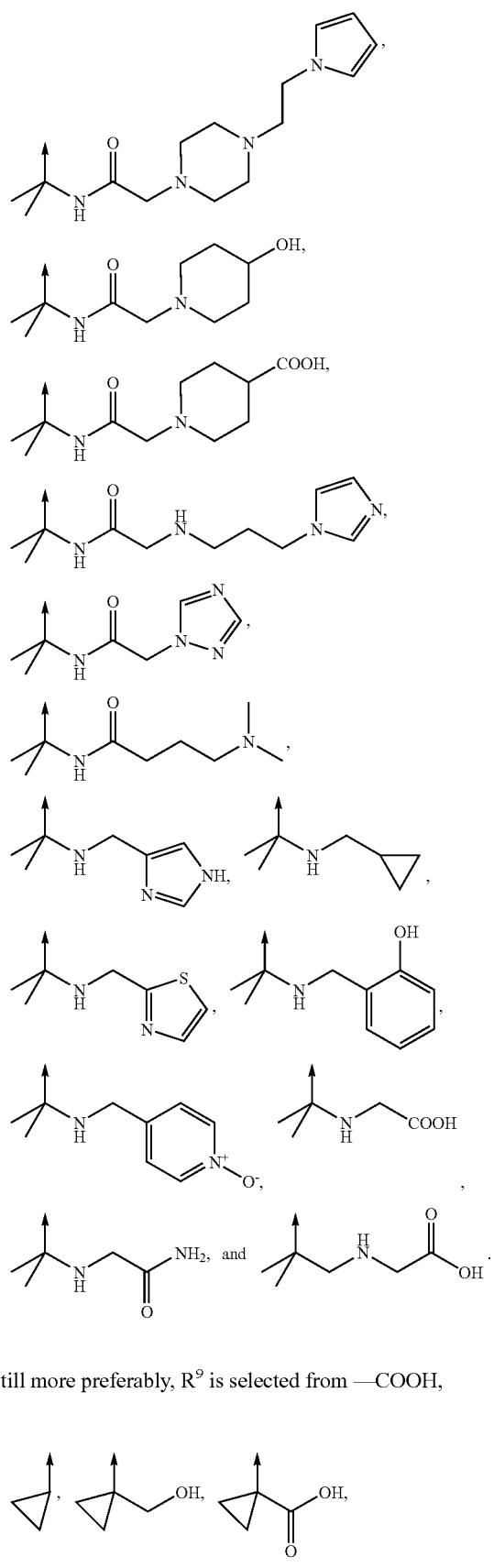
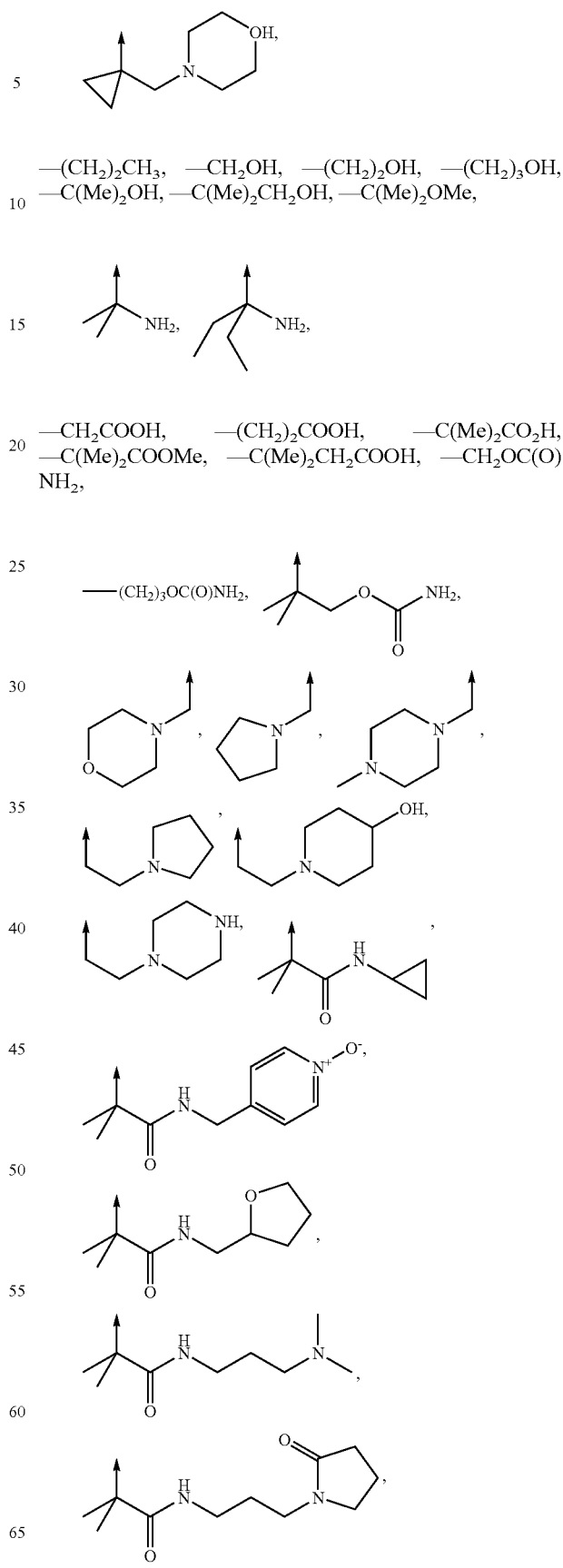
Still more preferably, $R^9$ is selected from —COOH,

-continued
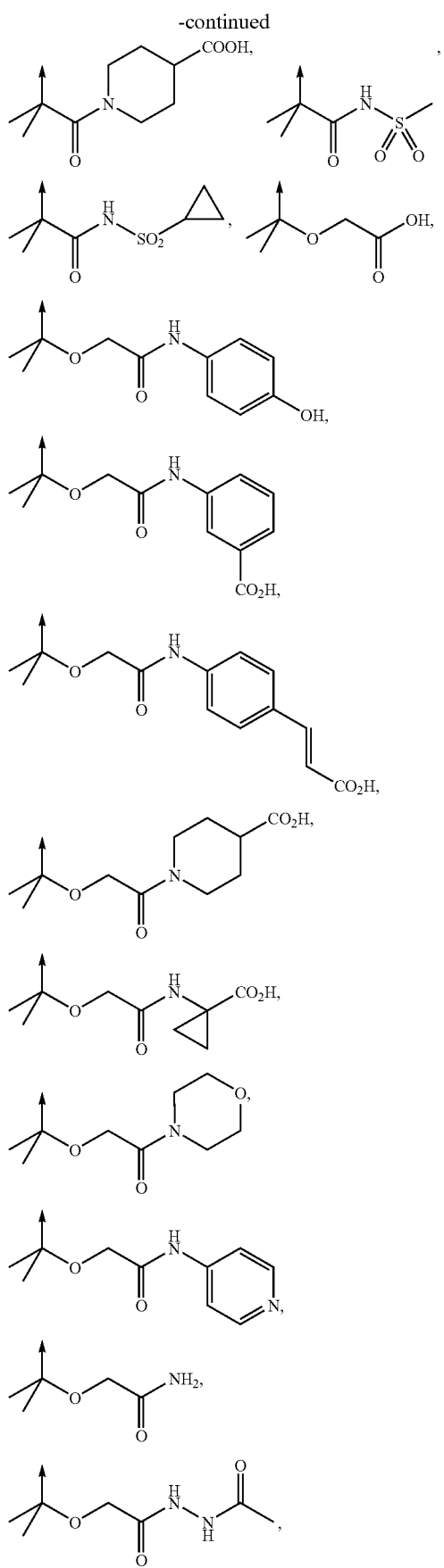
-continued
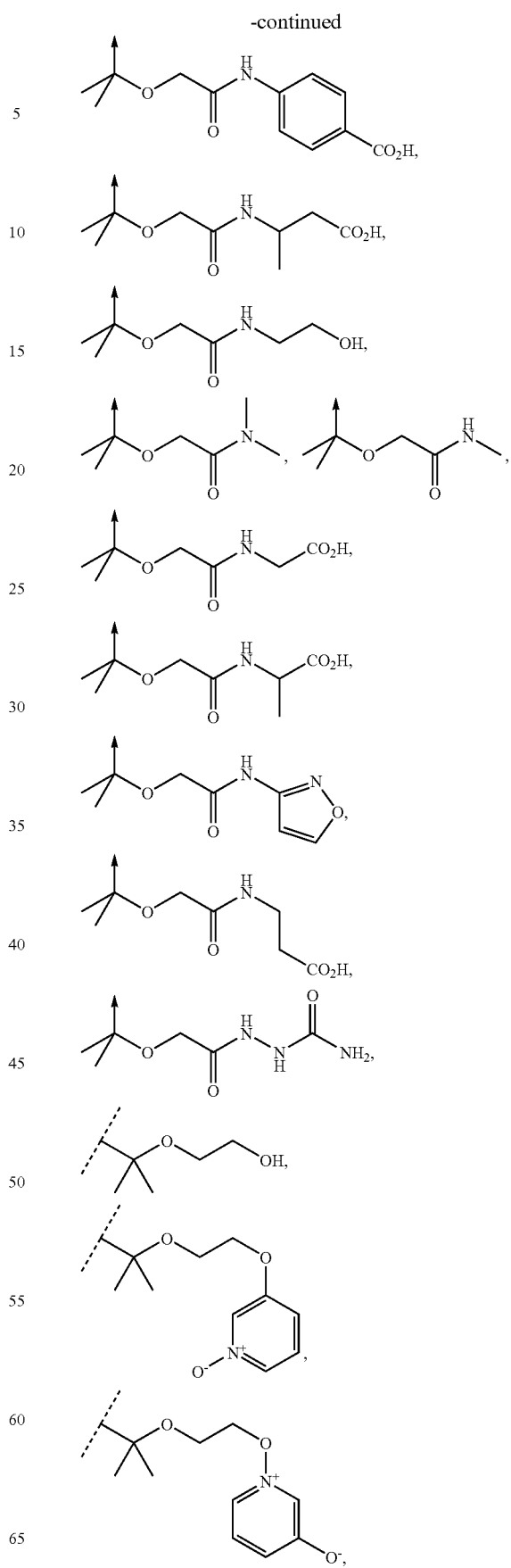

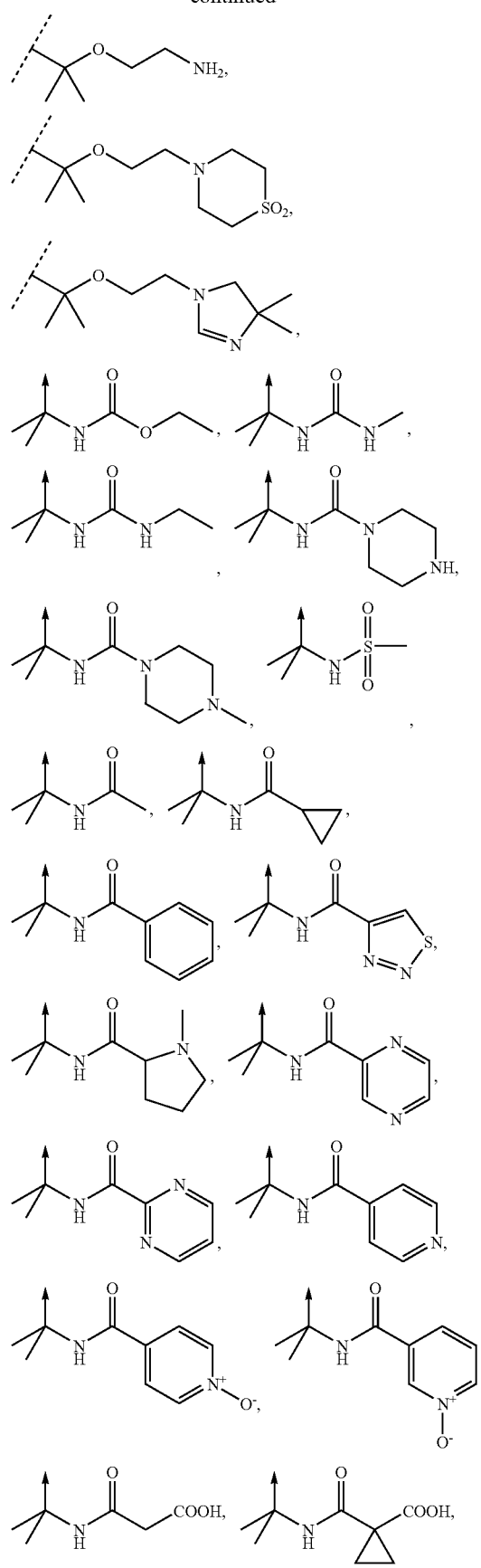
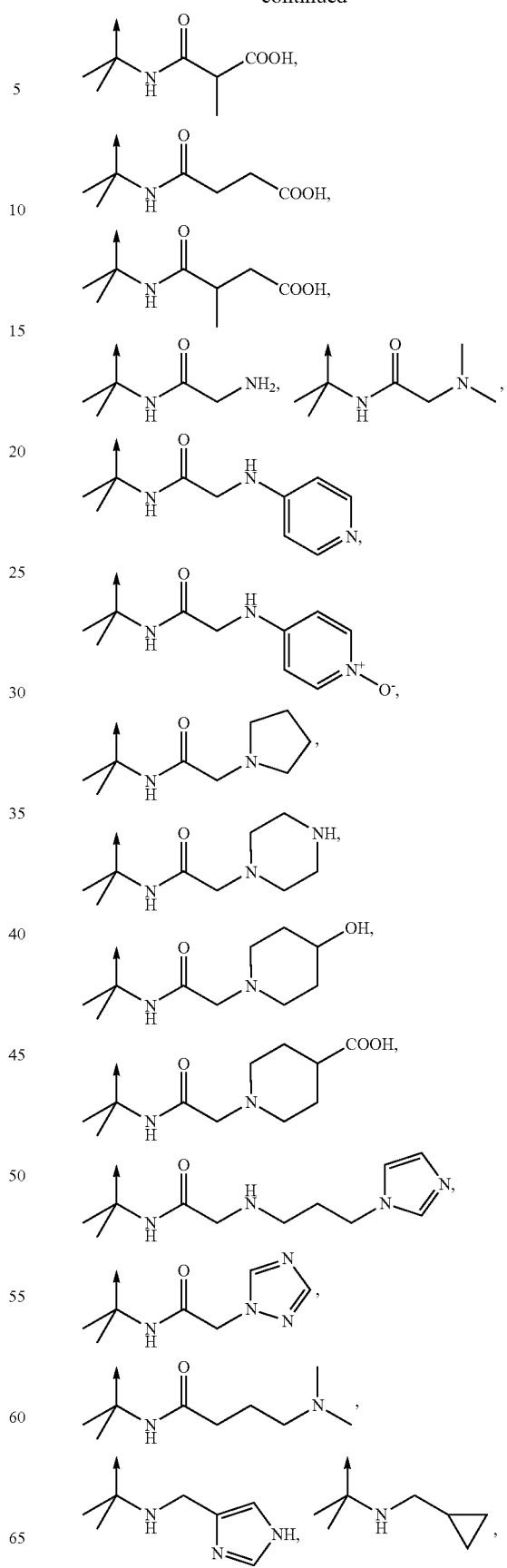

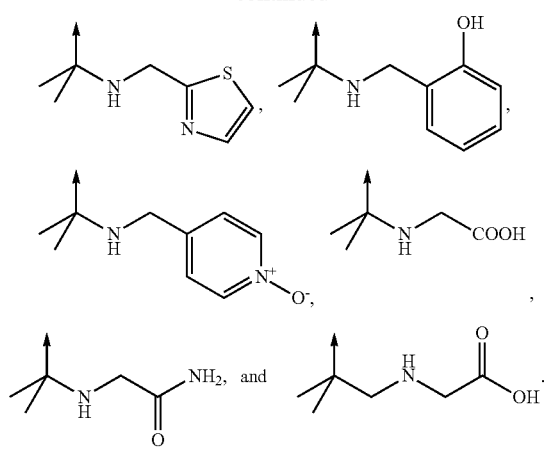

Most preferably, $R^9$ is selected from

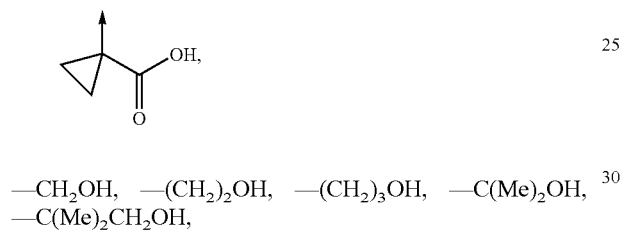

—$CH_2OH$, —$(CH_2)_2OH$, —$(CH_2)_3OH$, —$C(Me)_2OH$, —$C(Me)_2CH_2OH$,

—$C(Me)_2CO_2H$,

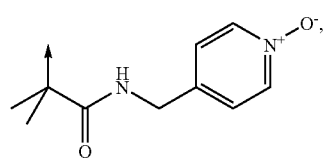

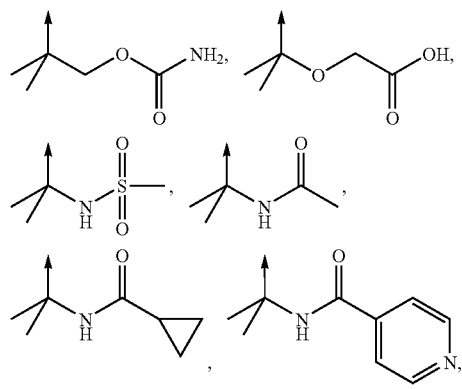

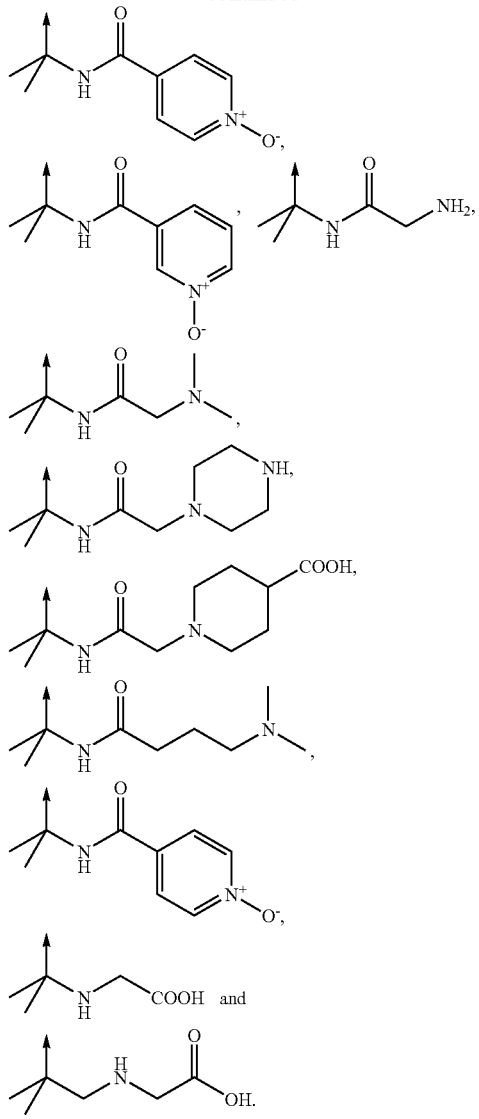

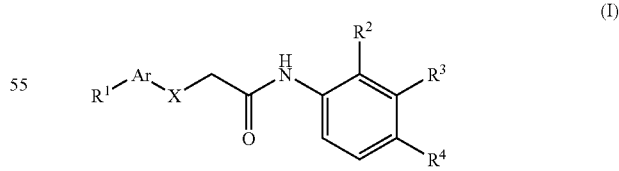

Any and each individual definition of $R^4$ as set out herein may be combined with any and each individual definition of Ar, X, $R^1$, $R^2$ and $R^3$ as set out herein.

Therefore, one embodiment of this invention provides a compound, represented by $$\text{(I)}$$

wherein

Ar is a 5-membered aromatic heterocycle containing 1 to 4 heteroatoms each independently selected from N, O and S; said heterocycle being optionally substituted at a substitutable position with $R^{Ar}$, wherein $R^{Ar}$ is H, $(C_{1-4})$alkyl, $CF_3$ or $(C_{3-7})$cycloalkyl and wherein the groups X and $R^1$ are attached to positions on the Ar ring which are immediately adjacent to each other;

X is selected from O and S;
R$^1$ is a group of formula:
R$^{11}$ is halo; and

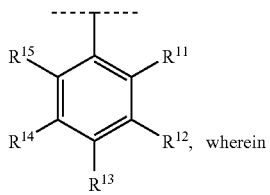

wherein

R$^{12}$, R$^{13}$, R$^{14}$ and R$^{15}$ are each independently selected from H, halo, (C$_{1-4}$)alkyl, CF$_3$, (C$_{3-7}$)cycloalkyl, (C$_{3-7}$)cycloalkyl-(C$_{1-4}$)alkyl-, cyano, —O—(C$_{1-4}$)alkyl, —OCF$_3$ and —N((C$_{1-4}$)alkyl)$_2$, wherein said (C$_{3-7}$)cycloalkyl is optionally substituted with (C$_{1-4}$)alkyl; or R$^{12}$ and R$^{13}$, R$^{13}$ and R$^{14}$, or R$^{14}$ and R$^{15}$ are linked, together with the carbon atoms to which they are attached, to form a five- or six-membered saturated, unsaturated or aromatic ring which optionally contains from one to three heteroatoms each independently selected from O, S and N, wherein the remaining of R$^{12}$, R$^{13}$, R$^{14}$ and R$^{15}$ are defined as hereinbefore;

R$^2$ is selected from halo, nitro and (C$_{1-4}$)alkyl;
R$^3$ is selected from H and halo;
R$^4$ is selected from:

a)

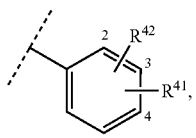

wherein R$^{42}$ is bonded to position 2 or position 3 of the phenyl ring and is selected from H, halo and (C$_{1-4}$)alkyl; and R$^{41}$ is bonded to position 3 or position 4 of the phenyl ring and is selected from:
 i) (C$_{1-4}$)alkyl substituted with —COOH, —COO(C$_{1-4}$)alkyl, —C(=O)NH$_2$, —C(=O)NHSO$_2$—(C$_{1-4}$)alkyl, or —OH;
 ii) (C$_{2-4}$)alkenyl substituted with —COOH or —COO(C$_{1-4}$)alkyl;
 iii) —O—(C$_{1-4}$)alkyl optionally substituted with —COOH, Het, or —N((C$_{1-6}$)alkyl)$_2$, wherein said Het is optionally substituted with —OH or —COOH and wherein either or both of the (C$_{1-6}$)alkyl groups in said —N((C$_{1-6}$)alkyl)$_2$ are optionally substituted with —COOH or —COO(C$_{1-4}$)alkyl; and
 iv) —OH, —COOH, —COO(C$_{1-4}$)alkyl, —SO$_2$NH$_2$, or —SO$_2$—(C$_{1-4}$)alkyl;
  provided that R$^{42}$ and R$^{41}$ may not both be bonded to position 3 of the phenyl ring at the same time;
b) (C$_{2-4}$)alkenyl substituted with —COOH or —COO(C$_{1-4}$)alkyl;
c) Het optionally substituted with (C$_{1-6}$)alkyl, —NH$_2$, —COOH, or (C$_{2-4}$)alkenyl substituted with —COOH;
d) —SO$_2$N(R$^{43}$)R$^{44}$, wherein R$^{43}$ is H or (C$_{1-4}$)alkyl and R$^{44}$ is selected from (C$_{1-6}$)alkyl, phenyl, phenyl-(C$_{1-4}$)alkyl-, —C(=O)NH(C$_{1-4}$)alkyl, —C(=O)O(C$_{1-4}$)alkyl, and Het; wherein said (C$_{1-6}$)alkyl is optionally substituted with —OH or —COOH and wherein said Het is optionally substituted with (C$_{1-6}$)alkyl;
 or R$^{43}$ and R$^{44}$, together with the N to which they are attached, are linked together to form a 5- or 6-membered heterocycle which may be saturated or unsaturated and which may optionally contain from one to three further heteroatoms each independently selected from N, O and S; said heterocycle being optionally substituted with (C$_{1-6}$)alkyl or —COOH;
e) —O—(C$_{1-4}$)alkyl substituted with —OH, —COOH or Het, wherein said Het is optionally substituted with —COOH or —COO(C$_{1-6}$)alkyl;
f) —C(=O)N(R$^5$)R$^6$ or —O—CH$_2$—C(=O)N(R$^5$)R$^6$ wherein R$^5$ is H or (C$_{1-6}$)alkyl and R$^6$ is selected from:
 i) phenyl optionally substituted with one or two substituents each independently selected from —OH, —COOH, —N((C$_{1-4}$)alkyl)$_2$, (C$_{1-4}$)alkyl, (C$_{2-4}$)alkenyl and Het; wherein said (C$_{1-4}$)alkyl is optionally substituted with —COOH and said (C$_{2-4}$)alkenyl is substituted with —COOH;
 ii) (C$_{1-4}$)alkyl optionally substituted with one or two substituents each independently selected from —COOH, —OH, —S—(C$_{1-6}$)alkyl and Het;
 iii) phenyl-(C$_{1-4}$)alkyl- wherein the phenyl portion of said phenyl-(C$_{1-4}$)alkyl- is optionally substituted with one or two substituents each independently selected from —OH, —NH$_2$, and —COOH;
 iv) (C$_{3-7}$)cycloalkyl-(C$_{1-4}$)alkyl- wherein the cycloalkyl portion of said (C$_{3-7}$)cycloalkyl-(C$_{1-4}$)alkyl- is optionally substituted with —COOH;
 v) Het optionally substituted with one or two substituents each independently selected from (C$_{1-6}$)alkyl, phenyl-(C$_{1-4}$)alkyl- and —COOH;
 vi) (C$_{3-7}$)cycloalkyl; and
 vii) —SO$_2$—R$^{61}$ wherein R$^{61}$ is (C$_{1-4}$)alkyl or phenyl;
 or R$^5$ and R$^6$, together with the N to which they are attached, are linked together to form a 5- or 6-membered heterocycle which may be saturated or unsaturated and which may optionally contain from one to three further heteroatoms each independently selected from N, O and S; said heterocycle being optionally substituted with one or two substituents each independently selected from (C$_{1-6}$)alkyl, —COOH and —COO(C$_{1-6}$)alkyl;
g) —NHC(=O)—R$^7$ wherein R$^7$ is selected from:
 i) (C$_{1-6}$)alkyl optionally substituted with one or two substituents each independently selected from —COOH, —O—(C$_{1-4}$)alkyl, —NHC(=O)—(C$_{1-4}$)alkyl, phenyl and Het; wherein said phenyl is optionally substituted with one or two substituents each independently selected from halo, —OH, —O—(C$_{1-4}$)alkyl —NO$_2$, —COOH —NH$_2$, —NH(C$_{1-4}$)alkyl, —N((C$_{1-4}$)alkyl)$_2$, and (C$_{1-6}$)alkyl optionally substituted with from one to three halo substituents;
 ii) phenyl optionally substituted with —OH, halo or —COOH;
 iii) —NHR$^{71}$ wherein R$^{71}$ is phenyl or phenyl-(C$_{1-4}$)alkyl-, wherein said phenyl is optionally substituted with —COOH or —COO(C$_{1-4}$)alkyl; and
 iv) (C$_{1-6}$)alkynyl, (C$_{3-7}$)cycloalkyl or (C$_{3-7}$)cycloalkyl-(C$_{1-4}$)alkyl-;
h) —NHSO$_2$R$^8$ wherein R$^8$ is selected from phenyl, phenyl-(C$_{1-4}$)alkyl- and Het; and
i) —C≡C—R$^9$ wherein R$^9$ is selected from:
 i) H, —COOH, —COO(C$_{1-6}$)alkyl, phenyl or (C$_{2-4}$)alkenyl;
 ii) (C$_{3-7}$)cycloalkyl optionally substituted with —OH, —COOH, —COO(C$_{1-6}$)alkyl, or (C$_{1-4}$)alkyl wherein said (C$_{1-4}$)alkyl is optionally substituted with —OH or —N(R$^{91}$)R$^{92}$, wherein R$^{91}$ is H and R$^{92}$ is (C$_{1-4}$)alkyl substituted with Het; or $R^{91}$ and $R^{92}$, together with the N to which they are attached, are linked together to form a 5- or 6-membered heterocycle which may be saturated, unsaturated or aromatic and which may optionally contain from one to three further heteroatoms each independently selected from N, O and S; said heterocycle being optionally substituted with one or two substituents each independently selected from $(C_{1-6})$alkyl and —OH; and iii) $(C_{1-6})$alkyl optionally substituted with one, two or three substituents each independently selected from:
a) —OH, —O(C=O)NH$_2$, —O(C=O)NH(C$_{1-4}$)alkyl, CF$_3$, —COOH or —COO—(C$_{1-4}$)alkyl;
b) Het optionally substituted with (C$_{1-6}$)alkyl or —OH;
c) —N(R$^{93}$)R$^{94}$ wherein R$^{93}$ is H or (C$_{1-4}$)alkyl and R$^{94}$ is selected from H, —(C$_{1-4}$)alkyl optionally substituted with R$^{941}$—SO$_2$—(C$_{1-4}$)alkyl and —C(=O)—R$^{942}$;
wherein R$^{941}$ is —COOH, —C(=O)NH$_2$, (C$_{3-7}$)cycloalkyl, Het, or phenyl optionally substituted with —OH,
and R$^{942}$ is —O—(C$_{1-4}$)alkyl, —NH—(C$_{1-4}$)alkyl, phenyl, (C$_{3-7}$)cycloalkyl or Het, wherein said (C$_{3-7}$)cycloalkyl is optionally substituted with —COOH and wherein said Het is optionally substituted with one or two substituents each independently selected from (C$_{1-6}$)alkyl and —OH; or
R$^{942}$ is (C$_{1-4}$)alkyl optionally substituted with —COOH, —NH$_2$, —NH(C$_{1-4}$)alkyl, —NH-Het, —N((C$_{1-4}$)alkyl)$_2$, or Het; wherein said Het is optionally substituted with one or two substituents each independently selected from —OH, —COOH and (C$_{1-6}$)alkyl optionally substituted with Het and wherein the (C$_{1-4}$)alkyl portion of said —NH(C$_{1-4}$)alkyl is optionally substituted with Het;
d) —C(=O)N(R$^{95}$)R$^{96}$, wherein R$^{95}$ is H and R$^{96}$ is selected from (C$_{3-7}$)cycloalkyl, —SO$_2$—R$^{961}$ and —(C$_{1-4}$)alkyl-R$^{962}$, wherein
R$^{961}$ is (C$_{1-4}$)alkyl, phenyl, (C$_{3-7}$)cycloalkyl, or —N((C$_{1-4}$)alkyl)$_2$; and
R$^{962}$ is phenyl, —COOH, —N((C$_{1-4}$)alkyl)$_2$, or Het, wherein said phenyl is optionally substituted with —N((C$_{1-4}$)alkyl)$_2$ and said Het is optionally substituted with oxo;
or R$^{95}$ and R$^{96}$, together with the N to which they are attached, are linked together to form a 5- or 6-membered heterocycle which may be saturated or unsaturated and which may optionally contain from one to three further heteroatoms each independently selected from N, O and S; said heterocycle being optionally substituted with —COOH; and
e) —O(C$_{1-4}$)alkyl optionally substituted with R$^{97}$ wherein R$^{97}$ is selected from —OH, —COOH, —C(=O)O—(C$_{1-4}$)alkyl-NH(C$_{1-4}$)alkyl, —C(=O)N(R$^{971}$)R$^{972}$—NH$_2$, —NH—(C$_{3-7}$)cycloalkyl, —O-Het, and Het wherein said Het is optionally substituted with one or two substituents each independently selected from halo, oxo, (C$_{1-4}$)alkyl, and —OH;
wherein R$^{971}$ is H or (C$_{1-4}$)alkyl and R$^{972}$ is selected from H, —OH, —NHC(=O)—(C$_{1-4}$)alkyl, —NHC(=O)—NH$_2$, (C$_{1-4}$)alkyl, (C$_{3-7}$)cycloalkyl, phenyl and Het, wherein said (C$_{1-4}$)alkyl is optionally substituted with —OH, —COOH, —N((C$_{1-4}$)alkyl)$_2$ or Het, and wherein said (C$_{3-7}$)cycloalkyl is optionally substituted with —COOH, and wherein said phenyl is optionally substituted with —OH, —COOH, or —(C$_{2-4}$)alkenyl-COOH;

or R$^{971}$ and R$^{972}$, together with the N to which they are attached, are linked together to form a 5- or 6-membered heterocycle which may be saturated or unsaturated and which may optionally contain from one to three further heteroatoms each independently selected from N, O and S; said heterocycle being optionally substituted with (C$_{1-4}$)alkyl or —COOH;

wherein Het is a 5- or 6-membered heterocycle or a 9- or 10-membered heterobicycle, each of which may be saturated, unsaturated or aromatic and each of which may optionally contain from one to four heteroatoms each independently selected from N, O and S. wherein each said N heteroatom may, independently and where possible, exist in an oxidized state such that it is further bonded to an O atom to form an N-oxide group and wherein each said S heteroatom may, independently and where possible, exist in an oxidized state such that it is further bonded to one or two oxygen atoms to form the groups SO or SO$_2$;

or an enantiomer, diastereoisomer or tautomer thereof, or a pharmaceutically acceptable salt or ester thereof.

A preferred embodiment provides a compound of formula (I) wherein:

Ar is selected from:

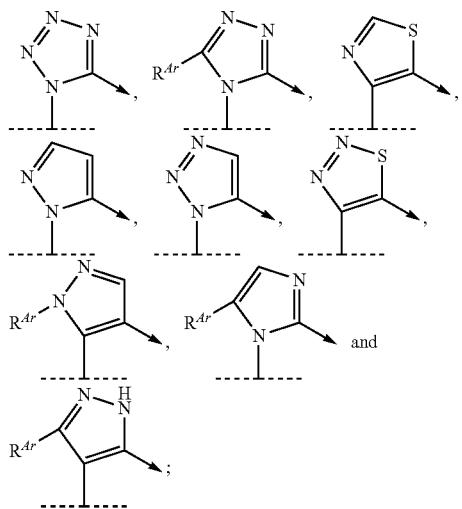

wherein R$^{Ar}$ is selected from H, CH$_3$, CF$_3$ and cyclopropyl and wherein the designation ┈┼┈ represents the bond to R$^1$ and the designation ╲ represents the bond to X;

X is S;

R$^1$ is a group of formula:

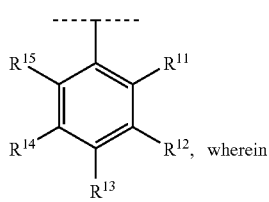

wherein

R$^{11}$ is chloro or bromo;
R$^{12}$ is selected from H, (C$_{1-4}$)alkyl, CF$_3$, (C$_{3-7}$)cycloalkyl and halo;

$R^{13}$ is selected from H, $(C_{1-4})$alkyl, $CF_3$, $(C_{3-7})$cycloalkyl, $(C_{3-7})$cycloalkyl-$(C_{1-4})$alkyl-, —O—$(C_{1-4})$alkyl, —N$((C_{1-4})$alkyl$)_2$ and —OCF$_3$; wherein the $(C_{3-7})$cycloalkyl is optionally substituted with $(C_{1-4})$alkyl;

$R^{14}$ is selected from H, halo, cyano, $(C_{1-4})$alkyl, $CF_3$, $(C_{3-7})$cycloalkyl, $(C_{3-7})$cycloalkyl-$(C_{1-4})$alkyl-, —O—$(C_{1-4})$alkyl, and —N$((C_{1-4})$alkyl$)_2$;

or $R^{12}$ and $R^{13}$ or $R^{13}$ and $R^{14}$ are linked, together with the carbon atoms to which they are attached, to form a five- or six-membered saturated, unsaturated or aromatic ring which optionally contains from one to three heteroatoms each independently selected from O, S and N;

$R^{15}$ is selected from H, halo, $(C_{1-4})$alkyl and $CF_3$;
$R^2$ is selected from halo, nitro and methyl;
$R^3$ is H or fluoro; and
$R^4$ is

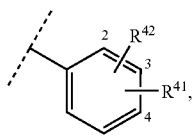

wherein $R^{42}$ is bonded to position 2 or position 3 of the phenyl ring and is selected from H, halo and $(C_{1-4})$alkyl; and $R^{41}$ is bonded to position 3 or position 4 of the phenyl ring and is selected from:
i) $(C_{1-4})$alkyl substituted with —COOH, —COO$(C_{1-4})$alkyl, —C(=O)NH$_2$, —C(=O)NHSO$_2$—$(C_{1-4})$alkyl, or —OH;
ii) $(C_{2-4})$alkenyl substituted with —COOH or —COO$(C_{1-4})$alkyl;
iii) —O—$(C_{1-4})$alkyl optionally substituted with —COOH, Het, or —N$((C_{1-6})$alkyl$)_2$, wherein Het is a 5- or 6-membered saturated, unsaturated or aromatic monocyclic heterocycle containing 1 to 4 heteroatoms each independently selected from O, S and N. wherein each said S heteroatom may, independently and where possible, exist in an oxidized state such that it is further bonded to one or two oxygen atoms to form the groups SO or SO$_2$, said Het being optionally substituted with —OH or —COOH; and wherein either or both of the $(C_{1-6})$alkyl groups in said —N$((C_{1-6})$alkyl$)_2$ are optionally substituted with —COOH or —COO$(C_{1-4})$alkyl; and
iv) —OH, —COOH, —COO$(C_{1-4})$alkyl, —SO$_2$NH$_2$, or —SO$_2$—$(C_{1-4})$alkyl;
provided that $R^{42}$ and $R^{41}$ may not both be bonded to position 3 of the phenyl ring at the same time.

An alternative preferred embodiment provides a compound of formula (I) wherein:
Ar is selected from:

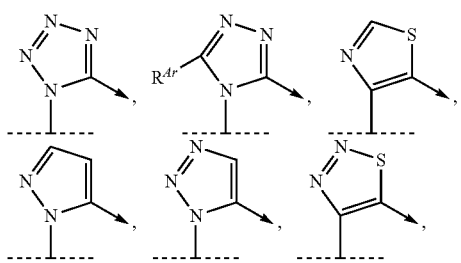

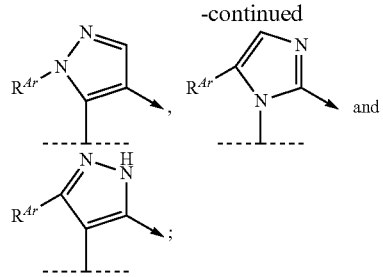

wherein $R^{Ar}$ is selected from H, $CH_3$, $CF_3$ and cyclopropyl
and wherein the designation ┼ represents the bond to $R^1$ and the designation ╲ represents the bond to X;
X is S;
$R^1$ is a group of formula:

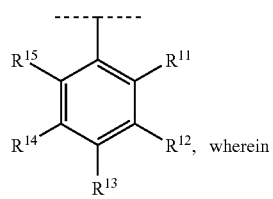

$R^{11}$ is chloro or bromo;
$R^{12}$ is selected from H, $(C_{1-4})$alkyl, $CF_3$, $(C_{3-7})$cycloalkyl and halo;
$R^{13}$ is selected from H, $(C_{1-4})$alkyl, $CF_3$, $(C_{3-7})$cycloalkyl, $(C_{3-7})$cycloalkyl-$(C_{1-4})$alkyl-, —O—$(C_{1-4})$alkyl, —N$((C_{1-4})$alkyl$)_2$ and —OCF$_3$; wherein the $(C_{3-7})$cycloalkyl is optionally substituted with $(C_{1-4})$alkyl;
$R^{14}$ is selected from H, halo, cyano, $(C_{1-4})$alkyl, $CF_3$, $(C_{3-7})$cycloalkyl, $(C_{3-7})$cycloalkyl-$(C_{1-4})$alkyl-, —O—$(C_{1-4})$alkyl, and —N$((C_{1-4})$alkyl$)_2$;
or $R^{12}$ and $R^{13}$ or $R^{13}$ and $R^{14}$ are linked, together with the carbon atoms to which they are attached, to form a five- or six-membered saturated, unsaturated or aromatic ring which optionally contains from one to three heteroatoms each independently selected from O, S and N;
$R^{15}$ is selected from H, halo, $(C_{1-4})$alkyl and $CF_3$;
$R^2$ is selected from halo, nitro and methyl;
$R^3$ is H or fluoro; and
$R^4$ is selected from:
b) $(C_{2-4})$alkenyl substituted with —COOH or —COO$(C_{1-4})$alkyl;
c) Het optionally substituted with $(C_{1-6})$alkyl, —NH$_2$, —COOH, or $(C_{2-4})$alkenyl substituted with —COOH, wherein Het is a 5- or 6-membered aromatic monocyclic heterocycle containing 1 to 4 heteroatoms each independently selected from O, S and N;
d) —SO$_2$N$(R^{43})R^{44}$, wherein $R^{43}$ is H or $(C_{1-6})$alkyl and $R^{44}$ is selected from $(C_{1-6})$alkyl, phenyl, phenyl-$(C_{1-4})$alkyl-, —C(=O)NH$(C_{1-4})$alkyl, —C(=O)O$(C_{1-4})$alkyl, and Het wherein Het is a 5- or 6-membered saturated, unsaturated or aromatic monocyclic heterocycle containing 1 to 4 heteroatoms each independently selected from O, S and N; wherein said $(C_{1-6})$alkyl is optionally substituted with —OH or —COOH and wherein said Het is optionally substituted with $(C_{1-6})$alkyl;
or $R^{43}$ and $R^{44}$, together with the N to which they are attached, are linked together to form a 5- or 6-membered heterocycle which may be saturated or unsaturated and which may optionally contain from one to three further heteroatoms each independently selected from N, O and S; said heterocycle being optionally substituted with (C$_{1-6}$)alkyl or —COOH;
e) —O—(C$_{1-4}$)alkyl substituted with —OH, —COOH or Het wherein Het is a 5- or 6-membered saturated, unsaturated or aromatic monocyclic heterocycle containing 1 to 4 heteroatoms each independently selected from O, S and N. wherein said Het is optionally substituted with —COOH or —COO(C$_{1-6}$)alkyl; provided that the carbon atom of —O—(C$_{1-4}$)alkyl which is directly bonded to O is not also directly bonded to —OH; and
h) —NHSO$_2$R$^8$ wherein R$^8$ is selected from phenyl, phenyl-(C$_{1-4}$)alkyl- and Het wherein Het is a 5- or 6-membered saturated, unsaturated or aromatic monocyclic heterocycle containing 1 to 4 heteroatoms each independently selected from O, S and N.

Another alternative preferred embodiment provides a compound of formula (I) wherein:
Ar is selected from:

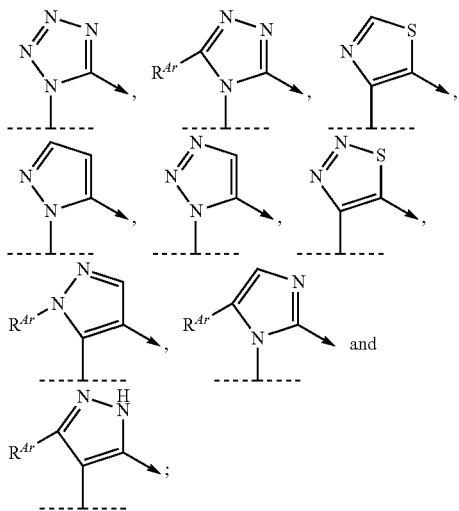

wherein R$^{Ar}$ is selected from H, CH$_3$, CF$_3$ and cyclopropyl and wherein the designation ┆ represents the bond to R$^1$ and the designation ⌒ represents the bond to X;
X is S;
R$^1$ is a group of formula:

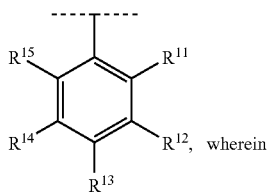, wherein

R$^{11}$ is chloro or bromo;
R$^{12}$ is selected from H(C$_{1-4}$)alkyl CF$_3$ (C$_{3-7}$)cycloalkyl and halo;
R$^{13}$ is selected from H(C$_{1-4}$)alkyl CF$_3$ (C$_{3-7}$)cycloalkyl (C$_{3-7}$)cycloalkyl-(C$_{1-4}$)alkyl-, —O—(C$_{1-4}$)alkyl, —N((C$_{1-4}$)alkyl)$_2$ and —OCF$_3$; wherein the (C$_{3-7}$)cycloalkyl is optionally substituted with (C$_{1-4}$)alkyl;

R$^{14}$ is selected from H, halo, cyano, (C$_{1-4}$)alkyl, CF$_3$ (C$_{3-7}$)cycloalkyl (C$_{3-7}$)cycloalkyl-(C$_{1-4}$)alkyl-, —O—(C$_{1-4}$)alkyl, and —N((C$_{1-4}$)alkyl)$_2$;
or R$^{12}$ and R$^{13}$ or R$^{13}$ and R$^{14}$ are linked, together with the carbon atoms to which they are attached, to form a five- or six-membered saturated, unsaturated or aromatic ring which optionally contains from one to three heteroatoms each independently selected from O, S and N;
R$^{15}$ is selected from H, halo, (C$_{1-4}$)alkyl and CF$_3$;
R$^2$ is selected from halo, nitro and methyl;
R$^3$ is H or fluoro; and
R$^4$ is —C(=O)N(R$^5$)R$^6$ or —O—CH$_2$—C(=O)N(R$^5$)R$^6$ wherein R$^5$ is H or (C$_{1-6}$)alkyl and R$^6$ is selected from:
 i) phenyl optionally substituted with one or two substituents each independently selected from —OH, —COOH, —N((C$_{1-4}$)alkyl)$_2$ (C$_{1-4}$)alkyl, (C$_{2-4}$)alkenyl and Het wherein Het is a 5- or 6-membered saturated, unsaturated or aromatic monocyclic heterocycle containing 1 to 4 heteroatoms each independently selected from O, S and N; wherein said (C$_{1-4}$)alkyl is optionally substituted with —COOH and said (C$_{2-4}$)alkenyl is substituted with —COOH;
 ii) (C$_{1-4}$)alkyl optionally substituted with one or two substituents each independently selected from —COOH, —OH, —S—(C$_{1-6}$)alkyl and Het wherein Het is a 5- or 6-membered saturated, unsaturated or aromatic monocyclic heterocycle containing 1 to 4 heteroatoms each independently selected from O, S and N wherein each said N heteroatom may, independently and where possible, exist in an oxidized state such that it is further bonded to an O atom to form an N-oxide group;
  provided that the carbon atom of (C$_{1-4}$)alkyl which is directly bonded to N is not also directly bonded to —OH;
 iii) phenyl-(C$_{1-4}$)alkyl- wherein the phenyl portion of said phenyl-(C$_{1-4}$)alkyl- is optionally substituted with one or two substituents each independently selected from —OH, —NH$_2$ and —COOH;
 iv) (C$_{3-7}$)cycloalkyl-(C$_{1-4}$)alkyl- wherein the cycloalkyl portion of said (C$_{3-7}$)cycloalkyl-(C$_{1-4}$)alkyl- is optionally substituted with —COOH;
 v) Het optionally substituted with one or two substituents each independently selected from (C$_{1-6}$)alkyl, phenyl-(C$_{1-4}$)alkyl- and —COOH wherein Het is a 5- or 6-membered heterocycle or a 9- or 10-membered heterobicycle, each of which may be saturated, unsaturated or aromatic and each of which may optionally contain from one to four heteroatoms each independently selected from N, O and S;
 vi) (C$_{3-7}$)cycloalkyl; and
 vii) —SO$_2$—R$^{61}$ wherein R$^{61}$ is (C$_{1-4}$)alkyl or phenyl;
 or R$^5$ and R$^6$, together with the N to which they are attached, are linked together to form a 5- or 6-membered heterocycle which may be saturated or unsaturated and which may optionally contain from one to three further heteroatoms each independently selected from N, O and S; said heterocycle being optionally substituted with one or two substituents each independently selected from (C$_{1-6}$)alkyl, —COOH and —COO(C$_{1-6}$)alkyl.

Yet another alternative preferred embodiment provides a compound of formula (I) wherein:

Ar is selected from:

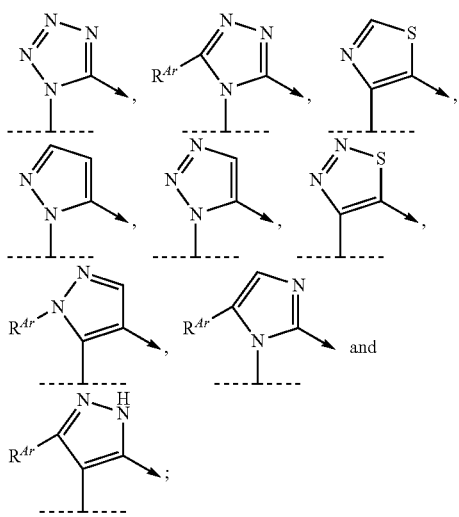

wherein $R^{Ar}$ is selected from H, $CH_3$, $CF_3$ and cyclopropyl and wherein the designation ┼ represents the bond to $R^1$ and the designation ↘ represents the bond to X;
X is S;
$R^1$ is a group of formula:

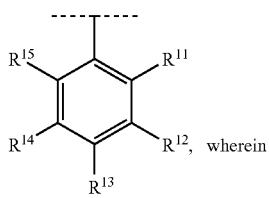

wherein $R^{11}$ is chloro or bromo;
$R^{12}$ is selected from H, $(C_{1-4})$alkyl, $CF_3$, $(C_{3-7})$cycloalkyl and halo;
$R^{13}$ is selected from H, $(C_{1-4})$alkyl, $CF_3$, $(C_{3-7})$cycloalkyl, $(C_{3-7})$cycloalkyl-$(C_{1-4})$alkyl-, —O—$(C_{1-4})$alkyl, —N$((C_{1-4})$alkyl$)_2$ and —$OCF_3$; wherein the $(C_{3-7})$cycloalkyl is optionally substituted with $(C_{1-4})$alkyl;
$R^{14}$ is selected from H, halo, cyano, $(C_{1-4})$alkyl, $CF_3$, $(C_{3-7})$cycloalkyl, $(C_{3-7})$cycloalkyl-$(C_{1-4})$alkyl-, —O—$(C_{1-4})$alkyl, and —N$((C_{1-4})$alkyl$)_2$;
or $R^{12}$ and $R^{13}$ or $R^{13}$ and $R^{14}$ are linked, together with the carbon atoms to which they are attached, to form a five- or six-membered saturated, unsaturated or aromatic ring which optionally contains from one to three heteroatoms each independently selected from O, S and N;
$R^{15}$ is selected from H, halo, $(C_{1-4})$alkyl and $CF_3$;
$R^2$ is selected from halo, nitro and methyl;
$R^3$ is H or fluoro; and
$R^4$ is —NHC(=O)—$R^7$ wherein $R^7$ is selected from:
i) $(C_{1-6})$alkyl optionally substituted with one or two substituents each independently selected from —COOH, —O—$(C_{1-4})$alkyl, —NHC(=O)—$(C_{1-4})$alkyl, phenyl and Het wherein Het is a 5- or 6-membered heterocycle or a 9- or 10-membered heterobicycle, each of which may be saturated, unsaturated or aromatic and each of which may optionally contain from one to four heteroatoms each independently selected from N, O and S wherein each said N heteroatom may, independently and where possible, exist in an oxidized state such that it is further bonded to an O atom to form an N-oxide group; and wherein said phenyl is optionally substituted with one or two substituents each independently selected from halo, —OH, —O—$(C_{1-4})$alkyl, —$NO_2$, —COOH, —$NH_2$, —NH$(C_{1-4})$alkyl, —N$((C_{1-4})$alkyl$)_2$, and $(C_{1-6})$alkyl optionally substituted with from one to three halo substituents;
ii) phenyl optionally substituted with —OH, halo or —COOH;
iii) —NH$R^{71}$ wherein $R^{71}$ is phenyl or phenyl-$(C_{1-4})$alkyl-, wherein said phenyl is optionally substituted with —COOH or —COO$(C_{1-4})$alkyl; and
iv) $(C_{1-6})$alkynyl, $(C_{3-7})$cycloalkyl or $(C_{3-7})$cycloalkyl-$(C_{1-4})$alkyl-.

Still another alternative preferred embodiment provides a compound of formula (I) wherein:
Ar is selected from:

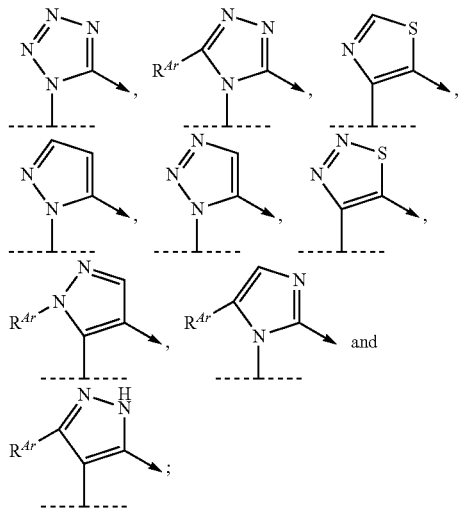

wherein $R^{Ar}$ is selected from H, $CH_3$, $CF_3$ and cyclopropyl and wherein the designation ┼ represents the bond to $R^1$ and the designation ↘ represents the bond to X;
X is S;
$R^1$ is a group of formula:

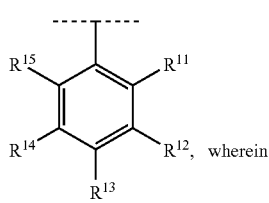

$R^{11}$ is chloro or bromo;
$R^{12}$ is selected from H, $(C_{1-4})$alkyl, $CF_3$, $(C_{3-7})$cycloalkyl and halo;
$R^{13}$ is selected from H, $(C_{1-4})$alkyl, $CF_3$, $(C_{3-7})$cycloalkyl, $(C_{3-7})$cycloalkyl-$(C_{1-4})$alkyl-, —O—$(C_{1-4})$alkyl, —N$((C_{1-4})$alkyl$)_2$ and —$OCF_3$; wherein the $(C_{3-7})$cycloalkyl is optionally substituted with $(C_{1-4})$alkyl;

$R^{14}$ is selected from H, halo, cyano, $(C_{1-4})$alkyl, $CF_3$, $(C_{3-7})$cycloalkyl, $(C_{3-7})$cycloalkyl-$(C_{1-4})$alkyl-, $-O-(C_{1-4})$alkyl, and $-N((C_{1-4})$alkyl$)_2$;

or $R^{12}$ and $R^{13}$ or $R^{13}$ and $R^{14}$ are linked, together with the carbon atoms to which they are attached, to form a five- or six-membered saturated, unsaturated or aromatic ring which optionally contains from one to three heteroatoms each independently selected from O, S and N;

$R^{15}$ is selected from H, halo, $(C_{1-4})$alkyl and $CF_3$;

$R^2$ is selected from halo, nitro and methyl;

$R^3$ is H or fluoro; and $R^4$ is $-C\equiv C-R^9$ wherein $R^9$ is selected from:

i) H, $-COOH$, $-COO(C_{1-6})$alkyl, phenyl or $(C_{2-4})$alkenyl;

ii) $(C_{3-7})$cycloalkyl optionally substituted with $-OH$, $-COOH$, $-COO(C_{1-6})$alkyl, or $(C_{1-4})$alkyl wherein said $(C_{1-4})$alkyl is optionally substituted with $-OH$ or $-N(R^{91})R^{92}$, wherein $R^{91}$ is H and $R^{92}$ is $(C_{1-4})$alkyl substituted with Het; or $R^{91}$ and $R^{92}$, together with the N to which they are attached, are linked together to form a 5- or 6-membered heterocycle which may be saturated, unsaturated or aromatic and which may optionally contain from one to three further heteroatoms each independently selected from N, O and S; said heterocycle being optionally substituted with one or two substituents each independently selected from $(C_{1-6})$alkyl and $-OH$; and iii) $(C_{1-6})$alkyl optionally substituted with one, two or three substituents each independently selected from:

a) $-OH$, $-O(C=O)NH_2$, $-O(C=O)NH(C_{1-4})$alkyl, $CF_3$, $-COOH$ or $-COO-(C_{1-4})$alkyl;

b) Het optionally substituted with $(C_{1-6})$alkyl or $-OH$;

c) $-N(R^{93})R^{94}$ wherein $R^{93}$ is H or $(C_{1-4})$alkyl and $R^{94}$ is selected from H, $-(C_{1-4})$alkyl optionally substituted with $R^{941}$—$SO_2$—$(C_{1-4})$alkyl and $-C(=O)-R^{942}$;

wherein $R^{941}$ is $-COOH$, $-C(=O)NH_2$, $(C_{3-7})$cycloalkyl, Het, or phenyl optionally substituted with $-OH$, and $R^{942}$ is $-O-(C_{1-4})$alkyl, $-NH-(C_{1-4})$alkyl, phenyl, $(C_{3-7})$cycloalkyl or Het, wherein said $(C_{3-7})$cycloalkyl is optionally substituted with $-COOH$ and wherein said Het is optionally substituted with one or two substituents each independently selected from $(C_{1-6})$alkyl and $-OH$; or $R^{942}$ is $(C_{1-4})$alkyl optionally substituted with $-COOH$, $-NH_2$, $-NH(C_{1-4})$alkyl, $-NH$-Het, $-N((C_{1-4})$alkyl$)_2$, or Het; wherein said Het is optionally substituted with one or two substituents each independently selected from $-OH$, $-COOH$ and $(C_{1-6})$alkyl optionally substituted with Het and wherein the $(C_{1-4})$alkyl portion of said $-NH(C_{1-4})$alkyl is optionally substituted with Het;

d) $-C(=O)N(R^{95})R^{96}$, wherein $R^{95}$ is H and $R^{96}$ is selected from $(C_{3-7})$cycloalkyl, $-SO_2-R^{961}$ and $-(C_{1-4})$alkyl-$R^{962}$, wherein $R^{961}$ is $(C_{1-4})$alkyl, phenyl, $(C_{3-7})$cycloalkyl, or $-N((C_{1-4})$alkyl$)_2$; and $R^{962}$ is phenyl, $-COOH$, $-N((C_{1-4})$alkyl$)_2$, or Het, wherein said phenyl is optionally substituted with $-N((C_{1-4})$alkyl$)_2$ and said Het is optionally substituted with oxo;

or $R^{95}$ and $R^{96}$, together with the N to which they are attached, are linked together to form a 5- or 6-membered heterocycle which may be saturated or unsaturated and which may optionally contain from one to three further heteroatoms each independently selected from N, O and S; said heterocycle being optionally substituted with $-COOH$; and e) $-O(C_{1-4})$alkyl optionally substituted with $R^{97}$ wherein $R^{97}$ is selected from $-OH$, $-COOH$, $-C(=O)O-(C_{1-4})$alkyl-$NH(C_{1-4})$alkyl, $-C(=O)N(R^{971})R^{972}$—$NH_2$, $-NH-(C_{3-7})$cycloalkyl, $-O$-Het, and Het;

provided that the carbon atom of $-O-(C_{1-4})$alkyl which is directly bonded to O is not also directly bonded to $-OH$, $-NH_2$ or $-NH-(C_{3-7})$cycloalkyl;

wherein each of said Het and the Het portion of said $-O$-Het is optionally substituted with one or two substituents each independently selected from halo, oxo, $(C_{1-4})$alkyl, and $-OH$; and wherein $R^{971}$ is H or $(C_{1-4})$alkyl and $R^{972}$ is selected from H, $-OH$, $-NHC(=O)-(C_{1-4})$alkyl, $-NHC(=O)-NH_2$, $(C_{1-4})$alkyl, $(C_{3-7})$cycloalkyl, phenyl and Het, wherein said $(C_{1-4})$alkyl is optionally substituted with $-OH$, $-COOH$, $-N((C_{1-4})$alkyl$)_2$ or Het, provided that when $R^{972}$ is $(C_{1-4})$alkyl, the carbon atom of $(C_{1-4})$alkyl which is directly bonded to N is not also directly bonded to $-OH$;

and wherein said $(C_{3-7})$cycloalkyl is optionally substituted with $-COOH$, and wherein said phenyl is optionally substituted with $-OH$, $-COOH$, or $-(C_{2-4})$alkenyl-$COOH$;

or $R^{971}$ and $R^{972}$, together with the N to which they are attached, are linked together to form a 5- or 6-membered heterocycle which may be saturated or unsaturated and which may optionally contain from one to three further heteroatoms each independently selected from N, O and S; said heterocycle being optionally substituted with $(C_{1-4})$alkyl or $-COOH$;

wherein Het is in each instance independently a 4,5- or 6-membered saturated, unsaturated or aromatic monocyclic heterocycle containing from one to four heteroatoms each independently selected from N, O and S. wherein each said N heteroatom may, independently and where possible, exist in an oxidized state such that it is further bonded to an O atom to form an N-oxide group and wherein each said S heteroatom may, independently and where possible, exist in an oxidized state such that it is further bonded to one or two oxygen atoms to form the groups SO or $SO_2$.

A more preferred embodiment provides a compound of formula (Ia)

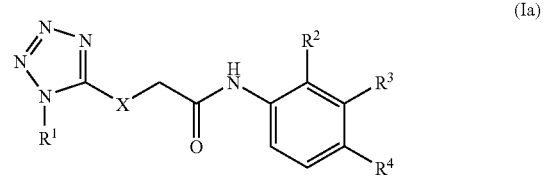

wherein
X is S;
R¹ is selected from:

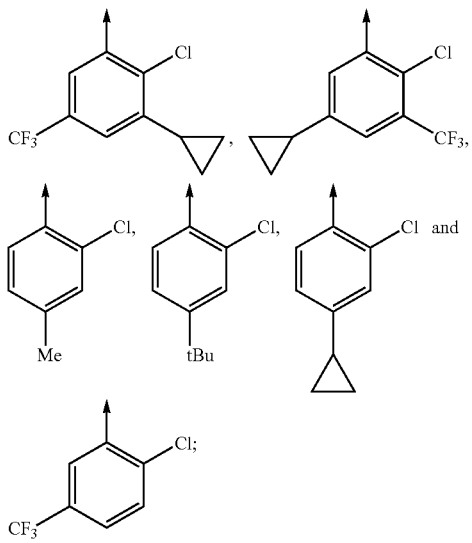

R² is chloro;
R³ is H or fluoro; and
R⁴ is

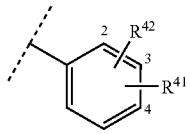

wherein R⁴² is bonded to position 2 or position 3 of the phenyl ring and is selected from H, Cl, F and CH₃; and R⁴¹ is bonded to position 4 of the phenyl ring and is selected from:
i) methyl, ethyl, propyl, 1-methylethyl, butyl, 1-methylpropyl, 2-methylpropyl and 1,1-dimethylethyl, each of which being substituted with —COOH, —COOCH₃, —COOCH₂CH₃—C(=O)NH₂, —C(=O)NHSO₂—CH₃, or —OH;
ii) —CH=CH—COOH, —CH=CH—COOCH₃ or —CH=CH—COOCH₂CH₃;
iii) —O—CH₃ or —O—CH₂CH₃, each of which being optionally substituted with —COOH, Het, or —N((C₁₋₄)alkyl)₂, wherein Het is selected from

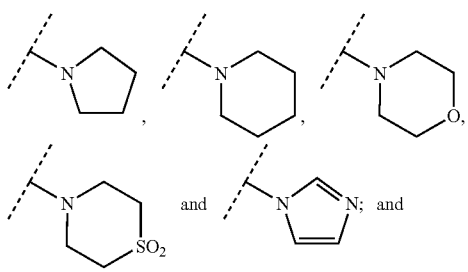

wherein said Het is optionally substituted with —OH or —COOH and wherein either or both of the (C₁₋₄)alkyl groups in said —N((C₁₋₄)alkyl)₂ are optionally substituted with —COOH, —COOCH₃ or —COOCH₂CH₃; and
iv) —OH, —COOH, —COOCH₃, —COOCH₂CH₃, —SO₂NH₂, or —SO₂—CH₃.

An alternative more preferred embodiment provides a compound of formula (Ia)

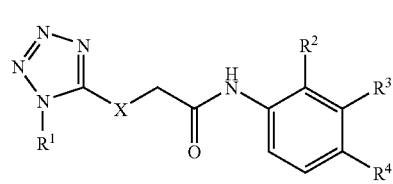

(Ia)

wherein
X is S;
R¹ is selected from:

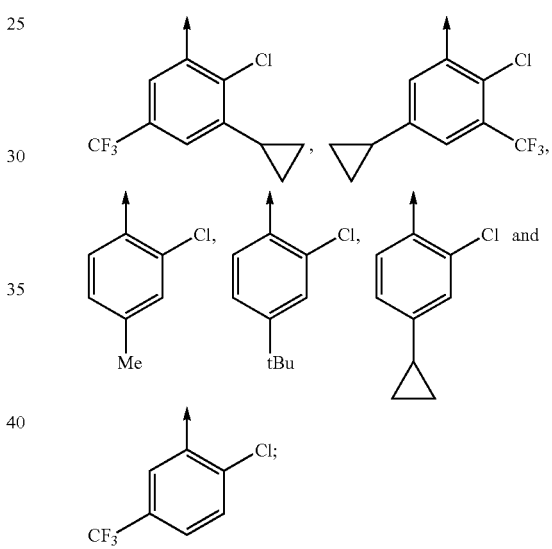

R² is chloro;
R³ is H or fluoro; and
R⁴ is —C(=O)N(R⁵)R⁶ wherein R⁵ is H or CH₃ and R⁶ is selected from
i) phenyl optionally substituted with one or two substituents each independently selected from —OH, —COOH, —N(CH₃)₂, CH₃, —CH₂COOH, —CH₂CH₂COOH,

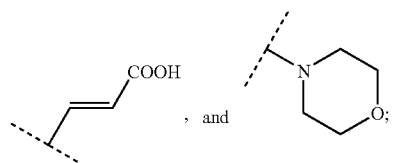

ii) (C₁₋₄)alkyl optionally substituted with one or two substituents each independently selected from —COOH, —OH, —S—CH₃ and Het, wherein Het is selected from

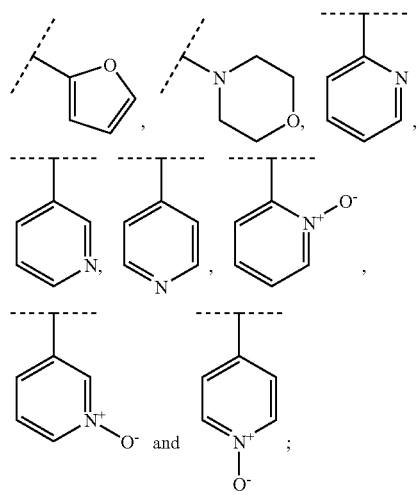

provided that the carbon atom of (C$_{1-4}$)alkyl which is directly bonded to N is not also directly bonded to —OH;

iii) phenyl-CH$_2$— or phenyl-CH$_2$CH$_2$—, wherein the phenyl portion of said phenyl-CH$_2$— or phenyl-CH$_2$CH$_2$— is optionally substituted with one or two substituents each independently selected from —OH, —NH$_2$, and —COOH;

iv) (4-carboxycyclohexyl)methyl;

v) Het optionally substituted with one or two substituents each independently selected from methyl, phenylmethyl- and —COOH, wherein said Het is selected from

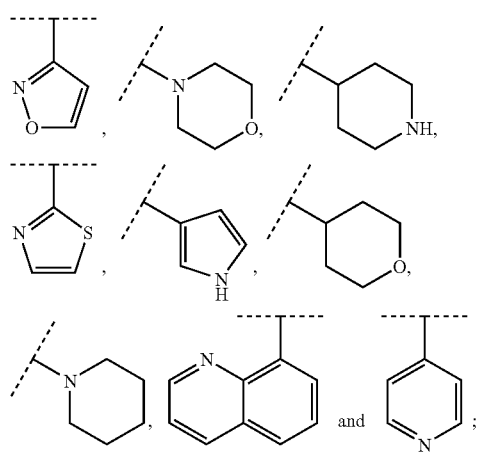

vi) cyclopropyl;

vii) —SO$_2$—CH$_3$ and —SO$_2$-Ph;

or R$^5$ and R$^6$, together with the N to which they are attached, are linked together to form a 6-membered saturated heterocycle which may optionally contain one further heteroatom independently selected from N and O; said heterocycle being optionally substituted with one or two substituents each independently selected from CH$_3$ and —COOH.

Another alternative more preferred embodiment provides a compound of formula (Ia)

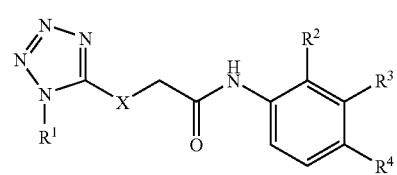

(Ia)

wherein

X is S;

R$^1$ is selected from:

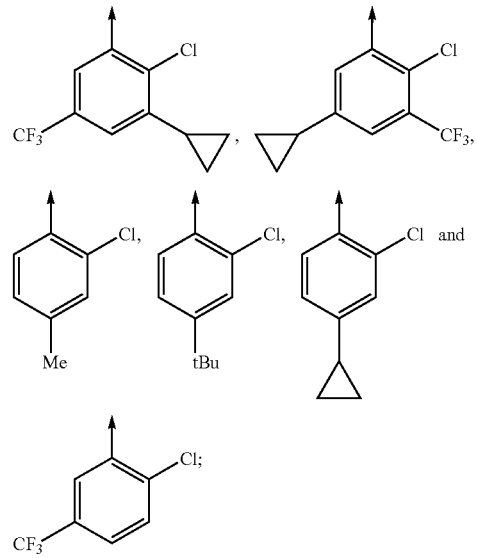

R$^2$ is chloro;

R$^3$ is H or fluoro; and

R$^4$ is —NHC(=O)—R$^7$ wherein R$^7$ is selected from:

i) methyl, ethyl, propyl, 1-methylethyl, butyl, 1-methylpropyl, 2-methylpropyl, 1,1-dimethylethyl, 1-methylbutyl, 2-methylbutyl or 3-methylbutyl, each of which being optionally substituted with one or two substituents each independently selected from —COOH, —O—CH$_3$, —NHC(=O)—CH$_3$, phenyl and Het; wherein Het is selected from

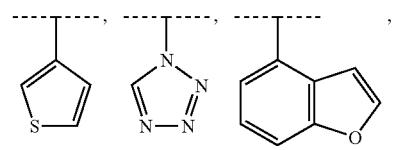

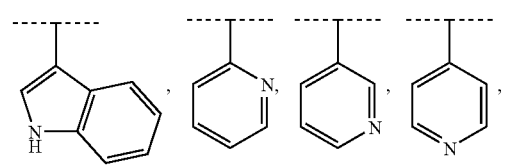

-continued

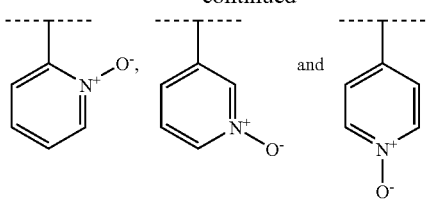

and wherein said phenyl is optionally substituted with one or two substituents each independently selected from halo, —OH, —O—CH$_3$, —NO$_2$, —COOH, —NH$_2$, —NHCH$_3$, —N(CH$_3$)$_2$, and CF$_3$;

ii) phenyl optionally substituted with —OH, Cl or —COOH;

iii) —NH-phenyl or phenyl-CH$_2$—NH—, wherein the phenyl portion of said —NH-phenyl and phenyl-CH$_2$—NH— is optionally substituted with —COOH, —COOCH$_3$ or —COOCH$_2$CH$_3$; and iv) ethynyl, 1-propynyl, 2-propynyl, 1-butynyl, 2-butynyl, 3-butynyl, cyclopropyl, cyclobutyl, cyclopentyl, cyclohexyl cyclopropylmethyl, cyclobutylmethyl, cyclopentylmethyl or cyclohexylmethyl.

Still another alternative more preferred embodiment provides a compound of formula (Ia)

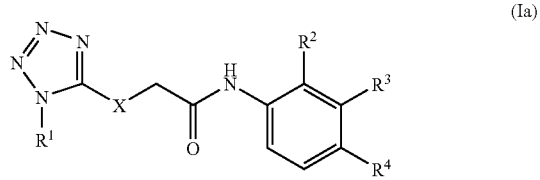

(Ia)

wherein
X is S;
R$^1$ is selected from:

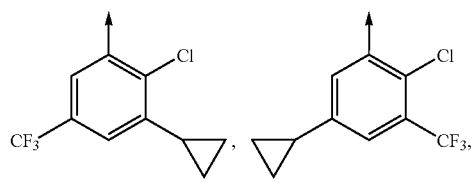

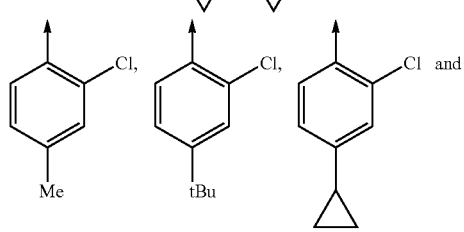

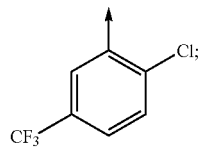

R$^2$ is chloro;
R$^3$ is H or fluoro; and
R$^4$ is —C≡C—R$^9$ wherein R$^9$ is selected from:
  i) H, —COOH, phenyl, ethenyl or 2-propenyl;
  ii) cyclopropyl, cyclobutyl, cyclopentyl or cyclohexyl, each of which being optionally substituted with —OH, —COOH or CH$_3$, wherein said CH$_3$ is optionally substituted with —OH or —N(R$^{91}$)R$^{92}$, wherein R$^{91}$ is H and
  R$^{92}$ is

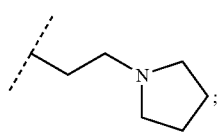

or R$^{91}$ and R$^{92}$, together with the N to which they are attached, are linked together to form a 5- or 6-membered heterocycle which may be saturated, unsaturated or aromatic and which may optionally contain one or two further heteroatoms each independently selected from N and O; said heterocycle being optionally substituted with one or two substituents each independently selected from CH$_3$ and —OH;

iii) methyl, ethyl, propyl, 1-methylethyl, butyl, 1-methylpropyl, 2-methylpropyl, 1,1-dimethylethyl, pentyl or 1-ethylpropyl, each of which being optionally substituted with one, two or three substituents each independently selected from:
    a) —OH, —O(C═O)NH$_2$, —O(C═O)NHCH$_3$, CF$_3$, —COOH, —COOCH$_3$ or —COOCH$_2$CH$_3$;
    b) Het optionally substituted with CH$_3$ or —OH; wherein Het is selected from

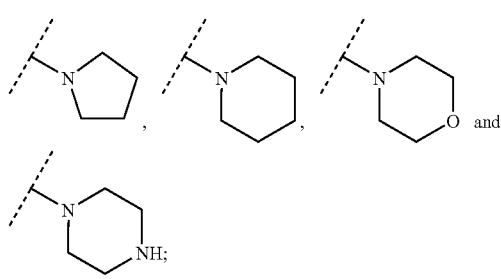

c) —N(R$^{93}$)R$^{94}$ wherein R$^{93}$ is H, CH$_3$ or CH$_2$CH$_3$ and R$^{94}$ is selected from H, —(C$_{1-4}$)alkyl optionally substituted with R$^{941}$, —SO$_2$—CH$_3$ and —C(═O)—R$^{942}$;
      wherein R$^{941}$ is —COOH, —C(═O)NH$_2$, cyclopropyl, Het, or phenyl optionally substituted with —OH; wherein Het is selected from

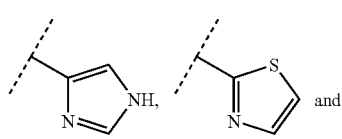

and

-continued

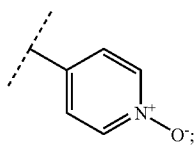

and $R^{942}$ is —O—$(C_{1-4})$alkyl, —NH—$(C_{1-4})$alkyl, phenyl, cyclopropyl or Het; wherein Het is selected from

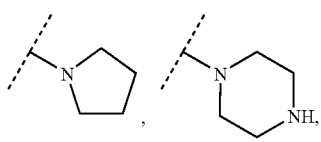

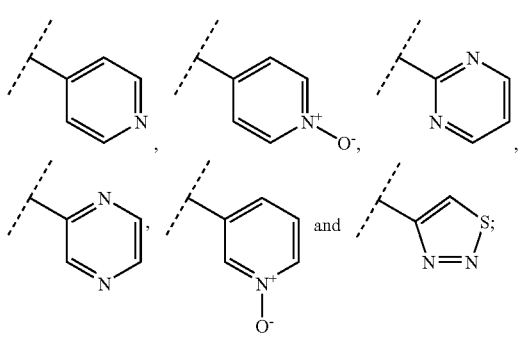

and wherein said cyclopropyl is optionally substituted with —COOH and wherein said Het is optionally substituted with $CH_3$ or —OH; or $R^{942}$ is $(C_{1-4})$alkyl optionally substituted with —COOH, —$NH_2$, —NH$(C_{1-4})$alkyl

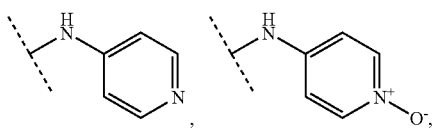

—N$((C_{1-4})$alkyl$)_2$, or Het; wherein Het is selected from

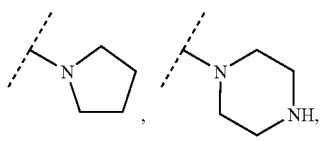

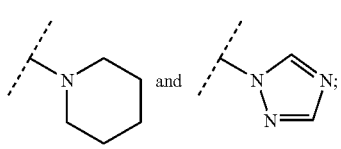

and wherein said Het is optionally substituted with one or two substituents each independently selected from —OH, —COOH and $(C_{1-4})$alkyl optionally substituted with

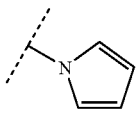

and wherein the $(C_{1-4})$alkyl portion of said —NH$(C_{1-4})$alkyl is optionally substituted with

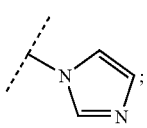

d) —C(=O)N($R^{95}$)$R^{96}$, wherein $R^{95}$ is H and $R^{96}$ is selected from cyclopropyl, —$SO_2$—$R^{961}$ and —$(C_{1-4})$alkyl-$R^{962}$, wherein
$R^{961}$ is $CH_3$, $CH_2CH_3$, phenyl, cyclopropyl, or —N$(CH_3)_2$; and
$R^{962}$ is phenyl, —COOH, —N$(CH_3)_2$, or Het; wherein Het is selected from

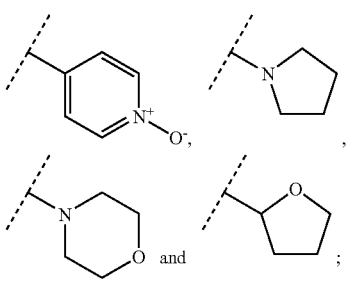

and wherein said phenyl is optionally substituted with —N$(CH_3)_2$ and said Het is optionally substituted with oxo; or $R^{95}$ and $R^{96}$, together with the N to which they are attached, are linked together to form a 6-membered heterocycle which may be saturated or unsaturated and which may optionally contain one or two further heteroatoms each independently selected from N and O; said heterocycle being optionally substituted with —COOH; and e) —O$(C_{1-4})$alkyl optionally substituted with $R^{97}$ wherein $R^{97}$ is selected from —OH, —COOH, —C(=O)O—$CH_2CH_2$—$NHCH_3$, —C(=O)N($R^{971}$)$R^{972}$—$NH_2$, —NH—$(C_{3-7})$cycloalkyl,

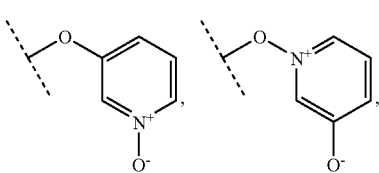

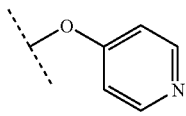

and Het;
provided that the carbon atom of —O—(C$_{1-4}$)alkyl which is directly bonded to O is not also directly bonded to —OH, —NH$_2$ or —NH—(C$_{3-7}$)cycloalkyl;
wherein Het is selected from

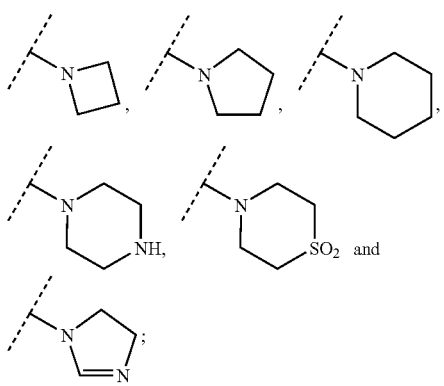

and wherein said Het is optionally substituted with one or two substituents each independently selected from halo, oxo, CH$_3$ and —OH; and
wherein R$^{971}$ is H or CH$_3$ and R$^{972}$ is selected from H, —OH, —NHC(=O)—CH$_3$, —NHC(=O)—NH$_2$, (C$_{1-4}$)alkyl, cyclopropyl, phenyl and Het; wherein Het is selected from

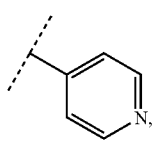

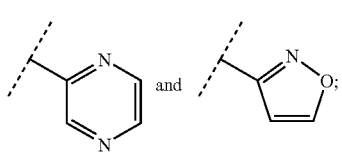

and wherein said (C$_{1-4}$)alkyl is optionally substituted with —OH, —COOH, —N(CH$_3$)$_2$ or

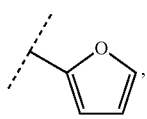

provided that when R$^{972}$ is (C$_{1-4}$)alkyl, the carbon atom of (C$_{1-4}$)alkyl which is directly bonded to N is not also directly bonded to —OH;

and wherein said cyclopropyl is optionally substituted with —COOH, and wherein said phenyl is optionally substituted with —OH, —COOH, or —CH=CH—COOH;
or R$^{971}$ and R$^{972}$, together with the N to which they are attached, are linked together to form a 5- or 6-membered heterocycle which may be saturated or unsaturated and which may optionally contain one or two further heteroatoms each independently selected from N and O; said heterocycle being optionally substituted with CH$_3$ or —COOH.

Specific Embodiments

Included within the scope of this invention is each single compound of formula (I) as presented in Tables 1 to 7.

The compounds of formula (I) are effective inhibitors of wild type HIV as well as of the double mutation enzyme K103N/Y181C. The compounds of the invention may also inhibit the single mutation enzymes V106A, Y188L, K103N, Y181C, P236L and G190A (among others). The compounds may also inhibit other double mutation enzymes including K103N/P225H, K103N/V108I and K103N/L100I.

The compounds of formula (I) possess inhibitory activity against HIV-1 replication. When administered in suitable dosage forms, they are useful in the treatment of AIDS, ARC and related disorders associated with HIV-1 infection. Another aspect of the invention, therefore, is a method for treating HIV-1 infection which comprises administering to a human being, infected by HIV-1, a therapeutically effective amount of a compound of formula (I), as described above. Whether it is termed treatment or prophylaxis, the compounds may also be used to prevent perinatal transmission of HIV-1 from mother to baby, by administration to the mother before giving birth and to the child within the first days of life.

The compounds of formula (I) may be administered in single or divided doses by the oral, parenteral or topical routes. A suitable oral dosage for a compound of formula (I) would be in the range of about 0.5 mg to 3g per day. A preferred oral dosage for a compound of formula (I) would be in the range of about 100 mg to 800 mg per day for a patient weighing 70 kg. In parenteral formulations, a suitable dosage unit may contain from 0.1 to 250 mg of said compounds, preferably 1 mg to 200 mg, whereas for topical administration, formulations containing 0.01 to 1% active ingredient are preferred. It should be understood, however, that the dosage administration from patient to patient would vary. The dosage for any particular patient will depend upon the clinician's judgment, who will use as criteria for fixing a proper dosage the size and condition of the patient as well as the patient's response to the drug.

When the compounds of the present invention are to be administered by the oral route, they may be administered as medicaments in the form of pharmaceutical preparations that contain them in association with a compatible pharmaceutical carrier material. Such carrier material can be an inert organic or inorganic carrier material suitable for oral administration. Examples of such carrier materials are water, gelatin, talc, starch, magnesium stearate, gum arabic, vegetable oils, polyalkylene-glycols, petroleum jelly and the like.

The compounds of formula (I) can be used in combination with one or more other antiretroviral drug known to one skilled in the art, as a combined preparation useful for simultaneous, separate or sequential administration for treating or preventing HIV infection in an individual. Examples of antiretroviral drugs, including approved and investigational drugs, that may be used in combination therapy with compounds of formula (I) include but are not limited to:

NRTIs (nucleoside or nucleotide reverse transcriptase inhibitors; including but not limited to zidovudine, didanosine, zalcitabine, stavudine, lamivudine, emtricitabine, abacavir, and tenofovir);

NNRTIs (non-nucleoside reverse transcriptase inhibitors; including but not limited to nevirapine, delavirdine, efavirenz, capravirine, etravirine, rilpivirine, GW695634 and BILR 355);

protease inhibitors (including but not limited to ritonavir, tipranavir, saquinavir, nelfinavir, indinavir, amprenavir, fosamprenavir, atazanavir, lopinavir, VX-385 and TMC-114);

entry inhibitors including but not limited to CCR5 antagonists (including but not limited to maraviroc (UK-427, 857), SCH-417690, GW873140 and TAK-652), CXCR4 antagonists (including but not limited to AMD-11070), fusion inhibitors (including but not limited to enfuvirtide (T-20)) and others (including but not limited to PRO-542 and BMS-488043);

integrase inhibitors (including but not limited to c-1605, BMS-538158 and JTK-303);

TAT inhibitors;

maturation inhibitors (including but not limited to PA-457);

immunomodulating agents (including but not limited to levamisole); and antifungal or antibacterial agents (including but not limited to fluconazole).

Moreover, a compound of formula (I) can be used with at least one other compound of formula (I).

The pharmaceutical preparations can be prepared in a conventional manner and finished dosage forms can be solid dosage forms, for example, tablets, dragees, capsules, and the like, or liquid dosage forms, for example solutions, suspensions, emulsions and the like. The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound of formula (I) can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include but are not limited to, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Microbial preservatives added may include benzalkonium chloride, thimerosal, chloro-butanol or phenylethyl alcohol.

Additionally, the compounds provided by the invention may be administerable by suppository.

Methodology and Synthesis

In general, the compounds of formula (I) are prepared by known methods from readily available starting materials, using reaction conditions known to be suitable for the reactants. Schemes 1-7 illustrate the general methods used to prepare the compounds of formula (I).

General methods for preparing a compound of formula (I), wherein Y is halo (e.g. Cl, Br or I), P is a protecting group, $R^1$, $R^2$, $R^3$, $R^4$, $R^5$, $R^6$, $R^7$, Ar, and X are as defined herein and $R^{4a}$ is a precursor of $R^4$ (or identical to $R^4$), are described in Scheme 1.

Scheme 1: General method for the synthesis of compound of formula (I)

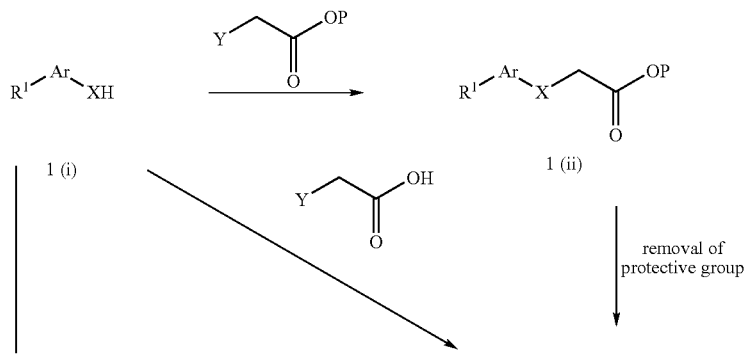

-continued
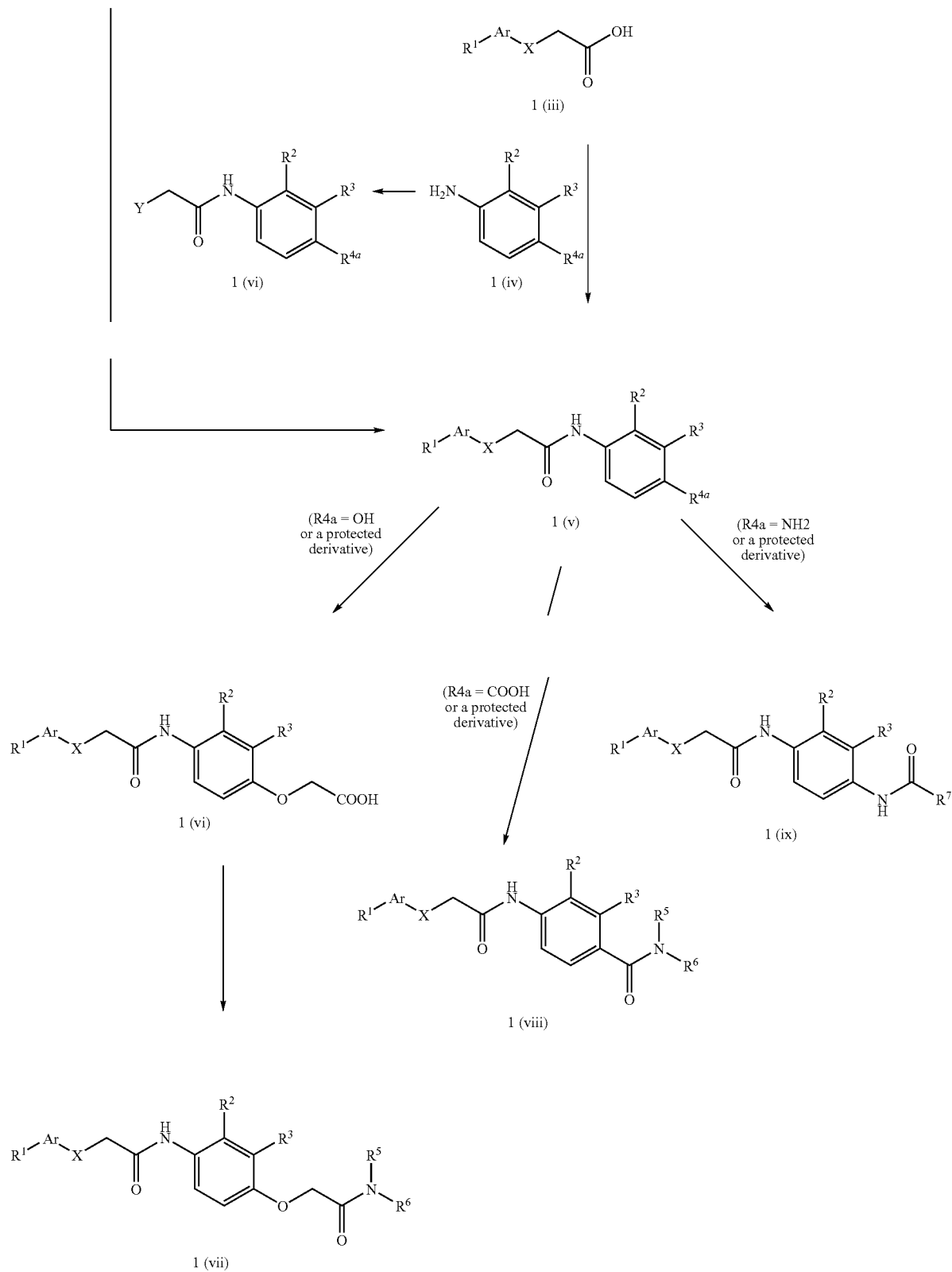

Briefly, thiol or alcohol 1(i) can be alkylated with an α-haloacetic acid ester in the presence of a base to give 1(ii), which can be transformed to acid 1(iii) after hydrolysis of the ester protecting group. Alternatively, 1(iii) can be obtained directly by alkylation with α-haloacetic acid. The reaction of acid 1(iii) with aniline 1(iv) can provide the amide 1(v) using the standard methods for preparing amides. Alternatively, amide 1(v) can also be obtained by the alkylation of 1(i) with 1(vi), which is readily available from aniline 1(iv) and α-haloacetyl chloride or bromide. Finally, amide 1(v) can be readily transformed to a compound of formula (I), if $R^{4a}$ is different from $R^4$, using methods known to the skilled in the art. For example, when $R^{4a}$ is —OH, or a protected form thereof, the group $R^{4a}$ may be transformed to an —OCH$_2$COOH group by alkylation with an α-haloacetic ester fragment, followed by deprotection of the ester, to give compound 1(vi). Coupling of the acid with amines of the formula HN(R$^5$)R$^6$, using methods well known in the art, provide compounds of general formula 1(vii). Alternatively, when $R^{4a}$ is —COOH or a protected form thereof, the group $R^{4a}$ may be transformed to a group of formula —CON(R$^5$)R$^6$ by coupling with amines of the formula HN(R$^5$)R$^6$, using methods well known in the art, to provide compounds of general formula 1(viii). Furthermore, when $R^{4a}$ is —NH$_2$, or a protected form thereof, the group $R^{4a}$ may be transformed to a group of formula —NH(C=O)R$^7$ by well known acylation procedures, to give compounds of general formula 1(ix). In addition, protecting group removal, alkylation, coupling, amide formation or functional group modifications are contemplated, to carry out other transformations of compound 1(v) to other compounds of formula (I).

Anilines such as 1(iv) are either commercially available or can be prepared by known methods. General methods for preparing substituted anilines 2(ii) and 2(iii), wherein Y is halo (e.g. Br or I), $R^2$, $R^3$, $R^9$, $R^{41}$ and $R^{42}$ are as defined herein and $R^{9a}$ and $R^{41a}$ are precursors of (or identical to) $R^9$ and $R^{41}$, respectively, are described in Scheme 2.

Scheme 2: Synthesis of substituted anilines

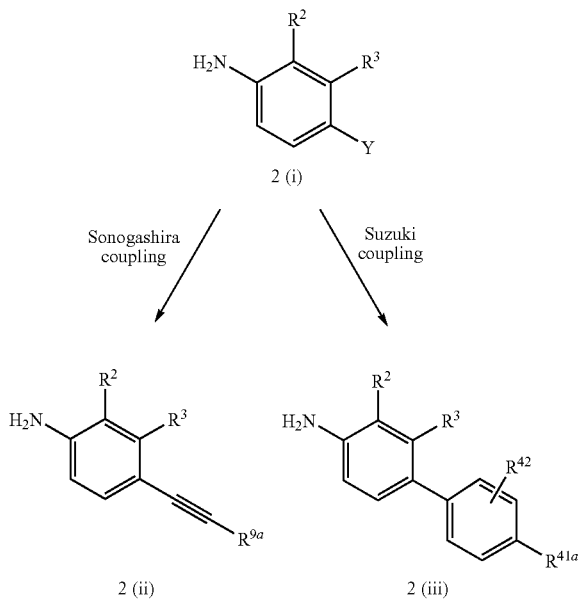

Briefly, 4-bromo or 4-iodoaniline 2(i) can be readily transformed to anilines 2(ii) or 2(iii) using the typical conditions of the Sonogashira reaction or the Suzuki coupling.

The preparation of compounds of formula (I) wherein Ar is tetrazole, 1,2,4-triazole, imidazole or 1,2,3-triazole and $R^{11}$, $R^{12}$, $R^{13}$, $R^{14}$, $R^{15}$ and $R^{Ar}$ are as defined herein is described in Scheme 3.

Scheme 3: Synthesis of tetrazole, 1,2,4-triazole, imidazole and 1,2,3- triazole derivatives

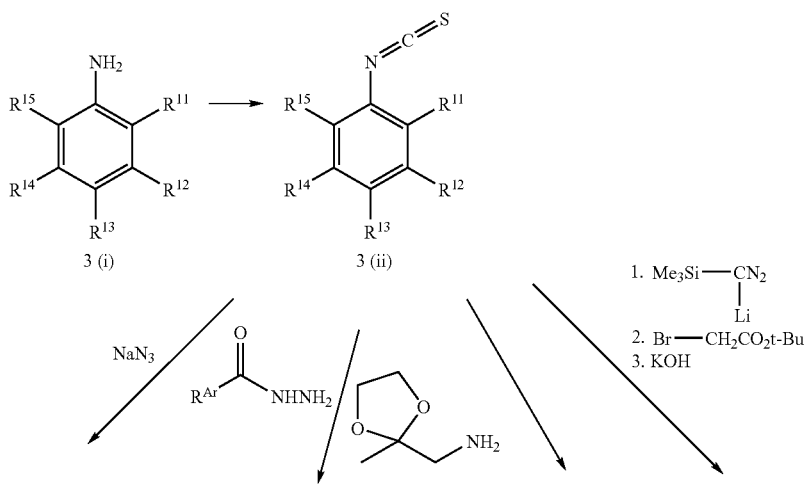

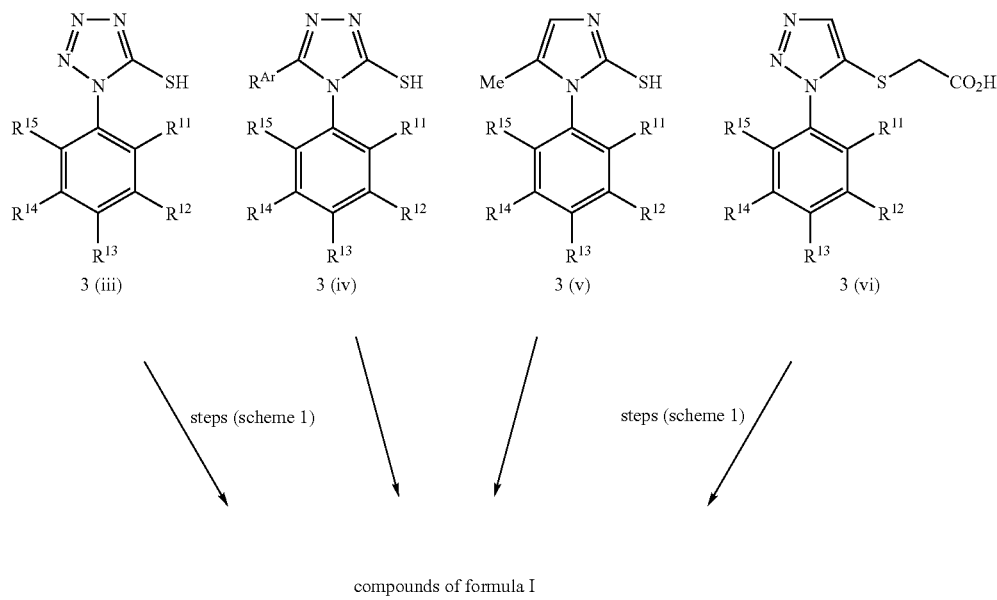

The key isocyanates 3(ii) are commercially available or can be easily prepared by known methods from aniline 3(i). Tetrazole 3(iii) can be prepared by reacting isocyanate 3(ii) with sodium azide. Triazole 3(iv) can be obtained from the condensation of isocyanate 3(ii) with acylhydrazide followed by treatment with base or acid. Imidazole 3(v) can be obtained from 3(ii) by treatment with 1-amino-2,2-ethylenedioxypropane. Triazole 3(vi) can be prepared by reacting the lithium salt of trimethylsilyldiazomethane with 3(ii) followed by the alkylation with tert-butyl bromoacetate and potassium hydroxide treatment. Finally, the compounds of formula (I) can be obtained from 3(iii), 3(iv), 3(v) and 3(vi) using the additional steps described in Scheme 1.

The preparation of compounds of formula (I) wherein Ar is thiazole or thiadiazole, P is a protecting group and $R^{11}$, $R^{12}$, $R^{13}$, $R^{14}$ and $R^{15}$ are as defined herein is described in Scheme 4.

Scheme 4: Preparation of thiazole and thiadiazole derivatives

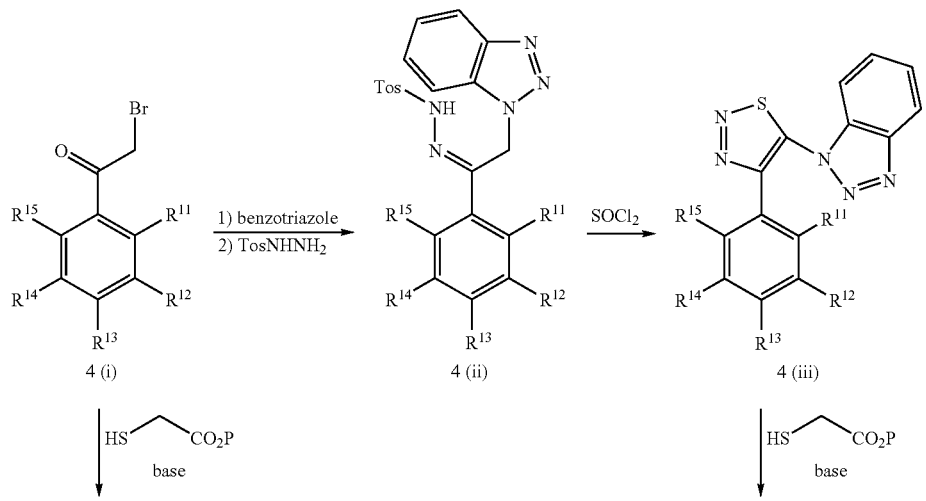

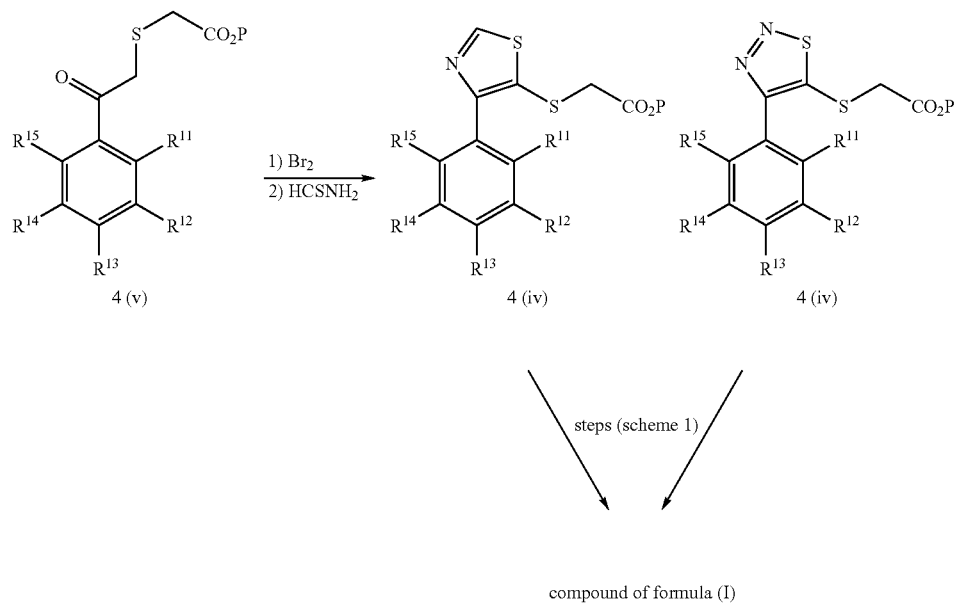

The reaction of bromomethylketone 4(i) with benzotriazole followed with the treatment with p-toluenesulfonyl hydrazide gives intermediate 4(ii). The thiadiazole 4(iii) can be prepared from 4(ii) by treatment with thionyl chloride. The treatment of 4(iii) with thioglycolate gives 4(iv) and finally a compound of formula (I) using the sequence described in Scheme 1. The bromomethylketone 4(i) can also be transformed to sulfide 4(v) by reaction with thioglycolate in the presence of a base. The bromination of 4(v) followed by the treatment with thioformamide gives 4(vi) that can easily be transformed to a compound of formula (I) using the sequence described in Scheme 1.

The preparation of compounds of formula (I) wherein Ar is pyrazole, P is a protecting group, and $R^{11}$, $R^{12}$, $R^{13}$, $R^{14}$ and $R^{15}$ are as defined herein is described in Schemes 5-7.

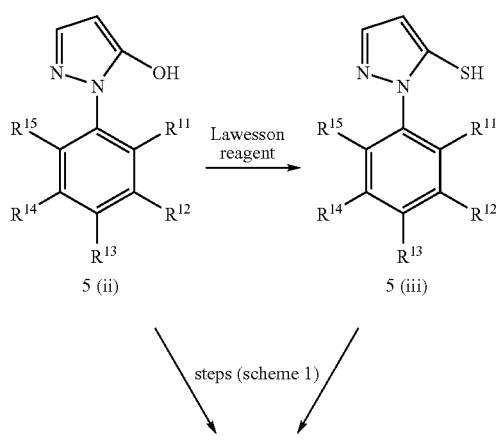

Pyrazole 5(ii) can be easily obtained by reacting hydrazine 5(i) with methyl 3,3-dimethoxypropionate. Hydroxypyrazole 5(ii) can be transformed to the corresponding thiol derivative 5(iii) with the Lawesson reagent. Finally, pyrazole derivatives 5(ii) and 5(iii) can be converted to compounds of formula (I) by using the sequence described in Scheme 1.

Scheme 5: Preparation of pyrazole derivatives (method 1)

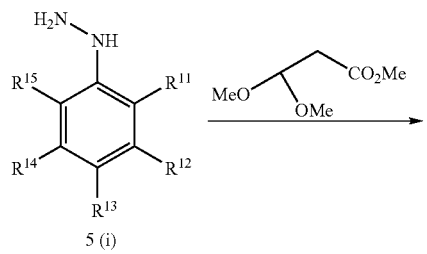

Scheme 6: Preparation of pyrazole derivatives (method 2)

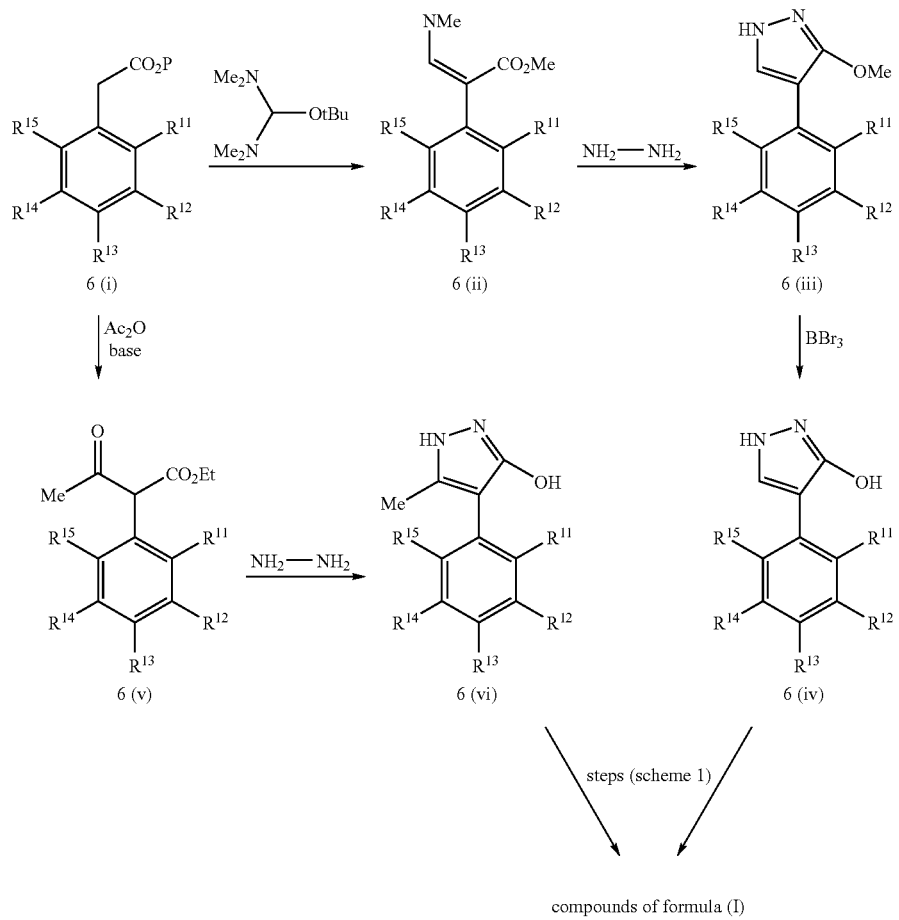

The pyrazole derivatives 6(iv) and 6(vi) can be obtained starting with phenylacetate 6(i). The reaction of 6(i) with the appropriate electrophile, tert-butoxybis(dimethylamino) methane or acetic anhydride, can give intermediates 6(ii) and 6(v), which can be easily transformed to pyrazoles 6(iii) and 6(vi) respectively upon treatment with hydrazine. The methyl ether derivative 6(iii) can be transformed to the corresponding hydroxypyrazole 6(iv). Finally, using the steps described in Scheme 1, 6(iv) and 6(vi) can be converted to compounds of formula (I).

Scheme 7: Preparation of pyrazole derivatives (method 3)

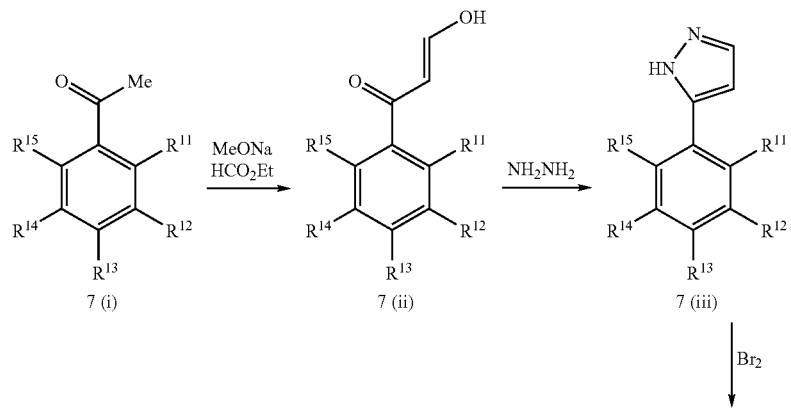

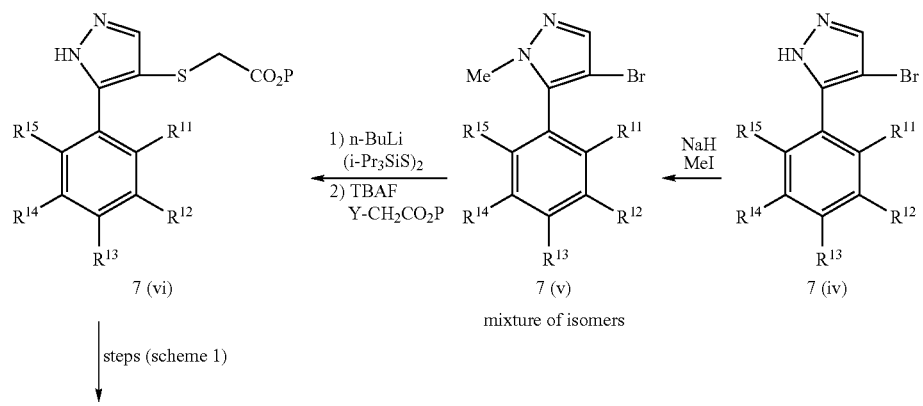

7 (vi)            7 (v)            7 (iv)

mixture of isomers

| steps (scheme 1)
↓ compounds of formula (I)

Pyrazole 7(iii) can be obtained from the Claisen condensation of acetophenone 7(i) with ethyl formate in the presence of a base such as sodium methoxide to give 7(ii) followed by condensation with hydrazine. Pyrazole 7(iii) can be converted to the bromo derivative 7(iv) upon treatment with bromine. Pyrazole 7(iv) can be transformed to a mixture of isomers (7(v) and isomer), which upon treatment with n-butyllitium in the presence of (i-Pr$_3$Si—S)$_2$, followed by the reaction with tetrabutylammonium fluoride in the presence of α-haloacetic acid ester can be converted to 7(vi). Finally, using the sequence of steps described in Scheme 1, 7(vi) can be transformed to compounds of formula (I).

Processes and reactants for preparing compounds of formula 1 are illustrated further by the examples hereinafter.

EXAMPLES

The present invention is illustrated in further detail by the following non-limiting examples. All reactions were performed in a nitrogen or argon atmosphere unless otherwise stated. Room temperature is 18 to 22° C. (degrees Celsius). Solution percentages or ratios express a volume to volume relationship, unless stated otherwise. Purification by reverse phase HPLC(RP-HPLC) was performed using a gradient of MeCN/H$_2$O containing TFA (0.06%) (CombiPrep ODS-AQ 50×20 mm, 5µ, 120 A). Analytical HPLC was carried out under standard conditions using a Combiscreen ODS-AQ C18 reverse phase column, YMC, 50×4.6 mm i.d., 5 µM, 120 Å at 220 nM, elution with a linear gradient as described in the following table (Solvent A is 0.06% TFA in H$_2$O; solvent B is 0.06% TFA in CH$_3$CN):

| Time (min) | Flow (mL/min) | Solvent A (%) | Solvent B (%) |
|---|---|---|---|
| 0 | 3.0 | 95 | 5 |
| 0.5 | 3.0 | 95 | 5 |
| 6.0 | 3.0 | 50 | 50 |
| 10.5 | 3.5 | 0 | 100 |

Abbreviations or symbols used herein include:
Ac: acetyl;
Boc: tert-butoxycarbonyl;
Bu: butyl;
tBu: 1,1-dimethylethyl (tert-butyl)
tBuOH: tert-butanol;
CHAPS: 3-{(3-cholamidopropyl)dimethylammonio}-1-propanesulfonate;
DEAD: diethyl azodicarboxylate;
DMF: N,N-dimethylformamide;
DMSO: dimethylsulfoxide;
dppf: 1,1'-bis(diphenylphosphino)ferrocene;
DTT: DL-dithiothreitol;
Et: ethyl;
Et$_2$O: diethyl ether;
EtOH: ethanol;
EtOAc: ethyl acetate;
GSH: glutathione;
HPLC: high performance liquid chromatography;
iPr: 1-methylethyl (isopropyl);
LiHMDS: lithium hexamethyldisilazide;
Me: methyl;
MeOH: methanol;
MeCN: acetonitrile;
n-BuLi: n-butyllithium;
NaHMDS: sodium hexamethyldisilazide;
NMR: nuclear magnetic resonance;
Ph: phenyl;
Pr: propyl;
RP-HPLC: reverse phase high performance liquid chromatography;
TBAF: tetrabutylammonium fluoride;
TFA: trifluoroacetic acid;
THF: tetrahydrofuran;
TLC: thin layer chromatography.

Syntheses

The following examples illustrate methods for preparing compounds of the invention.

Example 1

Entry 2015

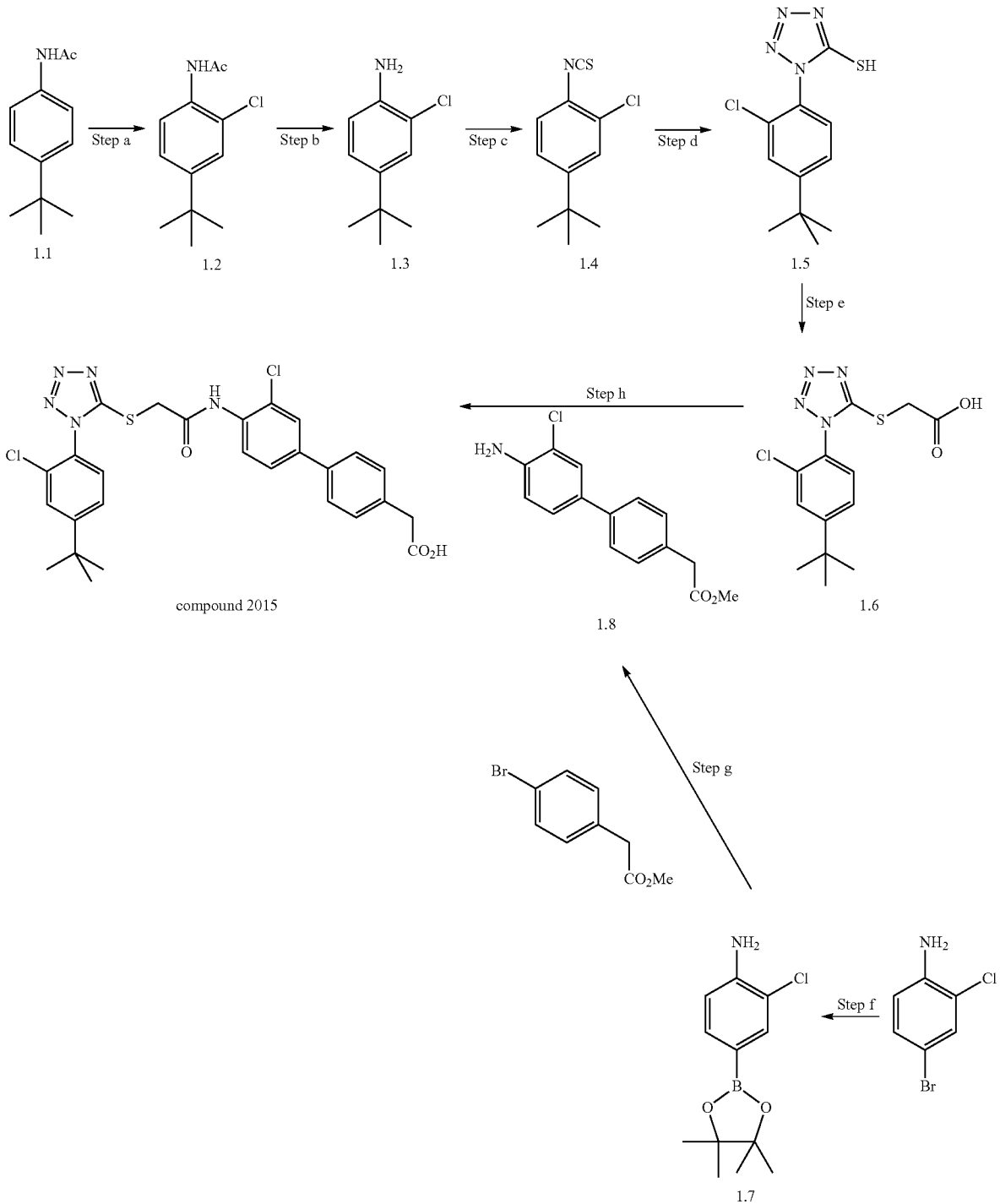

a) Compound 1.2

To a solution of N-[4-(tert-butyl)phenyl]acetamide 1.1 (2.00 g, 10.5 mmol) in a mixture of acetic acid (3.0 mL) and 12 N HCl (4.6 mL) was added dropwise a solution of $NaClO_3$ (170 mg, 1.60 mmol) in water (1 mL). After 30 min the resulting orange suspension was diluted with water (80 mL), the precipitate was filtered, washed with water and dried to give the compound 1.2 (2.0 g, 84% yield) as an off-white solid.

b) Compound 1.3

A solution of N-[4-(tert-butyl)-2-chlorophenyl]acetamide 1.2 (2.00 g, 8.86 mmol) in a mixture of 36 $NH_2SO_4$ (14 mL) and water (2.9 mL) was heated at 120° C. for 18 h. After cooling the reaction mixture was poured over ice, aqueous NaOH solution (10 M) was added until the pH was alkaline and the mixture was extracted with EtOAc. The organic phase was washed with brine, dried (MgSO$_4$), filtered and concentrated under reduced pressure. The resulting oil 1.3 (767 mg, 40% yield) was used as such in the next step.

c) Compound 1.4

To a solution of compound 1.3 (765 mg, 4.16 mmol) in CH$_2$Cl$_2$ (5 mL) was added di-2-pyridylthiocarbonate (966 mg, 4.16 mmol). The solution was stirred at room temperature overnight. The reaction mixture was washed successively with saturated aqueous NaHCO$_3$ solution and brine, dried (MgSO$_4$), filtered and concentrated under reduced pressure to give compound 1.4 (930 mg, 99% yield).

d) Compound 1.5

To a solution of compound 1.4 (925 mg, 4.10 mmol) in EtOH (200 mL) was added NaN$_3$ (4.3 g, 66 mmol) and the mixture was heated to 70° C. After 2 h the reaction mixture was cooled to room temperature and 12 N HCl (2 mL) was added. The mixture was concentrated and diluted with EtOAc. The organic layer was extracted with aqueous 1 N NaOH solution. The aqueous layer was acidified with aqueous 6 N HCl solution and a white precipitate formed. The suspension was filtered and the resulting solid was triturated with Et$_2$O/hexane (1/1) to give compound 1.5 (941 mg, 85% yield) as an off white solid.

e) Compound 1.6

To a solution of pyridine (0.34 mL, 4.20 mmol) and compound 1.5 (930 mg, 3.46 mmol) in DMSO (25 mL) was added ethyl 2-bromoacetate (392 µL, 3.46 mmol). The resulting light yellow solution was stirred at room temperature for 2 h. The reaction mixture was then diluted with EtOAc and was successively washed with water and brine, dried (MgSO$_4$), filtered and concentrated under reduced pressure. The crude ester was dissolved in THF (30 mL) and MeOH (10 mL) and aqueous 1 N NaOH solution (3 mL, 3 mmol) was added. The solution was stirred at 55° C. for 60 min. The THF/MeOH was evaporated under reduced pressure and the residue was dissolved in aqueous 1 N NaOH solution. The solution was slowly acidified to pH 2 at 0° C. with aqueous 1 N HCl solution. The suspension was filtered and the resulting solid was rinsed with water and dried under reduced pressure to give compound 1.6 (600 mg, 99% yield) as a white solid.

f) Compound 1.7

A solution of 4-bromo-2-chloroaniline (4.00 g, 19.37 mmol), bis(pinacolato)diboron (5.90 g, 23.2 mmol) and KOAc (12.3 g, 58.1 mmol) in DMSO (100 mL) was deoxygenated by bubbling nitrogen through it for 45 min. PdCl$_2$ (dppf) (1.42 g, 1.94 mmol) and dppf (1.07 g, 1.94 mmol) were then added and the mixture was heated at 100° C. for 4 h. After cooling to room temperature the reaction mixture was diluted with EtOAc, washed successively with water and brine, dried (MgSO$_4$), filtered and concentrated under reduced pressure. The crude product was purified twice by flash chromatography using CH$_2$Cl$_2$ to give intermediate 1.7 (2.15 g, 44% yield) as a white solid.

g) Compound 1.8

To a solution of methyl (4-bromophenyl)acetate (obtained from the corresponding acid (267.5 mg, 1.2 mmol) upon treatment with excess diazomethane) in 1,4-dioxane (5 mL) were added intermediate 1.7 (315 mg, 1.20 mmol) and K$_3$PO$_4$ (792 mg, 3.73 mmol). After degassing the reaction mixture for 45 min, PdCl$_2$(dppf) (137 mg, 0.19 mmol) and dppf (136 mg, 0.06 mmol) were added and the mixture was heated at 10° C. for 3 h. After cooling to room temperature the reaction mixture was diluted with EtOAc, washed successively with water and brine, dried (MgSO$_4$), filtered and concentrated under reduced pressure. The crude product was purified by flash chromatography using hexane/EtOAc (80/20) to give compound 1.8 (164 mg, 48% yield)

h) Compound 2015

To an ice-cold solution of acid 1.6 (30.6 mg, 0.09 mmol) and aniline 1.8 (25.8 mg, 0.09 mmol) in pyridine (3 mL) was added PCl$_3$ (8.3 µL). The mixture was stirred at 0° C. for 2 h, quenched with a few drops of water, and concentrated under reduced pressure. The crude product was dissolved in EtOAc and the resulting solution was successively washed with aqueous 10% citric acid solution, water and brine, dried (MgSO$_4$), filtered and concentrated under reduced pressure. The crude product was purified by flash chromatography using hexane/EtOAc (75/25) to afford the corresponding ester (20 mg, 37% yield) as a white solid.

To a solution of the ester (20 mg, 0.034 mmol) in THF (3 mL)/ MeOH (1 mL) was added 1 N NaOH (70 µL, 0.070 mmol). After 1 h at 55° C., the reaction was concentrated and the crude acid was purified by RP-HPLC The pure fractions were combined and concentrated to give compound 2015 (6.5 mg, 33% yield) as a white solid. $^1$H-NMR (DMSO-d$_6$): δ 12.35 (bs s, 1H); 10.03 (s, 1H); 7.83-7.79 (m, 3H); 7.73-7.63 (m, 5 H); 7.36-7.34 (m, 2H); 4.47 (s, 2H); 3.62 (s, 2H); 1.36 (s, 9H).

Example 2

Entry 2033

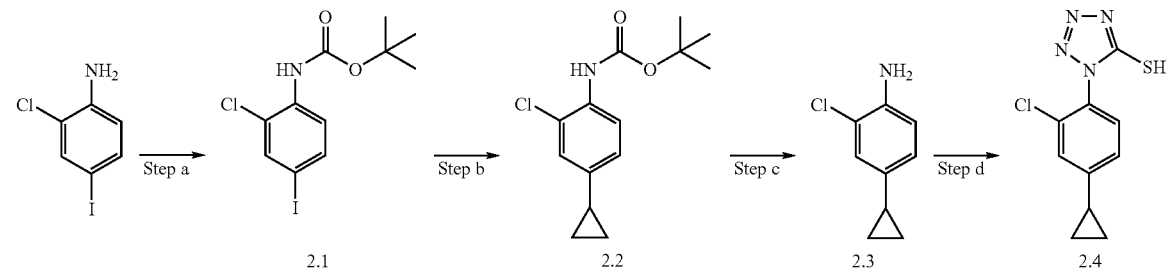

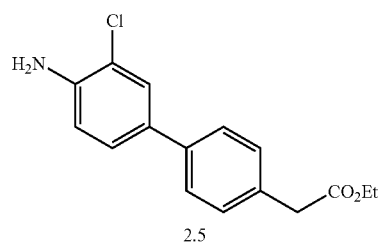
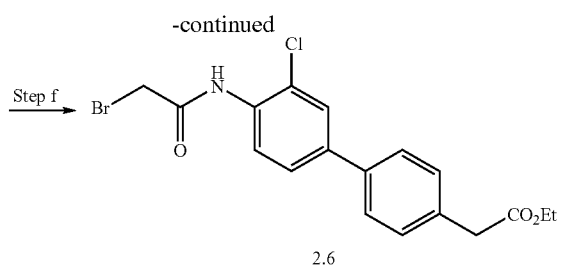

compound 2033 a) Compound 2.1

To a solution of 4-iodo-2-chloroaniline (5.00 g, 19.7 mmol) in THF (40 mL) was added dropwise NaHMDS (1 M in THF, 41.4 mL) and the mixture was stirred at room temperature for 90 min. Boc$_2$O (4.10 g, 19.0 mmol) in THF (30 mL) was added to the reaction mixture and the resulting solution was stirred overnight. The reaction mixture was diluted with water and extracted twice with EtOAc. The combined organic phase was successively washed with aqueous 1 N HCl, water and brine, dried (MgSO$_4$), filtered and concentrated under reduced pressure. The crude product was purified by flash chromatography using hexane/EtOAc (99/1 to 4:1) to give compound 2.1 as a light yellow oil (5.5 g, 79% yield).

b) Compound 2.2

To a solution of cyclopropylbromide (6.97 mL, 87.0 mmol) in THF (90 mL) cooled to −78° C. was added nBuLi (2.5 M in hexane, 34 mL) over 45 min. After 1 h, a solution of ZnBr$_2$ (flame dried under high vacuum, 23.2 g, 103 mmol) in THF (90 mL) was added by cannula and the mixture was allowed to warm to room temperature. After 1 h a solution of compound 2.1 dissolved in THF (90 mL) was added followed by Pd(PPh$_3$)$_4$ (2.15 g, 1.86 mmol) under stream of nitrogen. The reaction mixture was then heated at reflux for 1 h, cooled in an ice bath and quenched with a mixture of aqueous 1 N HCl solution and aqueous 5% Na$_2$S$_2$O$_3$ solution. The resulting mixture was extracted with Et$_2$O several times and the combined organic layers were successively washed with aqueous 1 N HCl solution, water and brine, dried (MgSO$_4$), filtered and concentrated under reduced pressure. The crude product was dissolved in hexane (100 mL) and filtered through a silica gel pad. The filtrate was concentrated to yield compound 2.2 (6.74 g, 87% yield) as a clear oil.

c) Compound 2.3

A solution of compound 2.2 (1.27 g, 4.74 mmol) in anhydrous HCl in dioxane (4 N. 20 mL) was heated at 45° C. for 30 min. The resulting suspension was concentrated to dryness and the viscous oil was partitioned between EtOAc and water. The aqueous layer was made alkaline using aqueous 1 N NaOH solution, and extracted with EtOAc. The organic phase was washed with brine, dried (MgSO$_4$), filtered and concentrated under reduced pressure to give aniline 2.3 (511.0 mg, 64% yield) as a beige oil.

d) Compound 2.4

Following the procedure described in Example 1, Steps c and d, compound 2.4 was obtained in 53% yield.

e) Compound 2.5

Following the procedure described in Example 1 Step g, but using the corresponding ethyl ester, aniline 2.5 was obtained as an orange solid in 35% yield.

f) Compound 2.6

To a mixture of aniline 2.5 (202 mg, 0.70 mmol) and Et$_3$N (110 µL, 0.79 mmol) in CH$_2$Cl$_2$ (8 mL) was added bromoacetyl chloride (65 µL, 0.75 mmol). After 18 h the reaction mixture was diluted with EtOAc, washed with water and brine, dried (MgSO$_4$), filtered and concentrated under reduced pressure. The crude product was purified by flash chromatography using hexane/EtOAc (75/25) to give compound 2.6 (247 mg, 86% yield) as a brown solid.

g) Compound 2033

To a solution of compound 2.4 (39.0 mg, 0.15 mmol) in DMF (2 mL) was added compound 2.6 (62.0 mg, 0.15 mmol) and K$_2$CO$_3$ (25 mg, 0.18 mmol). After 2 h, aqueous 1 N NaOH solution (0.5 mL) was added and stirring was continued for 2 h. The reaction mixture was quenched with TFA (0.5 mL). The resulting crude acid was purified by HPLC using a gradient of MeCN/H$_2$O containing TFA (0.06%) (CombiPrep ODS-AQ 50×20 mm, 5µ, 120 A). The pure fractions were combined and concentrated to give compound 2033 (42 mg, 51% yield) as a white solid. $^1$H-NMR (DMSO-d$_6$) δ 12.34 (br s, 1H); 10.02 (s, 1H); 7.81 (d, J=8.6 Hz, 1H); 7.79, (d, 2.0 Hz, 1H); 7.66-7.61 (m, 4H); 7.56 (d, J=2.2 Hz, 1H, 7.37-7.31 (m, 3H); 4.46 (s, 2H); 3.61 (s, 2H); 2.14-2.05 (m, 1H); 1.11-1.05 (m, 2H); 0.89-0.84 (m, 2H).

Example 3

General Procedure for the Chlorination of Anilines

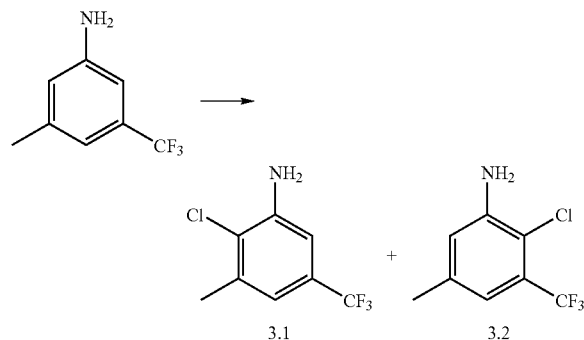

A solution of 3-methyl-5-(trifluoromethyl)aniline (2.0 g, 11.4 mmol) and N-chlorosuccinimide (1.7 g, 12.7 mmol) in MeCN (15 mL) was heated for 6 h. Upon cooling the reaction was concentrated to dryness and the resulting mixture was purified by flash chromatography using hexane/EtOAc (95/5) to give compound 3.1 (587.8 mg, 25% yield) as a clear oil, followed by hexane/EtOAc (90/10) to obtain compound 3.2 (611.9 mg, 26% yield) as a colorless oil.

Example 4

Entry 4067

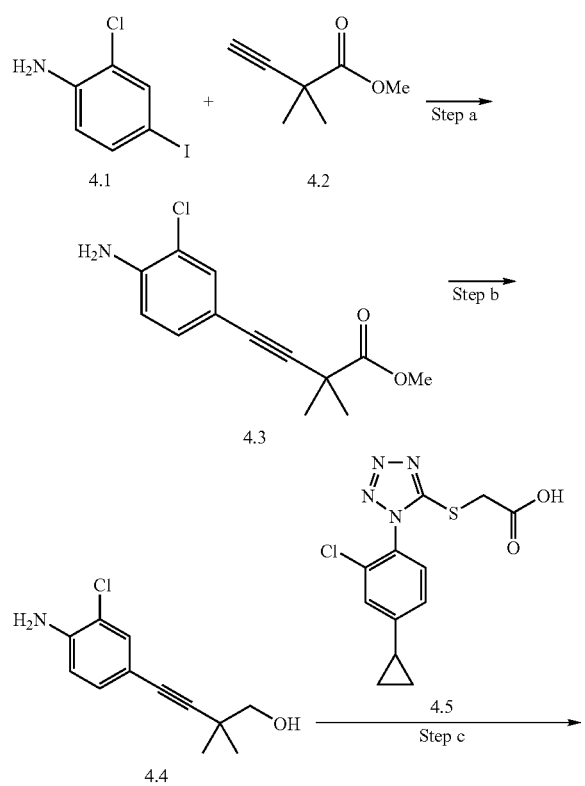

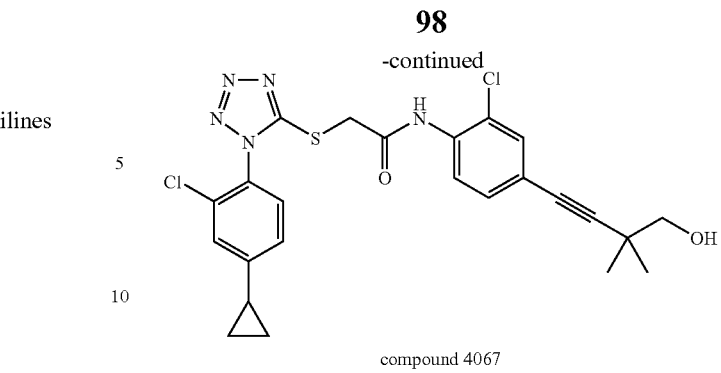

compound 4067 a) Compound 4.3

To a solution of aniline 4.1 (706.2 mg, 2.78 mmol) in THF (27 mL) was added cuprous iodide (55.8 mg, 0.29 mmol), $Et_2NH$ (2.37 mL, 22.9 mmol) and compound 4.2 (370 mg, 2.93 mmol). The mixture was degassed for 15 min by bubbling argon through the solution. $Pd(PPh_3)_4$ (339 mg, 0.29 mmol) was added and the reaction mixture was heated at reflux until total disappearance of the starting material as indicated by TLC. The black solution was cooled to room temperature, silica gel was added and all volatiles were removed under reduced pressure to give a dry powder which was applied at the top of a column. The crude compound was purified by flash chromatography (hexane/EtOAc, 75/25) to afford compound 4.3 (600 mg, 86% yield) as a brown oil.

b) Compound 4.4

$LiAlH_4$ (33.2 mg, 0.87 mmol) was added to an ice-cold $THF/Et_2O$ (1:2) solution of compound 4.3. The reaction mixture was stirred at room temperature for 1 h then was poured over aqueous 1 N Rochelle salt/$Et_2O$ (200 mL, 1:1). The organic phase was collected and the aqueous phase was extracted with $Et_2O$ (3×40 mL). The combined organic phases were washed with brine (50 mL), dried ($Na_2SO_4$), filtered and concentrated under reduced pressure to afford the alcohol 4.4 (77.0 mg, 79% yield) as a colorless oil which was used as such in the following step.

c) Compound 4067

Oxalyl chloride (40 μL, 45 μmol) and DMF (one drop) were successively added to an ice-cold solution of acid 4.5 (prepared from compound 2.4 using a procedure analogous to that described in Example 1 step e) (135 mg, 0.41 mmol) in $CH_2Cl_2$ (4 mL). The reaction mixture was stirred at room temperature for 1 h then was concentrated under reduced pressure. The residue was dissolved in THF (5 mL) and cooled to 0° C. A solution of amine 4.4 (77.0 mg, 0.34 mmol) in THF (1 mL) and pyridine (70 μL, 0.86 mmol) were successively added to the solution. The reaction mixture was stirred at room temperature for 2 h, diluted with saturated aqueous $NaHCO_3$ solution and extracted with $Et_2O$ (3×50 mL). The combined organic phases were washed with brine, dried ($Na_2SO_4$), filtered and concentrated under reduced pressure. The crude residue was purified by flash chromatography (hexane/EtOAc, 4/1) to afford the pure amide 4067 (60.0 mg, 27% yield) as a colorless oil. $^1$H-NMR (DMSO-$d_6$): δ 10.04 (s, 1H), 7.81 (d, J=8.6 Hz, 1H), 7.67 (d, J=8.6 Hz, 1H), 7.60 (d, J=1.8 Hz, 1H), 7.54 (d, J=1.8 Hz, 1H), 7.37 (dd, J=4.1, 2 Hz, 1H), 7.35 (dd, J=4.1, 2 Hz, 1H), 4.49 (s, 2H), 3.65 (broad s, 1H), 2.16-2.12 (m, 1H), 1.23 (s, 6H), 1.15-1.11 (m, 2H), 0.93-0.89 (m, 2H).

Example 5

Entry 4177

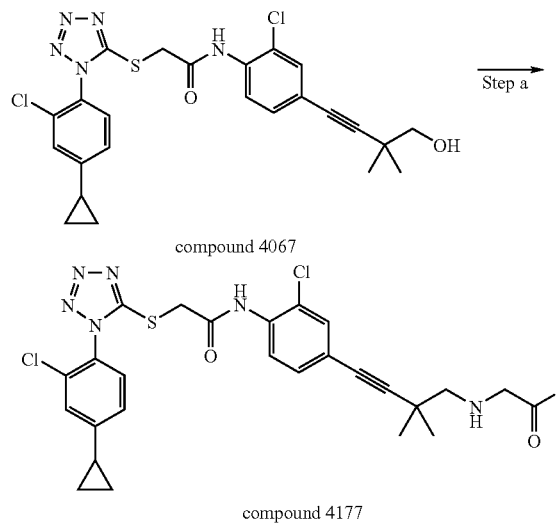

compound 4067 compound 4177 a) Compound 4177

To an ice-cold solution of alcohol 4067 (200 mg, 0.39 mmol) in $CH_2Cl_2$ (4 mL) was added Dess-Martin periodinane (328 mg, 0.77 mmol). The reaction mixture was stirred at room temperature for 30 min then diluted with saturated aqueous $Na_2S_2O_3$ solution (50 mL) and extracted with $Et_2O$ (3×50 mL). The combined organic phases were washed with brine, dried ($Na_2SO_4$), filtered and concentrated under reduced pressure. The crude oil was dissolved in EtOH (5 mL) and added to a solution of glycine methyl ester (72.9 mg, 0.58 mmol) and acetic acid (0.2 mL) in EtOH (5 mL) at room temperature. $NaCNBH_3$ (36.5 mg, 0.58 mmol) was then added and the resulting suspension was stirred at room temperature for 1 h. The reaction mixture was diluted with saturated aqueous $NaHCO_3$ solution (30 mL) and extracted with $Et_2O$ (3×30 mL). The combined organic phases were washed with brine, dried ($Na_2SO_4$), filtered and concentrated under reduced pressure. The crude oil was dissolved in DMSO (4 mL), cooled to 0° C. and aqueous 1 N LiOH solution (0.39 mL, 0.39 mmol) was added. The resulting mixture was stirred at room temperature for 30 min, diluted with TFA (0.5 mL) and purified by RP-HPLC to afford, after lyophilization, compound 4177 (38.0 mg, 14% yield) as a white solid. $^1$H-NMR (DMSO-$d_6$): δ 10.09 (s, 1H), 8.91 (broad s, 1H), 7.88 (d, J=8.6 Hz, 1H), 7.67 (dd, J=4.5, 2.7 Hz, 2H), 7.60 (d, J=1.8 Hz, 1H), 7.45 (dd, J=8.4, 1.6 Hz, 1H), 7.37 (dd, J=8.4, 1.7 Hz, 1H), 4.50 (s, 2H), 4.01 (s, 2H), 3.66 (broad s, 2H), 3.18 (s, 2H), 2.17-2.11 (m, 1H), 1.41 (s, 6H), 1.16-1.11 (m, 2H), 0.93-0.89 (m, 2H)

Example 6

Entry 4181

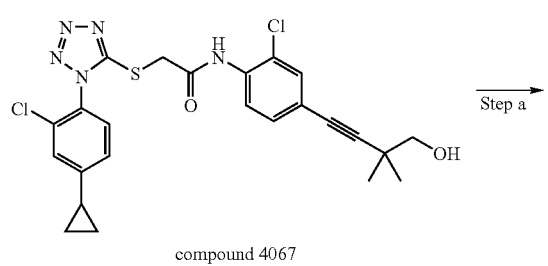

compound 4067

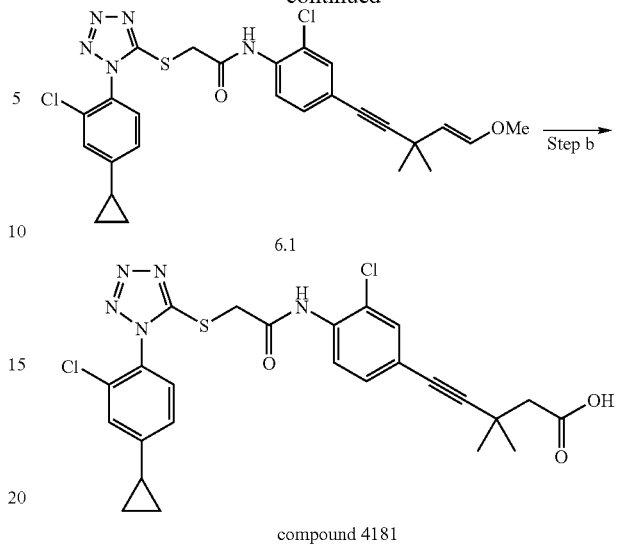

6.1 compound 4181 a) Compound 6.1

Dess-Martin periodinane (196 mg, 0.46 mmol) was added to an ice-cold solution of compound 4067 (217 mg, 0.42 mmol) in $CH_2Cl_2$ (4 mL). The resulting mixture was stirred at room temperature for 1 h, diluted with saturated aqueous $Na_2S_2O_3$ solution and extracted with $Et_2O$ (3×30 mL). The combined organic phases were washed with brine, dried ($Na_2SO_4$), filtered and concentrated under reduced pressure. The crude oil was dissolved in dry THF (2 mL) and transferred into an ice-cold solution of potassium tert-butoxide (182 mg, 1.62 mmol) and (methoxymethyl)triphenyl-phosphonium chloride (579 mg, 1.69 mmol) in THF (5 mL), which was previously stirred for 30 min. The resulting reaction mixture was stirred for 1 h at 0° C. then for 1 h at room temperature. Saturated aqueous $NaHCO_3$ solution (20 mL) was added and the mixture was extracted with $Et_2O$ (3×30 mL). The combined organic phases were washed with brine, dried ($Na_2SO_4$), filtered and concentrated under reduced pressure. Purification by flash chromatography using hexane/EtOAc (7/3) afforded compound 6.1 (80.0 mg, 35% yield) as a colorless oil.

b) Compound 4181

Aqueous 10% HCl solution (3 mL) was added to an ice-cold solution of compound 6.1 (79.7 mg, 0.15 mmol) in THF (2 mL). The reaction mixture was stirred for 30 min at 0° C., for 3 h at room temperature then extracted with $Et_2O$ (3×30 mL). The combined organic phases were washed with saturated aqueous $NaHCO_3$ solution, brine, dried ($Na_2SO_4$), filtered and concentrated under reduced pressure. The crude oil was dissolved in tBuOH/$CH_2Cl_2$ (3 mL, 3:1). Aqueous pH 7.0 potassium phosphate buffer (3 mL) was added, followed by 2-methyl-2-butene (5 mL) and $NaClO_2$ (66.5 mg, 0.74 mmol). The reaction mixture was stirred for 3 h at room temperature, diluted with aqueous 10% HCl solution (10 mL) and extracted with $CH_2Cl_2$ (5×10 mL). The combined organic phases were dried ($Na_2SO_4$), filtered and concentrated under reduced pressure. The crude product was purified by RP-HPLC to afford, after lyophilization, compound 4181 (44.0 mg, 55% yield) as a white solid. $^1$H-NMR (DMSO-$d_6$) δ 12.1 (s, 1H), 9.94 (s, 1H), 7.71 (d, J=8.4 Hz, 1H), 7.57 (d, J=8.2 Hz, 1H), 7.50 (d, J=1.5 Hz, 1H), 7.38 (d, J=1.7 Hz, 1H), 7.28-7.21

(m, 2H), 7.23 (dd, 1H), 4.38 (s, 2H), 2.06-2.01 (m, 1H), 1.30 (s, 6H), 1.05-1.01 (m, 2H), 0.83-0.80 (m, 2H).

Example 7

Entry 4012

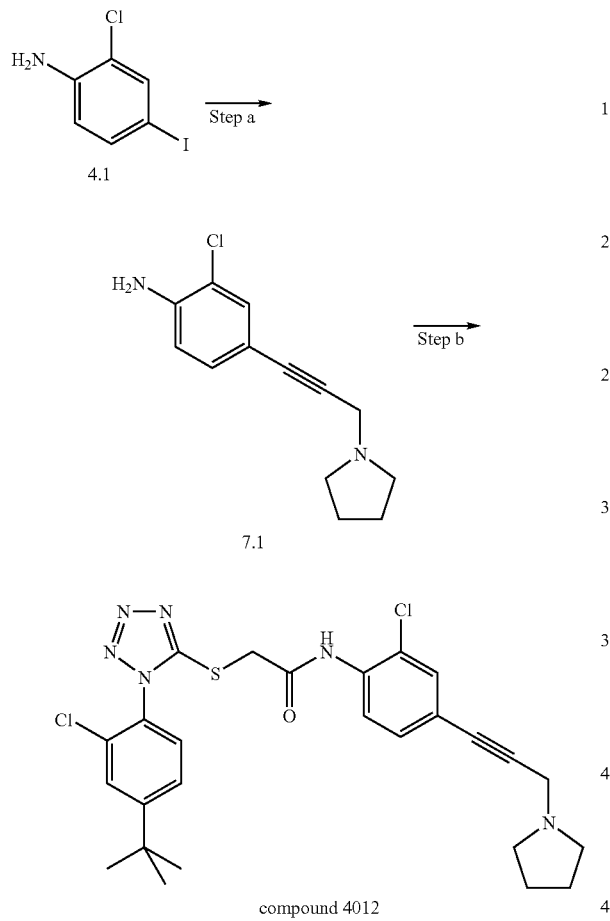

compound 4012 a) Compound 7.1

To a solution of aniline 4.1 (500 mg, 1.97 mmol) was added propargyl bromide (258 μL, 2.17 mmol), cuprous iodide (37.5 mg, 197 μmol) and pyrrolidine (0.82 mL, 9.82 mmol). The mixture was degassed by bubbling argon in the solution for 20 min. Pd(PPh$_3$)$_4$ (228 mg, 0.20 mmol) was added and the mixture was heated at reflux for 5 h. The reaction mixture was cooled to room temperature, silica gel was added and the volatiles were removed under reduced pressure to afford a dry powder. The crude compound was purified by flash chromatography using hexane/EtOAC/Et$_3$N (50/45/5) to afford compound 7.1 (281 mg, 61% yield) as a brown oil.

b) Compound 4012

Using a method similar to the one described in Example 1, Step h, but using aniline 7.1 in place of aniline 1.8, compound 4012 was obtained as a colorless oil (42% yield). $^1$H-NMR (DMSO-d$_6$): 10.03 (s, 1H), 7.82-7.78 (m, 2H), 7.72-7.66 (m, 2H), 7.57 (s, 2H), 7.39 (d, J=7.5 Hz, 1H), 4.46 (s, 2H), 3.60 (s, 2H), 2.51 (s, 4H), 1.72 (s, 4H), 1.36 (s, 9H).

Example 8

Entries 4069, 4072, 4130

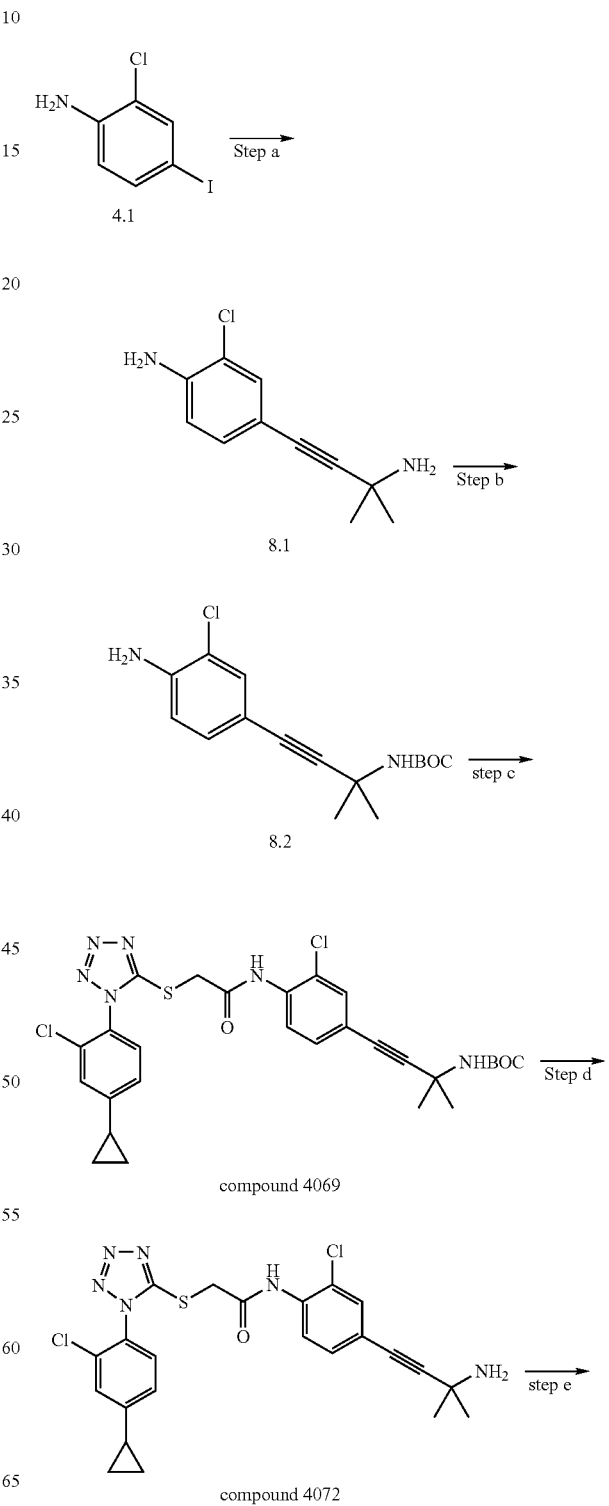

compound 4069 compound 4072

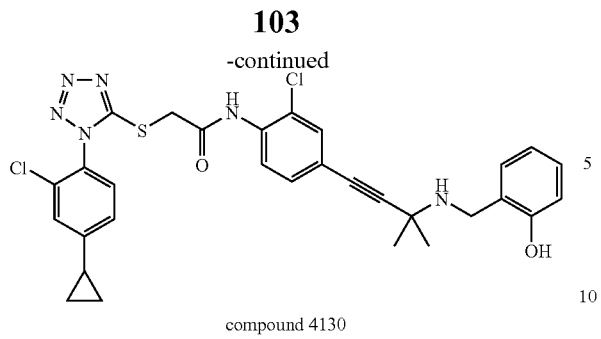

compound 4130 a) Compound 8.1

Using a method similar to the one described in Example 4, Step a, but replacing alkyne 4.2 with 3-amino-3-methyl-1-butyne, compound 8.1 was obtained as a brown oil (98% yield).

b) Compound 8.2

$Boc_2O$ (7.29 g, 33.4 mmol) was added to a solution of the propargylamine 8.1 (6.97 g, 33.4 mmol) in MeOH (100 mL) at room temperature. The resulting mixture was stirred at room temperature for 2 h, diluted with saturated aqueous $NaHCO_3$ solution (100 mL) and extracted with EtOAc (3×50 mL). The combined organic phases were washed with saturated aqueous $NaHCO_3$ solution and brine, dried ($Na_2SO_4$), filtered and concentrated under reduced pressure. The crude residue was purified by flash chromatography (hexane/EtOAc, 7/3) to afford the aniline 8.2 (5.64 g, 55% yield) as a colorless oil.

c) Compound 4069

Using a method similar to the one described in Example 4, Step c, aniline 8.2 (497 mg, 1.61 mmol) yielded compound 4069 (717 mg, 74% yield) as an off white solid. $^1$H-NMR (DMSO-$d_6$): δ 10.04 (s, 1H), 7.80 (d, J=8.4 Hz, 1H), 7.65 (d, J=8.3 Hz, 1H), 7.57 (d, J=1.8 Hz, 1H), 7.47 (d, J=1.8 Hz, 1H), 7.34 (dd, J=8.2, 1.8 Hz, 1H), 7.32 (dd, J=8.5, 1.7 Hz, 1H), 7.13 (broad s 1H), 4.46 (s, 2H), 2.13-2.07 (m, 1H), 1.52 (s, 6H), 1.41 (s, 9H), 1.11-1.09 (m, 2H), 0.90-0.86 (m, 2H).

d) Compound 4072

Anhydrous 4 N HCl in 1,4-dioxane (0.23 mL, 0.93 mmol) was added at room temperature to a solution of compound 4069 (56.0 mg, 93 μmol) in 1,4-dioxane (0.5 mL). The reaction mixture was stirred at room temperature overnight then concentrated under reduced pressure. The crude residue was purified by RP-HPLC to afford, after lyophilization, compound 4072 (33 mg, 70% yield) as a white solid. $^1$H-NMR (DMSO-$d_6$): δ 10.08 (s, 1H), 8.52 (broad s, 3H), 7.91 (d, J=8.4 Hz, 1H), 7.63 (d, J=8.4 Hz, 1H), 7.61 (d, J=5.6 Hz, 1H), 7.56 (d, J=1.86 Hz, 1H), 7.43 (dd, J=8.4, 1.6 Hz, 1H), 7.33 (dd, J=8.4, 2.0 Hz, 1H), 4.47 (s, 2H), 2.12-2.07 (m, 1H), 1.62 (s, 6H), 1.12-1.07 (m, 2H), 0.89-0.85 (m, 2H).

e) Compound 4130

Acetic acid (30 μL) was added to a solution of aniline 4071 in EtOH (2 mL) at room temperature. Salicylaldehyde (18.3 mg, 0.15 mmol) was then added, followed by $NaCNBH_3$ (5 pg. 75 μmol). The reaction was stirred at room temperature for 1 h then concentrated under reduced pressure. The crude residue was purified by RP-HPLC to afford, after lyophilization, compound 4130 (18.8 mg, 62% yield) as a white solid. $^1$H-NMR (DMSO-$d_6$): δ 10.26 (s, 1H), 10.14 (s, 1H), 9.17 (broad s, 2H), 7.95 (d, J=8.4 Hz, 1H), 7.75 (d, J=1.8 Hz, 1H), 7.67 (d, J=8.2 Hz, 1H), 7.60 (d, J=1.8 Hz, 1H), 7.54 (dd, J=8.6, 1.8 Hz, 1H), 7.40 (d, J=7.6 Hz, 1H), 7.38 (dd, J=8.4, 1.7 Hz, 1H), 7.31 (dt, J=8.2, 1.3 Hz, 1H), 6.97 (d, J=8.1 Hz, 1H), 6.91 (t, J=7.2 Hz, 1H), 4.51 (s, 2H), 4.33 (s, 2H), 2.17-2.11 (m, 1H), 1.76 (s, 6H), 1.16-1.11 (m, 2H), 0.93-0.89 (m, 2H).

Example 9

Entry 4062

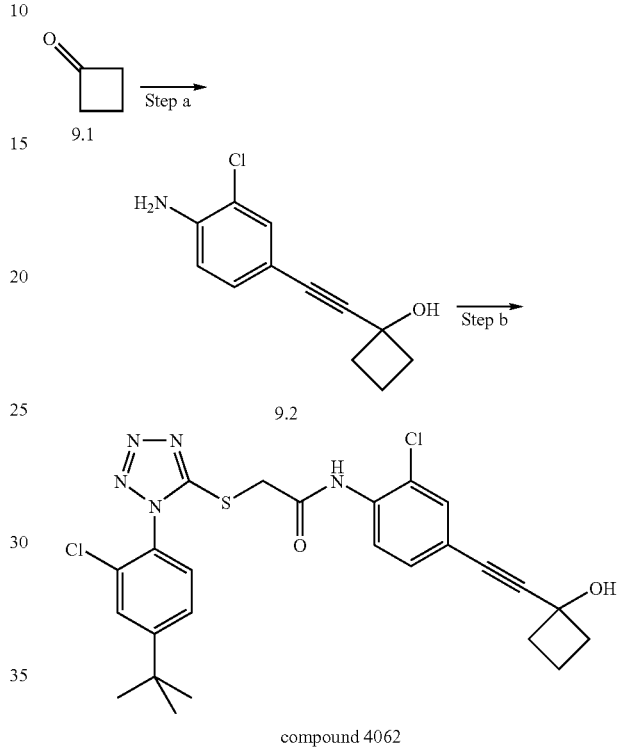

compound 4062 a) Compound 9.2

Cyclobutanone (1.00 g, 14.3 mmol) was added to a −78° C. solution of ethynyl magnesium bromide (0.5M in THF, 40 mL, 20 mmol). The reaction mixture was stirred at room temperature for 1 h, diluted with saturated aqueous $NH_4Cl$ solution and extracted with $Et_2O$ (4×30 mL). The combined organic phases were washed with brine, dried ($Na_2SO_4$), filtered and concentrated under reduced pressure. The crude oil was dissolved in THF (25 mL) and 2-chloro-4-iodoaniline (1.25 g, 4.93 mmol) was added, followed by cuprous iodide (94 mg, 190 mmol) and $Et_2NH$ (1.3 mL, 12 mmol). The mixture was degassed by bubbling argon through the solution for 15 min and $Pd(PPh_3)_4$ (570 mg, 0.49 mmol) was added. The solution was heated at reflux for 5 h. After cooling to room temperature, silica gel was added and the volatiles were removed under reduced pressure to give a dry brown powder. The crude product was purified by flash chromatography (hexane/EtOAc, 19/1) to afford compound 9.2 (269 mg, 25% yield) as a brown oil.

b) Compound 4062

Using a method similar to the one described in Example 7, Step b, aniline 9.2 (61 mg, 0.28 mmol) gave compound 4062 (10.0 mg, 6% yield) as an off white solid. $^1$H-NMR ($CDCl_3$): δ 9.39 (s, 1H), 8.31 (d, J=8.6 Hz, 1H), 7.61 (d, J=1.8 Hz, 1H), 7.49-7.47 (m, 2H), 7.36-7.31 (m, 2H), 4.16 (s, 2H), 2.55-2.50 (m, 2H), 2.36-2.30 (m, 2H), 2.23 (s, 1H), 1.91-1.83 (m, 2H), 1.38 (s, 9H).

Example 10

Entries 4098, 4082

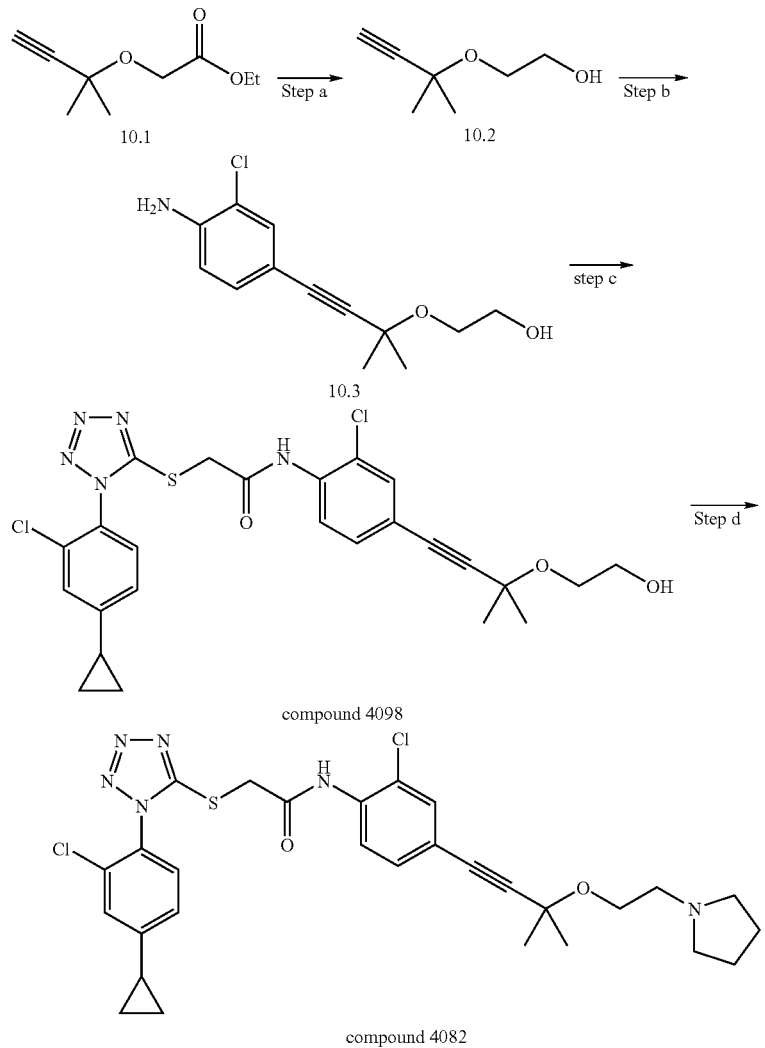

a) Compound 10.2

LiAlH$_4$ (446 mg, 11.7 mmol) was added to an ice-cold solution of compound 10.1 (2.00 g, 11.8 mmol) in Et$_2$O (100 mL). The reaction mixture was stirred at room temperature for 1 h then poured over aqueous 1 N Rochelle salt solution (200 mL). The solution was diluted with Et$_2$O (200 mL) and stirred vigourously for 1 h. The organic phase was collected, washed with brine, dried (Na$_2$SO$_4$), filtered and concentrated under reduced pressure. The crude oil was purified by flash chromatography (hexane/EtOAc, 4/1) to afford alcohol 10.2 (963 mg, 64% yield) as a colorless oil.

b) Compound 10.3

Using a method similar to the one described in Example 7, Step a, compound 10.2 (400 mg, 2.12 mmol) and 2-chloro-4-iodoaniline (791 mg, 3.12 mmol) gave alcohol 10.3 (585 mg, 74% yield) as a brown oil.

c) Compound 4098

Using a method similar to the one described in Example 4, Step c, aniline 10.3 (131 mg, 0.52 mmol) gave compound 4098 (160 mg, 57% yield) as an off white solid. $^1$H-NMR (DMSO-d$_6$): δ 10.04 (s, 1H), 7.83 (d, J=8.6 Hz, 1H), 7.64 (d, J=8.2 Hz, 1H), 7.57 (dd, J=7.2, 1.7 Hz, 2H), 7.39 (dd, J=8.4, 2.0 Hz, 1H), 7.33 (dd, J=8.4, 1.7 Hz, 1H), 4.58 (t, J=5.9 Hz, 1H), 4.46 (s, 2H), 3.58-3.49 (m, 4H), 2.12-2.07 (m, 1H), 1.48 (s, 6H), 1.12-1.07 (m, 2H), 0.89-0.85 (m, 2H).

d) Compound 4082

MsCl (1.2 μL, 15 μmol) was added to an ice cold solution of alcohol 4098 (7.8 mg, 14 μmol) and Et$_3$N (4 μL, 28 μmol) in CH$_2$Cl$_2$ (1 mL). The mixture was stirred at room temperature for 2 h, diluted with saturated aqueous NaHCO$_3$ solution (20 mL) and extracted with Et$_2$O (3×30 mL). The combined organic phases were washed with brine, dried (Na$_2$SO$_4$), filtered and concentrated under reduced pressure. The crude mesylate was dissolved in THF (5 mL) and pyrrolidine (0.1 mL) was added. The mixture was heated at reflux overnight, cooled to 0° C., concentrated under reduced pressure and purified by RP-HPLC to afford, after lyophilization, compound 4082 (3.7 mg, 44% yield). $^1$H-NMR (DMSO-d$_6$): δ 10.04 (s, 1H), 9.37 (broad s, 1H), 7.85 (d, J=8.4 Hz, 1H), 7.63 (d, J=8.2 Hz, 1H), 7.62 (s, 1H), 7.56 (d, J=1.8 Hz, 1H), 7.41 (dd, J=8.6, 1.8 Hz, 1H), 7.33 (dd, J=8.2, 1.7 Hz, 1H), 4.46 (s, 2H), 3.85-3.83 (m, 2H), 3.56-3.52 (m, 2H), 3.11-3.07 (m, 2H), 2.12-2.08 (m, 1H), 2.04-1.98 (m, 1H), 1.90-1.86 (m, 2H), 1.54 (s, 6H), 1.12-1.07 (m, 2H), 0.89-0.85 (m, 2H).

Example 11

Entry 4167

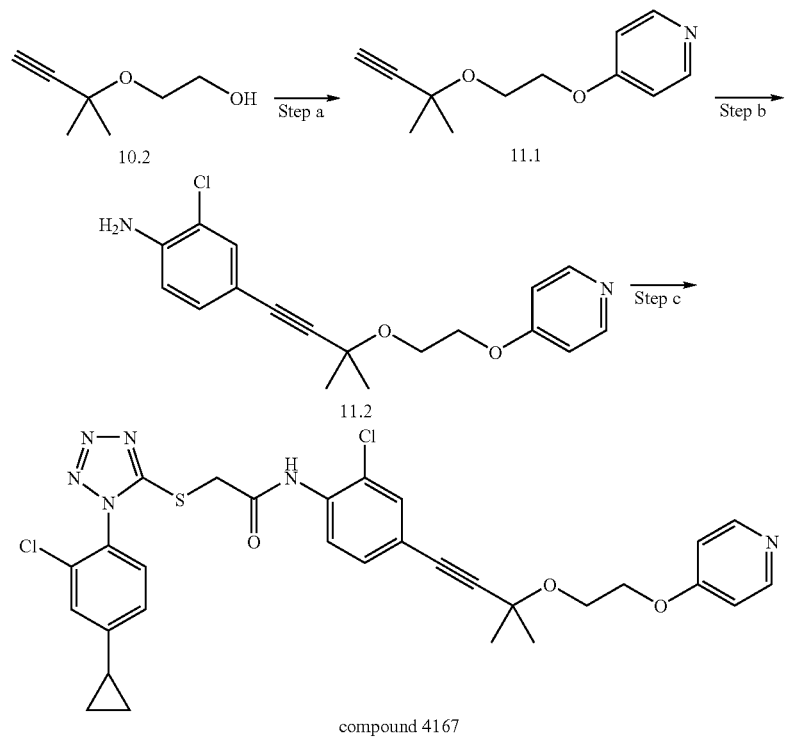

compound 4167 a) Compound 11.1

DEAD (424 mg, 2.43 mmol) was added to an ice-cold solution) solution of alcohol 10.2 (from Example 10) (240 mg, 1.87 mmol), 4-hydroxypyridine (196 mg, 2.06 mmol) and PPh$_3$ (638 mg, 2.43 mmol) in THF (20 mL). The reaction mixture was stirred for 1 h at room temperature. Silica gel was added and the volatiles were removed under reduced pressure to afford a dry powder which was applied on a pad of silica. Quick elution (hexane/EtOAc, 1/1) afforded alkyne 11.1 which was used as such in the following step.

b) Compound 11.2

Using a method similar to the one described in Example 7, Step a, compound 11.1 (88.0 mg, 0.43 mmol) and 2-chloro-4-iodoaniline (108.7 mg, 0.429 mmol) gave compound 11.2 (32.0 mg, 23% yield) as a brown oil.

c) Compound 4167

Using a method similar to the one described in Example 4, Step c, aniline 11.2 (32 mg, 97 µmol) yielded compound 4167 (24 mg, 40% yield) as an off white solid. $^1$H-NMR (DMSO-d$_6$): δ 9.99 (s, 1H), 8.65 (d, J=7.0 Hz, 2H), 7.78 (d, J=8.4 Hz, 1H), 7.57 (d, J=8.2 Hz, 1H), 7.51-7.47 (m, 4H), 7.31 (dd, J=8.4, 1.7 Hz, 1H), 7.27 (dd, J=8.3, 1.8 Hz, 1H), 4.46-4.45 (m, 2H), 4.40 (s, 2H), 3.91-3.89 (m, 2H), 2.05-2.00 (m, 1H), 1.44 (s, 6H), 1.05-1.00 (m, 2H), 0.83-0.79 (m, 2H).

Example 12

Entries 4083, 4084

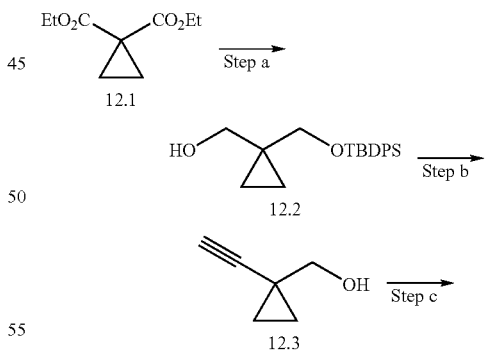

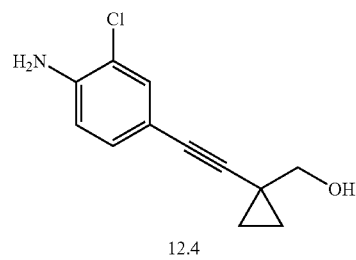

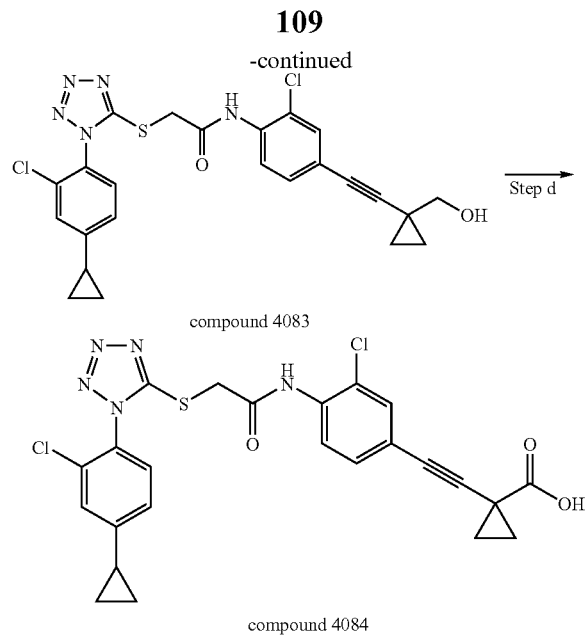

compound 4083 compound 4084 a) Compound 12.2

A solution of diethyl ester 12.1 (2.00 g, 10.7 mmol) in THF (15 mL) was slowly added to an ice-cold suspension of LiAlH$_4$ (1.35 g, 35.4 mmol) in THF (100 mL). The mixture was stirred at room temperature for 1 h then Na$_2$SO$_4$.6H$_2$O was added until no more gas was formed. The reaction mixture was filtered through Celite and concentrated under reduced pressure. The crude diol was dissolved in THF (100 mL), cooled to 0° C. and NaH (258 mg, 10.7 mmol) was added. The resulting suspension was stirred at room temperature for 1 h and tert-butyldiphenylsilyl chloride (2.95 g, 10.7 mmol) was added. The reaction mixture was stirred at room temperature for 1 h, diluted with saturated aqueous NH$_4$Cl solution (100 mL) and extracted with CH$_2$Cl$_2$ (3×100 mL). The combined organic phases were washed with brine, dried (Na$_2$SO$_4$), filtered and concentrated under reduced pressure. The crude residue was purified by flash chromatography (hexane/EtOAc, 4:1) to afford pure silylether 12.2 (1.2 g, 33% yield).

b) Compound 12.3

Dess-Martin periodinane (2.99 g, 7.05 mmol) was added to an ice-cold solution of compound 12.2 (2.40 g, 7.05 mmol) in CH$_2$Cl$_2$ (50 mL). The reaction mixture was stirred at room temperature for 1 h, diluted with saturated aqueous Na$_2$S$_2$O$_3$ solution (20 mL) and saturated aqueous NaHCO$_3$ solution (20 mL) then extracted with Et$_2$O (3×20 mL). The combined organic phases were washed with brine, dried (Na$_2$SO$_4$), filtered and concentrated under reduced pressure. The crude aldehyde was dissolved in CH$_2$Cl$_2$ (5 mL) and transferred into an ice-cold solution of PPh$_3$ (7.39 g, 7.05 mmol) and CBr$_4$ (4.67 g, 14.1 mmol) in CH$_2$Cl$_2$ (20 mL) that was previously stirred for 1 h at room temperature The resulting reaction mixture was stirred for 10 min at 0° C. and silica gel was added. The volatiles were removed under reduced pressure to afford a dry powder. The crude compound was purified by flash chromatography (hexane to hexane/EtOAc, 98:2) to afford the geminal dibromoalkene. To a cold (−78° C.) solution of this intermediate in THF (15 mL) was added n-BuLi solution (2 M in hexane, 5.6 mL). The reaction mixture was stirred for 1.5 h at −78° C., for 1 h at room temperature, then diluted with water (5 mL) and extracted with Et$_2$O (3×50 mL). The combined organic phases were washed with brine, dried (Na$_2$SO$_4$), filtered and concentrated under reduced pressure. The crude residue was purified by flash chromatography (100% hexane then 2% EtOAc/98% hexane) to afford the alkynyl-silyl ether, which was diluted in THF (10 mL) and treated with TBAF (1 M in THF, 8.46 mL, 8.46 mmol). The reaction mixture was stirred for 15 min at room temperature and concentrated under reduced pressure. The residue was purified by flash chromatography (hexane/EtOAc, 4/1) to afford compound 12.3 (240 mg, 35% yield, 4 steps).

c) Compound 12.4

Using a method similar to the one described in Example 7, Step a, compound 12.3 (240 mg, 2.50 mmol) and 2-chloro-4-iodoaniline (633 mg, 2.50 mmol) gave aniline 12.4 (370 mg, 67% yield) as a brown oil.

d) Compound 4083

Using a method similar to the one described in Example 4, Step c, aniline 12.4 (36.0 mg, 0.16 mmol) yielded compound 4083 (10 mg, 12% yield) as an off white solid. $^1$H-NMR (DMSO-d$_6$): δ 10.14 (s, 1H), 7.91 (d, J=8.6 Hz, 1H), 7.78 (d, J=8.2 Hz, 1H), 7.71 (d, J=1.7 Hz, 1H), 7.65 (d, J=1.7 Hz, 1H), 7.49-7.47 (m, 2H), 4.59 (s, 2H), 3.57 (s, 2H), 2.28-2.22 (m, 1H), 1.27-1.22 (m, 2H), 1.06-1.01 (m, 6H).

e) Compound 4084

Dess-Martin periodinane (16.9 mg, 40.0 μmol) was added to an ice-cold solution of compound 4083 (32.0 mg, 40.0 μmol) in CH$_2$Cl$_2$ (5 mL). The reaction mixture was stirred at room temperature for 1 h, diluted with saturated aqueous Na$_2$S$_2$O$_3$ solution and extracted with Et$_2$O (3×20 mL). The combined organic phases were washed with brine, dried (Na$_2$SO$_4$), filtered and concentrated under reduced pressure. The crude oil was dissolved in t-BuOH/CH$_2$Cl$_2$ (3 mL, 3:1). Aqueous pH 7.0 potassium phosphate buffer (3 mL) was added, followed by 2-methyl-2-butene (5 mL) and NaClO$_2$ (18 mg, 0.2 mmol). The reaction mixture was stirred for 3 h at room temperature, diluted with aqueous 10% HCl solution (10 mL) and extracted with CH$_2$Cl$_2$ (5×10 mL). The combined organic phases were dried (Na$_2$SO$_4$), filtered and concentrated under reduced pressure. The crude product was purified by RP-HPLC to afford, after lyophilization, the acid 4084 (2.1 mg, 10% yield) as a white solid. $^1$H-NMR (DMSO-d$_6$): δ 12.77 (s, 1H), 9.91 (s, 1H), 7.70 (d, J=8.6 Hz, 1H), 7.54 (d, J=8.3 Hz, 1H), 7.47 (d, J=1.8 Hz, 1H), 7.44 (d, J=1.8 Hz, 1H), 7.27 (dd, J=8.4, 1.8 Hz, 1H), 7.24 (dd, J=8.4, 1.7 Hz, 1H), 4.36 (s, 2H), 2.04-1.98 (m, 1H), 1.43-1.40 (m, 2H), 1.31-1.28 (m, 2H), 1.03-0.98 (m, 2H), 0.80-0.76 (m, 2H).

Example 13

Entry 4094

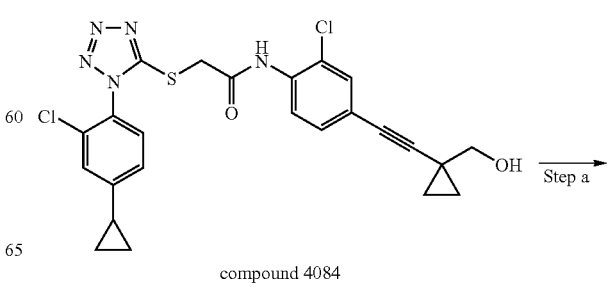

compound 4084

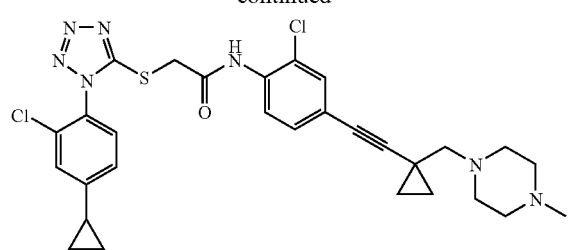
compound 4094
a) Compound 4094
Using a method analogous to the one described in Example 10, Step d, alcohol 4084 (26 mg, 0.05 mmol), afforded compound 4094 (13 mg, 43% yield) as a white solid. $^1$H-NMR (DMSO-$d_6$): δ 9.95 (s, 1H), 9.22 (broad s, 1H), 7.70 (d, J=8.2 Hz, 1H), 7.56 (d, J=8.4 Hz, 1H), 7.49 (d, J=1.8 Hz, 1H), 7.43-7.41 (m, 1H), 7.28-7.24 (m, 2H), 4.38 (s, 2H), 3.40 (s, 2H), 3.30-2.94 (m, 8H), 2.72 (s, 3H), 2.05-2.00 (m, 1H), 1.05-1.00 (m, 2H), 0.98 (s(br), 2H), 0.82-0.78 (m, 4H).
Example 14
Entry 1002
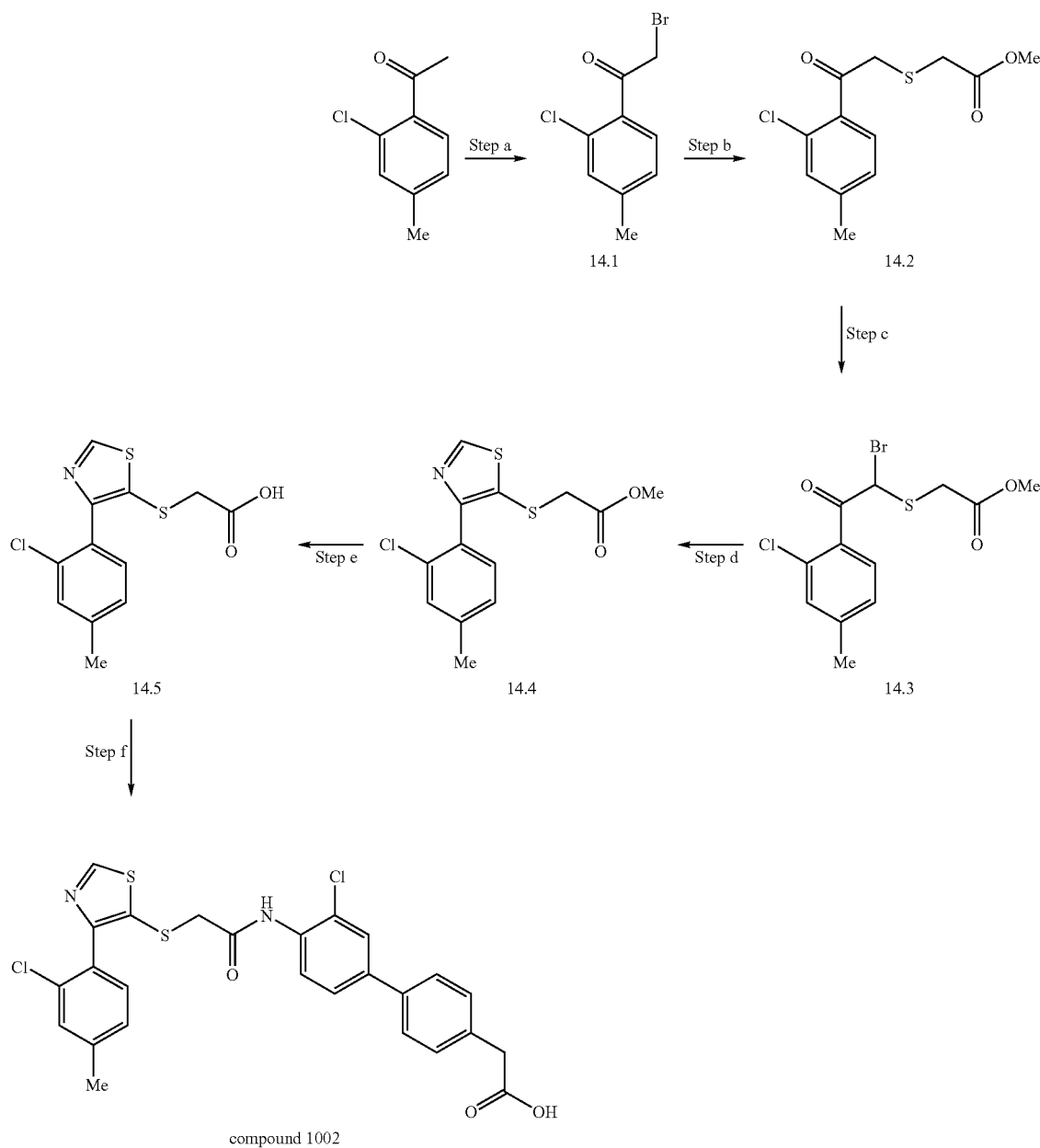

a) Compound 14.1

To a solution of 2-chloro-4-methylacetophenone (3.45 g, 20.4 mmol) in 1,4-dioxane (20 mL) was added at room temperature a solution of Br₂ (1.16 mL, 22.4 mmol) in 1,4-dioxane (50 mL) over a period of 1 h. The reaction mixture was stirred at room temperature for 20 min. The 1,4-dioxane was evaporated under reduced pressure and the residue was dissolved in Et₂O (100 mL). The resulting solution was successively washed with aqueous saturated NaHCO₃, water, and brine, dried (MgSO₄), filtered and concentrated under reduced pressure. The crude product was purified by flash chromatography (CH₂Cl₂:hexane, 7:3) to yield compound 14.1 (3.7 g, 73% yield) as a yellow oil.

b) Compound 14.2

Methyl thioglycolate (379 μL, 4.24 mmol) was added to a solution of compound 14.1 (1.00 g, 4.04 mmol) and Et₃N (619 μL, 4.44 mmol) in CH₂Cl₂. The reaction mixture was stirred at room temperature for 1 h. The mixture was then diluted with CH₂Cl₂ (100 mL), washed successively with aqueous 0.1 N HCl solution, aqueous saturated NaHCO₃, water and brine. The organic layer was dried (MgSO₄), filtered and concentrated under reduced pressure. The crude product was purified by flash chromatography (CH₂Cl₂:(CH₃)₂CO, 95:5) to afford compound 14.2 (1.1 g, 100% yield) as a pale yellow solid.

c) Compound 14.3

To a solution of compound 14.2 (1.07 g, 3.93 mmol) in AcOH (30 mL) was added at room temperature a solution of bromine (202 μL, 3.93 mmol) in AcOH (10 mL) over a period of 30 min. The reaction mixture was stirred at room temperature for 30 min and poured in ether (200 mL). The organic phase was successively washed with water, aqueous saturated NaHCO₃, water and brine, dried (MgSO₄), filtered and concentrated under reduced pressure. The crude product was purified by flash chromatography (CH₂Cl₂) to afford compound 14.3 (1.23 g, 89% yield) as a clear oil.

d) Compound 14.4

Thioformamide (521.3 mg, 8.53 mmol) was added to a solution of compound 14.3 (300.0 mg, 853.1 μmol) in iPrOH (20 mL). The reaction mixture was stirred at 60° C. for 1 h then was concentrated under reduced pressure. The residue was purified by flash chromatography (CH₂Cl₂:(CH₃)₂CO, 95:5) to afford compound 14.4 (207 mg, 78% yield) as a yellow oil.

e) Compound 14.5

Ester 14.4 (207 mg, 660.9 μmol) was dissolved in DMSO (6.0 mL) and aqueous 1 N NaOH (2.0 mL, 2.0 mmol) solution was added to the solution. The reaction mixture was stirred at room temperature for 1 h and acidified (pH=2) with TFA. The mixture was then diluted with EtOAc (100 mL) and successively washed with water and brine, dried (MgSO₄), filtered and concentrated under vacuum to give compound 14.5 (194 mg, 98% yield).

f) Compound 1002

PCl₃ (10.2 μL, 116 μmol) was added to an ice-cold solution of compound 14.5 (35.0 mg, 116 μmol) and compound 2.5 (from Example 2) (35.4 mg, 128 μmol) in pyridine (3.0 mL). The reaction mixture was stirred at room temperature for 30 min. Water (few drops) was added and the mixture was concentrated under reduced pressure. The crude ester was dissolved in DMSO (3.0 mL) and aqueous 1 N NaOH (1.0 mL, 1.0 mmol) solution was added to the solution. The reaction mixture was stirred at room temperature for 1 h and acidified (pH=2) with TFA. The solution was purified by RP-HPLC and the pure fractions were concentrated to give compound 1002 (6.2 mg, 10% yield) as an orange solid. ¹H NMR (DMSO-d₆) δ 12.27 (broad s, 1H), 9.65 (s, 1H), 9.22 (s, 1H), 7.83 (d, J=8.4 Hz, 1H), 7.77 (d, J=1.6 Hz, 1H), 7.65-7.63 (m, 3H), 7.38-7.30 (m, 4H), 7.16 (d, J=7.7 Hz, 1H), 3.76 (s, 2H), 3.61 (s, 2H), 2.34 (s, 3H).

Example 15

Entry 1003

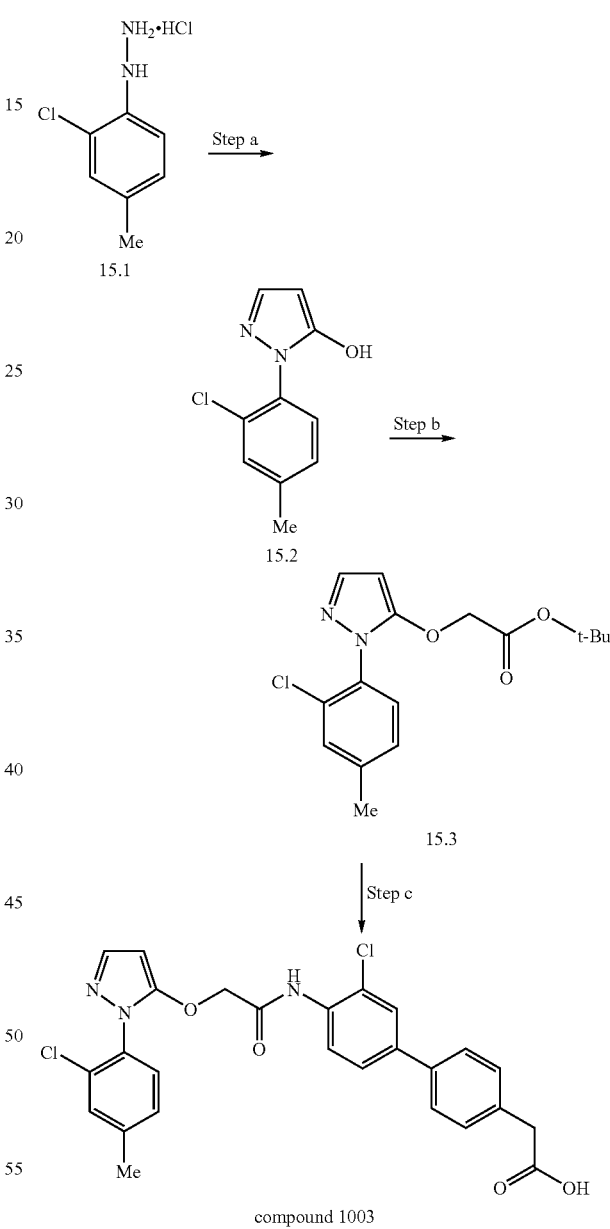

compound 1003 a) Compound 15.2

A mixture of compound 15.1 (400 mg, 2.07 mmol) and methyl 3,3-dimethoxypropionate (323 μL, 2.28 mmol) in MeOH (5.0 mL) was stirred at 70° C. for 24 h. The reaction mixture was concentrated under reduced pressure and the residue purified by flash chromatography (CH₂Cl₂:(CH₃)₂CO, 95:5) to afford compound 15.2 (104 mg, 24% yield) as a yellow solid.

b) Compound 15.3

To a solution of compound 15.2 (39.4 mg, 188.8 µmol) and tert-butyl bromoacetate (30.7 µL, 207.7 µmol) in DMF (3.0 mL) at room temperature was added potassium carbonate (39.1 mg, 283.3 µmol). The reaction mixture was stirred at room temperature for 16 h, then was diluted with EtOAc (50 mL) and successively washed with water and brine, dried (MgSO$_4$), filtered and concentrated under reduced pressure. The crude product was purified by flash chromatography (CH$_2$Cl$_2$:(CH$_3$)$_2$CO, 95:5) to afford compound 15.3 (21.4 mg, 35% yield) as a yellow oil.

c) Compound 1003

TFA (1.00 mL, 13.0 mmol) was added dropwise to a solution of compound 15.3 (13.2 mg, 41.0 µmol) in CH$_2$Cl$_2$ (2.0 mL) at room temperature. The reaction mixture was stirred for 16 h and then concentrated under vacuum. PCl$_3$ (10.2 µL, 116.7 µmol) was then added to an ice-cold solution of the resulting acid and compound 2.5 (Example 2) (11.3 mg, 41.0 µmol) in pyridine (3.0 mL). The reaction mixture was stirred at room temperature for 30 min. Water (few drops) was added and the mixture was concentrated under reduced pressure. The crude ester was dissolved in DMSO (2.0 mL) and aqueous 1 N NaOH (1.0 mL, 1.0 mmol) solution was added to the solution. The reaction mixture was stirred at room temperature for 1 h and acidified (pH=2) with TFA. The solution was purified by RP-HPLC and the pure fractions were concentrated to give compound 1003 (7.6 mg, 36% yield) as an orange solid. $^1$H NMR (DMSO-d$_6$) δ 12.36 (broad s, 1H), 9.36 (s, 1H), 8.00 (d, J=8.4 Hz, 1H), 7.79 (d, J=2.2 Hz, 1H), 7.66 (d, J=1.9 Hz, 1H), 7.63 (d, J=8.2 Hz, 2H), 7.52 (d, J=2.0 Hz, 1H), 7.50 (s, 1H), 7.44 (d, J=8.0 Hz, 1H), 7.34 (d, J=8.2 Hz, 2H), 7.31 (d, J=8.2 Hz, 1H), 4.88 (s, 2H), 3.60 (s, 2H), 2.39 (s, 3H).

Example 16

Entry 1004

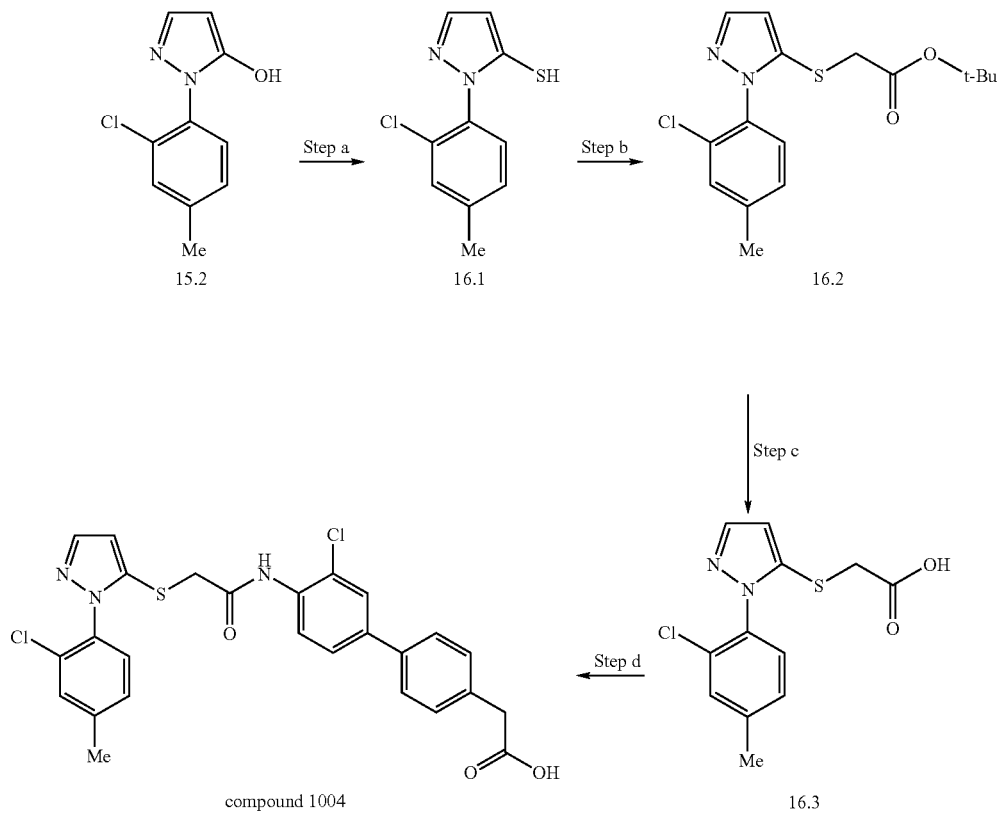

a) Compound 16.1

A mixture of compound 15.2 (250 mg, 1.20 mmol) and Lawesson's reagent (485 mg, 1.20 mmol) in toluene (15 mL) was heated under reflux for 4 h. The reaction mixture was then concentrated under reduced pressure and the residue purified by flash chromatography (CH$_2$Cl$_2$:(CH$_3$)$_2$CO, 95:5) to afford compound 16.1 (86 mg, 32% yield) as a yellow oil.

b) Compound 16.2

To a solution of 16.1 (86.1 mg, 383 µmol) in DMF (5.0 mL) at 0° C. was added K$_2$CO$_3$ (105.9 mg, 766.3 µmol). After stirring for 30 min, tert-butyl bromoacetate (62.2 µL, 421 µmol) was added and the reaction mixture was stirred at 0° C. for 1 h and then allowed to warm to room temperature and stirred for 2 h. EtOAc (50 mL) was added and the mixture was washed with water and brine, dried (MgSO$_4$), filtered and concentrated under reduced pressure. The residue was purified by flash chromatography (CH$_2$Cl$_2$:(CH$_3$)$_2$CO, 95:5) to afford compound 16.2 (64.0 mg, 49% yield) as a colorless oil.

c) Compound 16.3

TFA (1.00 mL, 13.0 mmol) was added dropwise to a solution of compound 16.2 (58.4 mg, 172.3 µmol) in CH$_2$Cl$_2$ (3.0 mL) at room temperature. The reaction mixture was stirred for 16 h and then concentrated under reduced pressure to afford compound 16.3 (48.7 mg, 100% yield).

d) Compound 1004

PCl₃ (10.2 μL, 116.7 μmol) was added to an ice-cold solution of compound 16.3 (29.0 mg, 102.6 μmol) and compound 2.5 (Example 2) (32.7 mg, 112.8 μmol) in pyridine (3.0 mL). The reaction mixture was stirred at room temperature for 30 min. Water (few drops) was added and the mixture was concentrated under reduced pressure. The crude ester was dissolved in DMSO (3.0 mL) and aqueous 1 N NaOH (1.0 mL, 1.0 mmol) solution was added to the solution. The reaction mixture was stirred at room temperature for 1 h and acidified (pH=2) with TFA. The solution was purified by RP-HPLC and the pure fractions were concentrated to give compound 1004 (15.8 mg, 29% yield) as a white solid. ¹H NMR (DMSO-d₆) δ 12.37 (broad s, 1H), 9.65 (s, 1H), 7.81 (d, J=8.4 Hz, 1H), 7.77 (d, J=2.0 Hz, 1H), 7.73 (d, J=1.9 Hz, 1H), 7.65-7.62 (m, 3H), 7.50 (s, 1H), 7.38 (d, J=8.1 Hz, 1H), 7.34 (d, J=8.3 Hz, 2H), 7.24 (dd, J=8.0, 1.0 Hz, 1H), 6.66 (d, J=1.7 Hz, 1H), 3.75 (s, 2H), 3.61 (s, 2H), 2.37 (s, 3H).

Example 17

Entry 1005

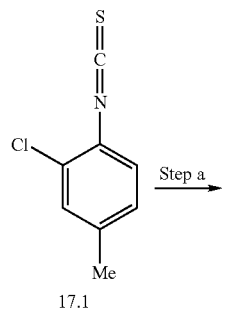
17.1

Step a

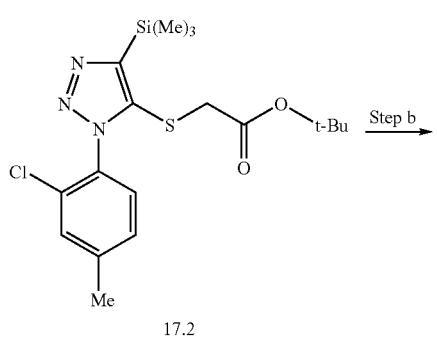
17.2

Step b

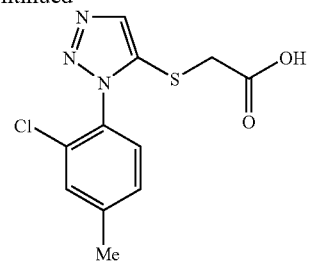
17.3

Step c

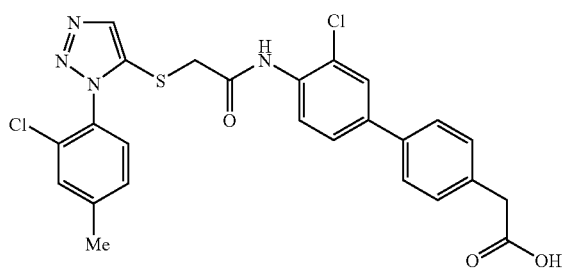
compound 1005 a) Compound 17.2

To a cold (−78° C.) solution of (trimethylsilyl)diazomethane (2.0 M in hexane) (6.53 mL, 13.07 mmol) in THF (50 mL) was added dropwise 2.5 M n-BuLi in hexane (5.23 mL, 13.07 mmol). After 20 min, a solution of compound 17.1 (2.0 g, 10.89 mmol) in THF (15 mL) was added dropwise and the reaction mixture was stirred at −78° C. for 1 h. tert-Butyl bromoacetate (1.93 mL, 13.07 mmol) was then added and the mixture was stirred at −78° C. for 30 min and then at 0° C. for another 30 min. The mixture was treated with ice-water (50 mL) and Et₂O (300 mL) was added. The mixture was washed with water and brine, dried (MgSO₄), filtered and concentrated under reduced pressure. The crude product was purified by flash chromatography (CH₂Cl₂:(CH₃)₂CO, 95:5) to afford compound 17.2 (3.7 g, 83% yield) as a yellow oil.

b) Compound 17.3

A mixture of compound 17.2 (1.0 g, 2.43 mmol) and aqueous 10% KOH solution (12.5 mL) in MeOH (25 mL) was heated under reflux for 2 h. The MeOH was removed under reduced pressure and the mixture was neutralized with aqueous 1 N HCl solution. The aqueous phase was then extracted with Et₂O (2×10 mL). The combined organic extracts were washed with brine, dried (MgSO₄), filtered and concentrated under reduced pressure to give compound 17.3 (683 mg, 99% yield) as a yellow solid.

c) Compound 1005

Using a method similar to the one described for Example 16, Step d, compound 17.3 (50.0 mg, 176.2 μmol) gave compound 1005 (42.7 mg, 46% yield) as a white solid. ¹H NMR (DMSO-d₆) δ 12.36 (broad s, 1H), 9.75 (s, 1H), 8.06 (s, 1H), 7.79-7.77 (m, 2H), 7.65-7.61 (m, 4H), 7.50 (d, J=8.0 Hz, 1H), 7.36-7.32 (m, 3H), 3.87 (s, 2H), 3.61 (s, 2H), 2.41 (s, 3H).

Example 18

Entry 1007

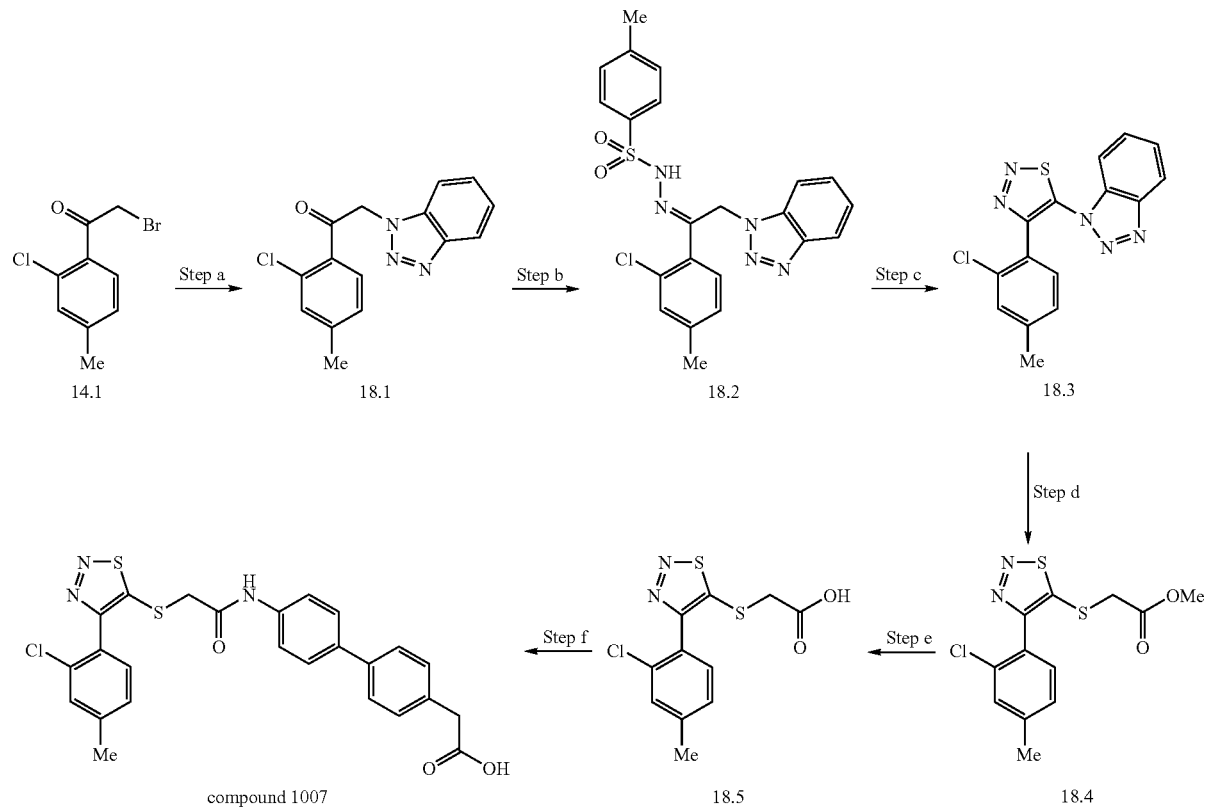

a) Compound 18.1

A mixture of compound 14.1 (Example 14) (1.00 g, 4.04 mmol), benzotriazole (529.4 mg, 4.44 mmol) and $K_2CO_3$ (558 mg, 4.04 mmol) in toluene (100 mL) was heated at reflux for 16 h. The cooled reaction mixture was washed with water and brine, dried ($MgSO_4$), filtered and concentrated under reduced pressure. The residue was purified by flash chromatography ($CH_2Cl_2$:($CH_3$)$_2$CO, 97:3) to afford compound 18.1 (781 mg, 68% yield) as a yellow oil.

b) Compound 18.2

A solution of compound 18.1 (781 mg, 2.73 mmol) and p-toluenesulfonyl hydrazide (509 mg, 2.73 mmol) in benzene (25.0 mL) was heated at reflux for 24 h. The mixture was cooled and concentrated under reduced pressure to give compound 18.2 (1.20 g, 97% yield) as a beige solid.

c) Compound 18.3

A solution of compound 18.2 (1.20 g, 2.65 mmol) in $SOCl_2$ (25 mL) was stirred at 60° C. for 8 h. The reaction mixture was then concentrated under reduced pressure and the residue purified by flash chromatography ($CH_2Cl_2$) to afford compound 18.3 (480 mg, 55% yield) as a yellow solid.

d) Compound 18.4

NaH (60% in oil) (33.5 mg, 838 μmol) was added to a solution of compound 18.3 (229 mg, 698 μmol) and methylthioglycolate (74.9 μL, 838 μmol) in DMF (7 mL) at room temperature. The reaction mixture was stirred for 2 h, quenched with aqueous 0.1 N HCl solution (2 mL) and then diluted with EtOAc (50 mL). The solution was successively washed with water and brine, dried ($MgSO_4$), filtered and concentrated under reduced pressure. The residue was purified by flash chromatography (hexane: EtOAc, 8:2) to afford compound 18.4 (162 mg, 74% yield) as a yellow oil.

e) Compound 18.5

Aqueous 1.0 N NaOH solution (800 μL, 800 μmol) was added to a solution of compound 18.4 (162 mg, 514 μmol) in DMF (5.0 mL). The reaction mixture was stirred at room temperature for 30 min. The mixture was then neutralized with aqueous 1.0 N HCl solution (800.0 μL) and diluted with EtOAc (60 mL). The solution was successively washed with water and brine, dried ($MgSO_4$), filtered and concentrated under reduced pressure to give compound 18.5 (149 mg, 97% yield) as a yellow oil.

f) Compound 1007

To a solution of compound 18.5 (75.0 mg, 249 μmol) in $CH_2Cl_2$ (5 mL) at room temperature was added $(COCl)_2$ (43.5 μL, 499 μmol) followed by DMF (5 μL). The reaction mixture was stirred for 15 min and was then concentrated under reduced pressure. The resulting acyl chloride was dissolved in THF (3 mL) and a solution of compound 2.5 (Example 2) (82.5 mg, 299 μmol) in THF (2 mL) was added followed by pyridine (60.5 μL, 748 μmol). The reaction mixture was stirred for 10 min and then quenched with a few drops of aqueous 0.1 N HCl solution. The reaction mixture was then concentrated under reduced pressure. The intermediate ester was diluted in DMSO (6 mL) and treated with aqueous 1.0N NaOH solution (1.0 mL, 1.0 mmol). The reaction mixture was stirred for 3 h and then neutralized with TFA. The solution was purified by RP-HPLC and the pure fractions were concentrated to give compound 1007 (32.4 mg, 24% yield) as a white solid. $^1$H NMR (DMSO-$d_6$) δ 12.34 (broad s, 1H), 10.00 (s, 1H), 7.81-7.79 (m, 2H), 7.66-7.63 (m, 3H), 7.53 (s, 1H), 7.45 (d, J=7.8 Hz, 1H), 7.36-7.32 (m, 3H), 4.21 (s, 2H), 3.61 (s, 2H), 2.40 (s, 3H).

Example 19

Entry 1008

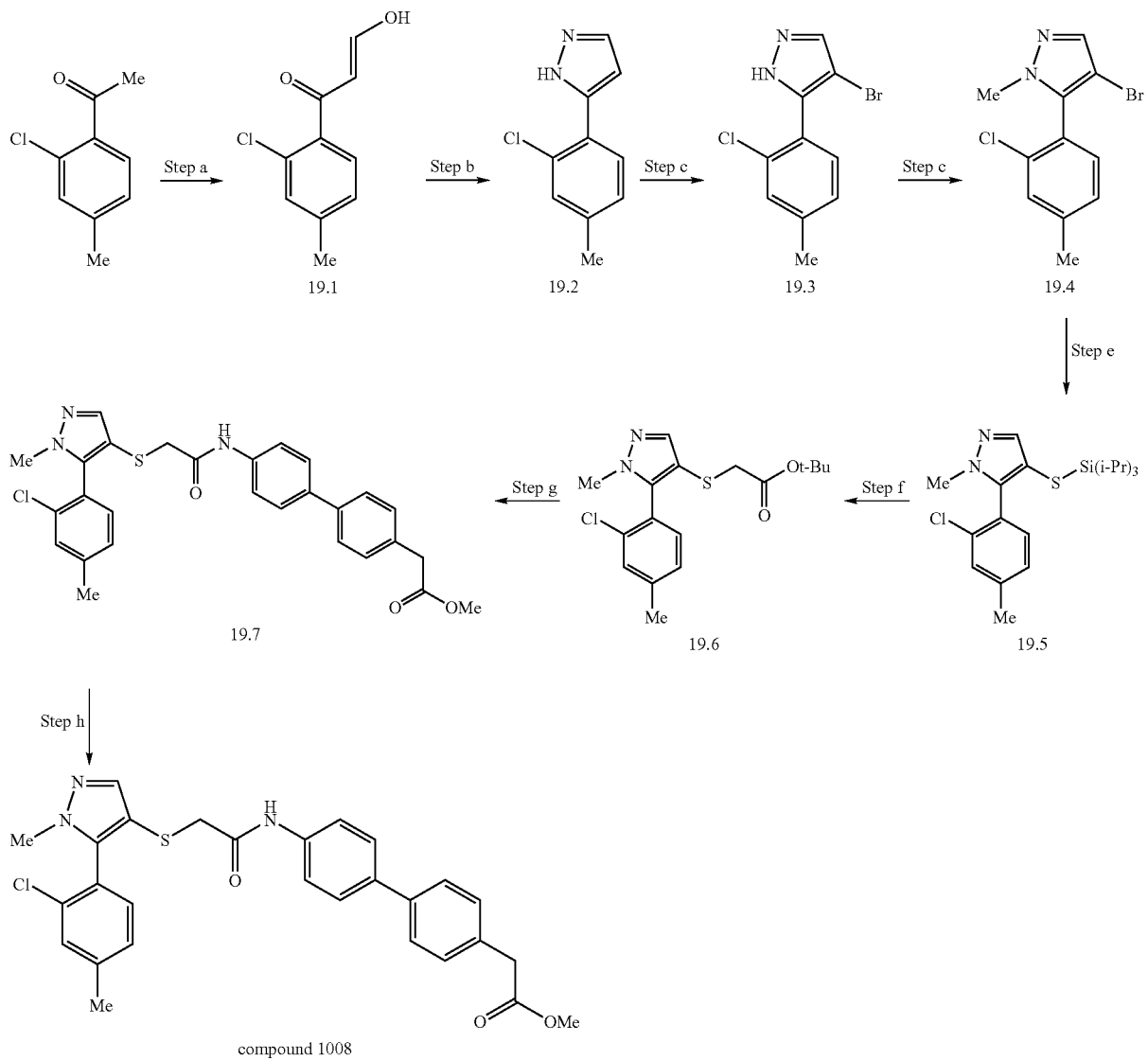

compound 1008 a) Compound 19.1

To a suspension of MeONa (384 mg, 7.12 mmol) in THF (18 mL) at room temperature was added ethyl formate (574.9 µL, 7.12 mmol) followed by a solution of 2-chloro-4-methylacetophenone (1.00 g, 5.93 mmol) in THF (6.0 mL). The reaction mixture was stirred at room temperature for 16 h, and then aqueous 1.0 N NaOH solution (60 mL) was added. The aqueous phase was washed with Et$_2$O (2×2 mL). These extracts were discarded, and the aqueous phase was acidified with aqueous 1.0 N HCl solution (65 mL). The mixture was then extracted with Et$_2$O (3×40 mL). The combined organic extracts were washed with water and brine, dried (MgSO$_4$), filtered, and concentrated under reduced pressure to give compound 19.1 (1.11 g, 95% yield) as a yellow oil.

b) Compound 19.2

Hydrazine hydrate (193.2 µL, 6.20 mmol) was added dropwise to a cold (0° C.) solution of compound 19.1 (1.11 g, 5.64 mmol) in ethanol (15.0 mL). The cooling bath was then removed and the reaction mixture was stirred at room temperature for 3 h. The mixture was concentrated under reduced pressure and the residue diluted in CH$_2$Cl$_2$ (150 mL). The solution was washed with brine, dried (MgSO$_4$), filtered and concentrated under reduced pressure. The crude product was purified by flash chromatography (CH$_2$Cl$_2$:(CH$_3$)$_2$CO, 95:5) to afford compound 19.2 (671 mg, 62% yield) as a yellow solid.

c) Compound 19.3

A solution of bromine (198 µL, 3.83 mmol) in CH$_2$Cl$_2$ (10 mL) was added dropwise to a solution of compound 19.2 (671 mg, 3.48 mmol) in CH$_2$Cl$_2$ (20 mL). The reaction mixture was stirred at room temperature for 1 h. The mixture was diluted with CH$_2$Cl$_2$ (60 mL) and the resulting solution was successively washed with water, aqueous saturated NaHCO$_3$ solution and brine, dried (MgSO₄), filtered and concentrated under reduced pressure. The crude product was purified by flash chromatography (CH₂Cl₂:(CH₃)₂CO, 95:5) to afford compound 19.3 (382 mg, 40% yield) as a yellow solid.

d) Compound 19.4

NaH (60% in oil) (59.9 mg, 1.50 mmol) was added to a cold (0° C.) solution of compound 19.3 (369.6 mg, 1.36 mmol) in DMF (5 mL). The reaction mixture was stirred at 0° C. for 30 min and then MeI (93.2 µL, 1.50 mmol) was added. The mixture was warmed to room temperature and stirred for 1 h. The reaction mixture was diluted with EtOAc (100 mL) and washed with water and brine, dried (MgSO₄), filtered and concentrated under reduced pressure. The crude product was purified by flash chromatography (CH₂Cl₂:(CH₃)₂CO, 95:5) to afford compound 19.4 (363 mg, 93% yield; 1.6:1 mixture of isomers) as a yellow solid.

e) Compound 19.5

To a cold (−78° C.) solution of compound 19.4 (75.0 mg, 262 µmol) in THF (4 mL) was added 2.5 M n-BuLi in hexane (115.6 µL, 288.9 µmol). After 15 min, a solution of (i-Pr₃SiS)₂ (199.0 mg, 525.3 µmol) in THF (1 mL) was added via cannula to the reaction mixture at −78° C. The reaction mixture was stirred for 15 min and then the cooling bath was removed and the solution stirred for 3 h. CH₂Cl₂ (50 mL) was added and the mixture was washed with water and brine, dried (MgSO₄), filtered and concentrated under reduced pressure to afford compound 19.5 (46.4 mg, 45% yield).

f) Compound 19.6

TBAF (1.0 M in THF) (294 µL, 294 µmol) was added to a solution of compound 19.5 (46.4 mg, 117 µmol) and tert-butyl bromoacetate (43.4 µL, 294 µmol) in DMF (3 mL). The reaction mixture was stirred for 30 min, quenched with water (10 mL), and diluted with EtOAc (60 mL). The organic phase was washed with water and brine, dried (MgSO₄), filtered and concentrated under reduced pressure. The crude product was purified by flash chromatography (CH₂Cl₂:(CH₃)₂CO, 95:5) to afford compound 19.6 (34.8 mg, 84% yield) as a yellow oil.

g) Compound 19.7

TFA (1.0 mL, 13.0 mmol) was added dropwise to a solution of compound 19.6 (34.8 mg, 98.6 µmol) in CH₂Cl₂ (2 mL) at room temperature. The reaction mixture stirred for 8 h and then concentrated under reduced pressure. The intermediate acid was diluted in CH₂Cl₂ (5 mL) and (COCl)₂ (25.8 µL, 295.8 µmol) was added followed by DMF (5 µL). The reaction mixture was stirred for 15 min and CH₂Cl₂ was removed under reduced pressure. The intermediate acyl chloride was dissolved in THF (3 mL) and a solution of compound 2.5 (Example 2) (40.8 mg, 147.9 µmol) in THF (1 mL) was added followed by pyridine (23.9 µL, 295.8 µmol). The reaction mixture was stirred for 1 h and then concentrated under reduced pressure to give compound 19.7 (50 mg, 91% yield).

h) Compound 1008

Ester 19.7 (50 mg, 90 µmol) was dissolved in DMSO (4 mL) and aqueous 1 N NaOH (500 µL, 500 µmol) solution was added to the solution. The reaction mixture was stirred at room temperature for 1 h and then acidified (pH=2) with TFA. The solution was purified by RP-HPLC and the pure fractions containing the desired isomer (slowest eluting isomer) were concentrated to give compound 1008 (18.8 mg, 39% yield). ¹H NMR (DMSO-d₆) δ 12.35 (broad s, 1H), 9.43 (s, 1H), 7.88 (d, J=8.6 Hz, 1H), 7.76 (d, J=2.0 Hz, 1H), 7.65-7.62 (m, 4H), 7.41 (s, 1H), 7.35 (d, J=8.0 Hz, 2H), 7.28 (d, J=7.8 Hz, 1H), 7.17 (d, J=7.2 Hz, 1H), 3.61 (s, 2H), 3.56 (s, 3H), 3.49 (s, 2H), 2.33 (s, 3H).

Example 20

Entry 1009

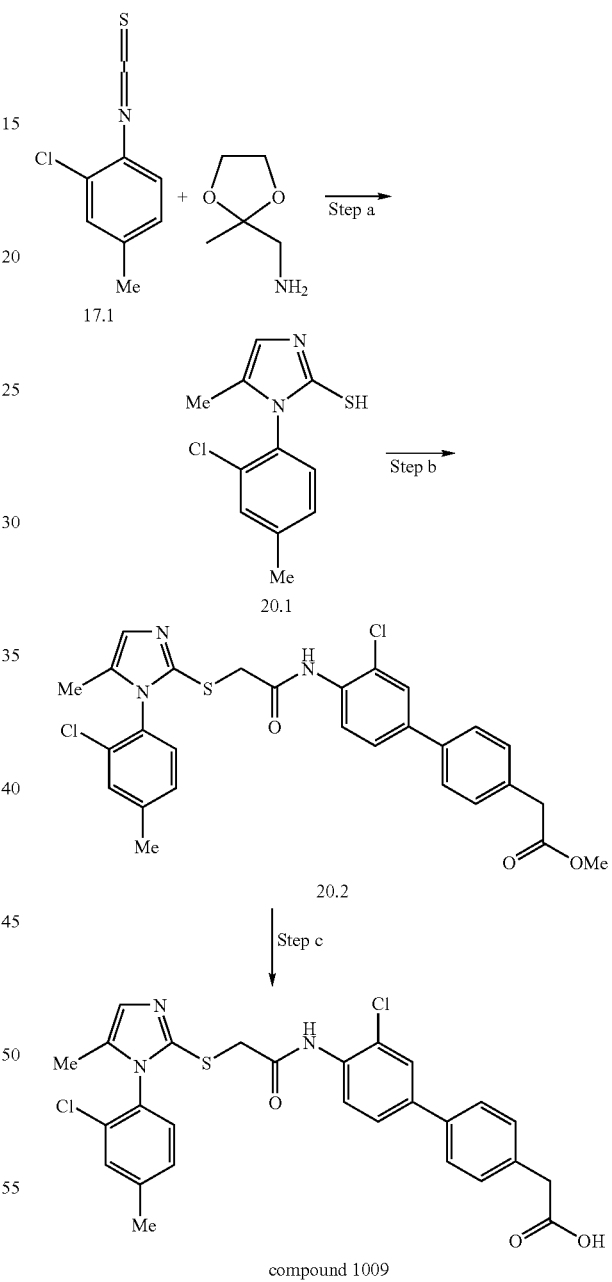

compound 1009 a) Compound 20.1

1-Amino-2,2-ethylenedioxypropane (2.00 g, 17.0 mmol) was added to a cooled (0° C.) solution of compound 17.1 (Example 17) (3.17 g, 17.1 mmol) in ethanol (14 mL). The reaction mixture was stirred at reflux for 30 min and then cooled to 0° C. (product precipitated as a white solid). Aqueous 12 N HCl solution (1.4 mL) was added and the mixture was again heated under reflux for 1 h (solution after heating). The solution was cooled to room temperature and the precipitate was collected by suction filtration to give compound 20.1 (2.01 g, 49% yield) as a white solid.

b) Compound 20.2

To a solution of compound 20.1 (90.3 mg, 378 μmol) in DMF (5 mL) was added $K_2CO_3$ (157 mg, 1.13 mmol) followed by the methyl ester analog of compound 2.6 (Example 2) (150 mg, 378 μmol). The reaction mixture was stirred at room temperature for 2 h. The mixture was then diluted with EtOAc (100 mL) and successively washed with water and brine, dried ($MgSO_4$), filtered and concentrated under reduced pressure. The crude product was purified by flash chromatography ($CH_2Cl_2$:($CH_3$)$_2$CO, 95:5) to afford compound 20.2 (172 mg, 82% yield) as a white solid.

c) Compound 1009

Using a method similar to the one described in Example 19, Step h, compound 20.2 (165 mg, 298 μmol) gave compound 1009 (160 mg, 99% yield) as a white solid. $^1$H NMR (DMSO-$d_6$) δ 10.14 (s, 1H), 7.95 (d, J=8.4 Hz, 1H), 7.79 (d, J=2.0 Hz, 1H), 7.66-7.63 (m, 4H), 7.50 (d, J=8.1 Hz, 1H), 7.37-7.33 (m, 4H), 4.03 (s, 2H), 3.63 (s, 2H), 2.42 (s, 3H), 1.98 (s, 3H).

Example 21

Entry 1010

The solvent was then carefully removed under reduced pressure and the residue dissolved in MeOH (100.0 mL). $Ag_2O$ (4.35 g, 18.8 mmol) was added to the solution and the reaction mixture was stirred at 0° C. for 1 h and then heated at 60° C. for 2 h. The reaction mixture was then cooled to room temperature and filtered through diatomaceous earth. The filtrate was concentrated under vacuum and the residue purified by flash chromatography (hexane:EtOAc, 8:2) to afford compound 21.1 (588 mg, 16% yield).

b) Compound 21.2 tert-Butoxybis(dimethylamino)methane (685 μL, 3.32 mmol) was added to a solution of compound 21.1 (589 mg, 2.96 mmol) in THF (7 mL) at room temperature. The reaction mixture was stirred at room temperature for 2 h then was concentrated under reduced pressure. The residue was purified by flash chromatography (hexane:EtOAc, 1:1) to afford compound 21.2 (38.3 mg, 72% yield) as an orange oil.

c) Compound 21.3

Hydrazine monohydrate (113 μL, 2.33 mmol) was added to a solution of compound 21.2 (538 mg, 2.12 mmol) in ethanol (5 mL). The reaction mixture was stirred at reflux for 3 h. The mixture was then concentrated under reduced pressure to give compound 21.3 (439 mg, 93% yield) as a yellow solid.

d) Compound 21.4

$BBr_3$ (1.0 M in $CH_2Cl_2$, 8.12 mL, 8.12 mmol) was added to a cold (0° C.) solution of compound 21.3 (452.3 mg, 2.03

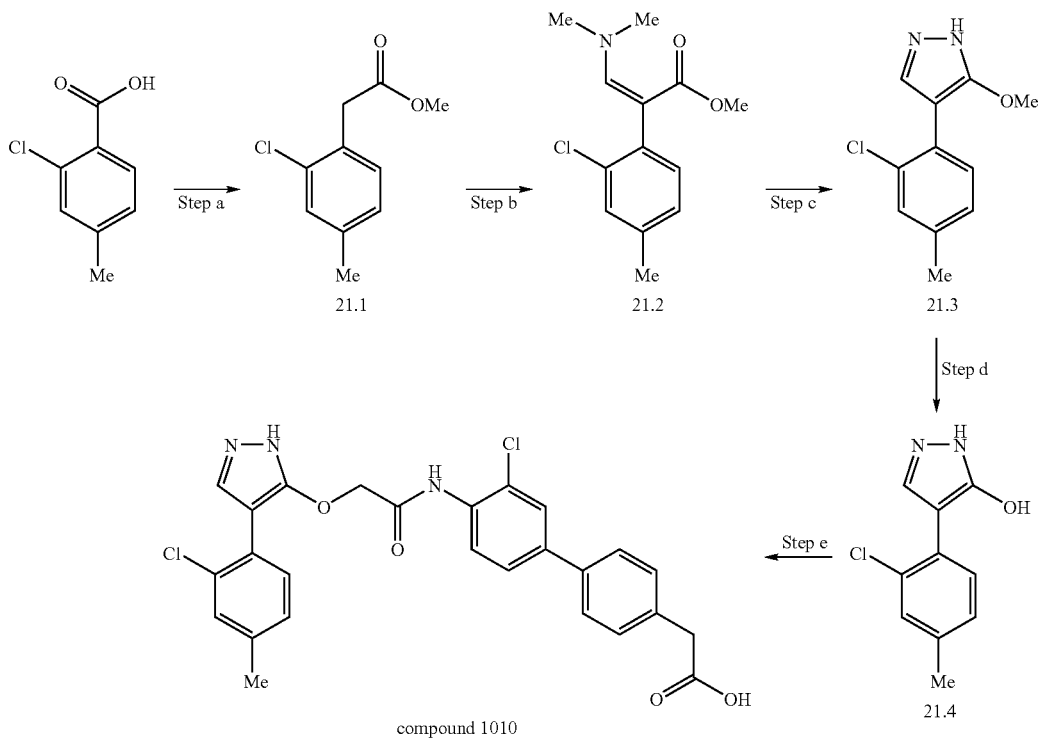

a) Compound 21.1

To a solution of 2-chloro-4-methylbenzoic acid (3.21 g, 18.8 mmol) in $CH_2Cl_2$ (80 mL) at room temperature was added $(COCl)_2$ (3.28 mL, 37.6 mmol) followed by DMF (100 μL). The reaction mixture was stirred for 3 h then was concentrated under reduced pressure. The intermediate acyl chloride was dissolved in THF (40 mL) and added dropwise to a cold (0° C.) solution of $CH_2N_2$ in $Et_2O$ (ca. 0.6 M, 75 mL). The reaction mixture was stirred at room temperature for 4 h.

mmol) in $CH_2Cl_2$ (20.0 mL). The reaction mixture was heated to room temperature and stirred for 3 h. The mixture was then cooled to 0° C. and quenched with MeOH (5 mL). The solution was diluted with $CH_2Cl_2$ (100 mL) and successively washed with water, aqueous saturated $NaHCO_3$ and brine, dried ($MgSO_4$), filtered and concentrated under reduced pressure to give compound 21.4 (238 mg, 56% yield).

e) Compound 1010

To a solution of compound 21.4 (60.0 mg, 287.6 µmol) in DMF (5 mL) at room temperature was added CsCO$_3$ (281.1 mg, 862.7 µmol) followed by compound 2.6 (Example 2) (114.1 mg, 287.6 µmol). The reaction mixture was stirred at 50° C. for 2 h. The mixture was then filtered through diatomaceous earth and to the filtrate was added aqueous 1 N NaOH solution (1.0 mL, 1.0 mmol). The reaction mixture was stirred at room temperature for 30 min and acidified (pH=2) with TFA. The solution was purified by RP-HPLC and the pure fractions were concentrated to give compound 1010 (6.8 mg, 5% yield) as a yellow solid. $^1$H NMR (DMSO-d$_6$) δ 12.40 (broad s, 1H), 9.20 (s, 1H), 8.13 (d, J=8.6 Hz, 1H), 7.79 (d, J=1.9 Hz, 1H), 7.67-7.62 (m, 4H), 7.42 (d, J=7.9 Hz, 1H), 7.38 (s, 1H), 7.34 (d, 8.2 Hz, 2H), 7.21 (d, J=7.7 Hz, 1H), 4.64 (s, 2H), 3.60 (s, 2H), 2.34 (s, 3H).

Example 22

Entry 1015

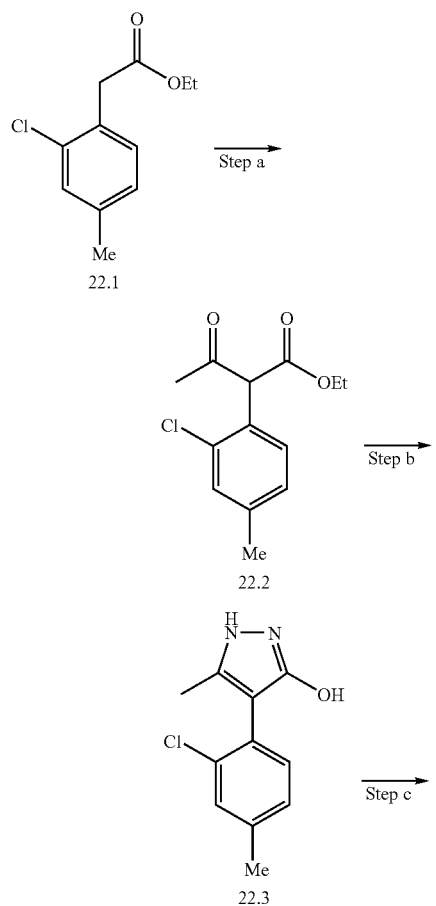

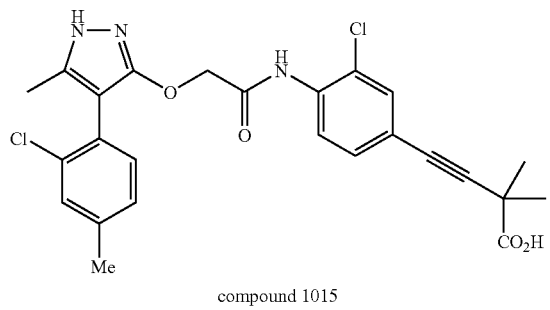

compound 1015 a) Compound 22.2

To a cold (−78° C.) solution of compound 22.1 (2.50 g, 11.8 mmol) in THF (50 mL) was added 1.0 M LiHMDS in hexane (24.7 mL, 24.7 mmol). The reaction mixture was stirred at −78° C. for 1 h and then acetic anhydride (1.33 mL, 14.1 mmol) was added dropwise. The reaction mixture was warmed to room temperature and stirred for 30 min. The mixture was then poured in aqueous 1 N HCl solution (50 mL), and extracted with EtOAc (2×50 mL). The organic extracts were washed with water, brine, dried (MgSO$_4$), filtered and concentrated under vacuum. The crude product was purified by flash chromatography (hexane:EtOAc, 8:2) to afford compound 22.2 (2.37 g, 79% yield) as a clear oil.

b) Compound 22.3

Hydrazine hydrate (122 µL, 3.93 mmol) was added to a solution of compound 22.2 (500 mg, 1.96 mmol) in ethanol (3.0 mL). The reaction mixture was stirred under reflux for 2 h. The reaction mixture was then cooled to room temperature and the white precipitate was collected under suction filtration to give compound 22.3 (255 mg, 59% yield).

c) Compound 1015

Using a method analogous to the one described in Example 2, Step g, compound 22.3 (24.8 mg, 111 µmol) and benzyl 4-[4-(2-bromoacetamido)-3-chlorophenyl]-2,2-dimethyl-but-3-ynoate (50.0 mg, 111 µmol) (prepared from the benzyl ester analog of compound 4.3 and bromoacetyl bromide using a method similar to the one described in Example 2, Step f) gave compound 1015 (19.1 mg, 34% yield) as a white solid. $^1$H NMR (DMSO-d$_6$) δ 12.88 (broad s, 1H), 11.96 (s, 1H), 9.18 (s, 1H), 8.11 (d, J=8.5 Hz, 1H), 7.49 (d, J=2.0 Hz, 1H), 7.36 (d, J=1.8 Hz, 1H), 7.34 (s, 1H), 7.27 (d, J=7.8 Hz, 1H), 7.17 (d, J=7.8 Hz, 1H), 4.79 (s, 2H), 2.32 (s, 3H), 2.07 (s, 3H), 1.45 (s, 6H).

Example 23

Entry 1017

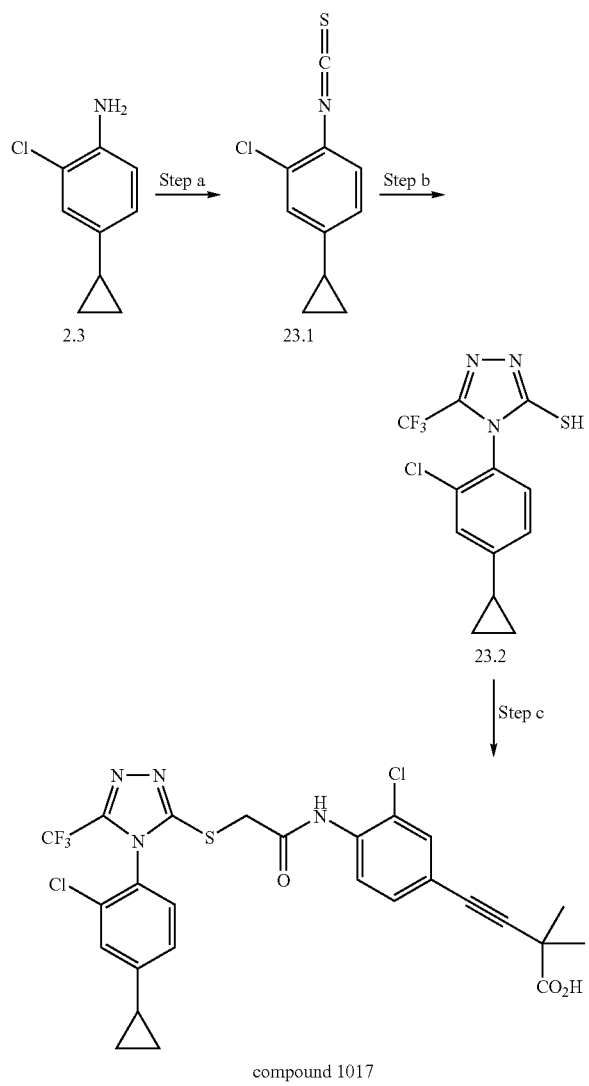

compound 1017 a) Compound 23.1

To a solution of compound 2.3 (Example 2) (600 mg, 3.58 mmol) in MeCN (15 mL) at room temperature was added Et$_3$N (1.1 mL, 7.9 mmol) followed by thiophosgene (300 µL, 3.94 mmol). The reaction mixture was stirred at room temperature for 3 h. The mixture was diluted with EtOAc (100 mL) and successively washed with water and brine, dried (MgSO$_4$), filtered and concentrated under reduced pressure to afford compound 23.1 (750 mg, 100% yield) as a brown oil.

b) Compound 23.2

To a solution of compound 23.1 (150 mg, 715 µmol) in EtOH (15. mL) was added trifluoroacetylhydrazine (101 mg, 787 µmol) and the reaction mixture was stirred at reflux for 2 h. The mixture was then concentrated under reduced pressure and the residue diluted with TFA (10 mL). The mixture was stirred at reflux for 2 h and the excess TFA was removed under reduced pressure. The mixture was diluted with EtOAc (50 mL) and successively washed with saturated aqueous NaHCO$_3$, water and brine, dried (MgSO$_4$), filtered and concentrated under reduced pressure. The crude product was purified by flash chromatography (CH$_2$Cl$_2$:(CH$_3$)$_2$CO, 9:1) to afford compound 23.2 (134 mg, 59% yield) as a pale yellow solid.

c) Compound 1017

Using a method analogous to the one described in Example 22, Step c, compound 23.2 (49.1 mg, 153.6 µmol) gave compound 1017 (59.0 mg, 64% yield) as a white solid. $^1$H NMR (DMSO-d$_6$) δ 9.97 (s, 1H), 7.83 (d, J=8.4 Hz, 1H), 7.67 (d, J=8.3 Hz, 1H), 7.52 (d, J=1.8 Hz, 1H), 7.51 (d, J=1.9 Hz, 1H), 7.35 (dd, J=8.4, 1.8 Hz, 1H), 7.28 (dd, J=8.2, 1.8 Hz, 1H), 4.35 (s, 2H), 2.08-2.02 (m, 1H), 1.45 (s, 6H), 1.09-1.05 (m, 2H), 0.87-0.83 (m, 2H).

Example 24

Reverse Transcriptase (RT) Assays

Enzymatic Assay (IC$_{50}$)

The enzymatic assay employed is described as follows: The reverse transcriptase (RT) enzyme assay has been adapted to a 96-well microtiter plate format and uses PicoGreen™ as a fluorescent intercalator. More explicitly, the HIV-1 RT enzyme was thawed and appropriately diluted into Tris/HCl 50 mM pH 7.8 containing NaCl 60 mM, MgCl$_2$.6H$_2$O 2 mM, DTT 6 mM, GSH 2 mM and 0.02% w/v Chaps to give 10 nM enzyme. To 10 µL of this enzyme solution was added 10 µL of inhibitor solution (40 µM to 2.032 nM inhibitor in the same assay buffer as above containing 4% v/v DMSO). The plate was pre-incubated for 15 minutes at room temperature before proceeding to the next step. In this pre-incubation step, the highest and lowest inhibitor concentrations were 20 µM and 1.016 nM respectively and the concentration of DMSO was 2% v/v. Then the enzymatic reaction was initiated by addition of 20 µL of substrate solution. The final reaction mixture contained Tris/HCl 50 mM pH 7.8, NaCl 60 mM, MgCl$_2$.6H$_2$O 2 mM, DTT 6 mM, GSH 2 mM, CHAPS 0.02% w/v, DMSO 1% v/v, poly rC 45 nM, dG$_{15}$ 4.5 nM, dGTP 3.6 µM, and 2.5 nM enzyme. In this incubation step, the highest and lowest inhibitor concentrations were 10 µM and 0.508 nM respectively. After addition of the substrate cocktail, the plate was covered with a plastic seal and incubated for 50 minutes at 37° C. in a dry incubator. The reaction was then quenched by addition of 5 µL of EDTA 0.5 M. The plate was shaken for 30 seconds at medium speed and incubated for 5 minutes at room temperature. Then 160 µL of PicoGreen™ 1:400 dilution from commercial stock (diluted in Tris 20 mM pH 7.5 with EDTA 1 mM) was added and the plate was shaken for 30 seconds and incubated for 10 minutes at room temperature. The plate was then analyzed using a POLARstar Galaxy fluorometer (BMG Labtechnologies) with $\lambda_{ex}$ and $\lambda_{em}$ of 485 nm and 520 nm respectively. Each well was read for 1.25 second. Each row contained at its extremities a blank and a control well.

P24 Cellular Assay (EC$_{50}$)

The p24 assay is as described in WO 01/96338.

C8166 HIV-1 Luciferase Assay (EC$_{50}$)

Plasmid: pGL3 Basic LTR/TAR #12

Plasmid is the pGL3 Basic Vector (a promoterless luciferase expression vector from Promega catalogue #E1751) with the addition of HIV-1 HxB2 LTR sequence from nucleotide −138 to +80 (Sca1-HindIII) upstream of the luciferase gene and the gene for blasticidine resistance cloned in.
Cells: C8166 LTRluc#A8-F5-G7

C8166 cells are a human T-lymphotrophic virus type 1 immortalized but nonexpressing line of cord blood lymphocytes and are highly permissive to HIV-1 infection. The reporter cells were made by electroporating C8166 cells with pGL3 Basic LTR/TAR and then selecting positive clones with blasticidine. The clone C8166-LTRluc #A8-F5-G7 was selected by 3 consecutive rounds of limiting dilution under blasticidine selection.

Media: Complete media consisting of: RPMI 1640+10% FBS+$10^{-5}$ M β-mercaptoethanol+10 μg/mL gentamycin. Cultures are maintained in complete media with 5 μg/mL blasticidine, however, selection is removed for the assay.
Luciferase Assay Protocol
Preparation of Compounds Serial dilutions of HIV-1 inhibitor compounds are prepared in complete media from 10 mM DMSO stock solutions. Eleven serial dilutions of 2.5× are made at 8× desired final concentration in a 1 mL deep well titer plate (96 wells). The $12^{th}$ well contains complete media with no inhibitor and serves as the positive control. All samples contain the same concentration of DMSO (≦0.1% DMSO). A 25 μL aliquot of inhibitor is added, to triplicate wells, of a 96 well tissue culture treated clear view black microtiter plate (Corning Costar catalogue # 3904). The last row is reserved for uninfected C8166 LTRluc cells to serve as the background blank control and the first row is media alone.
Infection of Cells Count C8166 LTRluc cells and place in a minimal volume of complete RPMI 1640 in a tissue culture flask (ex. 30×$10^6$ cells in 10 ml media/25 cm² flask). Infect cells with HIV-1 at a moi of 0.005. Incubate cells for 1.5 h at 37° C. on a rotating rack in a 5% $CO_2$ incubator. Resuspend cells in complete RPMI to give a final concentration of 25,000-cells/175 μL. Add 175 μL of cell mix to wells of 96 well microtiter plate containing 25 μL 8× inhibitors. Add 25,000 uninfected C8166-LTRluc cells/well in 200 μL complete RPMI to last row for background control. Incubate cells at 37° C. in 5% $CO_2$ incubator for 3 days.
Luciferase Assay Add 50 μL Steady Glo (luciferase substrate $T_{1/2}$=5 h Promega catalogue # E2520) to each well of the 96 well plate. Determine the relative light units (RLU) of luciferase using the BMG LUMIstar Galaxy luminometer. Plates are read from the bottom for 2 seconds per well with a gain of 240.

The level of inhibition (% inhibition) of each well containing inhibitor was calculated with the following equation:

$$\% \cdot \text{inhibition} = \left(1 - \left[\frac{RLU \cdot \text{well} - RLU \cdot \text{blank}}{RLU \cdot \text{control} - RLU \cdot \text{blank}}\right]\right) * 100$$

The calculated % inhibition values were then used to determine $EC_{50}$, slope factor (n) and maximum inhibition ($I_{max}$) by the non-linear regression routine NLIN procedure of SAS using the following equation:

$$\% \cdot \text{inhibition} = \frac{I_{max} \times [\text{inhibitor}]^n}{[\text{inhibitor}]^n + IC_{50}^n}$$

Tables

Tables 1 to 7 illustrate further compounds of the present invention, which can be synthesized in analogy to the methods as described hereinbefore, optionally modified by procedures known to the one skilled in the art. All compounds shown in the tables show $IC_{50}$ values in the enzymatic assay described in Example 24 of less than 1 μM against the K103N/Y181C mutant reverse transcriptase. As well, most compounds shown in Tables 1 to 7 below show $IC_{50}$ values in the enzymatic assay described in Example 24 of less than 1 μM against the wild type HIV reverse transcriptase. All compounds shown in Tables 1 to 7 below are also active in at least one of the cellular assays described in Example 24.

Retention times ($t_R$) for each compound were measured using the standard analytical HPLC conditions described in the Examples. As is well known to one skilled in the art, retention time values are sensitive to the specific measurement conditions. Therefore, even if identical conditions of solvent, flow rate, linear gradient, and the like are used, the retention time values may vary when measured, for example, on different HPLC instruments. Even when measured on the same instrument, the values may vary when measured, for example, using different individual HPLC columns, or, when measured on the same instrument and the same individual column, the values may vary, for example, between individual measurements taken on different occasions.

TABLE 1 wherein R¹, Ar, X and R⁴ are given in the table below:

| Cpd | R¹—Ar | X | R⁴ | $t_R$ (min) | MS (MH⁺) |
|---|---|---|---|---|---|
| 1001 | 4-(4-tBu-2-Cl-phenyl)-3,5-dimethyl-4H-1,2,4-triazol-3-yl | S | 4-(carboxymethoxy)phenyl | 6.9 | 599.1 601.1 603.1 |
| 1002 | 4-(2-Cl-4-Me-phenyl)thiazol-5-yl | S | 4-(carboxymethyl)phenyl | 6.5 | 543.0 544.0 547.0 |
| 1003 | 1-(2-Cl-4-Me-phenyl)-1H-pyrazol-5-yl | O | 4-(carboxymethyl)phenyl | 6.4 | 510.1 512.1 514.0 |
| 1004 | 1-(2-Cl-4-Me-phenyl)-1H-pyrazol-5-yl | S | 4-(carboxymethyl)phenyl | 6.2 | 526.0 528.0 530.0 |
| 1005 | 1-(2-Cl-4-Me-phenyl)-1H-1,2,3-triazol-5-yl | S | 4-(carboxymethyl)phenyl | 6.6 | 527.1 529.1 531.0 |

TABLE 2
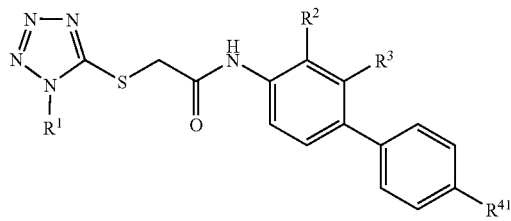
wherein R¹, R², R³ and R⁴¹ are given in the table below:
| Cpd | R¹ | R² | R³ | R⁴¹ | $t_R$ (min) | MS (MH⁺) |
|---|---|---|---|---|---|---|
| 2001 | 2-Cl, 4-Me phenyl | Cl | H | —COOMe | 6.0 | 528.1 530.0 532.0 |
| 2002 | 2-Cl, 4-Me phenyl | Cl | H | —COOH | 5.2 | 514.0 516.0 518.0 |
| 2003 | 2-Cl, 4-Me phenyl | Cl | H | —CH₂COOMe | 5.9 | 542.1 544.0 546.0 |
| 2004 | 2-Cl, 4-Me phenyl | Cl | H | —CH₂COOH | 5.3 | 528.0 530.0 532.0 |
| 2005 | 2-Cl, 4-Me phenyl | Cl | H | —OMe | 9.3 | 500.1 502.1 504.0 |
| 2006 | 2-Cl, 4-Me phenyl | Cl | H | —OH | 7.7 | 486.0 488.0 490.0 |

TABLE 2-continued
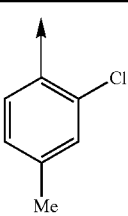
wherein R¹, R², R³ and R⁴¹ are given in the table below:
| Cpd | R¹ | R² | R³ | R⁴¹ | $t_R$ (min) | MS (MH⁺) |
|---|---|---|---|---|---|---|
| 2007 | 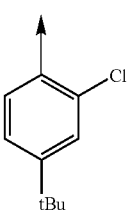 2-Cl, 4-Me phenyl | Cl | H | —O—CH₂COOH | 7.5 | 544.0 546.0 548.0 |
| 2008 | 2-Cl, 4-tBu phenyl | Cl | H | —COOMe | 8.3 | 570.0 572.1 574.1 |
| 2009 | 2-Cl, 4-Me phenyl | Cl | H | —CH₂CH₂OH | 7.6 | 514.1 516.1 518.0 |
| 2010 | 2-Cl, 4-Me phenyl | NO₂ | H | —CH₂COOMe | 8.7 | 553.1 555.1 |
| 2011 | 2-Cl, 4-Me phenyl | NO₂ | H | —CH₂COOH | 7.4 | 539.1 541.1 |
| 2012 | 2-Cl, 4-Me phenyl | Cl | H | —CH₂CONH₂ | 6.8 | 527.1 529.1 631.0 |

TABLE 2-continued
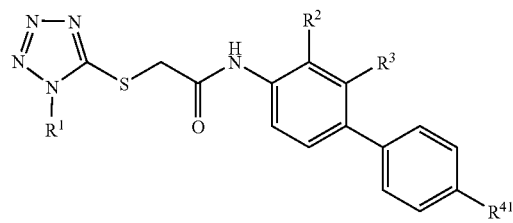
wherein R¹, R², R³ and R⁴¹ are given in the table below:
| Cpd | R¹ | R² | R³ | R⁴¹ | $t_R$ (min) | MS (MH⁺) |
|---|---|---|---|---|---|---|
| 2013 | 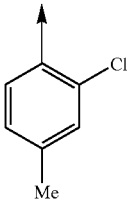 | NO₂ | H | —CH₂CONH₂ | 6.8 | 538.1 540.1 |
| 2014 | 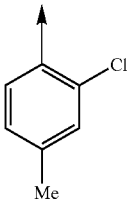 | NO₂ | H | —SO₂NH₂ | 6.9 | 560.0 562.0 |
| 2015 | 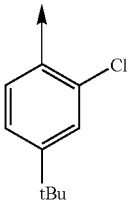 | Cl | H | —CH₂COOH | 7.6 | 570.1 572.1 574.0 |
| 2016 | 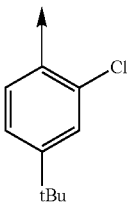 | Cl | H | —O—CH₂COOH | 7.6 | 586.0 588.0 590.0 |
| 2017 | 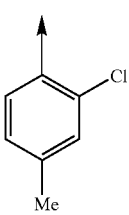 | Cl | H | —CH₂CONHSO₂Me | 6.6 | 605.0 607.0 609.0 |
| 2018 | 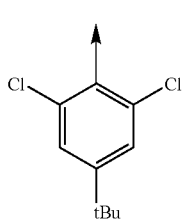 | Cl | H | —O—CH₂COOH | 7.5 | 620.1 622.1 624.0 |

TABLE 2-continued
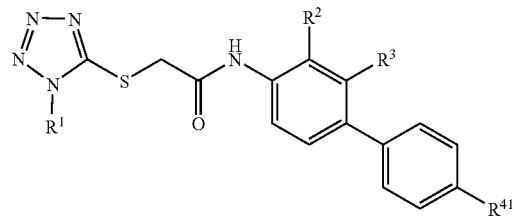
wherein R¹, R², R³ and R⁴¹ are given in the table below:
| Cpd | R¹ | R² | R³ | R⁴¹ | $t_R$ (min) | MS (MH⁺) |
|---|---|---|---|---|---|---|
| 2019 | 2-Cl, 4-tBu-phenyl | Cl | H | —C(Me)₂COOH | 7.7 | 598.1 600.1 602.0 |
| 2020 | 2,6-diCl, 4-tBu-phenyl | Cl | H | —CH₂COOH | 7.6 | 604.0 606.0 608.0 |
| 2021 | 2-Cl, 4,6-diMe-phenyl | Cl | H | —CH₂COOH | 6.9 | 540.0 542.0 544.0 (M − H)⁻ |
| 2022 | 2-Cl, 4-tBu-phenyl | Cl | H | —O-CH₂CH₂-morpholine | 6.5 | 641.2 643.2 645.2 |
| 2023 | 2-Cl, 4-CF₃-phenyl | Cl | H | —CH₂COOH | 6.9 | 582.0 584.0 586.0 |
| 2024 | 2-Cl, 4-tBu-phenyl | Cl | H | —O-CH₂CH₂-N(Et)₂ | 6.1 | 627.3 629.3 631.0 |

TABLE 2-continued
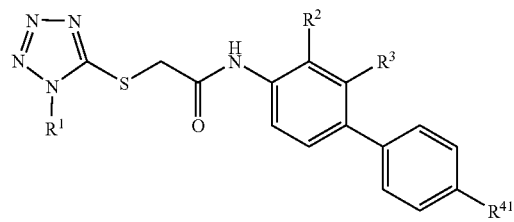
wherein R¹, R², R³ and R⁴¹ are given in the table below:
| Cpd | R¹ | R² | R³ | R⁴¹ | $t_R$ (min) | MS (MH⁺) |
|---|---|---|---|---|---|---|
| 2025 | 2,6-dimethyl-4-Cl-phenyl (Me, Cl, Me) | Cl | H | —C(Me)₂COOH | 7.3 | 570.1 572.1 574.0 |
| 2026 | 2-F-6-Cl-4-Me-phenyl | Cl | H | —C(Me)₂COOH | 7.1 | 574.1 576.1 578.1 |
| 2027 | 2-Cl-4-tBu-phenyl | Cl | H | —SO₂Me | 8.7 | 588.0 590.0 592.1 (M − H)⁻ |
| 2028 | 2-Cl-4-tBu-phenyl | Cl | H | —CH₂CH₂COOH | 8.8 | 582.1 584.1 586.1 (M − H)⁻ |
| 2029 | 2-Cl-4-tBu-phenyl | Cl | H | —O-CH₂CH₂-N(pyrrolidine) | 6.1 | 625.1 627.2 629.2 |
| 2030 | 2-Cl-naphthyl | Cl | H | —CH₂COOH | 7.7 | 564.1 566.1 568.1 |

TABLE 2-continued
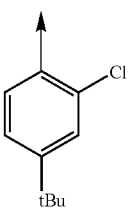
wherein R¹, R², R³ and R⁴¹ are given in the table below:
| Cpd | R¹ | R² | R³ | R⁴¹ | $t_R$ (min) | MS (MH⁺) |
|---|---|---|---|---|---|---|
| 2031 | 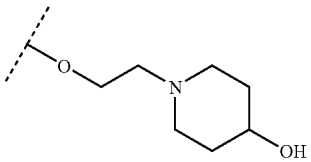 | Cl | H | 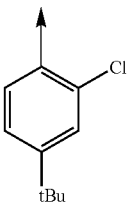 | 5.7 | 655.3 657.3 658.2 |
| 2032 | 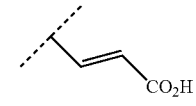 | Cl | H | 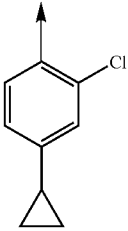 | 8.7 | 580.1 582.1 582.0 (M − H)⁻ |
| 2033 | 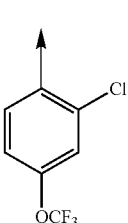 | Cl | H | —CH₂COOH | 7.4 | 554.2 556.2 558.2 |
| 2034 | 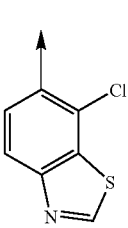 | Cl | H | —CH₂COOH | 6.9 | 598.1 600.1 602.1 |
| 2035 | 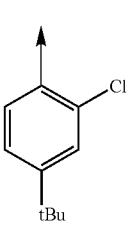 | Cl | H | —CH₂COOH | 5.4 | 571.0 573.0 575.0 |
| 2036 | 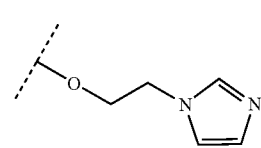 | Cl | H | 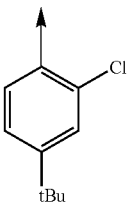 | 5.9 | 622.2 624.2 626.0 |

TABLE 2-continued
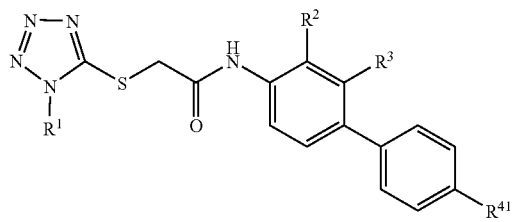
wherein $R^1$, $R^2$, $R^3$ and $R^{41}$ are given in the table below:
| Cpd | $R^1$ | $R^2$ | $R^3$ | $R^{41}$ | $t_R$ (min) | MS (MH$^+$) |
|---|---|---|---|---|---|---|
| 2037 | 3-Cl, 2-CF$_3$, 5-iPr-phenyl | Cl | H | —CH$_2$COOH | 7.3 | 624.1 626.1 628.1 |
| 2038 | 3-Cl-naphthyl | Cl | H | —CH$_2$COOH | 7.4 | 562.0 564.0 566.0 (M − H)$^-$ |
| 2039 | 2-Cl-4-tBu-phenyl | Cl | H | —O-CH$_2$CH$_2$-piperidinyl | 6.1 | 639.2 641.2 643.3 |
| 2040 | 2-Cl-4-tBu-phenyl | Cl | H | —O-CH$_2$CH$_2$-(4-CO$_2$H-piperidinyl) | 5.7 | 683.1 685.1 687.1 |
| 2041 | 2-Cl-4-tBu-phenyl | Cl | H | —O-CH$_2$CH$_2$-(3-OH-pyrrolidinyl) (S) | 5.8 | 641.1 643.1 645.0 |
| 2042 | 2-Cl-4-tBu-phenyl | Cl | H | —O-CH$_2$CH$_2$-(3-OH-pyrrolidinyl) (R) | 5.7 | 641.2 643.2 645.0 |

TABLE 2-continued
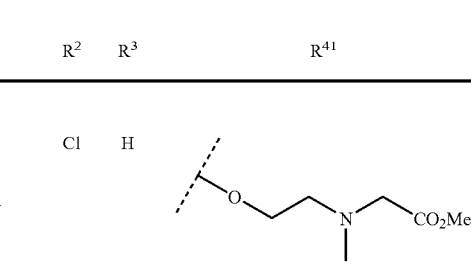
wherein R¹, R², R³ and R⁴¹ are given in the table below:
| Cpd | R¹ | R² | R³ | R⁴¹ | $t_R$ (min) | MS (MH⁺) |
|---|---|---|---|---|---|---|
| 2043 | 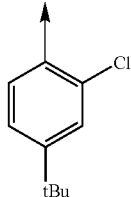 | Cl | H | 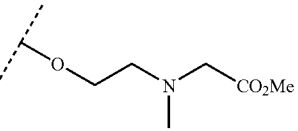 | 5.9 | 657.2<br>659.2<br>661.0 |
| 2044 | 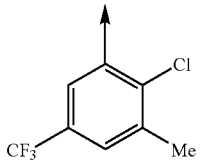 | Cl | H | —CH₂COOH | 6.9 | 594.0<br>596.0<br>598.0<br>(M − H)⁻ |
| 2045 | 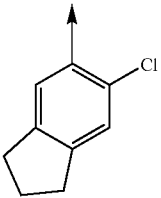 | Cl | H | —CH₂COOH | 6.9 | 554.1<br>556.1<br>558.1 |
| 2046 | 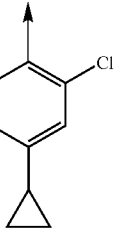 | Cl | H | 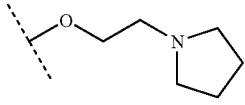 | 6.2 | 609.2<br>611.2<br>613.2 |
| 2047 | 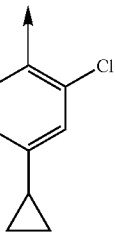 | Cl | H | 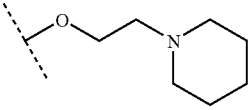 | 6.3 | 623.1<br>625.1<br>627.1 |

TABLE 2-continued
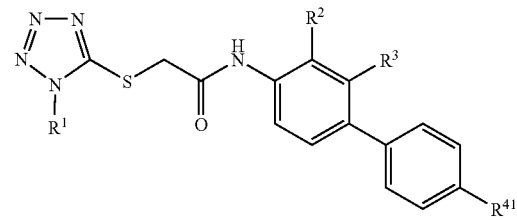
wherein R¹, R², R³ and R⁴¹ are given in the table below:
| Cpd | R¹ | R² | R³ | R⁴¹ | $t_R$ (min) | MS (MH⁺) |
|---|---|---|---|---|---|---|
| 2048 | | Br | H | —CH₂COOH | 6.7 | 598.0 600.0 602.0 |
| 2049 | ![](2-chloro-5-trifluoromethylphenyl) | Cl | H | | 5.8 | 651.1 653.1 655.0 |
| 2050 | ![](2-chloro-4-trifluoromethylphenyl) | Cl | H | | 5.9 | 651.1 653.1 655.1 (M − H)⁻ |
| 2051 | | Cl | F | | 6.1 | 641.1 643.1 645.1 |
| 2052 | | Cl | H | —C(Me)₂COOH | 7.0 | 582.1 584.1 586.0 |

TABLE 2-continued
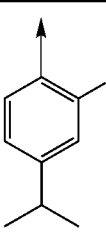
wherein R¹, R², R³ and R⁴¹ are given in the table below:
| Cpd | R¹ | R² | R³ | R⁴¹ | $t_R$ (min) | MS (MH⁺) |
|---|---|---|---|---|---|---|
| 2053 | 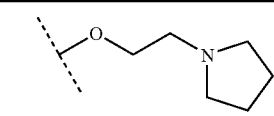 | Cl | H | 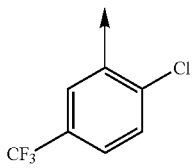 | 6.2 | 655.1 657.1 659.0 |
| 2054 | 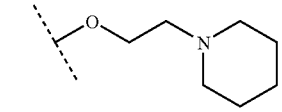 | Cl | F | 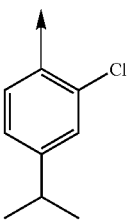 | 5.9 | 669.1 671.1 673.0 |
| 2055 | 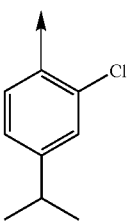 | Cl | H | —C(Me)₂COOH | 7.2 | 582.1 584.1 586.0 (M − H)⁻ |
| 2056 | 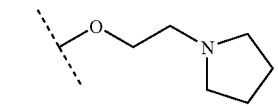 | Cl | H | 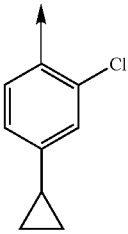 | 6.1 | 611.2 613.2 615.0 |
| 2057 | 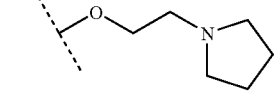 | Cl | F | 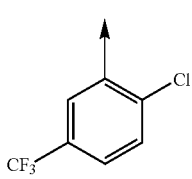 | 5.9 | 627.2 629.2 631.0 |
| 2058 | 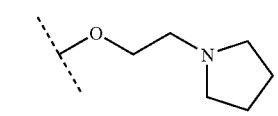 | Cl | F | 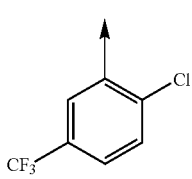 | 5.7 | 655.1 657.1 659.0 |

TABLE 2-continued
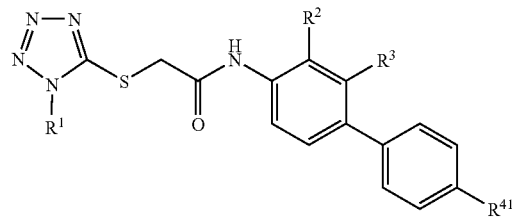
wherein $R^1$, $R^2$, $R^3$ and $R^{41}$ are given in the table below:
| Cpd | $R^1$ | $R^2$ | $R^3$ | $R^{41}$ | $t_R$ (min) | MS (MH$^+$) |
|---|---|---|---|---|---|---|
| 2059 | 2-Cl, 4-cyclopropyl-phenyl | Cl | F | -O-CH$_2$CH$_2$-N(thiomorpholine-1,1-dioxide) | 5.9 | 691.0 693.0 695.0 |
TABLE 3
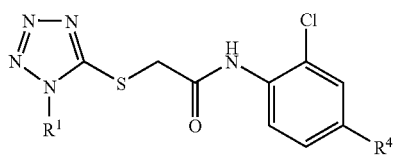
wherein $R^1$ and $R^4$ are given in the table below:
| Cpd | $R^1$ | $R^4$ | $t_R$ (min) | MS (MH$^+$) |
|---|---|---|---|---|
| 3001 | 2-Cl, 4-Me-phenyl | 3-CO$_2$Me-phenyl | 9.3 | 528.0 530.0 532.0 |
| 3002 | 2-Cl, 4-Me-phenyl | 3-CH$_2$CO$_2$Me-phenyl | 9.0 | 542.1 544.1 546.1 |
| 3003 | 2-Cl, 4-Me-phenyl | 3-CO$_2$H-phenyl | 7.7 | 512.0 514.0 516.0 (M − H)$^-$ |

TABLE 3-continued
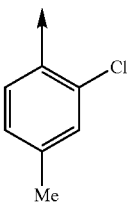
wherein R¹ and R⁴ are given in the table below:
| Cpd | R¹ | R⁴ | $t_R$ (min) | MS (MH⁺) |
|---|---|---|---|---|
| 3004 | 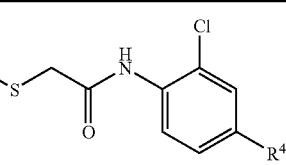 2-Cl, 4-Me phenyl | 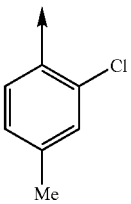 3-CH₂CO₂H phenyl | 7.7 | 528.0 530.0 532.0 |
| 3005 | 2-Cl, 4-Me phenyl | 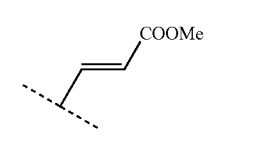 -CH=CH-COOMe | 8.2 | 478.0 480.0 482.0 |
| 3006 | 2-Cl, 4-Me phenyl | 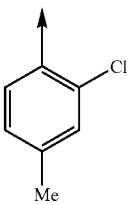 -CH=CH-COOH | 6.7 | 464.0 466.0 468.0 |
| 3007 | 2-Cl, 4-Me phenyl | —CONHMe | 6.1 | 451.0 453.0 455.0 |
| 3008 | 2-Cl, 4-Me phenyl | —CONHEt | 6.4 | 465.0 467.0 469.0 |
| 3009 | 2-Cl, 4-tBu phenyl | 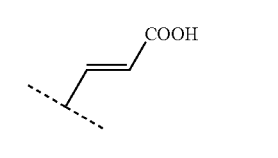 3-Cl, 4-OCH₂CO₂H phenyl | 7.8 | 619.9 621.9 623.9 |

TABLE 3-continued
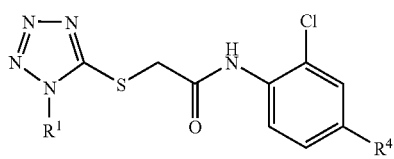
wherein R[1] and R[4] are given in the table below:
| Cpd | R[1] | R[4] | $t_R$ (min) | MS (MH[+]) |
|---|---|---|---|---|
| 3010 | 2-Cl, 4-tBu-phenyl | 4-(OCH$_2$CO$_2$H), 3-Me-phenyl | 7.7 | 600.1 602.1 604.1 |
| 3011 | 2-Cl, 4-tBu-phenyl | 3-Me, 4-(OCH$_2$CO$_2$H)-phenyl | 7.6 | 598.0 600.0 602.0 (M − H)[−] |
| 3012 | 2-Cl, 4-tBu-phenyl | 3-F, 4-(OCH$_2$CO$_2$H)-phenyl | 7.6 | 604.1 606.1 608.1 |
| 3013 | 2-Cl, 4-tBu-phenyl | 3-Cl, 4-(OCH$_2$CO$_2$H)-phenyl | 7.7 | 617.9 619.9 621.0 (M − H)[−] |
| 3014 | 2-Cl, 4-Me-phenyl | thiazol-4-yl | 8.9 | 477.1 479.0 481.1 |
| 3015 | 2-Cl, 4-Me-phenyl | 2-amino-thiazol-4-yl | 5.0 | 492.1 494.1 496.0 |

TABLE 3-continued
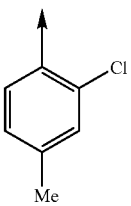
wherein R¹ and R⁴ are given in the table below:
| Cpd | R¹ | R⁴ | $t_R$ (min) | MS (MH⁺) |
|---|---|---|---|---|
| 3016 | 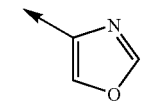 | 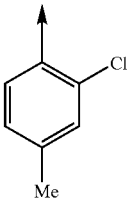 | 6.3 | 461.1 463.1 465.0 |
| 3017 | 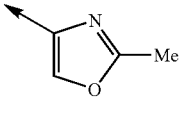 | 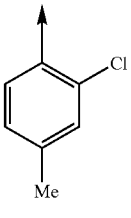 | 6.4 | 475.1 477.1 479.0 |
| 3018 | 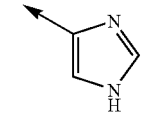 | 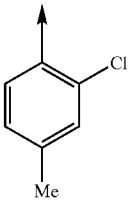 | 4.7 | 460.1 462.1 464.0 |
| 3019 | 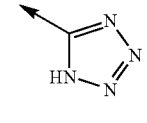 | 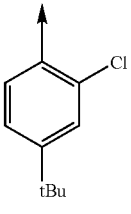 | 5.5 | 462.1 464.0 466.0 |
| 3020 | 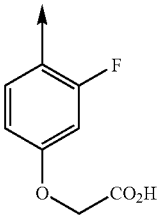 | 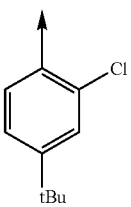 | 7.4 | 604.1 606.1 608.1 |
| 3021 |  | —SO₂NHMe | 7.9 | 529.1 531.0 533.0 |

TABLE 3-continued
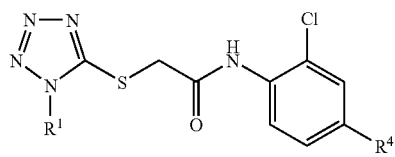
wherein R¹ and R⁴ are given in the table below:
| Cpd | R¹ | R⁴ | $t_R$ (min) | MS (MH⁺) |
|---|---|---|---|---|
| 3022 | 2-Cl-4-tBu-phenyl | 3-CO₂H-phenyl | 7.4 | 556.1 558.1 560.0 |
| 3023 | 2-Cl-4-tBu-phenyl | —SO₂NHCH(Me)₂ | 10.4 | 557.1 559.1 561.0 |
| 3024 | 2-Cl-4-tBu-phenyl | —SO₂NH-CH₂CH₂-Ph | 11.2 | 619.2 621.2 623.2 |
| 3025 | 2-Cl-4-tBu-phenyl | —SO₂N(Me)₂ | 10.5 | 543.1 545.1 547.1 |
| 3026 | 2-Cl-4-tBu-phenyl | —SO₂NH-Ph | 10.8 | 591.2 593.2 595.2 |
| 3027 | 2-Cl-4-tBu-phenyl | —SO₂NH(CH₂)₂OH | 8.7 | 559.1 561.1 563.1 |

TABLE 3-continued wherein R[1] and R[4] are given in the table below:

| Cpd | R[1] | R[4] | $t_R$ (min) | MS (MH+) |
|---|---|---|---|---|
| 3028 | 2-Cl, 4-tBu phenyl | benzyl-NH-SO2- | 11.0 | 605.1 607.1 610.0 |
| 3029 | 2-Cl, 4-tBu phenyl | 1H-imidazol-2-yl | 5.7 | 502.0 504.0 506.0 |
| 3030 | 2-Cl, 4-tBu phenyl | 5-carboxy-thiophen-2-yl | 8.0 | 562.0 564.0 566.0 |
| 3031 | 2-Cl, 4-tBu phenyl | 5-(2-carboxyvinyl)-thiophen-2-yl | 8.4 | 586.1 588.1 590.0 |
| 3032 | 2-Cl, 4-tBu phenyl | —SO2NHCH2COOH | 6.3 | 571.0 573.0 575.0 |
| 3033 | 2-Cl, 4-tBu phenyl | —O-CH2CH2-piperidin-1-yl | 5.7 | 563.1 565.1 567.1 |

TABLE 3-continued
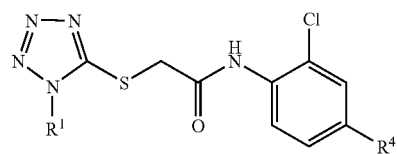
wherein R¹ and R⁴ are given in the table below:
| Cpd | R¹ | R⁴ | t_R (min) | MS (MH⁺) |
|---|---|---|---|---|
| 3034 | 2-Cl, 4-tBu phenyl | -O-CH₂CH₂-morpholine | 5.4 | 565.2 567.2 569.0 |
| 3035 | 2-Cl, 4-tBu phenyl | -O-CH₂CH₂-N(piperidine-4-COOMe) | 5.7 | 619.1 621.1 623.0 (M − H)⁻ |
| 3036 | 2-Cl, 4-cyclopropyl phenyl | 4-methylpiperazine-1-SO₂- | 5.1 | 582.0 584.1 586.0 |
| 3037 | 2-Cl, 4-cyclopropyl phenyl | 4-methylpiperazine-1-NH-SO₂- | 5.0 | 597.1 599.1 601.1 |
| 3038 | 2-Cl, 4-cyclopropyl phenyl | 2-Cl, 4-(O-CH₂CH₂-piperidine) phenyl | 6.3 | 657.1 659.1 661.1 |

TABLE 3-continued
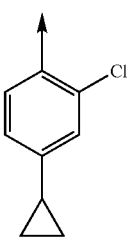
wherein R¹ and R⁴ are given in the table below:
| Cpd | R¹ | R⁴ | $t_R$ (min) | MS (MH⁺) |
|---|---|---|---|---|
| 3039 | 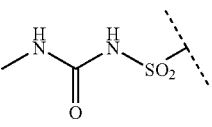 | 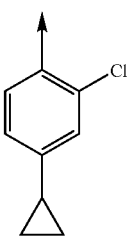 | 5.5 | 554.0 556.0 558.0 (M − H)⁻ |
| 3040 | 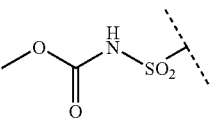 | 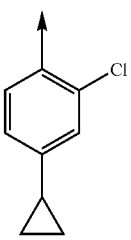 | 5.9 | 555.0 557.0 559.0 (M − H)⁻ |
| 3041 | 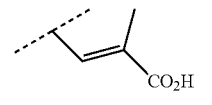 | 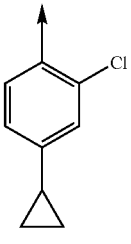 | 7.6 | 504.0 506.0 508.0 |
| 3042 | 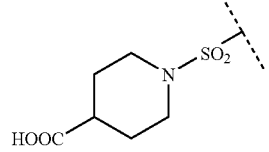 | 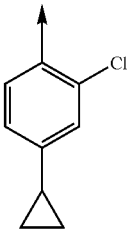 | 7.4 | 609.0 611.0 613.0 (M − H)⁻ |
| 3043 | 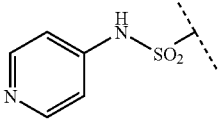 | | 5.9 | 576.0 578.0 580.0 |

TABLE 3-continued
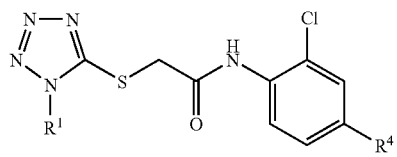
wherein R¹ and R⁴ are given in the table below:
| Cpd | R¹ | R⁴ | $t_R$ (min) | MS (MH⁺) |
|---|---|---|---|---|
| 3044 | 2-Cl, 4-cyclopropyl-phenyl | =C(Me)-CO₂Me | 9.0 | 518.0 520.0 522.0 |
| 3045 | 2-Cl, 4-cyclopropyl-phenyl | -O-C(Me)₂-CH₂OH | 5.9 | 516.2 518.1 520.1 |
| 3046 | 2-Cl, 4-cyclopropyl-phenyl | -O-CH₂-C(Me)₂-COOH | 7.2 | 536.1 538.1 540 |
TABLE 4
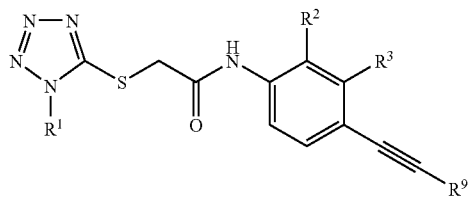
wherein R¹, R², R³ and R⁹ are given in the table below:
| Cpd | R¹ | R² | R³ | R⁹ | $t_R$ (min) | MS (MH⁺) |
|---|---|---|---|---|---|---|
| 4001 | 2-Cl, 4-tBu-phenyl | Cl | H | —(CH₂)₂OH | 7.3 | 504.3 506.3 508.3 |

TABLE 4-continued
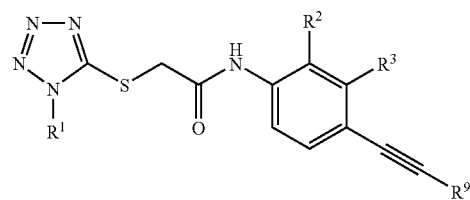
wherein R[1], R[2], R[3] and R[9] are given in the table below:
| Cpd | R[1] | R[2] | R[3] | R[9] | $t_R$ (min) | MS (MH+) |
|---|---|---|---|---|---|---|
| 4002 | 2-Cl-4-tBu-phenyl | Cl | H | phenyl | 8.7 | 536.1 538.1 540.1 |
| 4003 | 2-Cl-4-tBu-phenyl | Cl | H | —(CH$_2$)$_4$OH | 8.4 | 532.1 534.1 536.0 |
| 4004 | 2-Cl-4-tBu-phenyl | Cl | H | —(CH$_2$)$_3$OH | 6.4 | 518.1 520.1 522.1 |
| 4005 | 2-Cl-4-tBu-phenyl | Cl | H | —C(Me)$_2$OH | 6.4 | 518.1 520.1 522.1 |
| 4006 | 2-Cl-4-tBu-phenyl | Cl | H | —CH$_2$OH | 6.0 | 490.2 492.2 494 |
| 4007 | 2,6-Me-4-Cl... (2-Cl-4,6-Me-phenyl) | Cl | H | —C(Me)$_2$OH | 5.8 | 490.2 492.1 494.0 |

TABLE 4-continued
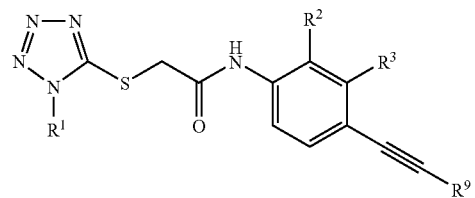
wherein R[1], R[2], R[3] and R[9] are given in the table below:
| Cpd | R[1] | R[2] | R[3] | R[9] | $t_R$ (min) | MS (MH[+]) |
|---|---|---|---|---|---|---|
| 4008 | 2-Cl,4-tBu-phenyl | Cl | H | —CH$_2$N(Et)$_2$ | 5.5 | 545.2 547.2 549.2 |
| 4009 | 2-Cl,4-tBu-phenyl | Cl | H | —(CH$_2$)$_2$CH$_3$ | 8.1 | 502.1 504.1 506.1 |
| 4010 | 2-Cl,4-tBu-phenyl | Cl | H | —CH$_2$-morpholinyl | 5.3 | 559.1 561.1 563.2 |
| 4011 | 2-Cl,4-tBu-phenyl | Cl | H | —C(Me)$_2$CO$_2$H | 6.5 | 546.1 548.1 550.0 |
| 4012 | 2-Cl,4-tBu-phenyl | Cl | H | —CH$_2$-pyrrolidinyl | 5.5 | 543.2 545.2 547.2 |
| 4013 | 2-Cl,4-tBu-phenyl | Cl | H | —C(Me)$_2$C(O)NHCH$_2$CH$_2$-morpholinyl | 5.8 | 658.3 660.3 662.0 |

TABLE 4-continued
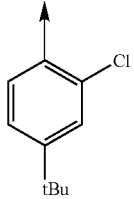
wherein R¹, R², R³ and R⁹ are given in the table below:
| Cpd | R¹ | R² | R³ | R⁹ | $t_R$ (min) | MS (MH⁺) |
|---|---|---|---|---|---|---|
| 4014 | 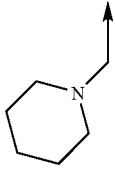 | Cl | H | 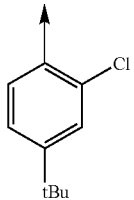 | 5.6 | 557.2 559.2 561.2 |
| 4015 | 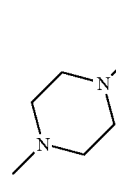 | Cl | H | 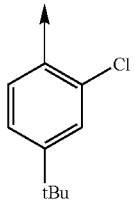 | 5.4 | 572.2 574.2 576.2 |
| 4016 | 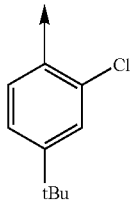 | Cl | H | —C(Me)₂CH₂OH | 6.6 | 532.2 534.2 536.2 |
| 4017 | 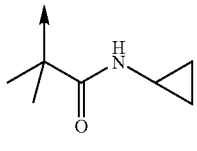 | Cl | H | 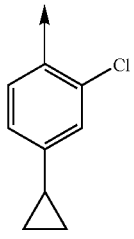 | 6.8 | 585.2 587.2 589.2 |
| 4018 | 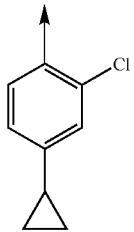 | Cl | H | —C(Me)₂OH | 5.9 | 502.1 504.1 506.1 |
| 4019 | 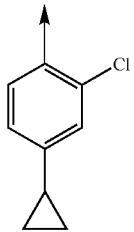 | Cl | H | —C(Me)₂COOH | 6.0 | 530.1 532.1 534.1 |

TABLE 4-continued
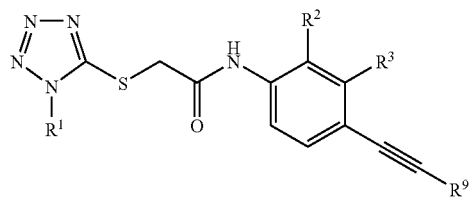
wherein R¹, R², R³ and R⁹ are given in the table below:
| Cpd | R¹ | R² | R³ | R⁹ | $t_R$ (min) | MS (MH⁺) |
|---|---|---|---|---|---|---|
| 4020 | 2-Cl, 4-tBu-phenyl | Cl | H | —C(Me)₂—O—CH₂—C(O)OH | 7.1 | 574, 576, 578 (M − H)⁻ |
| 4021 | 3-CN, 4-Cl-phenyl | Cl | H | —C(Me)₂OH | 5.7 | 487.0, 489.0, 491.0 |
| 4022 | 2-F, 3-Cl, 4-CF₃-phenyl | Cl | H | —C(Me)₂OH | 6.6 | 548.0, 550.0, 552.0 |
| 4023 | 2-Cl, 4-tBu-phenyl | Cl | H | —C(Me)₂—O—CH₂—C(O)-(4-methylpiperazin-1-yl) | 5.8 | 658.2, 660.2, 662.2 |
| 4024 | 2-Cl, 4-tBu-phenyl | Cl | H | —C(Me)₂—O—CH₂—C(O)NH-(4-hydroxyphenyl) | 7.2 | 665.2, 667.2, 669.2 (M − H)⁻ |
| 4025 | 2-Cl, 4-tBu-phenyl | Cl | H | —C(Me)₂—O—CH₂—C(O)NH-(3-CO₂H-phenyl) | 7.3 | 693.2, 695.2, 697.2 (M − H)⁻ |

TABLE 4-continued
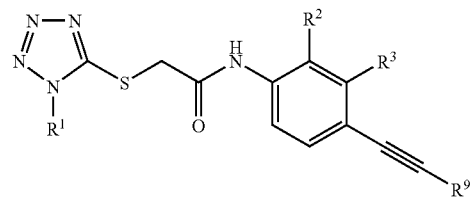
wherein R¹, R², R³ and R⁹ are given in the table below:
| Cpd | R¹ | R² | R³ | R⁹ | $t_R$ (min) | MS (MH⁺) |
|---|---|---|---|---|---|---|
| 4026 | ![2-Cl-4-tBu-phenyl] | Cl | H | ![tBuO-CH2-C(O)-NH-C6H4-CH=CH-CO2H] | 6.3 | 719.2 721.2 723.2 (M − H)⁻ |
| 4027 | ![2-Cl-4-tBu-phenyl] | Cl | H | ![tBuO-CH2-C(O)-N(piperidine-4-CO2H)] | 6.9 | 685.2 687.2 689.2 (M − H)⁻ |
| 4028 | ![2-Cl-3-CF3-6-Me-phenyl] | Cl | H | —C(Me)₂OH | 6.8 | 542.0 544.0 546.0 (M − H)⁻ |
| 4029 | ![2-Cl-3-CF3-5-F-phenyl] | Cl | H | —C(Me)₂OH | 6.7 | 548.0 550.0 552.0 |
| 4030 | ![2-Cl-3-Me-5-CF3-phenyl] | Cl | H | —C(Me)₂OH | 6.9 | 542.0 544.0 546.0 (M − H)⁻ |
| 4031 | ![2-Cl-3-CF3-5-Me-phenyl] | Cl | H | —C(Me)₂OH | 6.9 | 542.0 544.0 546.0 (M − H)⁻ |

TABLE 4-continued
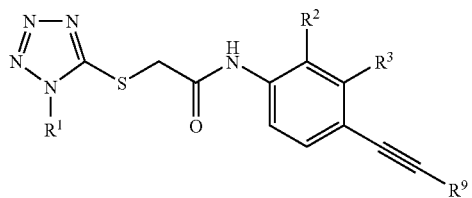
wherein R¹, R², R³ and R⁹ are given in the table below:
| Cpd | R¹ | R² | R³ | R⁹ | $t_R$ (min) | MS (MH⁺) |
|---|---|---|---|---|---|---|
| 4032 | 2-Cl-4-tBu-phenyl | Cl | H | cyclopropyl | 7.4 | 500.1 502.1 504.1 |
| 4033 | 2-Cl-4-tBu-phenyl | Cl | H | —C(CH₃)₂CH₂OC(O)NH₂ | 6.5 | 575.1 577.1 579.1 |
| 4034 | 2-Cl-4-tBu-phenyl | Cl | H | —CH₂OC(O)NH₂ | 6.0 | 533.1 535.0 537.0 |
| 4035 | 2-Cl-4-tBu-phenyl | Cl | H | —C(CH₃)₂OCH₂C(O)OCH₂CH₂NHCH₃ | 6.0 | 633.2 635.2 637.2 |
| 4036 | 2-Cl-4-tBu-phenyl | Cl | H | —C(CH₃)₂OCH₂C(O)NH-cyclopropyl-CO₂H | 7.2 | 657.2 659.2 661 |
| 4037 | 2-Cl-4-tBu-phenyl | Cl | H | —C(CH₃)₂OCH₂C(O)NHCH₂-furan-2-yl | 7.7 | 653.2 655.2 657 (M − H)⁻ |

TABLE 4-continued
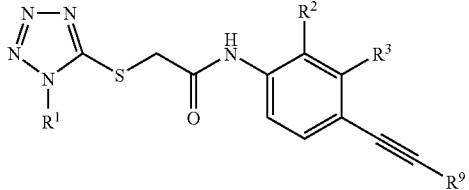
wherein R¹, R², R³ and R⁹ are given in the table below:
| Cpd | R¹ | R² | R³ | R⁹ | $t_R$ (min) | MS (MH⁺) |
|---|---|---|---|---|---|---|
| 4038 | 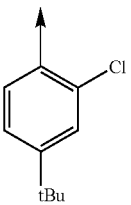 2-Cl, 4-tBu phenyl | Cl | H | 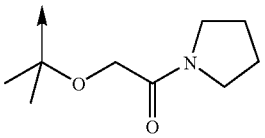 | 7.4 | 627.2 629.2 631.0 (M − H)⁻ |
| 4039 | 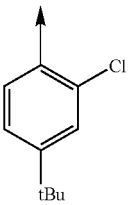 2-Cl, 4-tBu phenyl | Cl | H | 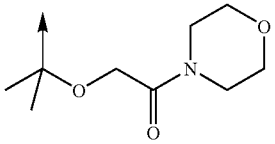 | 7.3 | 643.2 645.2 647.0 (M − H)⁻ |
| 4040 | 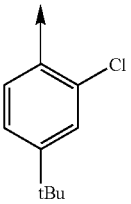 2-Cl, 4-tBu phenyl | Cl | H | 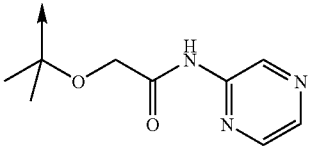 | 7.7 | 653.2 655.2 657.0 |
| 4041 | 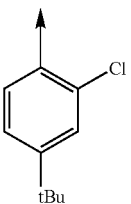 2-Cl, 4-tBu phenyl | Cl | H | 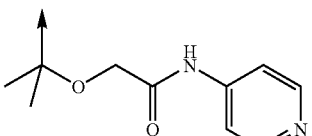 | 6.1 | 652.2 654.2 656.0 |
| 4042 | 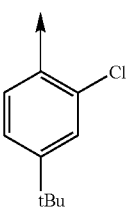 2-Cl, 4-tBu phenyl | Cl | H | 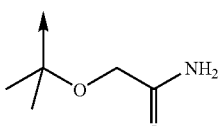 | 7.1 | 573.2 575.2 577.0 (M − H)⁻ |
| 4043 | 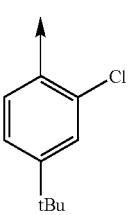 2-Cl, 4-tBu phenyl | Cl | H | 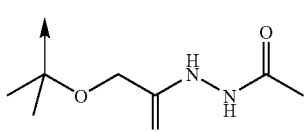 | 6.8 | 654.3 (M + Na) |

TABLE 4-continued
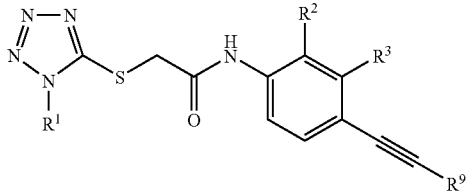
wherein R¹, R², R³ and R⁹ are given in the table below:
| Cpd | R¹ | R² | R³ | R⁹ | $t_R$ (min) | MS (MH⁺) |
|---|---|---|---|---|---|---|
| 4044 | 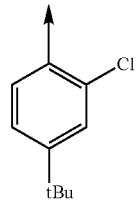 | Cl | H | 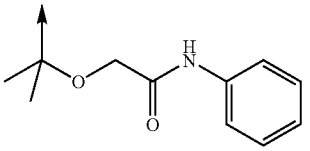 | 8.0 | 649.2 651.2 653.0 (M − H)⁻ |
| 4045 | 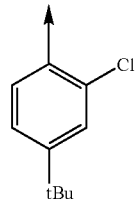 | Cl | H | 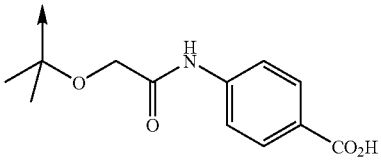 | 7.5 | 693.2 695.2 697.0 (M − H)⁻ |
| 4046 | 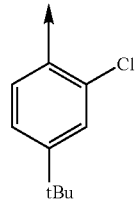 | Cl | H | 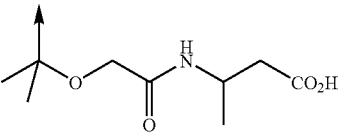 | 7.2 | 659.2 661.2 663.0 (M − H)⁻ |
| 4047 | 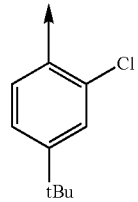 | Cl | H | 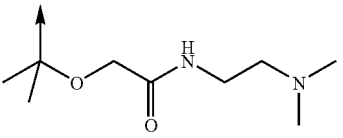 | 5.8 | 646.3 648.3 650.0 |
| 4048 | 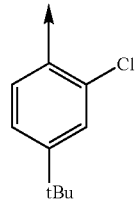 | Cl | H | 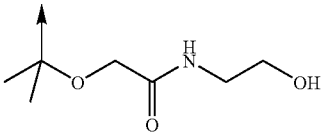 | 6.9 | 617.2 619.2 621.0 (M − H)⁻ |
| 4049 | 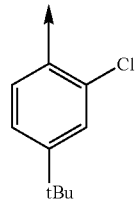 | Cl | H | 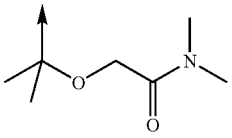 | 7.3 | 601.2 603.2 605.0 (M − H)⁻ |

TABLE 4-continued wherein R¹, R², R³ and R⁹ are given in the table below:

| Cpd | R¹ | R² | R³ | R⁹ | $t_R$ (min) | MS (MH⁺) |
|---|---|---|---|---|---|---|
| 4050 | 2-Cl-4-tBu-phenyl | Cl | H | tBuO-CH₂-C(O)-N(OH)(Me) | 6.9 | 603.2 605.2 607.0 (M − H)⁻ |
| 4051 | 2-Cl-4-tBu-phenyl | Cl | H | tBuO-CH₂-C(O)-NHMe | 7.3 | 587.2 589.2 591.0 (M − H)⁻ |
| 4052 | 2-Cl-4-tBu-phenyl | Cl | H | tBuO-CH₂-C(O)-NH-CH₂-CO₂H | 7.0 | 631.2 633.2 635.0 (M − H)⁻ |
| 4053 | 2-Cl-4-tBu-phenyl | Cl | H | tBuO-CH₂-C(O)-NH-CH(Me)-CO₂H | 7.2 | 645.2 647.2 649.0 (M − H)⁻ |
| 4054 | 2-Cl-4-tBu-phenyl | Cl | H | tBuO-CH₂-C(O)-NH-isoxazol-3-yl | 7.7 | 640.2 642.2 644.0 (M − H)⁻ |
| 4055 | 2-Cl-4-tBu-phenyl | Cl | H | tBuO-CH₂-C(O)-NH-CH₂-CH₂-CO₂H | 7.0 | 645.2 647.2 649.0 (M − H)⁻ |

TABLE 4-continued
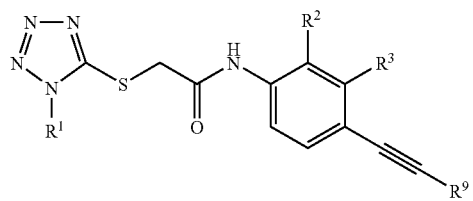
wherein R¹, R², R³ and R⁹ are given in the table below:
| Cpd | R¹ | R² | R³ | R⁹ | $t_R$ (min) | MS (MH⁺) |
|---|---|---|---|---|---|---|
| 4056 | 2-Cl-4-tBu-phenyl | Cl | H | -CH₂-O-C(Me)₂-... -C(O)-NH-NH-C(O)-NH₂ (tBuO-CH₂-C(O)-NH-NH-C(O)-NH₂) | 6.6 | 631.2 633.2 635.0 (M − H)⁻ |
| 4057 | 2-Cl-4-tBu-phenyl | Me | H | —C(Me)₂COOH | 6.1 | 524.1 526.0 528.0 |
| 4058 | 2-Cl-3-Me-5-CF₃-phenyl | Cl | H | —C(Me)₂COOH | 7.0 | 570.0 572.0 574.0 |
| 4059 | 2-Cl-3-CF₃-4-Me-phenyl | Cl | H | —C(Me)₂OH | 6.7 | 544.1 546.1 548.0 |
| 4060 | 2-Cl-4-Me-5-CF₃-phenyl | Cl | H | —C(Me)₂OH | 6.8 | 544.1 546.1 548.0 |
| 4061 | 2-Cl-4-tBu-phenyl | Cl | H | —(CH₂)₃OC(O)NH₂ | 6.3 | 561.1 563.1 565.0 |

TABLE 4-continued
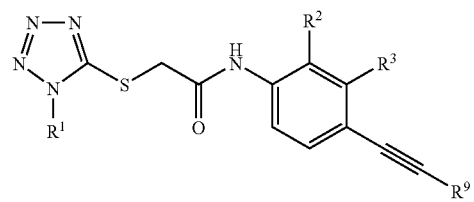
wherein R¹, R², R³ and R⁹ are given in the table below:
| Cpd | R¹ | R² | R³ | R⁹ | $t_R$ (min) | MS (MH⁺) |
|---|---|---|---|---|---|---|
| 4062 | 2-Cl, 4-tBu phenyl | Cl | H | 1-hydroxycyclobutyl | 6.4 | 530.1 532.1 534.0 |
| 4063 | 2-Cl, 4-Me, 5-CF₃ phenyl | Cl | H | —C(Me)₂COOH | 6.9 | 572.1 574.1 576.0 |
| 4064 | 2-Cl, 4-cyclopropyl phenyl | Cl | H | neopentyl carbamate | 6.9 | 559.1 561.1 563.1 |
| 4065 | 6-Cl-indanyl | Cl | H | —C(Me)₂OH | 6.7 | 502.1 504.1 506.1 |
| 4066 | 2-Cl, 4-cyclopropyl phenyl | Cl | H | 3-(Boc-amino)pentan-3-yl | 7.5 | 627.2 629.2 631.0 (M − H)⁻ |

TABLE 4-continued
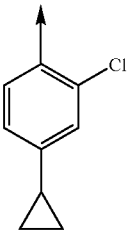
wherein R¹, R², R³ and R⁹ are given in the table below:
| Cpd | R¹ | R² | R³ | R⁹ | $t_R$ (min) | MS (MH⁺) |
|---|---|---|---|---|---|---|
| 4067 | 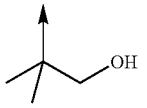 | Cl | H | 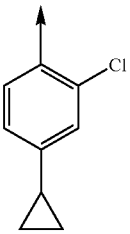 | 5.9 | 516.2<br>518.1<br>520.1 |
| 4068 | 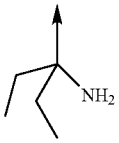 | Cl | H | 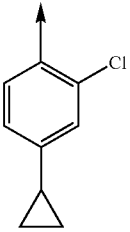 | 5.1 | 527.1<br>529.1<br>531.0<br>(M − H)⁻ |
| 4069 | 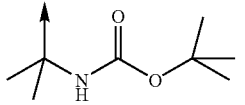 | Cl | H | 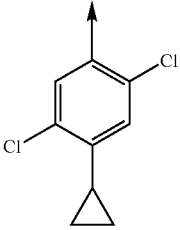 | 6.7 | 601.1<br>603.1<br>605.0 |
| 4070 | 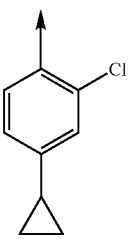 | Cl | H | —C(Me)₂OH | 7.1 | 536.0<br>538.0<br>540.0 |
| 4071 | 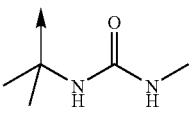 | Cl | H | | 5.6 | 558.1<br>560.1<br>562.0 |

TABLE 4-continued
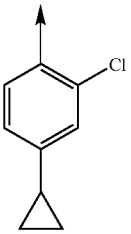
wherein R¹, R², R³ and R⁹ are given in the table below:
| Cpd | R¹ | R² | R³ | R⁹ | $t_R$ (min) | MS (MH⁺) |
|---|---|---|---|---|---|---|
| 4072 | 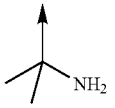 | Cl | H | 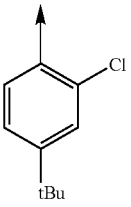 | 4.7 | 499.0 501.0 503.0 (M − H)⁻ |
| 4073 | 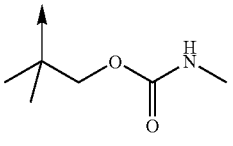 | Cl | H | 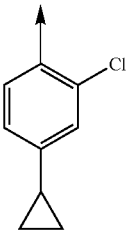 | 6.6 | 532.1 534.1 536.0 |
| 4074 | 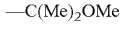 | Cl | H | —C(Me)₂OMe | 6.4 | 516.1 518.1 520.0 |
| 4075 | 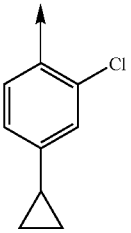 | Cl | H | 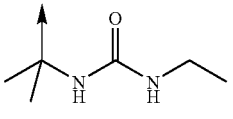 | 5.8 | 572.1 574.1 576.0 |
| 4076 | 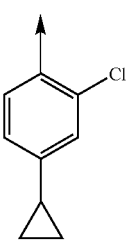 | Cl | H | 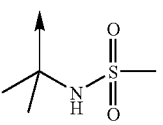 | 5.8 | 578.9 581.9 583 |

TABLE 4-continued
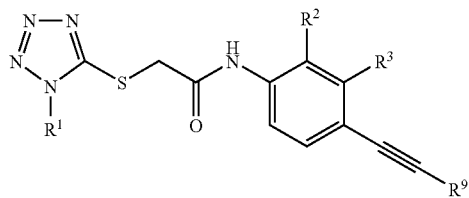
wherein $R^1$, $R^2$, $R^3$ and $R^9$ are given in the table below:
| Cpd | $R^1$ | $R^2$ | $R^3$ | $R^9$ | $t_R$ (min) | MS (MH⁺) |
|---|---|---|---|---|---|---|
| 4077 | 2-Cl, 4-CF₃-phenyl | Cl | H | —C(Me)₂COOMe | 7.3 | 572.0 574.0 576.0 |
| 4078 | 2-Cl, 4-cyclopropyl-phenyl | Br | H | —C(Me)₂OH | 6.5 | 546.0 548.0 550.0 |
| 4079 | 2-Cl, 4-cyclopropyl-phenyl | Cl | H | —C(Me)₂NHC(O)-cyclopropyl | 5.9 | 569.1 572.1 574.0 |
| 4080 | 2-Cl, 4-cyclopropyl-phenyl | Cl | H | —C(Me)₂NHC(O)Me | 5.6 | 543.1 545.1 547.0 |
| 4081 | 2-Cl, 4-cyclopropyl-phenyl | Cl | H | —C(Me)₂NHC(O)OEt | 6.1 | 573.1 575.1 577.0 |

TABLE 4-continued
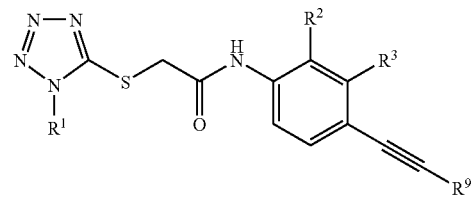
wherein R¹, R², R³ and R⁹ are given in the table below:
| Cpd | R¹ | R² | R³ | R⁹ | $t_R$ (min) | MS (MH⁺) |
|---|---|---|---|---|---|---|
| 4082 | 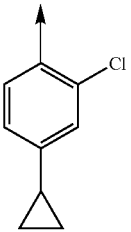 | Cl | H | 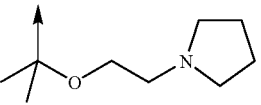 | 5.5 | 599.0 601.0 603.0 |
| 4083 | 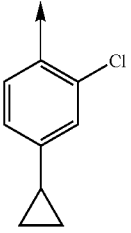 | Cl | H | 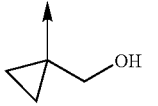 | 5.6 | 514.0 516.0 518.0 |
| 4084 | 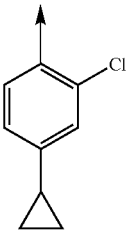 | Cl | H | 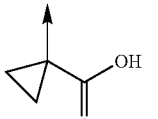 | 5.6 | 528.0 530.0 532 |
| 4085 | 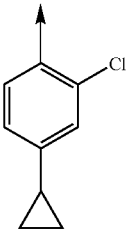 | Cl | H | 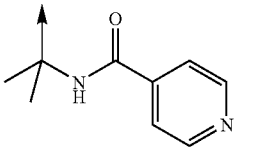 | 5.2 | 606.0 608.0 610.0 |
| 4086 | 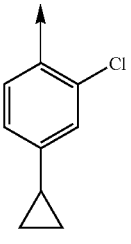 | Cl | H | 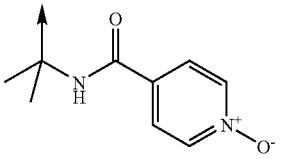 | 5.6 | 622.0 624.0 626.0 |

TABLE 4-continued
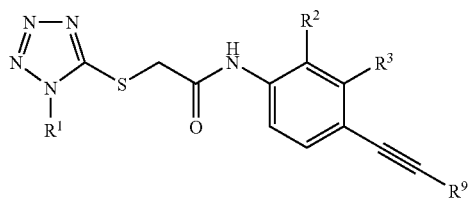
wherein $R^1$, $R^2$, $R^3$ and $R^9$ are given in the table below:
| Cpd | $R^1$ | $R^2$ | $R^3$ | $R^9$ | $t_R$ (min) | MS ($MH^+$) |
|---|---|---|---|---|---|---|
| 4087 | 2-Cl, 4-cyclopropyl-phenyl | Cl | H | -C(CH3)2-NH-C(O)-CH2-N(CH3)2 | 5.0 | 586.0 588.0 590.0 |
| 4088 | 2-Cl, 4-tBu-phenyl | Cl | H | —COOH | 5.8 | 504.0 506.0 508.0 |
| 4089 | 2-Cl, 4-tBu-phenyl | Cl | H | —H | 6.4 | 460.0 462.0 464.0 |
| 4090 | 2-Cl, 4-cyclopropyl-phenyl | Cl | H | -C(CH3)2-O-CH2-COOH | 6.5 | 558.0 560.0 562.0 |
| 4091 | 2-Cl, 4-cyclopropyl-phenyl | Cl | H | —CH2OH | 5.3 | 474.0 476.0 478.0 |

TABLE 4-continued
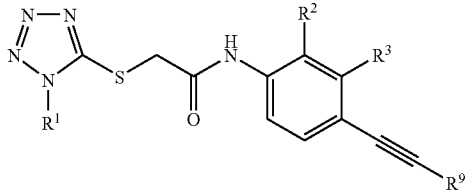
wherein R¹, R², R³ and R⁹ are given in the table below:
| Cpd | R¹ | R² | R³ | R⁹ | $t_R$ (min) | MS (MH⁺) |
|---|---|---|---|---|---|---|
| 4092 | 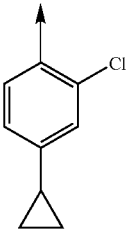 | Cl | H | 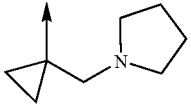 | 5.2 | 567.1 569.1 571.1 |
| 4093 | 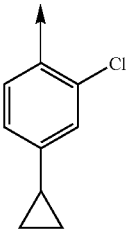 | Cl | H | —COOH | 5.3 | 488.0 490.0 492.0 |
| 4094 | 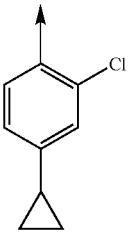 | Cl | H | 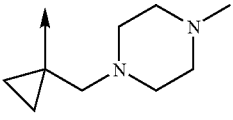 | 4.6 | 596.2 598.2 600 |
| 4095 | 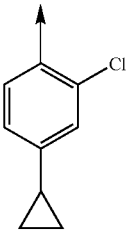 | Cl | H | 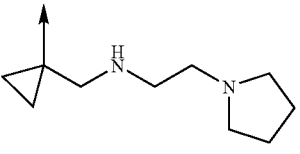 | 4.5 | 610.2 612.2 614.0 |
| 4096 | 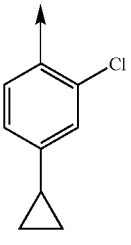 | Cl | H | 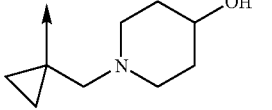 | 4.9 | 597.1 599.1 601.0 |

TABLE 4-continued
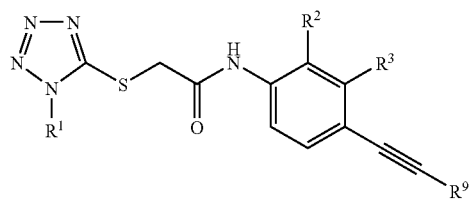
wherein $R^1$, $R^2$, $R^3$ and $R^9$ are given in the table below:
| Cpd | $R^1$ | $R^2$ | $R^3$ | $R^9$ | $t_R$ (min) | MS (MH$^+$) |
|---|---|---|---|---|---|---|
| 4097 | 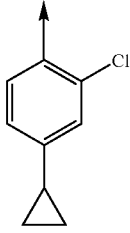 | Cl | H | H | 5.9 | 444.1 446.0 448.0 |
| 4098 | 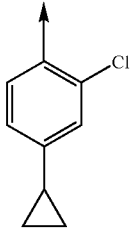 | Cl | H | 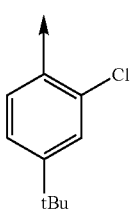 | 5.7 | 544.1 546.1 548.0 (M − H)$^-$ |
| 4099 | 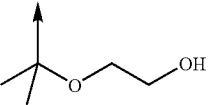 | Cl | H | —C(Me)$_2$COOH | 6.9 | 574.0 576.0 578.0 (M − H)$^-$ |
| 4100 | 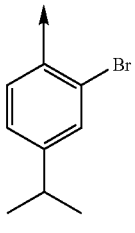 | Cl | F | —C(Me)$_2$COOH | 6.7 | 548.1 550.1 552.0 |
| 4101 | 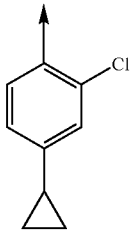 | Cl | F | —C(Me)$_2$COOH | 6.6 | 575.9 577.9 579.0 |
| 4102 | 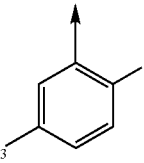 | Cl | H | —(CH$_2$)$_2$COOH | 5.9 | 532.1 534.1 536.0 |

TABLE 4-continued
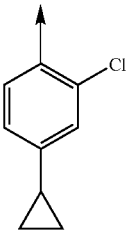
wherein R¹, R², R³ and R⁹ are given in the table below:
| Cpd | R¹ | R² | R³ | R⁹ | $t_R$ (min) | MS (MH⁺) |
|---|---|---|---|---|---|---|
| 4103 | 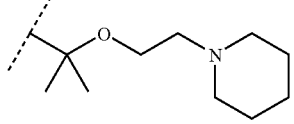 | Cl | H | 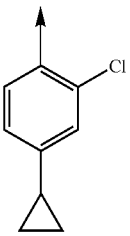 | 5.5 | 613.2 615.2 617.0 |
| 4104 | 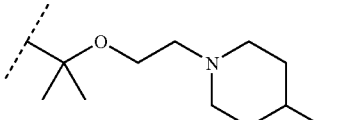 | Cl | H | 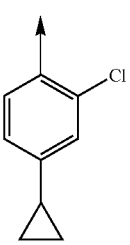 | 5.2 | 629.2 631.2 633.0 |
| 4105 | 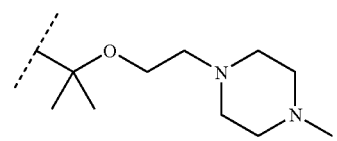 | Cl | H | 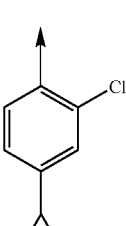 | 4.7 | 628.2 630.2 632.0 |
| 4106 | 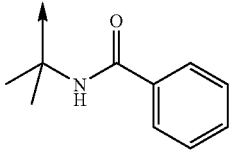 | Cl | H | 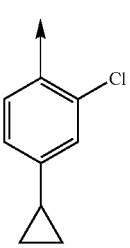 | 6.2 | 605.1 607.1 609.0 |
| 4107 | 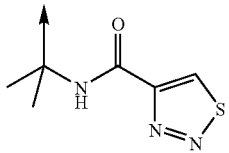 | Cl | H |  | 6..0 | 613.1 615.1 617.0 |

TABLE 4-continued

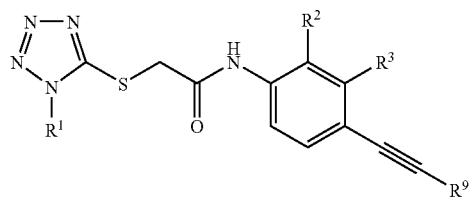

wherein $R^1$, $R^2$, $R^3$ and $R^9$ are given in the table below:

| Cpd | $R^1$ | $R^2$ | $R^3$ | $R^9$ | $t_R$ (min) | MS ($MH^+$) |
|---|---|---|---|---|---|---|
| 4108 | 2-chloro-4-cyclopropylphenyl | Cl | H | tert-butyl-NHC(O)CH₂CH₂CH₂N(CH₃)₂ | 5.1 | 614.2 616.2 618.0 |
| 4109 | 2-chloro-4-cyclopropylphenyl | Cl | H | tert-butyl-NHC(O)CH₂-(1,2,4-triazol-1-yl) | 5.4 | 610.1 612.1 614.0 |
| 4110 | 2-chloro-4-cyclopropylphenyl | Cl | H | tert-butyl-NHC(O)-(1-methylpyrrolidin-2-yl) | 5.0 | 612.2 614.2 616.2 |
| 4111 | 2-chloro-4-cyclopropylphenyl | Cl | H | tert-butyl-NHC(O)-pyrazin-2-yl | 6.0 | 607.1 609.1 610.2 |
| 4112 | 2-chloro-4-cyclopropylphenyl | Cl | H | isopropenyl | 6.8 | 484.1 486.1 488.0 |

TABLE 4-continued

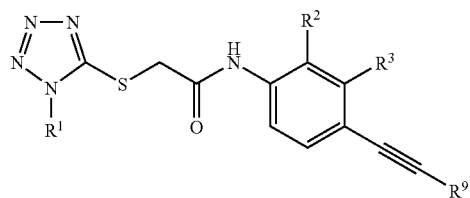

wherein R¹, R², R³ and R⁹ are given in the table below:

| Cpd | R¹ | R² | R³ | R⁹ | $t_R$ (min) | MS (MH⁺) |
|---|---|---|---|---|---|---|
| 4113 | 4-cyclopropyl-2-chlorophenyl | Cl | H | tert-butyl-NH-CH₂-(1H-imidazol-4-yl) | 4.3 | 581.1 583.1 585.1 |
| 4114 | 2-chloro-5-methoxyphenyl | Cl | H | —C(Me)₂COOH | 6.1 | 520.0 522.0 524.0 |
| 4115 | 4-cyclopropyl-2-chlorophenyl | Cl | H | —C(Me)₂-O-CH₂CH₂-(4,4-dimethyl-4,5-dihydroimidazol-1-yl) | 5.5 | 626.2 628.2 630.0 |
| 4116 | 4-cyclopropyl-2-chlorophenyl | Cl | H | —C(Me)₂-O-CH₂CH₂-(piperazin-1-yl) | 4.7 | 614.2 616.2 618.0 |
| 4117 | 4-cyclopropyl-2-chlorophenyl | Cl | H | —C(Me)₂-O-CH₂CH₂-NH-cyclopropyl | 5.2 | 585.2 587.2 589.0 |

TABLE 4-continued
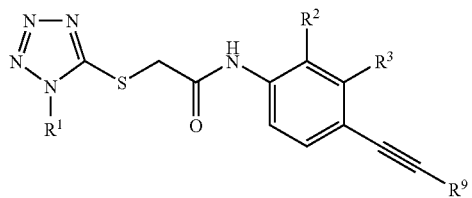
wherein R¹, R², R³ and R⁹ are given in the table below:
| Cpd | R¹ | R² | R³ | R⁹ | $t_R$ (min) | MS (MH⁺) |
|---|---|---|---|---|---|---|
| 4118 | 2-Cl, 4-cyclopropyl-phenyl | Cl | N | -C(Me)₂-O-CH₂CH₂-NH-cyclobutyl | 5.4 | 599.2<br>601.2<br>603.2 |
| 4119 | 2-Cl, 4-cyclopropyl-phenyl | Cl | H | -C(Me)₂-O-CH₂CH₂-N(azetidinyl) | 5.4 | 585.1<br>587.1<br>589.1 |
| 4120 | 2-Cl, 4-CF₃-phenyl | Cl | H | -C(Me)₂-NH-C(O)-(pyridine-N-oxide) | 5.9 | 650.1<br>652.1<br>654.0 |
| 4121 | 2-Cl, 4-iPr-phenyl | Cl | H | —C(Me)₂COOH | 6.9 | 530.0<br>532.0<br>534.0<br>(M – H)⁻ |
| 4122 | 2-Cl, 4-tBu-phenyl | Cl | F | —C(Me)₂COOH | 7.1 | 564.1<br>566.1<br>568.0 |

TABLE 4-continued
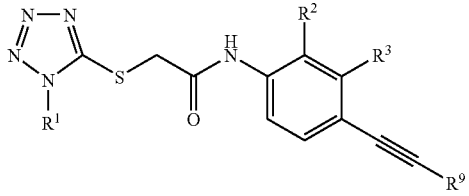
wherein R¹, R², R³ and R⁹ are given in the table below:
| Cpd | R¹ | R² | R³ | R⁹ | $t_R$ (min) | MS (MH⁺) |
|---|---|---|---|---|---|---|
| 4123 | 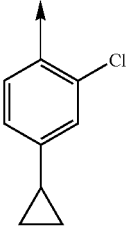 | Cl | H | 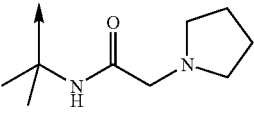 | 5.1 | 612.1 614.1 616.0 |
| 4124 | 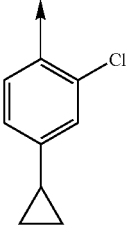 | Cl | H | 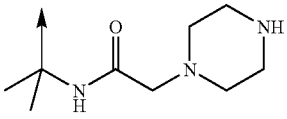 | 4.6 | 627.1 629.1 631.0 |
| 4125 | 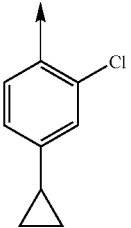 | Cl | H | 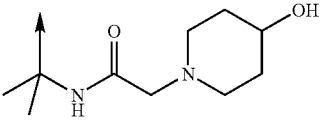 | 4.9 | 642.2 644.1 646.0 |
| 4126 | 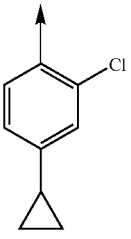 | Cl | H | 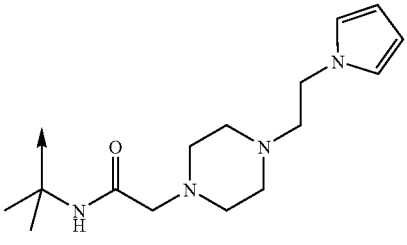 | 5.2 | 720.2 722.2 724.0 |
| 4127 | 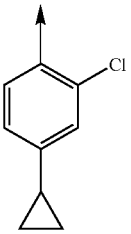 | Cl | H | 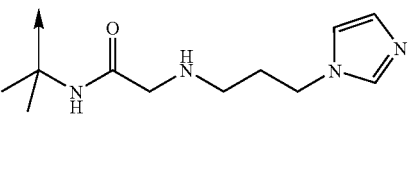 | 4.5 | 666.2 668.2 670.0 |

TABLE 4-continued
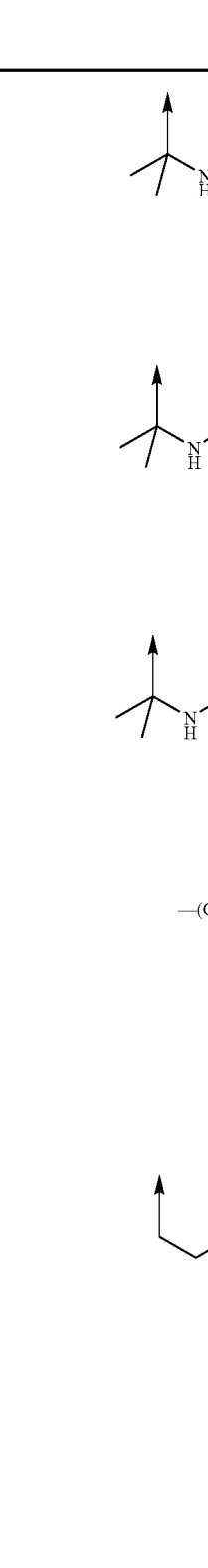
wherein R¹, R², R³ and R⁹ are given in the table below:
| Cpd | R¹ | R² | R³ | R⁹ | $t_R$ (min) | MS (MH⁺) |
|---|---|---|---|---|---|---|
| 4128 | 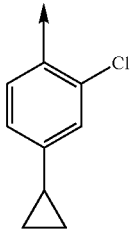 | Cl | H | 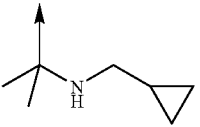 | 5.1 | 553.1 555.1 557.1 (M − H)⁻ |
| 4129 | 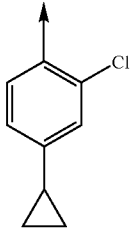 | Cl | H | 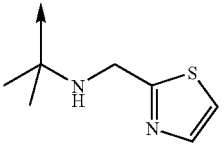 | 4.9 | 598.1 600.1 602.1 |
| 4130 | 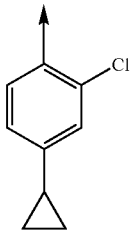 | Cl | H | 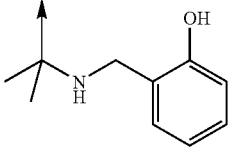 | 5.2 | 607.2 609.2 611.0 |
| 4131 | 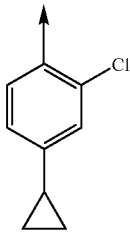 | Cl | H | —(CH₂)₂OH | 5.4 | 488.1 490.1 492.0 |
| 4132 | 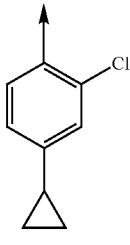 | Cl | H | 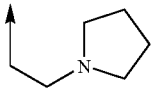 | 4.9 | 541.1 543.1 545.0 |

TABLE 4-continued
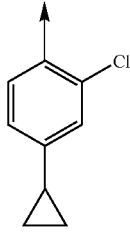
wherein R¹, R², R³ and R⁹ are given in the table below:
| Cpd | R¹ | R² | R³ | R⁹ | $t_R$ (min) | MS (MH⁺) |
|---|---|---|---|---|---|---|
| 4133 |  | Cl | H | 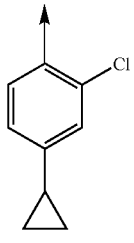 | 6.4 | 470.0 472.1 474.0 |
| 4134 | 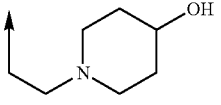 | Cl | H | 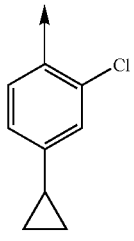 | 4.6 | 571.1 573.1 575.0 |
| 4135 | 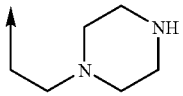 | Cl | H | 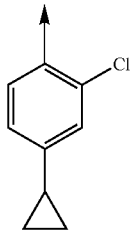 | 4.1 | 556.1 558.1 560.0 |
| 4136 | 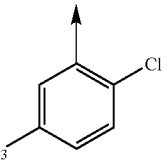 | Cl | H | —CH₂COOH | 5.3 | 502.1 504.1 506.0 |
| 4137 | 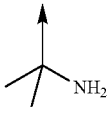 | Cl | H | 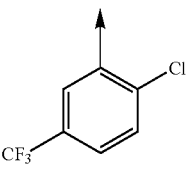 | 4.3 | 527.0 529.0 531.0 (M − H)⁻ |
| 4138 | 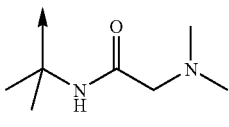 | Cl | H | | 4.7 | 614.1 616.1 618.0 |

TABLE 4-continued
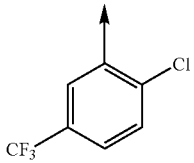
wherein R¹, R², R³ and R⁹ are given in the table below:
| Cpd | R¹ | R² | R³ | R⁹ | $t_R$ (min) | MS (MH⁺) |
|---|---|---|---|---|---|---|
| 4139 | 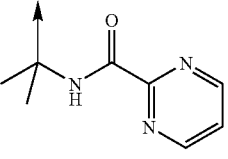 | Cl | H | 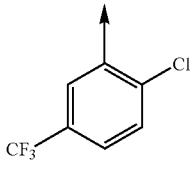 | 5.8 | 635.1 637.1 639.1 |
| 4140 | 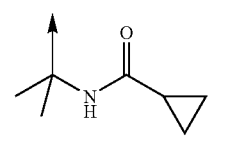 | Cl | H | 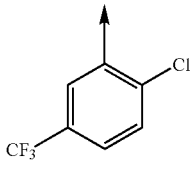 | 5.6 | 597.1 599.1 601.0 |
| 4141 | 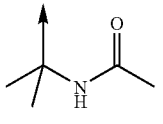 | Cl | H | 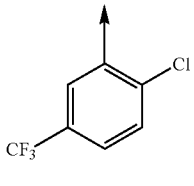 | 5.3 | 571.1 573.1 575.1 |
| 4142 | 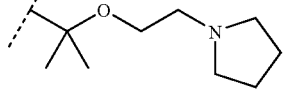 | Cl | H | 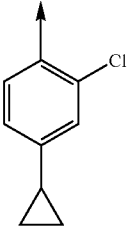 | 5.1 | 627.2 629.2 631.0 |
| 4143 | 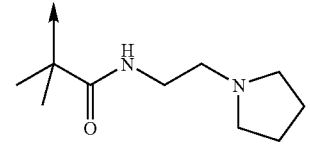 | Cl | H | 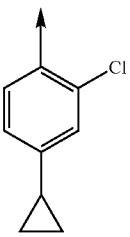 | 6.6 | 626.2 628.2 630.2 |
| 4144 | 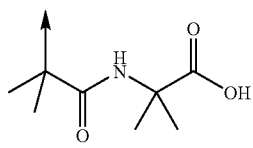 | Cl | H | | 8.2 | 615.1 617.1 619.1 |

TABLE 4-continued

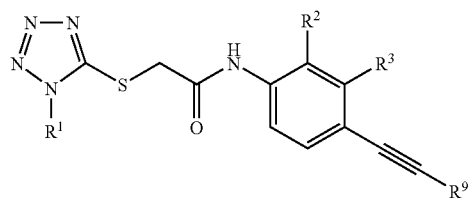

wherein R¹, R², R³ and R⁹ are given in the table below:

| Cpd | R¹ | R² | R³ | R⁹ | $t_R$ (min) | MS (MH⁺) |
|---|---|---|---|---|---|---|
| 4145 | 2-chloro-4-cyclopropylphenyl | Cl | H | -C(CH₃)₂-C(O)NH-CH₂CH₂CH₂-N(CH₃)₂ | 6.4 | 614.2 616.2 618.2 |
| 4146 | 2-chloro-4-cyclopropylphenyl | Cl | H | -C(CH₃)₂-C(O)NH-CH₂-(tetrahydrofuran-2-yl) | 8.7 | 613.2 615.2 617.2 |
| 4147 | 2-chloro-5-trifluoromethylphenyl | Cl | H | -C(CH₃)₂-NH-C(O)-CH₂CH₂CH₂-N(CH₃)₂ | 5.3 | 642.2 644.2 645.2 |
| 4148 | 2-chloro-4-cyclopropylphenyl | Cl | H | -C(CH₃)₂-C(O)NH-CH₂-(pyridine-4-yl N-oxide) | 6.9 | 634.1 636.1 638.1 (M − H)⁻ |
| 4149 | 2-chloro-4-cyclopropylphenyl | Cl | H | -C(CH₃)₂-C(O)-N(piperidine-4-COOH) | 7.9 | 639.1 641.1 643.1 (M − H)⁻ |

TABLE 4-continued
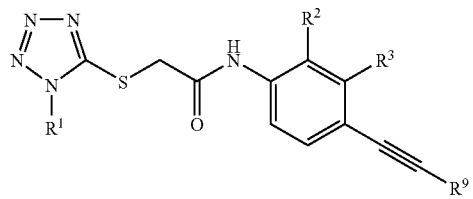
wherein R¹, R², R³ and R⁹ are given in the table below:
| Cpd | R¹ | R² | R³ | R⁹ | $t_R$ (min) | MS (MH⁺) |
|---|---|---|---|---|---|---|
| 4150 | 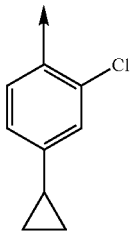 | Cl | H | 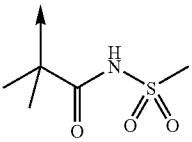 | 8.3 | 605.1 607.0 609.0 (M − H)⁻ |
| 4151 | 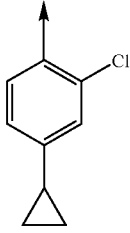 | Cl | F | 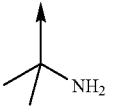 | 4.7 | 517.1 519.1 520.1 (M − H)⁻ |
| 4152 | 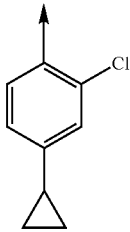 | Cl | H | 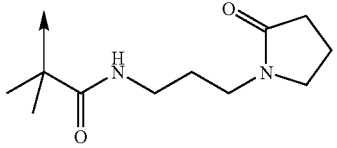 | 7.8 | 654.2 656.2 658.2 |
| 4153 | 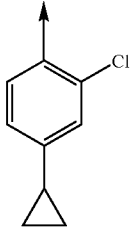 | Cl | H | 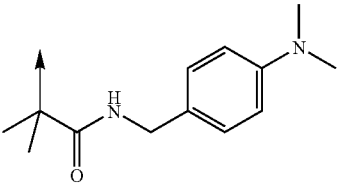 | 6.77 | 662.2 664.2 666.2 |
| 4154 | 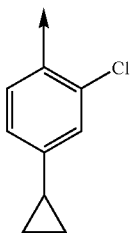 | Cl | H | 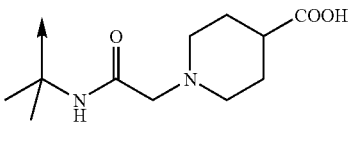 | 4.9 | 670.1 672.1 674.0 |

TABLE 4-continued
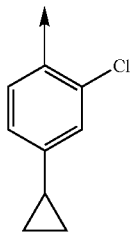
wherein R¹, R², R³ and R⁹ are given in the table below:
| Cpd | R¹ | R² | R³ | R⁹ | t$_R$ (min) | MS (MH⁺) |
|---|---|---|---|---|---|---|
| 4155 | 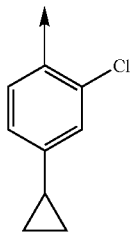 | Cl | F | 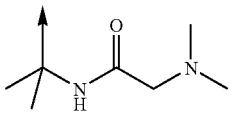 | 5.0 | 604.1 606.1 608.0 |
| 4156 | 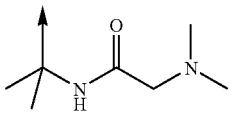 | Cl | F | 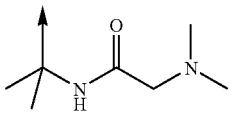 | 5.13 | 632.2 634.2 636.0 |
| 4157 | 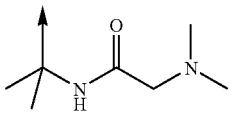 | Cl | F | 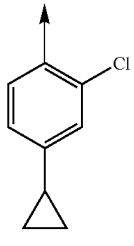 | 5.6 | 640.1 642.1 644.0 |
| 4158 | 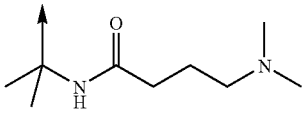 | Cl | H | —C(Me)₂COOH | 7.0 | 598.1 600.1 602.0 |
| 4159 | 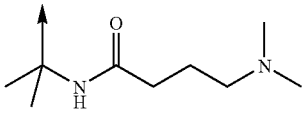 | Cl | H | —C(Me)₂COOH | 7.0 | 598.1 600.1 602.1 |
| 4160 | 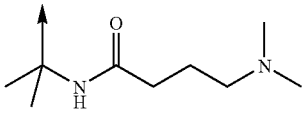 | Cl | F | 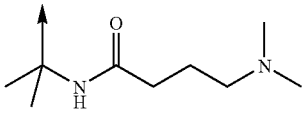 | 5.6 | 672.1 674.1 676.0 |

TABLE 4-continued

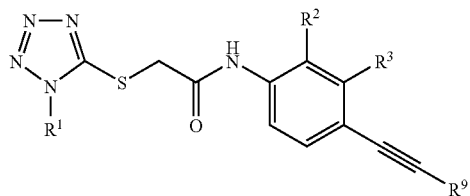

wherein R¹, R², R³ and R⁹ are given in the table below:

| Cpd | R¹ | R² | R³ | R⁹ | $t_R$ (min) | MS (MH⁺) |
|---|---|---|---|---|---|---|
| 4161 | 2,3-dichlorophenyl | Cl | H | —C(Me)₂COOH | 6.3 | 524.0 526.0 528.0 |
| 4162 | 2,5-dichlorophenyl | Cl | H | —C(Me)₂COOH | 6.3 | 524.0 526.0 528.0 529.0 |
| 4163 | 2-chloro-5-(trifluoromethyl)phenyl | Cl | F | —C(Me)₂NH₂ | 4.4 | 545.1 547.1 549.0 (M − H)⁻ |
| 4164 | 2-chloro-5-(trifluoromethyl)phenyl | Cl | F | —C(Me)₂NHC(O)-pyridyl N-oxide | 5.4 | 668.1 670.1 672.1 |
| 4165 | 2-chloro-4-cyclopropylphenyl | Cl | F | —C(Me)₂OCH₂CH₂O-(4-pyridyl) | 5.5 | 641.2 643.2 645.0 |
| 4166 | 2-chloro-5-(trifluoromethyl)phenyl | Cl | F | —C(Me)₂OCH₂CH₂O-(4-pyridyl) | 5.4 | 669.2 671.2 673.0 |

TABLE 4-continued

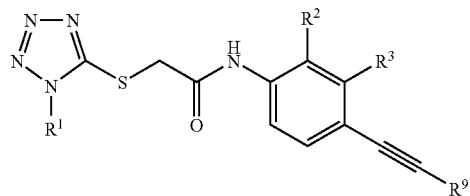

wherein R[1], R[2], R[3] and R[9] are given in the table below:

| Cpd | R[1] | R[2] | R[3] | R[9] | $t_R$ (min) | MS (MH+) |
|---|---|---|---|---|---|---|
| 4167 | 2-chloro-4-cyclopropylphenyl | Cl | H | –C(Me)₂–O–CH₂CH₂–O–(4-pyridyl) | 5.4 | 623.2 625.2 627.0 |
| 4168 | 2-chloro-5-trifluoromethylphenyl | Cl | H | –C(Me)₂–O–CH₂CH₂–O–(4-pyridyl) | 5.3 | 651.2 653.2 655.0 |
| 4169 | 2-chloro-4-cyclopropylphenyl | Cl | F | –C(Me)₂–O–CH₂CH₂–OH | 5.8 | 562.1 564.1 566.0 (M – H)⁻ |
| 4170 | 2-chloro-5-trifluoromethylphenyl | Cl | F | –C(Me)₂–NHC(O)–CH₂CH₂CH₂–N(Me)₂ | 4.8 | 660.2 662.2 664.0 |
| 4171 | 2-chloro-5-trifluoromethylphenyl | Cl | F | –C(Me)₂–NHC(O)–CH₂–N(Me)₂ | 4.8 | 632.2 634.2 636.0 |
| 4172 | 6-chloroquinolin-5-yl | Cl | H | —C(Me)₂COOH | 5.7 | 602.2 604.2 606.0 |

TABLE 4-continued

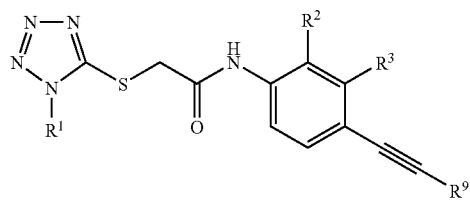

wherein R¹, R², R³ and R⁹ are given in the table below:

| Cpd | R¹ | R² | R³ | R⁹ | $t_R$ (min) | MS (MH⁺) |
|---|---|---|---|---|---|---|
| 4173 | ![R1 structure: 2-chloro-4-(1-methylcyclopropyl)phenyl] | Cl | H | —C(Me)₂COOH | 9.0 | 544.2 546.1 548.2 |
| 4174 | ![R1 structure: 2-chloro-5-cyclopropylphenyl] | Cl | H | —C(Me)₂COOH | 6.6 | 530.1 532.1 534.1 |
| 4175 | ![R1 structure: 2-chloro-4-cyclopropylphenyl] | Cl | F | ![R9: -C(Me)2-O-CH2CH2-pyrrolidine] | 5.5 | 617.2 619.2 621.1 |
| 4176 | ![R1 structure: 2-chloro-4-cyclopropylphenyl] | Cl | F | ![R9: -C(Me)2-O-CH2CH2-piperazine] | 4.7 | 632.2 634.2 636.0 |
| 4177 | ![R1 structure: 2-chloro-4-cyclopropylphenyl] | Cl | H | ![R9: -C(Me)2-CH2-NH-CH2-COOH] | 4.9 | 571.1 573.1 575.0 (M − H)⁻ |

TABLE 4-continued

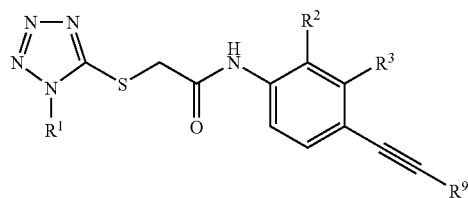

wherein R¹, R², R³ and R⁹ are given in the table below:

| Cpd | R¹ | R² | R³ | R⁹ | $t_R$ (min) | MS (MH⁺) |
|---|---|---|---|---|---|---|
| 4178 | 2-Cl-4-cyclopropyl-phenyl | CH₃ | F | N-tert-butyl pyridine-4-carboxamide N-oxide | 5.8 | 620.2 622.2 624.0 |
| 4179 | 2-Cl-3-cyclopropyl-phenyl | Cl | H | —C(Me)₂COOH | 6.5 | 530.1 532.1 534.0 |
| 4180 | 2-Cl-4-cyclopropyl-phenyl | CH₃ | H | N-tert-butyl pyridine-4-carboxamide N-oxide | 5.7 | 602.2 604.2 606.0 |
| 4181 | 2-Cl-4-cyclopropyl-phenyl | Cl | H | —C(Me)₂CH₂COOH | 5.8 | 544.1 546.1 548.0 |
| 4182 | 2-Cl-4-cyclopropyl-phenyl | Cl | H | —C(Me)₂OCH₂CH₂-(2-oxopyrrolidin-1-yl) | 6.8 | 613.2 615.2 617.0 |

TABLE 4-continued
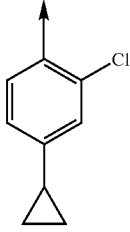
wherein R¹, R², R³ and R⁹ are given in the table below:
| Cpd | R¹ | R² | R³ | R⁹ | $t_R$ (min) | MS (MH⁺) |
|---|---|---|---|---|---|---|
| 4183 | 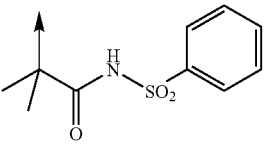 | Cl | H | 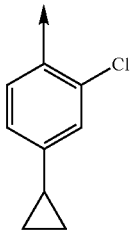 | 9.3 | 669.1 671.1 673.1 |
| 4184 | 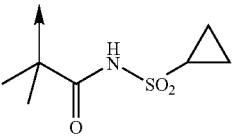 | Cl | H | 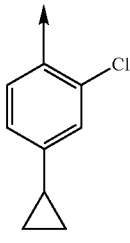 | 8.8 | 631.1 633.1 635.1 (M − H)⁻ |
| 4185 | 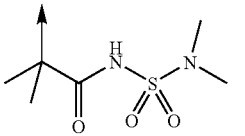 | Cl | H | 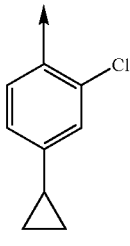 | 8.9 | 636.1 638.1 640.1 |
| 4186 | 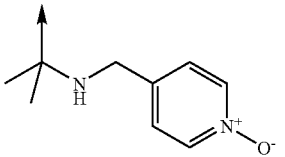 | Cl | H | 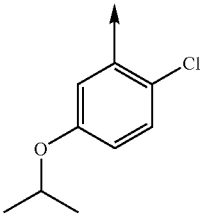 | 4.7 | 608.2 610.2 612.0 |
| 4187 |  | Cl | H | —C(Me)₂COOH | 6.7 | 548.1 550.1 552.0 |

TABLE 4-continued
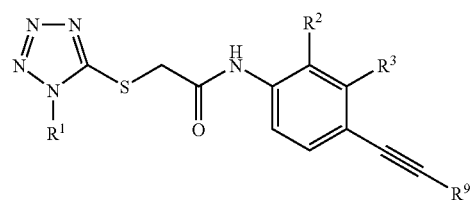
wherein R¹, R², R³ and R⁹ are given in the table below:
| Cpd | R¹ | R² | R³ | R⁹ | $t_R$ (min) | MS (MH⁺) |
|---|---|---|---|---|---|---|
| 4188 | 2-Cl-4-cyclopropylphenyl | Cl | H | t-Bu-NHC(O)CH₂NH-(4-pyridyl) | 5.1 | 635.2 637.2 639.0 |
| 4189 | 2,5-dichlorophenyl | Cl | H | t-Bu-NHC(O)-(pyridine-4-yl N-oxide) | 5.7 | 616.1 618.1 620.1 |
| 4190 | 2-Cl-4-cyclopropylphenyl | Cl | H | -C(CH₃)₂-O-CH₂CH₂NH₂ | 5.5 | 545.2 547.2 549.0 |
| 4191 | 2-Cl-4-cyclopropylphenyl | Cl | H | t-Bu-NHC(O)-(pyridine-3-yl N-oxide) | 6.0 | 622.2 624.2 626.0 |
| 4192 | 2-Cl-4-cyclopropylphenyl | Cl | H | t-Bu-NHC(O)CH₂NH₂ | 4.7 | 558.2 560.2 562.0 |

TABLE 4-continued
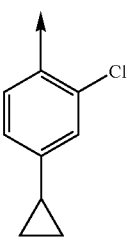
wherein R¹, R², R³ and R⁹ are given in the table below:
| Cpd | R¹ | R² | R³ | R⁹ | t_R (min) | MS (MH⁺) |
|---|---|---|---|---|---|---|
| 4193 | 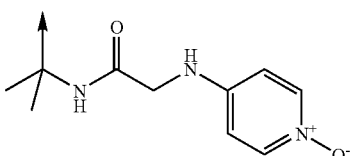 | Cl | H | 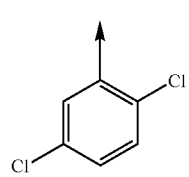 | 5.1 | 651.2 653.2 655.0 |
| 4194 | 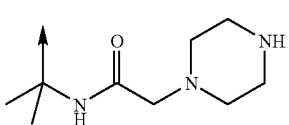 | Cl | H | 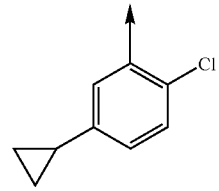 | 4.7 | 621.1 623.1 625.1 626.1 |
| 4195 | 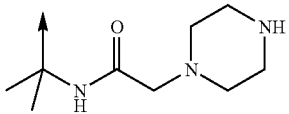 | Cl | H | 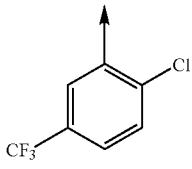 | 5.0 | 627.2 629.2 631.0 |
| 4196 | 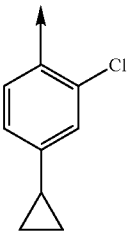 | Cl | H | —C(Me)₂COOH | 7.3 | 558.1 560.1 562.1 |
| 4197 | 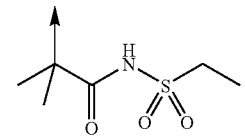 | Cl | H | 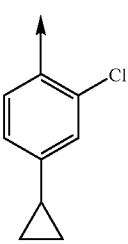 | 8.6 | 619.1 621.1 623.1 (M − H)⁻ |
| 4198 | 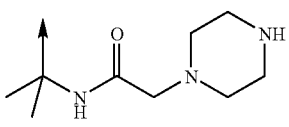 | Cl | F | | 4.8 | 645.2 647.2 649.2 |

TABLE 4-continued
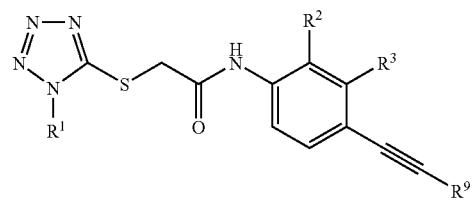
wherein R[1], R[2], R[3] and R[9] are given in the table below:
| Cpd | R[1] | R[2] | R[3] | R[9] | $t_R$ (min) | MS (MH[+]) |
|---|---|---|---|---|---|---|
| 4199 | 2-Cl-5-tBu-phenyl | Cl | H | —C(Me)$_2$OH | 8.6 | 518.1 520.1 522.0 |
| 4200 | 2-Cl-5-tBu-phenyl | Cl | H | —C(Me)$_2$COOH | 8.8 | 546.1 520.1 522.0 |
| 4201 | 2-Cl-5-tBu-phenyl | Cl | H | —C(Me)$_2$NH$_2$ | 6.4 | 515.1 517.1 519.0 (M − H)[−] |
| 4202 | 2-Cl-5-tBu-phenyl | Cl | H | —C(Me)$_2$NHC(O)CH$_2$-piperazinyl | 6.4 | 643.2 645.2 647.1 |
| 4203 | 2-Cl-5-tBu-phenyl | Cl | H | —C(Me)$_2$NHC(O)CH$_2$NH-(pyridin-4-yl N-oxide) | 6.9 | 667.1 669.1 671.0 |
| 4204 | 2-Cl-5-tBu-phenyl | Cl | H | —C(Me)$_2$NHC(O)CH$_2$-(4-COOH-piperidin-1-yl) | 6.6 | 686.2 688.2 690.1 |

TABLE 4-continued
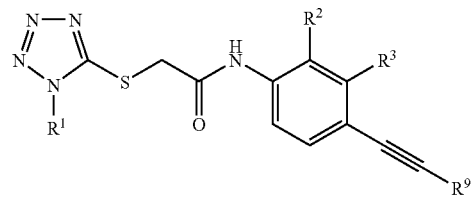
wherein R[1], R[2], R[3] and R[9] are given in the table below:
| Cpd | R[1] | R[2] | R[3] | R[9] | $t_R$ (min) | MS (MH[+]) |
|---|---|---|---|---|---|---|
| 4205 | 2-Cl, 5-tBu-phenyl | Cl | H | tBu-NH-C(O)-(pyridine-4-yl N-oxide) | 7.6 | 638.1 640.1 642.1 |
| 4206 | 2,5-diCl, 4-cyclopropyl-phenyl | Cl | H | —C(Me)$_2$COOH | 7.0 | 564.1 566.1 568.1 |
| 4207 | 2-Cl-phenyl | Cl | H | —C(Me)$_2$COOH | 5.8 | 490.1 492.1 494.0 |
| 4208 | 2-Cl, 4-cyclopropyl-phenyl | Cl | H | tBu-NH-C(O)-(pyridine-4-yl N-oxide) | 6.0 | 622.2 624.1 626.0 |
| 4209 | 2-Cl, 4-cyclopropyl-phenyl | Cl | F | —C(Me)$_2$-O-CH$_2$CH$_2$-piperazine | 4.6 | 632.0 634.0 636.0 |
| 4210 | 2,3-diCl, 5-CF$_3$-phenyl | Cl | H | tBu-NH-C(O)-(pyridine-4-yl N-oxide) | 6.2 | 684.0 686.0 688.0 |

TABLE 4-continued
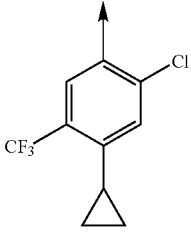
wherein R¹, R², R³ and R⁹ are given in the table below:
| Cpd | R¹ | R² | R³ | R⁹ | $t_R$ (min) | MS (MH⁺) |
|---|---|---|---|---|---|---|
| 4211 | 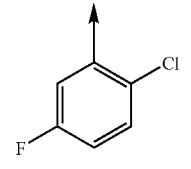 | Cl | H | —C(Me)₂COOH | 7.0 | 598.1 600.1 602.0 |
| 4212 | 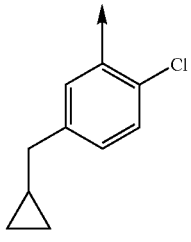 | Cl | H | —C(Me)₂COOH | 6.0 | 508.0 510.0 512.0 |
| 4213 | 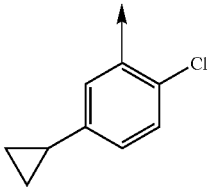 | Cl | H | —C(Me)₂COOH | 5.9 | 544.1 546.0 548.0 |
| 4214 | 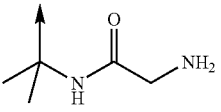 | Cl | H | 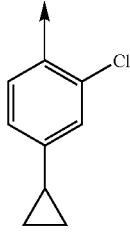 | 5.2 | 558.0 560.0 562.0 |
| 4215 | 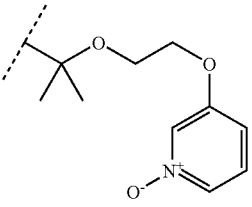 | Cl | F | 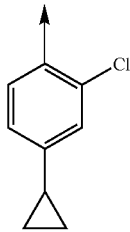 | 6.7 | 656.9 658.9 660.0 |
| 4216 | 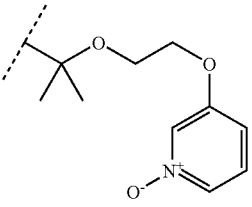 | Cl | F | 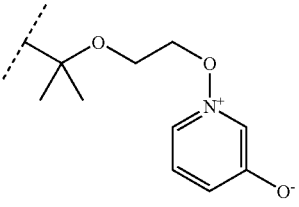 | 5.9 | 656.9 658.9 660.0 |

TABLE 4-continued
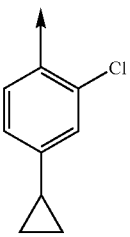
wherein R¹, R², R³ and R⁹ are given in the table below:
| Cpd | R¹ | R² | R³ | R⁹ | $t_R$ (min) | MS (MH⁺) |
|---|---|---|---|---|---|---|
| 4217 | 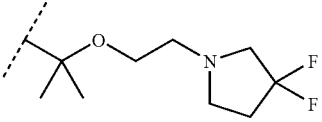 | Cl | F | 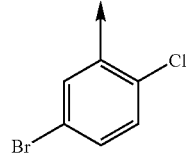 | 6.0 | 653.0<br>655.0<br>657.0 |
| 4218 | 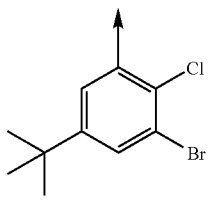 | Cl | H | —C(Me)₂COOH | 7.6 | 567.9<br>569.9<br>571.9<br>573.0 |
| 4219 | 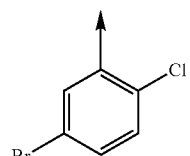 | Cl | H | —C(Me)₂COOH | 9.2 | 624.0<br>626.0<br>628.0<br>630.0 |
| 4220 | 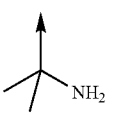 | Cl | H | 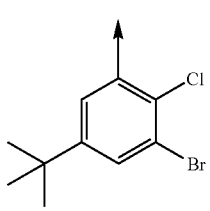 | 5.6 | 537.0<br>538.9<br>540.9<br>(M − H)⁻ |
| 4221 | 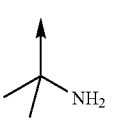 | Cl | H | 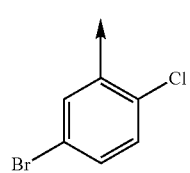 | 6.9 | 593.0<br>595.0<br>596.9<br>599.0<br>(M − H)⁻ |
| 4222 | 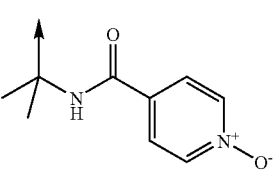 | Cl | H |  | 6.5 | 660.0<br>662.0<br>664.0<br>666.0 |

TABLE 4-continued wherein R¹, R², R³ and R⁹ are given in the table below:

| Cpd | R¹ | R² | R³ | R⁹ | t_R (min) | MS (MH⁺) |
|---|---|---|---|---|---|---|
| 4223 | 2-Cl-3-Br-5-tert-butylphenyl | Cl | H | N-tert-butyl pyridine-4-carboxamide N-oxide | 8.3 | 716.0 718.0 720.0 722.0 |
| 4224 | 2-Cl-3-Br-5-tert-butylphenyl | Cl | H | N-tert-butyl-2-(piperazin-1-yl)acetamide | 6.5 | 721.0 723.0 725.0 727.0 |
| 4225 | 2-Cl-3-Br-5-tert-butylphenyl | Cl | H | N-tert-butyl-2-((1-oxidopyridin-4-yl)amino)acetamide | 7.5 | 745.0 747.0 749.0 751.0 |
| 4226 | 2-Cl-3-Br-5-tert-butylphenyl | Cl | H | 1-(2-(tert-butylamino)-2-oxoethyl)piperidine-4-carboxylic acid | 7.2 | 764.0 766.0 768.0 770.0 |
| 4227 | 2-Cl-4-cyclopropylphenyl | Cl | H | N-tert-butylglycine | 5.8 | 557.0 559.0 561.0 |
| 4228 | 2-Cl-4-cyclopropylphenyl | Cl | H | N-tert-butylpiperazine-1-carboxamide | 5.3 | 613.1 615.1 617.0 |

TABLE 4-continued

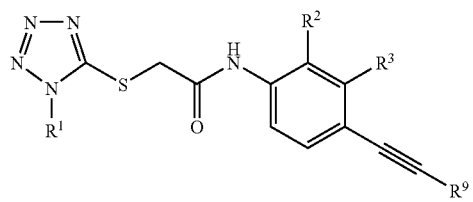

wherein $R^1$, $R^2$, $R^3$ and $R^9$ are given in the table below:

| Cpd | $R^1$ | $R^2$ | $R^3$ | $R^9$ | $t_R$ (min) | MS ($MH^+$) |
|---|---|---|---|---|---|---|
| 4229 | 4-Cl, 2-Cl-phenyl-cyclopropyl | Cl | H | tBu-NH-C(O)-N(4-methylpiperazinyl) | 5.4 | 625.0 627.0 629.0 |
| 4230 | 2-Cl, 5-CF3, 3-cyclopropyl-phenyl | Cl | F | tBu-NH-C(O)-pyridinyl N-oxide | 6.5 | 708.0 710.0 712.0 |
| 4231 | 4-Cl, 2-Cl-phenyl-cyclopropyl | Cl | H | tBu-NH-CH2-C(O)NH2 | 5.6 | 556.0 558.0 560.0 (M − H)⁻ |
| 4232 | 4-Cl, 2-Cl-phenyl-cyclopropyl | Cl | H | tBu-NH-C(O)-CH2-COOH | 6.9 | 587.1 589.0 591.0 |
| 4233 | 4-Cl, 2-Cl-phenyl-cyclopropyl | Cl | H | tBu-NH-C(O)-cyclopropyl-COOH | 7.8 | 613.1 615.1 617.0 |

US 8,198,458 B2
TABLE 4-continued
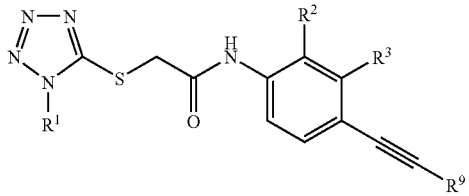
wherein R[1], R[2], R[3] and R[9] are given in the table below:
| Cpd | R[1] | R[2] | R[3] | R[9] | t$_R$ (min) | MS (MH[+]) |
|---|---|---|---|---|---|---|
| 4234 | 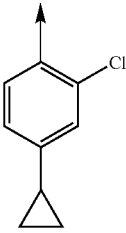 | Cl | H | 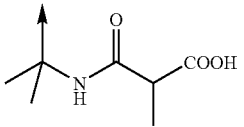 | 7.1 | 601.1 603.1 605.0 |
| 4235 | 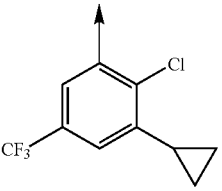 | Cl | H | 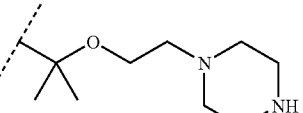 | 5.4 | 682.1 684.1 686.0 |
| 4236 | 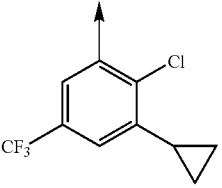 | Cl | F | 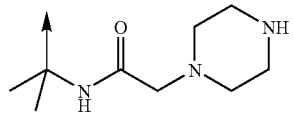 | 5.5 | 713.0 715.0 717.0 |
| 4237 | 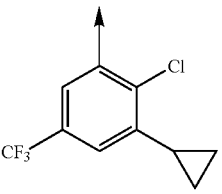 | Cl | F | 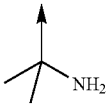 | 5.7 | 570.0 572.0 574.0 |
| 4238 | 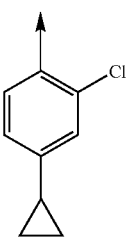 | Cl | H | 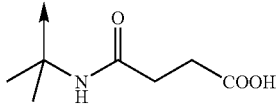 | 6.9 | 601.1 603.1 605.0 |
| 4239 | 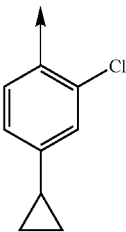 | Cl | H | 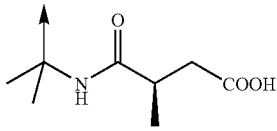 | 7.1 | 615.1 617.1 619.0 |

TABLE 4-continued

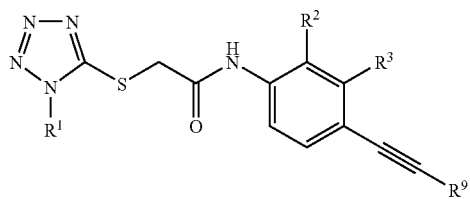

wherein $R^1$, $R^2$, $R^3$ and $R^9$ are given in the table below:

| Cpd | $R^1$ | $R^2$ | $R^3$ | $R^9$ | $t_R$ (min) | MS ($MH^+$) |
|---|---|---|---|---|---|---|
| 4240 | 2-Cl-4-(cyclopropylmethyl)phenyl | Cl | H | —C(Me)₂COOH | 8.7 | 544.1 546.1 548.1 |
| 4241 | 2-Cl-4-cyclopropylphenyl | Cl | H | —C(Me)₂—O—CH₂CH₂—N(thiomorpholine-1,1-dioxide) | 6.5 | 663.2 665.2 667.0 |
| 4242 | 2-Cl-3-cyclopropyl-5-CF₃-phenyl | Cl | H | —C(Me)₂—O—CH₂CH₂—N(3,3-difluoropyrrolidinyl) | 7.2 | 703.1 705.1 707.0 |
| 4243 | 4-Cl-3-(dimethylamino)phenyl | Cl | H | —C(Me)₂COOH | 7.4 | 533.1 535.1 537.0 |
| 4244 | 2-Cl-4-(cyclopropylmethyl)phenyl | Cl | H | —C(Me)₂—C(O)NH—CH₂CH₂CH₂—N(2-oxopyrrolidinyl) | 8.3 | 668.2 670.2 672.0 |

TABLE 4-continued

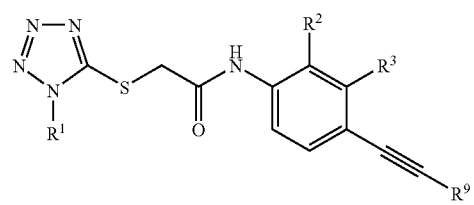

wherein R¹, R², R³ and R⁹ are given in the table below:

| Cpd | R¹ | R² | R³ | R⁹ | $t_R$ (min) | MS (MH⁺) |
|---|---|---|---|---|---|---|
| 4245 | 2-chloro-4-(cyclopropylmethyl)phenyl | Cl | H | C(CH₃)₂C(O)NH(CH₂)₃N(CH₃)₂ | 6.5 | 628.2 630.2 632.0 |
| 4246 | 2-chloro-4-(cyclopropylmethyl)phenyl | Cl | H | C(CH₃)₂OCH₂CH₂-pyrrolidinyl | 6.9 | 613.2 615.2 617.0 |
| 4247 | 2-chloro-4-(cyclopropylmethyl)phenyl | Cl | H | C(CH₃)₂NHC(O)-pyridyl-N-oxide | 7.4 | 636.2 638.2 640.0 |
| 4248 | 2-chloro-3-trifluoromethyl-5-cyclopropylphenyl | Cl | F | C(CH₃)₂NHC(O)-pyridyl-N-oxide | 7.3 | 708.1 710.1 712.0 |
| 4249 | 2-chloro-4-cyclopropylphenyl | Cl | H | C(CF₃)₂OH | 8.3 | 610.1 612.1 614.0 |

TABLE 4-continued
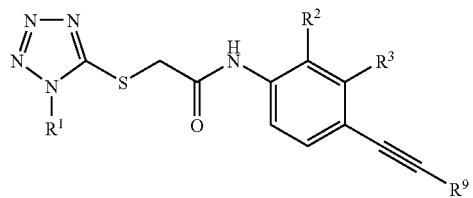
wherein $R^1$, $R^2$, $R^3$ and $R^9$ are given in the table below:
| Cpd | $R^1$ | $R^2$ | $R^3$ | $R^9$ | $t_R$ (min) | MS (MH$^+$) |
|---|---|---|---|---|---|---|
| 4250 | 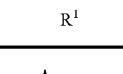 | Cl | F | 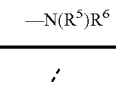 | 6.3 | 585.1 587.1 589.0 (M − H)$^-$ |
TABLE 5
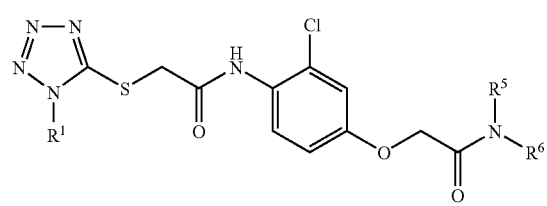
wherein $R^1$, $R^5$ and $R^6$ are given in the table below:
| Cpd | $R^1$ | —N(R$^5$)R$^6$ | $t_R$ (min) | MS (MH$^+$) |
|---|---|---|---|---|
| 5001 | 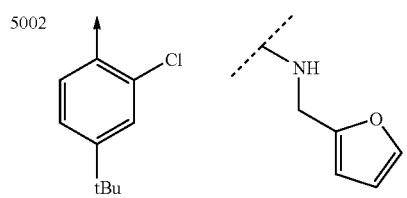 |  | 7.0 | 590.1 592.1 594.0 |
| 5002 | 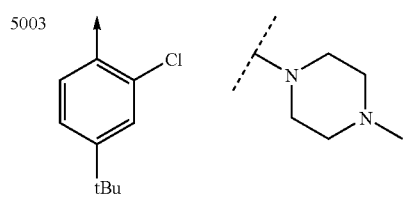 | 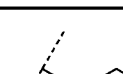 | 7.0 | 589.1 591.1 593.0 |
| 5003 | 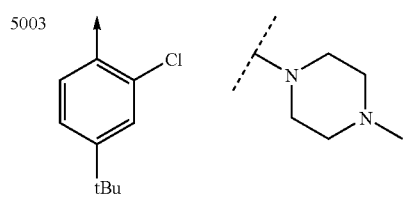 | 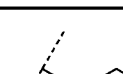 | 5.2 | 592.2 594.2 596.0 |
TABLE 5-continued
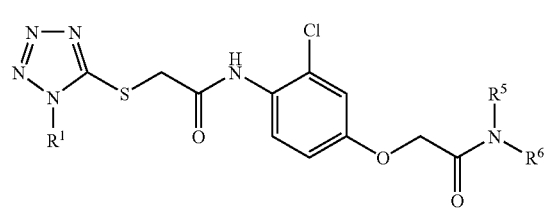
wherein $R^1$, $R^5$ and $R^6$ are given in the table below:
| Cpd | $R^1$ | —N(R$^5$)R$^6$ | $t_R$ (min) | MS (MH$^+$) |
|---|---|---|---|---|
| 5004 | 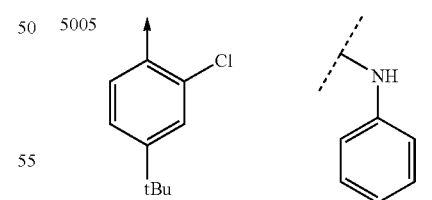 | | 6.7 | 579.1 581.1 583.1 |
| 5005 |  | | 6.5 | 670.2 672.2 674.0 |

TABLE 5-continued

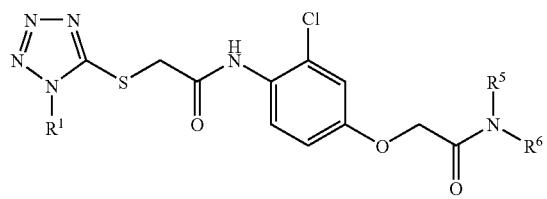

wherein R¹, R⁵ and R⁶ are given in the table below:

| Cpd | R¹ | —N(R⁵)R⁶ | $t_R$ (min) | MS (MH⁺) |
|---|---|---|---|---|
| 5006 | 2-Cl-4-tBu-phenyl | NH-morpholine | 5.4 | 594.1 596.1 598.0 |
| 5007 | 2-Cl-4-tBu-phenyl | NH-CH₂CH₂-morpholine | 5.3 | 622.2 624.2 626.2 |
| 5008 | 2-Cl-4-tBu-phenyl | NH-(1-benzylpiperidin-4-yl) | 6.8 | 682.2 684.2 686.2 |
| 5009 | 2-Cl-4-tBu-phenyl | NH-(2-hydroxyphenyl) | 7.1 | 601.1 603.1 605.1 |
| 5010 | 2-Cl-4-tBu-phenyl | NH-(2-carboxyphenyl) | 7.1 | 629.1 631.1 633.0 |

TABLE 5-continued

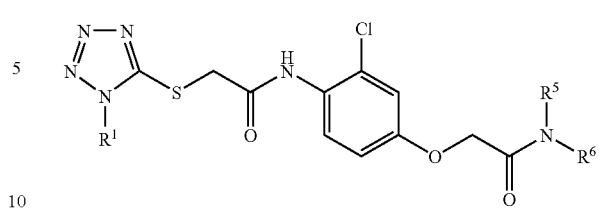

wherein R¹, R⁵ and R⁶ are given in the table below:

| Cpd | R¹ | —N(R⁵)R⁶ | $t_R$ (min) | MS (MH⁺) |
|---|---|---|---|---|
| 5011 | 2-Cl-4-tBu-phenyl | NH-(3-hydroxyphenyl) | 6.9 | 601.1 603.1 605.1 |
| 5012 | 2-Cl-4-tBu-phenyl | NH-(4-dimethylaminophenyl) | 5.7 | 628.2 630.2 632.0 |
| 5013 | 2-Cl-4-tBu-phenyl | NH-(4-hydroxyphenyl) | 6.8 | 601.1 603.1 605.0 |
| 5014 | 2-Cl-4-tBu-phenyl | NH-CH(CH₃)CH₂CO₂H | 6.5 | 595.1 597.1 599.1 |
| 5015 | 2-Cl-4-tBu-phenyl | NH-CH₂CH₂OH | 6.1 | 553.1 555.1 557.0 |

TABLE 5-continued

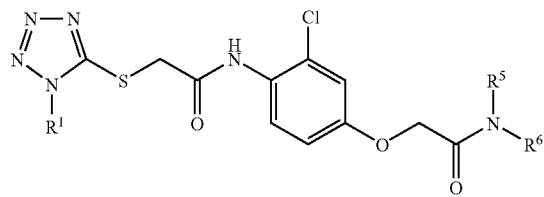

wherein $R^1$, $R^5$ and $R^6$ are given in the table below:

| Cpd | $R^1$ | —N($R^5$)$R^6$ | $t_R$ (min) | MS (MH$^+$) |
|---|---|---|---|---|
| 5016 | 2-Cl, 4-tBu phenyl | NH-CH$_2$CH$_2$-(4-OH-phenyl) | 6.9 | 629.2 631.2 633.0 |
| 5017 | 2-Cl, 4-tBu phenyl | NH-(4-CO$_2$H-thiazol-2-yl) | 6.7 | 664.1 666.1 668.1 |
| 5018 | 2-Cl, 4-tBu phenyl | NH-CH(CH$_2$OH)CO$_2$H | 6.1 | 597.1 599.1 601.1 |
| 5019 | 2-Cl, 4-tBu phenyl | NH-CH$_2$-(3,4-diOH-phenyl) | 6.6 | 631.1 633.1 635.1 |
| 5020 | 2-Cl, 4-tBu phenyl | NH-CH$_2$CO$_2$H | 6.3 | 567.1 569.1 571.1 |

TABLE 5-continued

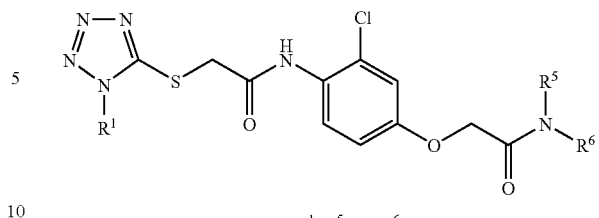

wherein $R^1$, $R^5$ and $R^6$ are given in the table below:

| Cpd | $R^1$ | —N($R^5$)$R^6$ | $t_R$ (min) | MS (MH$^+$) |
|---|---|---|---|---|
| 5021 | 2-Cl, 4-tBu phenyl | NH-CH$_2$CH$_2$-(3,4-diOH-phenyl) | 6.7 | 645.2 647.1 649.1 |
| 5022 | 2-Cl, 4-tBu phenyl | NH-(3-CO$_2$H-phenyl) | 6.9 | 629.1 631.1 633.0 |
| 5023 | 2-Cl, 4-tBu phenyl | NH-(4-CH$_2$CO$_2$H-phenyl) | 6.9 | 643.1 645.1 647.1 |
| 5024 | 2-Cl, 4-tBu phenyl | NH-CH$_2$CH$_2$-(pyridin-4-yl) | 5.3 | 612.2 614.2 616.0 |
| 5025 | 2-Cl, 4-tBu phenyl | NH-CH$_2$CH$_2$CO$_2$H | 6.3 | 581.1 583.1 585.0 |

TABLE 5-continued

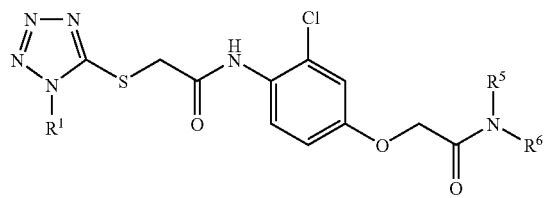

wherein R¹, R⁵ and R⁶ are given in the table below:

| Cpd | R¹ | —N(R⁵)R⁶ | $t_R$ (min) | MS (MH⁺) |
|---|---|---|---|---|
| 5026 | 2-Cl-4-tBu-phenyl | -NH-CH2-(4-NH2-phenyl) | 5.5 | 614.2, 616.2, 618.0 |
| 5027 | 2-Cl-4-tBu-phenyl | -NH-CH2-(4-CO2H-phenyl) | 6.7 | 643.1, 645.1, 647.1 |
| 5028 | 2-Cl-4-tBu-phenyl | 4-CO2H-piperidin-1-yl | 6.5 | 621.2, 623.2, 625.2 |
| 5029 | 2-Cl-4-tBu-phenyl | -NH-(1-methyl-2-CO2H-pyrrol-4-yl) | 6.7 | 632.1, 634.1, 636.0 |
| 5030 | 2-Cl-4-tBu-phenyl | -NH-(tetrahydropyran-4-yl) | 6.7 | 593.2, 595.2, 597.0 |
| 5031 | 2-Cl-4-tBu-phenyl | -NH-CH2-(trans-4-CO2H-cyclohexyl) | 6.7 | 649.2, 651.2, 653.0 |

TABLE 5-continued

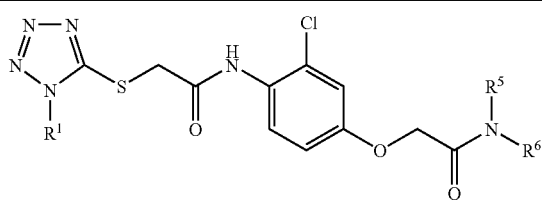

wherein R¹, R⁵ and R⁶ are given in the table below:

| Cpd | R¹ | —N(R⁵)R⁶ | $t_R$ (min) | MS (MH⁺) |
|---|---|---|---|---|
| 5032 | 2-Cl-4-cyclopropyl-phenyl | 4-CO2H-piperidin-1-yl | 5.7 | 605.1, 607.1, 609.1 |
| 5033 | 2-Cl-4-cyclopropyl-phenyl | -NH-CH2-(pyridin-3-yl) | 5.0 | 584.1, 566.0, 588.0 |
| 5034 | 2-Cl-4-cyclopropyl-phenyl | -NH-CH2CH2-(pyridin-2-yl) | 5.1 | 598.1, 600.0, 602.0 |
| 5035 | 2-Cl-4-cyclopropyl-phenyl | -NH-CH2CH2-(pyridin-3-yl) | 5.0 | 598.1, 600.1, 602.0 |
| 5036 | 2-Cl-4-cyclopropyl-phenyl | -NH-CH2CH2-(pyridin-4-yl) | 5.0 | 598.1, 600.1, 602.0 |

TABLE 5-continued

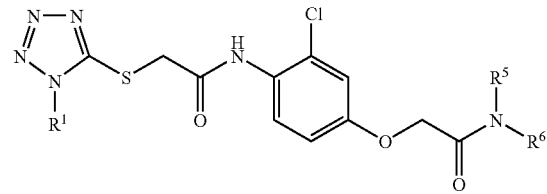

wherein R¹, R⁵ and R⁶ are given in the table below:

| Cpd | R¹ | —N(R⁵)R⁶ | $t_R$ (min) | MS (MH⁺) |
|---|---|---|---|---|
| 5037 | 2-Cl, 4-cyclopropyl phenyl | N-methyl-N-(2-(pyridin-4-yl)ethyl) | 5.0 | 612.2, 614.2, 616.0 |
| 5038 | 2-Cl, 4-cyclopropyl phenyl | NH-(2-(2-(1-oxido-pyridin-2-yl))ethyl) | 5.5 | 614.0, 616.0, 618.0 |
| 5039 | 2-Cl, 4-cyclopropyl phenyl | NH-(2-(3-(1-oxido-pyridin-3-yl))ethyl) | 5.4 | 614.0, 616.0, 618.0 |
| 5040 | 2-Cl, 4-cyclopropyl phenyl | NH-(2-(4-(1-oxido-pyridin-4-yl))ethyl) | 5.4 | 614.1, 616.0, 618.0 |

TABLE 5-continued

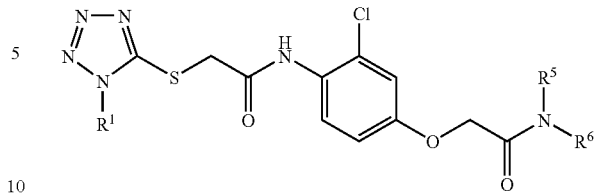

wherein R¹, R⁵ and R⁶ are given in the table below:

| Cpd | R¹ | —N(R⁵)R⁶ | $t_R$ (min) | MS (MH⁺) |
|---|---|---|---|---|
| 5041 | 2-Cl, 4-cyclopropyl phenyl | N-methyl-N-(2-(1-oxido-pyridin-4-yl)ethyl) | 5.5 | 628.1, 630.0, 632.0 |

TABLE 6

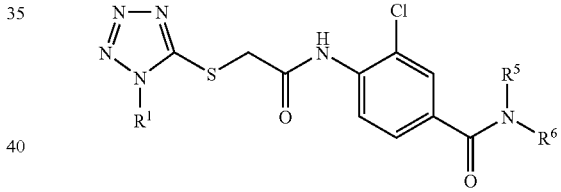

wherein R¹, R⁵ and R⁶ are given in the table below:

| Cpd | R¹ | —N(R⁵)R⁶ | $t_R$ (min) | MS (MH⁺) |
|---|---|---|---|---|
| 6001 | 2-Cl, 4-tBu phenyl | NH-(4-(carboxymethyl)phenyl) | 7.2 | 613.1, 615.1, 617.0 |
| 6002 | 2-Cl, 4-tBu phenyl | NH-cyclopropyl | 6.9 | 519.2, 521.2, 523.0 |

TABLE 6-continued

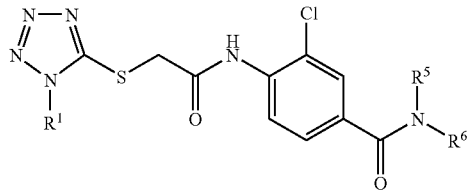

wherein R¹, R⁵ and R⁶ are given in the table below:

| Cpd | R¹ | —N(R⁵)R⁶ | $t_R$ (min) | MS (MH⁺) |
|---|---|---|---|---|
| 6003 | 2-Cl, 4-tBu phenyl | CH₂-(2-furyl)NH— | 7.1 | 559.2 561.2 563.2 |
| 6004 | 2-Cl, 4-tBu phenyl | 4-Me-piperazin-1-yl | 5.1 | 562.2 564.2 566.0 |
| 6005 | 2-Cl, 4-tBu phenyl | morpholin-4-yl | 6.9 | 549.2 551.2 553.0 |
| 6006 | 2-Cl, 4-tBu phenyl | 4-(morpholin-4-yl)phenyl-NH— | 6.7 | 640.3 642.3 644.0 |
| 6007 | 2-Cl, 4-tBu phenyl | morpholin-4-yl-NH— | 6.2 | 564.2 566.2 568.0 |

TABLE 6-continued

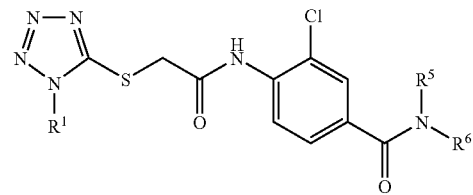

wherein R¹, R⁵ and R⁶ are given in the table below:

| Cpd | R¹ | —N(R⁵)R⁶ | $t_R$ (min) | MS (MH⁺) |
|---|---|---|---|---|
| 6008 | 2-Cl, 4-tBu phenyl | (pyridin-3-yl)methyl-NH— | 5.3 | 570.2 572.2 574.0 |
| 6009 | 2-Cl, 4-tBu phenyl | 1-benzyl-piperidin-4-yl-NH— | 5.9 | 652.3 654.3 656.0 |
| 6010 | 2-Cl, 4-tBu phenyl | quinolin-8-yl-NH— | 7.5 | 570.2 572.2 574.0 |
| 6011 | 2-Cl, 4-tBu phenyl | 2-hydroxyphenyl-NH— | 7.2 | 571.2 573.2 575.0 |
| 6012 | 2-Cl, 4-tBu phenyl | 4-(dimethylamino)phenyl-NH— | 5.8 | 598.3 600.3 602.0 |

TABLE 6-continued

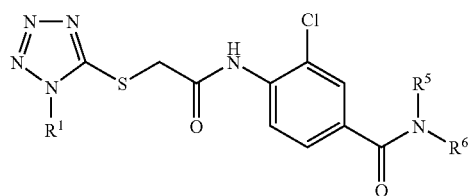

wherein R¹, R⁵ and R⁶ are given in the table below:

| Cpd | R¹ | —N(R⁵)R⁶ | $t_R$ (min) | MS (MH⁺) |
|---|---|---|---|---|
| 6013 | 2-Cl-4-tBu-phenyl | 4-HO-phenyl-NH– | 6.9 | 571.2 573.2 575.0 |
| 6014 | 2-Cl-4-tBu-phenyl | 4-CO₂H-phenyl-NH– | 7.0 | 599.2 601.2 603.0 |
| 6015 | 2-Cl-4-tBu-phenyl | CH₃CH(NH–)CH₂CO₂H | 6.6 | 565.2 567.2 569.2 |
| 6016 | 2-Cl-4-tBu-phenyl | —NH(CH₂)₂OH | 6.1 | 523.2 525.2 527.0 |
| 6017 | 2-Cl-4-tBu-phenyl | 4-HO-phenyl-(CH₂)₂-NH– | 6.9 | 599.3 601.3 603.0 |
| 6018 | 2-Cl-4-tBu-phenyl | HOCH₂CH(CO₂H)NH– | 6.0 | 567.2 569.2 571.2 |
| 6019 | 2-Cl-4-tBu-phenyl | 3,4-diHO-phenyl-CH₂-NH– | 6.7 | 601.2 603.2 605.2 |
| 6020 | 2-Cl-4-tBu-phenyl | 3,4-diHO-phenyl-(CH₂)₂-NH– | 6.7 | 615.3 617.3 619.3 |
| 6021 | 2-Cl-4-tBu-phenyl | 3-CO₂H-phenyl-NH– | 7.0 | 599.2 601.2 603.0 |
| 6022 | 2-Cl-4-tBu-phenyl | 4-(CH=CHCO₂H)-phenyl-NH– | 7.0 | 625.2 627.2 629.0 |

TABLE 6-continued

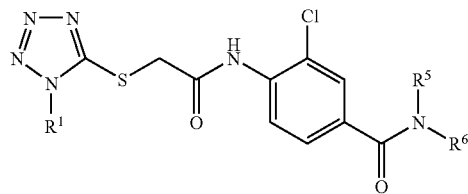

wherein R¹, R⁵ and R⁶ are given in the table below:

| Cpd | R¹ | —N(R⁵)R⁶ | $t_R$ (min) | MS (MH⁺) |
|---|---|---|---|---|
| 6023 | 2-Cl-4-tBu-phenyl | 2-(pyridin-4-yl)ethyl-NH- | 5.3 | 584.3 586.3 588.0 |
| 6024 | 2-Cl-4-tBu-phenyl | —NH(CH₂)₂CO₂H | 6.3 | 551.2 553.2 555.0 |
| 6025 | 2-Cl-4-tBu-phenyl | MeS-CH₂CH₂-CH(CO₂H)-NH- | 6.9 | 611.2 613.2 615.0 |
| 6026 | 2-Cl-4-tBu-phenyl | 4-aminobenzyl-NH- | 5.6 | 584.1 586.1 588.1 |
| 6027 | 2-Cl-4-tBu-phenyl | 1-methyl-5-CO₂H-pyrrol-3-yl-NH- | 6.7 | 606.2 608.2 610.0 |

TABLE 6-continued

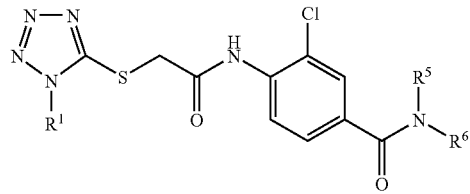

wherein R¹, R⁵ and R⁶ are given in the table below:

| Cpd | R¹ | —N(R⁵)R⁶ | $t_R$ (min) | MS (MH⁺) |
|---|---|---|---|---|
| 6028 | 2-Cl-4-tBu-phenyl | 2-morpholinoethyl-NH- | 5.2 | 592.2 594.2 596.0 |
| 6029 | 2-Cl-4-tBu-phenyl | pyridin-4-yl-NH- | 5.5 | 556.1 558.1 560.1 |
| 6030 | 2-Cl-4-tBu-phenyl | 4-CO₂H-piperidin-1-yl | 6.4 | 591.2 593.2 595.2 |
| 6031 | 2-Cl-4-tBu-phenyl | 4-(2-carboxyethyl)phenyl-NH- | 7.1 | 627.2 629.2 631.0 |
| 6032 | 2-Cl-4-tBu-phenyl | 4-(2-carboxyvinyl)-3-methylphenyl-NH- | 7.3 | 639.2 641.2 643.0 |

TABLE 6-continued

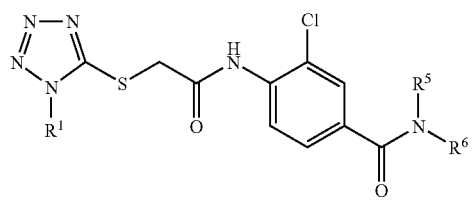

wherein R¹, R⁵ and R⁶ are given in the table below:

| Cpd | R¹ | —N(R⁵)R⁶ | $t_R$ (min) | MS (MH⁺) |
|---|---|---|---|---|
| 6033 | 2-Cl, 4-cyclopropyl-phenyl | —NHC(Me)₂COOH | 5.5 | 546.9 548.9 550.9 |
| 6034 | 2-Cl, 4-cyclopropyl-phenyl | (4-pyridyl N-oxide)CH₂NH— | 5.4 | 568.1 570.1 572.1 (M − H)⁻ |
| 6035 | 2-Cl, 4-cyclopropyl-phenyl | 2-(4-pyridyl N-oxide)ethylNH— | 5.4 | 582.1 584.1 586.1 (M − H)⁻ |
| 6036 | 2-Cl, 4-cyclopropyl-phenyl | —NHSO₂CH₃ | 6.5 | 539.0 541.0 543.0 (M − H)⁻ |
| 6037 | 2-Cl, 4-cyclopropyl-phenyl | —NHSO₂Ph | 7.5 | 601.0 603.0 605.0 (M − H)⁻ |

TABLE 6-continued

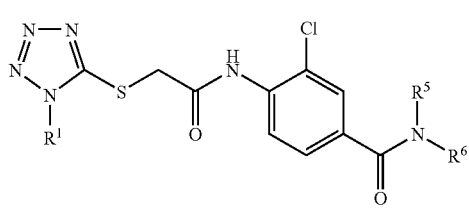

wherein R¹, R⁵ and R⁶ are given in the table below:

| Cpd | R¹ | —N(R⁵)R⁶ | $t_R$ (min) | MS (MH⁺) |
|---|---|---|---|---|
| 6038 | 2-Cl, 4-cyclopropyl-phenyl | (2-pyridyl N-oxide)CH₂NH— | 6.1 | 570.1 572.1 574.0 |
| 6039 | 2-Cl, 4-cyclopropyl-phenyl | (3-pyridyl N-oxide)CH₂NH— | 5.9 | 568.1 570.1 572.1 (M − H)⁻ |

TABLE 7

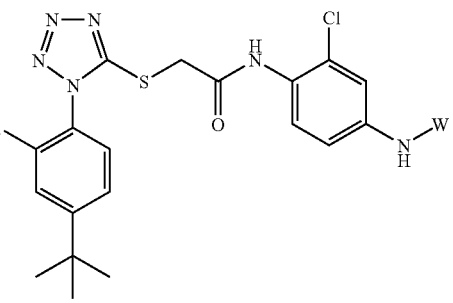

wherein W is given in the table below:

| Cpd | W | $t_R$ (min) | MS (MH⁺) |
|---|---|---|---|
| 7001 | —C(O)CH₂Ph | 10.4 | 570.0 572.0 574.0 |

TABLE 7-continued
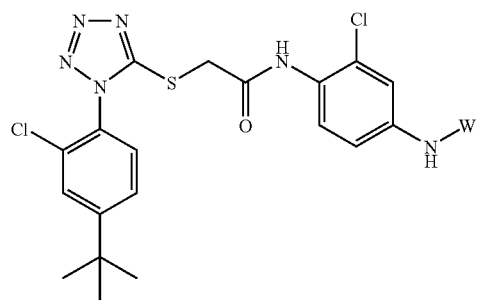
wherein W is given in the table below:
| Cpd | W | $t_R$ (min) | MS (MH+) |
|---|---|---|---|
| 7002 | | 10.4 | 570.1 572.1 574.0 |
| 7003 | | 9.9 | 591.1 593.0 595.0 |
| 7004 | | 10.0 | 605.1 607.0 609.0 |
| 7005 | | 10.5 | 555.1 557.1 559.1 |
| 7006 | | 11.0 | 642.2 644.0 646.0 |
TABLE 7-continued
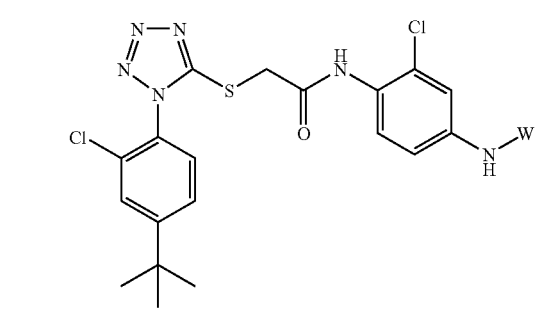
wherein W is given in the table below:
| Cpd | W | $t_R$ (min) | MS (MH+) |
|---|---|---|---|
| 7007 | | 9.8 | 597.0 599.0 601.0 |
| 7008 | | 10.0 | 582.1 584.0 586.0 (M − H)− |
| 7009 | | 9.2 | 612.1 614.1 616.0 (M − H)− |
| 7010 | | 9.7 | 521.1 523.1 525.0 |
| 7011 | | 9.9 | 571.1 573.1 575.0 |

TABLE 7-continued

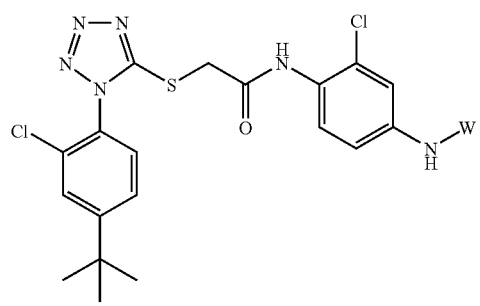

wherein W is given in the table below:

| Cpd | W | $t_R$ (min) | MS (MH$^+$) |
|---|---|---|---|
| 7012 | 3-hydroxybenzoyl | 10.0 | 571.2 573.2 574.2 |
| 7013 | 2-chlorobenzoyl | 11.3 | 589.0 591.1 593.1 595.0 |
| 7014 | 2-hydroxybenzoyl | 11.5 | 571.2 573.2 575.0 |
| 7015 | (4-methoxyphenyl)acetyl | 11.0 | 599.1 601.1 603.0 |
| 7016 | (3-methoxyphenyl)acetyl | 11.0 | 599.2 601.2 603.0 |

TABLE 7-continued

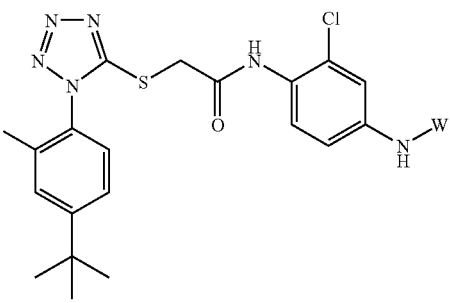

wherein W is given in the table below:

| Cpd | W | $t_R$ (min) | MS (MH$^+$) |
|---|---|---|---|
| 7017 | (3-nitrophenyl)acetyl | 11.1 | 614.2 616.2 618.0 |
| 7018 | (2-methoxyphenyl)acetyl | 11.1 | 559.2 601.2 603.0 |
| 7019 | (2-nitrophenyl)acetyl | 11.0 | 614.1 616.1 618.0 |
| 7020 | pent-4-ynoyl | 10.3 | 531.2 533.2 533.0 |
| 7021 | cyclopentylcarbonyl | 11.2 | 547.1 549.1 551.0 |
| 7022 | cyclohexylcarbonyl | 11.6 | 561.1 563.1 565.0 |
| 7023 | cyclopentylacetyl | 11.6 | 561.2 563.1 565.0 |

TABLE 7-continued

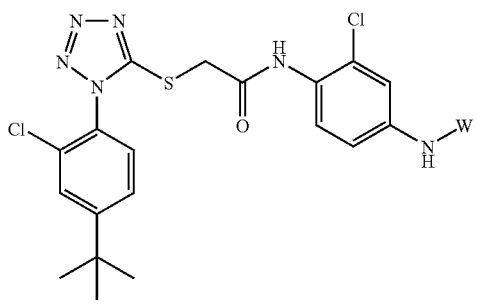

wherein W is given in the table below:

| Cpd | W | $t_R$ (min) | MS (MH+) |
|---|---|---|---|
| 7024 | (isobutyl ketone) | 11.5 | 549.2 / 551.2 / 553.0 |
| 7025 | (4-nitrobenzyl ketone) | 11.1 | 612.2 / 614.2 / 616.2 (M − H)− |
| 7026 | (3-thienylmethyl ketone) | 10.8 | 575.2 / 577.2 / 579.0 |
| 7027 | (3-carboxyphenyl ketone) | 9.9 | 599.1 / 601.1 / 603.0 |
| 7028 | (4-carboxybutyl ketone) | 8.7 | 551.1 / 553.1 / 555.0 |
| 7029 | (4-carboxyphenyl ketone) | 9.9 | 599.1 / 601.1 / 603.0 |

TABLE 7-continued

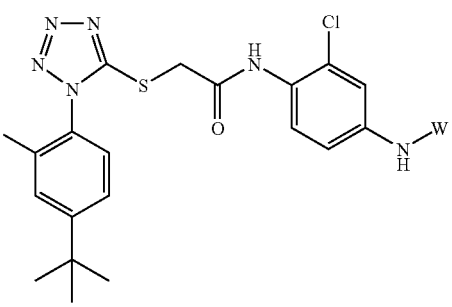

wherein W is given in the table below:

| Cpd | W | $t_R$ (min) | MS (MH+) |
|---|---|---|---|
| 7030 | (4-pyridylmethyl ketone) | 7.7 | 570.1 / 572.1 / 574.0 |
| 7031 | (3-pyridylmethyl ketone) | 7.7 | 570.1 / 572.1 / 573.1 |
| 7032 | (2-pyridylmethyl ketone) | 7.8 | 570.1 / 572.1 / 574.0 |
| 7033 | (N-acetyl phenylglycyl) | 6.3 | 626.0 / 628.0 / 630.0 |
| 7034 | (benzofuran-4-ylmethyl ketone) | 6.8 | 609.0 / 611.0 / 613.0 |

TABLE 7-continued

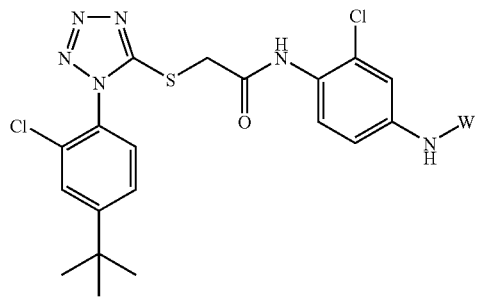

wherein W is given in the table below:

| Cpd | W | $t_R$ (min) | MS (MH$^+$) |
|---|---|---|---|
| 7035 | 2-chlorobenzyl ketone | 6.8 | 603.0 605.0 607.0 609.0 |
| 7036 | 2,6-dichlorobenzyl ketone | 6.2 | 637.0 639.0 641.0 643.0 |
| 7037 | 4-(dimethylamino)benzyl ketone | 5.3 | 612.1 614.0 616.0 |
| 7038 | phenethyl ketone | 6.8 | 583.1 585.0 587.0 |
| 7039 | α-methoxybenzyl ketone | 6.8 | 599.0 601.0 603.0 |

TABLE 7-continued

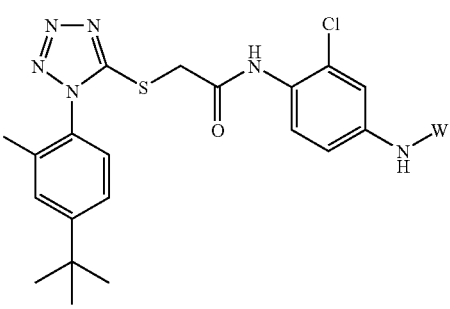

wherein W is given in the table below:

| Cpd | W | $t_R$ (min) | MS (MH$^+$) |
|---|---|---|---|
| 7040 | tetrazolylmethyl ketone | 5.9 | 561.0 563.0 565.0 |
| 7041 | α,α-dimethylbenzyl ketone | 7.0 | 597.1 599.0 601.0 |
| 7042 | 2-hydroxybenzyl ketone | 6.5 | 585.0 587.0 589.0 |
| 7043 | indol-3-ylmethyl ketone | 6.6 | 608.1 610.0 612.0 |
| 7044 | α-methylbenzyl ketone | 6.9 | 583.0 585.0 587.0 |

TABLE 7-continued

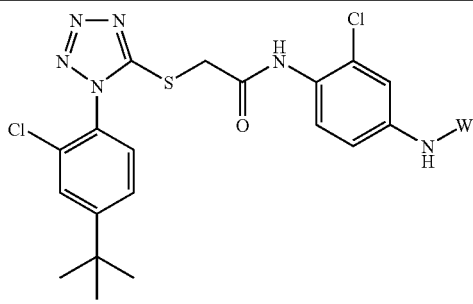

wherein W is given in the table below:

| Cpd | W | $t_R$ (min) | MS (MH$^+$) |
|---|---|---|---|
| 7045 | 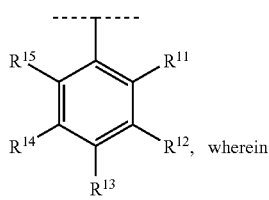 | 102 | 637.2<br>639.0<br>641.0 |
| 7046 | | 8.2 | 584.1<br>586.1<br>588.0<br>(M − H)$^-$ |
| 7047 | | 7.9 | 586.0<br>588.0<br>590.0 |
| 7048 | | 7.8 | 586.0<br>588.0<br>590.0 |

What is claimed is:
1. A compound of formula (I):

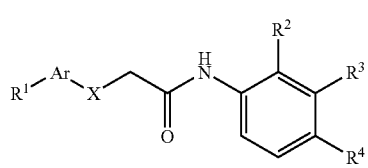

(I)

wherein
Ar is a 5-membered aromatic heterocycle containing 1 to 4 N heteroatoms; said heterocycle being optionally substituted at a substitutable position with R$^{Ar}$, wherein R$^{Ar}$ is H, (C$_{1-4}$)alkyl, CF$_3$ or (C$_{3-7}$)cycloalkyl and wherein the groups X and R$^1$ are attached to positions on the Ar ring which are immediately adjacent to each other;
X is selected from O and S;
R$^1$ is a group of formula:

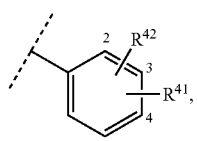

R$^{11}$ is halo; and
R$^{12}$, R$^{13}$, R$^{14}$ and R$^{15}$ are each independently selected from H, halo, (C$_{1-4}$)alkyl, CF$_3$, (C$_{3-7}$)cycloalkyl, (C$_{3-7}$)cycloalkyl-(C$_{1-4}$)alkyl-, cyano, —O—(C$_{1-4}$)alkyl, —OCF$_3$ and —N((C$_{1-4}$)alkyl)$_2$, wherein said (C$_{3-7}$)cycloalkyl is optionally substituted with (C$_{1-4}$) alkyl; or
R$^{12}$ and R$^{13}$, R$^{13}$ and R$^{14}$, or R$^{14}$ and R$^{15}$ are linked, together with the carbon atoms to which they are attached, to form a five- or six-membered saturated, unsaturated or aromatic ring which optionally contains from one to three heteroatoms each independently selected from O, S and N, wherein the remaining of R$^{12}$, R$^{13}$, R$^{14}$ and
R$^{15}$ are defined as hereinbefore;
R$^2$ is selected from halo, nitro and (C$_{1-4}$)alkyl;
R$^3$ is selected from H and halo;
R$^4$ is selected from:
a)

wherein R$^{42}$ is bonded to position 2 or position 3 of the phenyl ring and is selected from H, halo and (C$_{1-4}$)alkyl; and R$^{41}$ is bonded to position 3 or position 4 of the phenyl ring and is selected from:
i) (C$_{1-4}$)alkyl substituted with —COOH, —COO(C$_{1-4}$) alkyl, —C(=O)NH$_2$, —C(=O)NHSO$_2$—(C$_{1-4}$) alkyl, or —OH;
ii) (C$_{2-4}$)alkenyl substituted with —COOH or —COO (C$_{1-4}$)alkyl;
iii) —O—(C$_{1-4}$)alkyl optionally substituted with —COOH, Het, or —N((C$_{1-6}$)alkyl)$_2$, wherein said Het is optionally substituted with —OH or —COOH and wherein either or both of the (C$_{1-6}$)alkyl groups in said —N((C$_{1-6}$)alkyl)$_2$ are optionally substituted with —COOH or —COO(C$_{1-4}$)alkyl; and
iv) —OH, —COOH, —COO(C$_{1-4}$)alkyl, —SO$_2$NH$_2$, or —SO$_2$—(C$_{1-4}$)alkyl;
b) (C$_{2-4}$)alkenyl substituted with —COOH or —COO(C$_{1-4}$)alkyl;
c) —O—(C$_{1-4}$)alkyl substituted with —OH, —COOH or Het, wherein said Het is optionally substituted with —COOH or —COO($C_{1-6}$)alkyl; provided that the carbon atom of —O—($C_{1-4}$)alkyl which is directly bonded to O is not also directly bonded to —OH; and d) —O—$CH_2$—C(=O)N($R^5$)$R^6$ wherein $R^5$ is H or ($C_{1-6}$)alkyl and $R^6$ is selected from:
   i) phenyl optionally substituted with one or two substituents each independently selected from —OH, —COOH, —N(($C_{1-4}$)alkyl)$_2$, ($C_{1-4}$)alkyl, ($C_{2-4}$)alkenyl and Het; wherein said ($C_{1-4}$)alkyl is optionally substituted with —COOH and said ($C_{2-4}$)alkenyl is substituted with —COOH;
   ii) ($C_{1-4}$)alkyl optionally substituted with one or two substituents each independently selected from —COOH, —OH, —S—($C_{1-6}$)alkyl and Het; provided that the carbon atom of ($C_{1-4}$)alkyl which is directly bonded to N is not also directly bonded to —OH;
   iii) phenyl-($C_{1-4}$)alkyl- wherein the phenyl portion of said phenyl-($C_{1-4}$)alkyl- is optionally substituted with one or two substituents each independently selected from —OH, —$NH_2$, and —COOH;
   iii) ($C_{3-7}$)cycloalkyl-($C_{1-4}$)alkyl- wherein the cycloalkyl portion of said ($C_{3-7}$)cycloalkyl-($C_{1-4}$)alkyl- is optionally substituted with —COOH;
   iv) Het optionally substituted with one or two substituents each independently selected from ($C_{1-6}$)alkyl, phenyl-($C_{1-4}$)alkyl- and —COOH;
   v) ($C_{3-7}$)cycloalkyl; and
   vi) —$SO_2$—$R^{61}$ wherein $R^{61}$ is ($C_{1-4}$)alkyl or phenyl;
   or $R^5$ and $R^6$, together with the N to which they are attached, are linked together to form a 5- or 6-membered heterocycle which may be saturated or unsaturated and which may optionally contain from one to three further heteroatoms each independently selected from N, O and S; said heterocycle being optionally substituted with one or two substituents each independently selected from ($C_{1-6}$)alkyl, —COOH and —COO($C_{1-6}$)alkyl;
   wherein Het is a 5- or 6-membered heterocycle or a 9- or 10-membered heterobicycle, each of which may be saturated, unsaturated or aromatic and each of which containing from one to four heteroatoms each independently selected from N, O and S, wherein each said N heteroatom may, independently and where possible, exist in an oxidized state such that it is further bonded to an O atom to form an N-oxide group and wherein each said S heteroatom may, independently and where possible, exist in an oxidized state such that it is further bonded to one or two oxygen atoms to form the groups SO or $SO_2$;
   or a tautomer, salt or ester thereof.

2. The compound according to claim 1 wherein Ar is selected from:

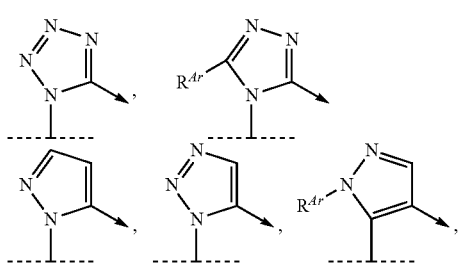

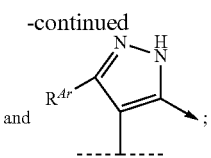

wherein $R^{Ar}$ is defined as in claim 1 and wherein the designation ⊥ represents the bond to $R^1$ and the designation ↘ represents the bond to X.

3. The compound according to claim 2 wherein Ar is selected from

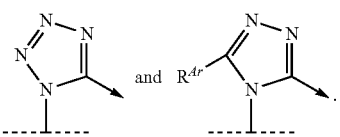

4. The compound according to claim 3 wherein Ar is

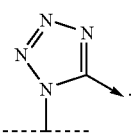

5. The compound according to claim 1 wherein $R^{Ar}$ is selected from H, $CH_3$, $CF_3$ and cyclopropyl.

6. The compound according to claim 1 wherein X is S.

7. The compound according to claim 1 wherein $R^{11}$ is chloro or bromo.

8. The compound according to claim 1 wherein $R^{12}$ is selected from H, ($C_{1-4}$)alkyl, $CF_3$, ($C_{3-7}$)cycloalkyl and halo or $R^{12}$ and $R^{13}$ are linked, together with the carbon atoms to which they are attached, to form a five- or six-membered saturated, unsaturated or aromatic ring which optionally contains from one to three heteroatoms each independently selected from O, S and N.

9. The compound according to claim 8 wherein $R^{12}$ is H, $CF_3$ or cyclopropyl.

10. The compound according to claim 1 wherein $R^{13}$ is selected from H, ($C_{1-4}$)alkyl, $CF_3$, ($C_{3-7}$)cycloalkyl, ($C_{3-7}$)cycloalkyl-($C_{1-4}$)alkyl-, —O—($C_{1-4}$)alkyl, —N(($C_{1-4}$)alkyl)$_2$ and —$OCF_3$; wherein the ($C_{3-7}$)cycloalkyl is optionally substituted with ($C_{1-4}$)alkyl; or wherein $R^{12}$ and $R^{13}$ or $R^{13}$ and $R^{14}$ are linked, together with the carbon atoms to which they are attached, to form a five- or six-membered saturated, unsaturated or aromatic ring which optionally contains from one to three heteroatoms each independently selected from O, S and N.

11. The compound according to claim 10 wherein $R^{13}$ is H, methyl, 1,1-dimethylethyl or cyclopropyl.

12. The compound according to claim 1 wherein $R^{14}$ is selected from H, halo, cyano, ($C_{1-4}$)alkyl, $CF_3$, ($C_{3-7}$)cycloalkyl, ($C_{3-7}$)cycloalkyl-($C_{1-4}$)alkyl-, —O—($C_{1-4}$)alkyl, and —N(($C_{1-4}$)alkyl)$_2$ or $R^{13}$ and $R^{14}$ are linked, together with the carbon atoms to which they are attached, to form a five- or six-membered saturated, unsaturated or aromatic ring which optionally contains from one to three heteroatoms each independently selected from O, S and N.

13. The compound according to claim 12 wherein $R^{14}$ is H, cyclopropyl or $CF_3$.

14. The compound according to claim 1 wherein $R^{15}$ is selected from H, halo, $(C_{1-4})$alkyl and $CF_3$.

15. The compound according to claim 1 wherein $R^2$ is selected from halo, nitro and methyl.

16. The compound according to claim 15 wherein $R^2$ is chloro.

17. The compound according to claim 1 wherein $R^3$ is H or fluoro.

18. The compound according to claim 1 wherein $R^4$ is

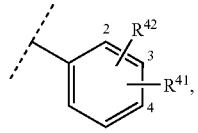

wherein $R^{42}$ is bonded to position 2 or position 3 of the phenyl ring and is selected from H, halo and $(C_{1-4})$alkyl; and $R^{41}$ is bonded to position 3 or position 4 of the phenyl ring and is selected from:
  i) $(C_{1-4})$alkyl substituted with —COOH, —COO$(C_{1-4})$alkyl, —C(=O)NH$_2$, —C(=O)NHSO$_2$—$(C_{1-4})$alkyl, or —OH;
  ii) $(C_{2-4})$alkenyl substituted with —COOH or —COO$(C_{1-4})$alkyl;
  iii) —O—$(C_{1-4})$alkyl optionally substituted with —COOH, Het, or —N($(C_{1-6})$alkyl)$_2$, wherein Het is a 5- or 6-membered saturated, unsaturated or aromatic monocyclic heterocycle containing 1 to 4 heteroatoms each independently selected from O, S and N, wherein each said S heteroatom may, independently and where possible, exist in an oxidized state such that it is further bonded to one or two oxygen atoms to form the groups SO or SO$_2$, said Het being optionally substituted with —OH or —COOH; and wherein either or both of the $(C_{1-6})$ alkyl groups in said —N($(C_{1-6})$alkyl)$_2$ are optionally substituted with —COOH or —COO($(C_{1-4})$alkyl; and
  iv) —OH, —COOH, —COO$(C_{1-4})$alkyl, —SO$_2$NH$_2$, or —SO$_2$—$(C_{1-4})$alkyl.

19. The compound according to claim 18 wherein $R^{42}$ is selected from H, Cl, F and CH$_3$.

20. The compound according to claim 18 wherein $R^{41}$ is selected from:
  i) methyl, ethyl, propyl, 1-methylethyl, butyl, 1-methylpropyl, 2-methylpropyl and 1,1-dimethylethyl, each of which being substituted with —COOH, —COOCH$_3$, —COOCH$_2$CH$_3$ —C(=O)NH$_2$, —C(=O)NHSO$_2$—CH$_3$, or —OH;
  ii) —CH=CH—COOH, —CH=CH—COOCH$_3$ or —CH=CH—COOCH$_2$CH$_3$;
  iii) —O—CH$_3$ or —O—CH$_2$CH$_3$, each of which being optionally substituted with —COOH, Het, or —N($(C_{1-4})$alkyl)$_2$, wherein Het is selected from

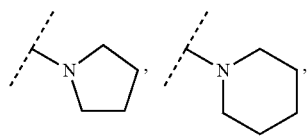

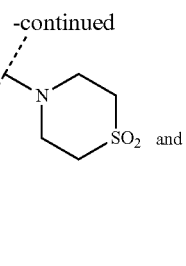

and wherein said Het is optionally substituted with —OH or —COOH and wherein either or both of the $(C_{1-4})$alkyl groups in said —N($(C_{1-4})$alkyl)$_2$ are optionally substituted with —COOH, —COOCH$_3$ or —COOCH$_2$CH$_3$; and
  iv) —OH, —COOH, —COOCH$_3$, —COOCH$_2$CH$_3$, —SO$_2$NH$_2$, or —SO$_2$—CH$_3$.

21. The compound according to claim 18 wherein $R_{41}$ is bonded to position 4 of the phenyl ring.

22. The compound according to claim 1 wherein $R^4$ is selected from:
  b) $(C_{2-4})$alkenyl substituted with —COOH or —COO$(C_{1-4})$alkyl; and
  c) —O—$(C_{1-4})$alkyl substituted with —OH, —COOH or Het wherein Het is a 5- or 6-membered saturated, unsaturated or aromatic monocyclic heterocycle containing 1 to 4 heteroatoms each independently selected from O, S and N, wherein said Het is optionally substituted with —COOH or —COO$(C_{1-6})$alkyl;
    provided that the carbon atom of —O—$(C_{1-4})$alkyl which is directly bonded to O is not also directly bonded to —OH.

23. The compound according to claim 22 wherein $R^4$ is selected from:
  b) $(C_{2-4})$alkenyl substituted with —COOH or —COOCH$_3$; and
  c) —O—$(C_{1-4})$alkyl substituted with —OH, —COOH or Het, wherein Het is selected from

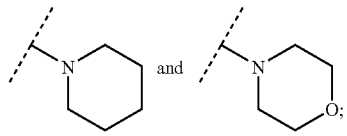

and wherein said Het is optionally substituted with —COOH, —COOCH$_3$ or —COOCH$_2$CH$_3$;
    provided that the carbon atom of —O—$(C_{1-4})$alkyl which is directly bonded to O is not also directly bonded to —OH.

24. The compound according to claim 1 wherein $R^4$ is —O—CH$_2$—C(=O)N(R$^5$)R$^6$ wherein R$^5$ is H or $(C_{1-6})$alkyl and R$^6$ is selected from:
  i) phenyl optionally substituted with one or two substituents each independently selected from —OH, —COOH, —N($(C_{1-4})$alkyl)$_2$, $(C_{1-4})$alkyl, $(C_{2-4})$alkenyl and Het wherein Het is a 5- or 6-membered saturated, unsaturated or aromatic monocyclic heterocycle containing 1 to 4 heteroatoms each independently selected from O, S and N; wherein said $(C_{1-4})$alkyl is optionally substituted with —COOH and said $(C_{2-4})$alkenyl is substituted with —COOH;
  ii) $(C_{1-4})$alkyl optionally substituted with one or two substituents each independently selected from —COOH, —OH, —S—($C_{1-6}$)alkyl and Het wherein Het is a 5- or 6-membered saturated, unsaturated or aromatic monocyclic heterocycle containing 1 to 4 heteroatoms each independently selected from O, S and N wherein each said N heteroatom may, independently and where possible, exist in an oxidized state such that it is further bonded to an O atom to form an N-oxide group;

provided that the carbon atom of ($C_{1-4}$)alkyl which is directly bonded to N is not also directly bonded to —OH;

iii) phenyl-($C_{1-4}$)alkyl- wherein the phenyl portion of said phenyl-($C_{1-4}$)alkyl- is optionally substituted with one or two substituents each independently selected from —OH, —$NH_2$ and —COOH;

iv) ($C_{3-7}$)cycloalkyl-($C_{1-4}$)alkyl- wherein the cycloalkyl portion of said ($C_{3-7}$)cycloalkyl-($C_{1-4}$)alkyl- is optionally substituted with —COOH;

v) Het optionally substituted with one or two substituents each independently selected from ($C_{1-6}$)alkyl, phenyl-($C_{1-4}$)alkyl- and —COOH wherein Het is a 5-or 6-membered heterocycle or a 9- or 10-membered heterobicycle, each of which may be saturated, unsaturated or aromatic and each of which may optionally contain from one to four heteroatoms each independently selected from N, O and S;

vi) ($C_{3-7}$)cycloalkyl; and vii) —$SO_2$—$R^{61}$ wherein $R^{61}$ is ($C_{1-4}$)alkyl or phenyl;

or $R^5$ and $R^6$, together with the N to which they are attached, are linked together to form a 5- or 6-membered heterocycle which may be saturated or unsaturated and which may optionally contain from one to three further heteroatoms each independently selected from N, O and S; said heterocycle being optionally substituted with one or two substituents each independently selected from ($C_{1-6}$)alkyl, —COOH and —COO($C_{1-6}$)alkyl.

25. The compound according to claim 24 wherein $R^5$ is H or $CH_3$ and $R^6$ is selected from:

i) phenyl optionally substituted with one or two substituents each independently selected from —OH, —COOH, —N($CH_3$)$_2$, $CH_3$, —$CH_2$COOH, —$CH_2CH_2$COOH,

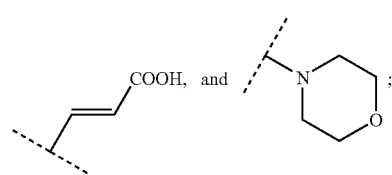

ii) ($C_{1-4}$)alkyl optionally substituted with one or two substituents each independently selected from —COOH, —OH, —S—$CH_3$ and Het, wherein Het is selected from

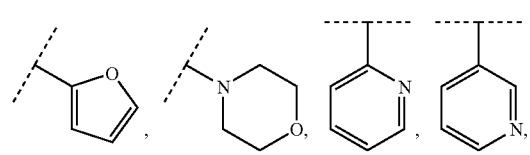

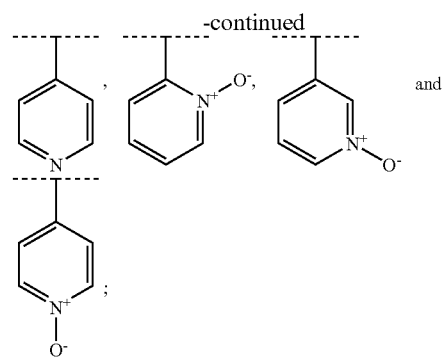

provided that the carbon atom of ($C_{1-4}$)alkyl which is directly bonded to N is not also directly bonded to —OH;

iii) phenyl-$CH_2$— or phenyl-$CH_2CH_2$—, wherein the phenyl portion of said phenyl-$CH_2$— or phenyl-$CH_2CH_2$— is optionally substituted with one or two substituents each independently selected from —OH, —$NH_2$, and —COOH;

iv) (4-carboxycyclohexyl)methyl;

v) Het optionally substituted with one or two substituents each independently selected from methyl, phenylmethyl- and —COOH, wherein said Het is selected from

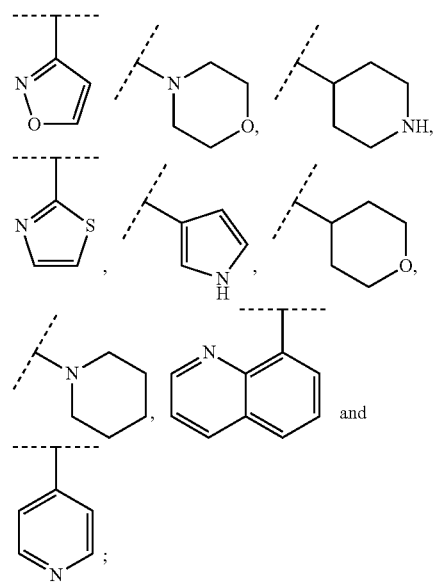

vi) cyclopropyl;

vii) —$SO_2$—$CH_3$ and —$SO_2$-Ph;

or $R^5$ and $R^6$, together with the N to which they are attached, are linked together to form a 6-membered saturated heterocycle which may optionally contain one further heteroatom independently selected from N and O; said heterocycle being optionally substituted with one or two substituents each independently selected from $CH_3$ and —COOH.

26. A pharmaceutical composition, comprising a compound according to claim 1, or a pharmaceutically acceptable salt or ester thereof, and a pharmaceutically acceptable carrier.

27. The composition according to claim 26 additionally comprising at least one antiretroviral drug, wherein said antiretroviral drug is selected from the group consisting of NRTIs, NNRTIs, protease inhibitors, entry inhibitors, integrase inhibitors, TAT inhibitors, maturation inhibitors, immunomodulating agents and antifungal or antibacterial agents.

28. A method of treating HIV infection in a mammal by administering to the mammal an anti-HIV effective amount of a compound according to claim 1 or a pharmaceutically acceptable salt or ester thereof.

* * * * *